US009266942B2

(12) United States Patent
Granoff et al.

(10) Patent No.: US 9,266,942 B2
(45) Date of Patent: Feb. 23, 2016

(54) CHIMERIC FACTOR H BINDING PROTEINS (FHBP) AND METHODS OF USE

(75) Inventors: Dan M. Granoff, Berkeley, CA (US); Peter Beernink, Walnut Creek, CA (US)

(73) Assignee: Children's Hospital & Research Center Oakland, Oakland, CA (US)

( * ) Notice: Subject to any disclaimer, the term of this patent is extended or adjusted under 35 U.S.C. 154(b) by 149 days.

(21) Appl. No.: 13/259,063

(22) PCT Filed: Apr. 29, 2010

(86) PCT No.: PCT/US2010/033048
§ 371 (c)(1),
(2), (4) Date: Dec. 13, 2011

(87) PCT Pub. No.: WO2010/127172
PCT Pub. Date: Nov. 4, 2010

(65) Prior Publication Data
US 2012/0121637 A1    May 17, 2012

Related U.S. Application Data

(60) Provisional application No. 61/174,424, filed on Apr. 30, 2009.

(51) Int. Cl.
*A61K 39/095*     (2006.01)
*C07K 19/00*      (2006.01)
*C07K 16/12*      (2006.01)
*A61K 39/00*      (2006.01)

(52) U.S. Cl.
CPC ........... *C07K 16/1217* (2013.01); *A61K 39/095* (2013.01); *A61K 2039/55555* (2013.01)

(58) Field of Classification Search
None
See application file for complete search history.

(56) References Cited

U.S. PATENT DOCUMENTS

| | | | |
|---|---|---|---|
| 8,470,340 B2 * | 6/2013 | Beernink et al. | 424/250.1 |
| 2005/0222385 A1 | 10/2005 | Pizza | |
| 2006/0166344 A1* | 7/2006 | Pizza et al. | 435/183 |
| 2006/0251670 A1 | 11/2006 | Comanducci et al. | |
| 2007/0148729 A1 | 6/2007 | Farley et al. | |
| 2008/0248065 A1 | 10/2008 | Granoff et al. | |
| 2009/0035328 A1 | 2/2009 | Granoff | |
| 2009/0104150 A1 | 4/2009 | Pepinsky et al. | |
| 2009/0285845 A1 | 11/2009 | Masignani | |
| 2011/0256180 A1 | 10/2011 | Beernink et al. | |

FOREIGN PATENT DOCUMENTS

| | | |
|---|---|---|
| WO | WO 9957280 | 11/1999 |
| WO | WO 2004048404 | 10/2004 |
| WO | WO 2006024954 | 3/2006 |
| WO | WO 2007060548 | 5/2007 |
| WO | 2008125985 | 10/2008 |
| WO | WO 2010027872 | 3/2010 |
| WO | WO 2010046715 | 4/2010 |

OTHER PUBLICATIONS

Greenspan et al. Nature Biotechnology 17: 936-937, 1999.*
Welsch et al. Molecular Immunology 44: p. 256, #251, 2007.*
Beernink & Granoff (2008) "Bactericidal antibody responses induced by meningococcal recombinant chimeric factor H-binding protein vaccines" *Infect. Immun.* 76(6):2568-2575.
Beernink & Granoff (2009) "The modular architecture of meningococcal factor H-binding protein" *Microbiology* 155(Pt. 9):2873-2883.
Beernink et al (2010) "Impaired immunogenicity of a meningococcal factor H-binding protein vaccine engineered to eliminate factor h binding" *Clin Vaccine Immunol* 17(7):1074-1078.
Beernink et al. (2008) "Fine antigenic specificity and cooperative bactericidal activity of monoclonal antibodies directed at the meningococcal vaccine candidate factor h-binding protein" *Infect. Immun.* 76(9):4232-4240.
Beernink et al. (2009) "A region of the N-terminal domain of meningococcal factor H-binding protein that elicits bactericidal antibody across antigenic variant groups" *Mol Immunol* 46(8-9):1647-1653.
Borrow, et al. (2001) "Serological Basis for Use of Meningococcal Serogroup C Conjugate Vaccines in the U.K..: Reevaluation of Correlates of Protection" *Infect. Immun.* 69(3):1568-1573.
Davila et al. (2010) "Genome-wide association study identifies variants in the CFH region associated with host susceptibility to meningococcal disease" *Nat Genetics* 42(9):772-776. doi:10.1038/ng.640.
Fletcher, et al. (2004) "Vaccine potential of the Neisseria meningitidis 2086 lipoprotein" *Infect Immun.* 72(4):2088-2100.
GenBank Accession No. AY548370 "Neisseria meningitidis strain H44/76 lipoprotein (gna1870) gene, complete cds" (AAT01289.1) (from N. meningitidis strain H44/76), dated May 1, 2004.
GenBank Accession No. AY548371 "Neisseria meningitidis strain CU385 lipoprotein (gna1870) gene, complete cd" (AAT01290.1) (from N. meningitidis strain CU385), dated May 1, 2004.
GenBank Accession No. AY548372 "Neisseria meningitidis strain BZ83 lipoprotein GNA1870 (gna1870) gene, complete cd" (AAS56915.1) (from N. meningitidis strain BZ83), dated Apr. 22, 2004.
GenBank Accession No. AY548373 "Neisseria meningitidis strain 4243 lipoprotein GNA1870 (gna1870) gene, complete cd" (AAS56916.1) (from N. meningitidis strain 4243), dated Apr. 22, 2004.
GenBank Accession No. AY548374 "Neisseria meningitidis strain M6190 lipoprotein GNA1870 (gna1870) gene, complete cd" (AAS56917.1) (from N. meningitidis strain M6190), dated Apr. 22, 2004.
GenBank Accession No. AY548375 "Neisseria meningitidis strain N98/254 lipoprotein GNA1870 (gna1870) gene, complete cd" (AAS56918.1) (from N. meningitidis strain NZ98/254), dated Apr. 22, 2004.

(Continued)

*Primary Examiner* — S. Devi
(74) *Attorney, Agent, or Firm* — Shweta Chandra; Carol L. Francis; Bozicevic, Field & Francis, LLP

(57) ABSTRACT

Chimeric fHbps that can elicit antibodies that are bactericidal for different fHbp variant strains of *N. meningitidis*, and methods of use, are provided.

18 Claims, 39 Drawing Sheets

(56) References Cited

OTHER PUBLICATIONS

GenBank Accession No. AY548376 "Neisseria meningitidis strain M1390 lipoprotein GNA1870 (gna1870) gene, complete cds" (AAS56919.1) (from N. meningitidis strain M1390), dated Apr. 22, 2004.
GenBank Accession No. AY548377 "Neisseria meningitidis strain M4105 lipoprotein GNA1870 (gna1870) gene, complete cd" (AAS56920.1) (fHbp ID 4 from N. meningitidis strain M4105), dated Apr. 22, 2004.
GenBank Accession No. NC_003112, "Neisseria meningitidis MC58, complete genom" GeneID: 904318 (NCBI Ref. NP_274866), fHbp ID 1 from N. meningitidis strain MC58, ), dated May 24, 2010.
GenBank Accession No. NP_000177 (P08603), and its encoding nucleic acid as NM_000186, "complement factor H isoform a precursor [*Homo sapiens*]" dated Mar. 21, 2010.
Giuliani, et al. (2005) "The region comprising amino acids 100 to 255 of Neisseria meningitidis lipoprotein GNA 1870 elicits bactericidal antibodies" *Infect. Immun.* 73(2):1151-1160.
Goldschneider, et al. (1969) "Human Immunity to the Meningococcus: I. The Role of the Humoral Antibodies" *J. Exp. Med.* 129(6):1307-1326.
Granoff, et al. (1998) "Bacterial Monoclonal Antibodies That Define Unique Meningococcal B Polysaccharide Epitopes That Do Not Cross-React with Human Polysialic Acid" *J. Immunol.* 160(10):5028-5036.
Granoff, et al. (2009) "Binding of complement factor H (fH) to Neisseria meningitidis is specific for human fH and inhibits complement activation by rat and rabbit sera" *Infect. Immun.* 77(2):764-769.
Masignani, et al. (2003) "Vaccination against Neisseria meningitidis using three variants of the lipoprotein GNA1870" *J. Exp. Med.* 197(6):789-799.
Pajon, et al. (2010) "Frequency of factor H-binding protein modular groups and susceptibility to cross-reactive bactericidal activity in invasive meningococcal isolates" *Vaccine* 28(9):2122-2129.
Scarselli, et al. (2009) "Epitope mapping of a bactericidal monoclonal antibody against the factor H binding protein of Neisseria meningitidis" *J. Mol. Biol.* 386(1):97-108.
Shaughnessy, et al. (2009) "Functional comparison of the binding of factor H short consensus repeat 6 (SCR 6) to factor H binding protein from Neisseria meningitidis and the binding of factor H SCR 18 to 20 to Neisseria gonorrhoeae porin" *Infect. Immun.* 77(5):2094-2103.
Welsch, et al. (2004) "Protective activity of monoclonal antibodies to genome-derived neisseria) antigen 1870, a Neisseria meningitidis candidate vaccine" *J. Immunol.* 172(9):5606-5615.
U.S. Appl. No. 12/921,123, filed Nov. 22, 2011, Granoff, et al.
U.S. Appl. No. 13/058,283, filed Apr. 7, 2011, Beernink, et al.
U.S. Appl. No. 13/279,006, filed Oct. 10, 2011, Granoff, et al.
Beernink (2006) "Rapid genetic grouping of factor h-binding protein (genome-derived neisseria) antigen 1870), a promising group B meningococcal vaccine candidate" *Clin. Vaccine Immunol.* 13(7):758-763.
McDowell, et al. (2004) "Demonstration of the involvement of outer surface protein E coiled coil structural domains and higher order structural elements in the binding of infection-induced antibody and the complement-regulatory protein, factor H" *J. Immunol.* 173:7471-7480.
Schneider et al. (2009) "*Neisseria meningitidis* recruits factor H using protein mimicry of host carbohydrates" *Nature* 458(7240):890-893.
Tettelin, et al. (2000) Uniprot Q9JXV4, Oct. 1, 2000, http://www.uniprot.org/uniprot/Q9JXV4.txt.
Welsch, et al. (2008) "Complement-dependent synergistic bactericidal activity of antibodies against factor H-binding protein, a sparsely distributed meningococcal vaccine antigen" *J. Infect. Dis.* 197(7):1053-1061.
Beernink, et al. (2007) "Prevalence of Factor H-Binding Protein Variants and NadA Among Meningococcal Group B Isolates from the United States: Implications for the Development of a Multicomponent Group B Vaccine" *J. Infect. Dis.* 195(10):1472-1479.
Fukasawa, et al., Immune Response to Naitive NadA from Neisseria Meningitidis and its Expression in Clinical Isolates in Mrazil, Journal of Medical Microbiology, 2003, 52:121-125.
Genbank Accession No. AAS56918 "Lipoprotein GNA1870 [Neisseria meningitidis]" dated Apr. 22, 2004.
Genbank Accession No. ABC59063 "Factor H Binding Protein [Neisseria meningitidis]" dated Jun. 20, 2006.
Genbank Accession No. ACI46937 "Factor H Binding Protein Variant A72_001 [Neisseria meningitidis]" dated Aug. 4, 2009.
Genbank Accession No. ACJ45782 "Factor H Binding Protein [Neisseria meningitidis]" dated Nov. 23, 2008.
Genbank Accession No. ACZ93150 "Factor H Binding Protein [Neisseria meningitidis]" dated Dec. 15, 2009.
Genbank Accession No. ACZ93290 "Factor H Binding Protein [Neisseria meningitidis]" dated Dec. 15, 2009.
Lewis, et al. (2010) "The Meningococcal Vaccine Candidate Neisserial Surface Protein A (NspA) Binds to Factor H and Enhances Meningococcal Resistance to Complement" *PLoS Pathog.* 6(7):e1001027:1-20.
Madico, et al. (2006) "The Meningococcal Vaccine Candidate GNA1870 Binds the Complement Regulatory Protein Factor H and Enhances Serum Resistance" *J. Immunol.* 177:501-510.
Maslanka, et al. (1997) "Standardization and a Multilaboratory Comparison of Neisseria Meningitidis Serogroup A and C Serum Bactericidal Assays" *Clin. Diagn. Lab. Immunol.* 4(2):156-157.
Ngampasutadol, et al. (2007) "A Novel Interaction Between Factor H SCR 6 and the Meningococcal Vaccine Candidate GNA 1870: Implications for Meningococcal Pathogenesis and Vaccine Development" *Mol. Immunol.* 44(1-3):220. Abstract.
Ngampasutadol, et al. (2008) "Human Factor H Interacts Selectively with *Neisseria gonorrhoeae* and Results in Species-Specific Complement Evasion" *J. Immunol.* 180(5):3426-3435.
Schneider, et al. (2009) "Supplemental Methods for *Neisseria meningitides* Recruits Factor H Using Protein Mimicry of Host Carbohydrates" *Nature* doi:10.1038/nature07769:1-17.

\* cited by examiner

Fig. 1A: Table 7, Source strains and characteristics of unique factor H binding protein variants.

| Strain (reference) | Country | Capsular Group | MLST ST | MLST Clonal Cpx. | PorA Variable Region ST | fHbp Characteristics Variant Group | fHbp Characteristics Sub-family | fHbp Characteristics Peptide ID | fHbp Characteristics Modular Group[2] | GenBank Acc. No. | N-term Element[3] | fHbp Variable Segment[1] A | B | C | D | E |
|---|---|---|---|---|---|---|---|---|---|---|---|---|---|---|---|---|
| MC58 (Tettelin et al., 2000) | UK | B | 74 | 32 | 7,16-2 | 1 | B | 1 | I | NP 274866 | G | A.α.2 | B.α.1 | C.α.5 | D.α.5 | E.α.8 |
| M2197 | US | C | 11 | 11 | 7,1 | 1 | B | 2 | I | None* | G | A.α.3 | B.α.1 | C.α.2 | D.α.2 | E.α.1 |
| 4243 (Welsch et al., 2004) | US | C | 11 | 11 | 5,2 | 1 | B | 3 | I | AAS569 16 | G | A.α.3 | B.α.1 | C.α.6 | D.α.1 | E.α.1 |
| M4105 (Welsch et al., 2004) | US | B | 154 | 41/44 | 7,4 | 1 | B | 4 | I | AAS569 20 | G | A.α.1 | B.α.1 | C.α.2 | D.α.4 | E.α.2 |
| 72491 (Parkhill et al., 2000) | Gambia | A | 4 | 4 | 7,13-1 | 1 | B | 5 | I | NP 283399 | G | A.α.13 | B.α.1 | C.α.2 | D.α.4 | E.α.2 |
| M6190 (Welsch et al., 2004) | US | B | 1988 | 11 | 5,2 | 1 | B | 6 | I | AAS569 17 | G | A.α.2 | B.α.7 | C.α.14 | D.α.3 | E.α.17 |
| M2937 | US | B | 35 | 35 | 23,14 | 1 | B | 7 | I | None* | G | A.α.12 | B.α.1 | C.α.10 | D.α.3 | E.α.12 |

[1] For each variable segment, distinct sequence variants were assigned a unique identifier beginning with a letter, A through E, to represent the segment; followed by an α or β to indicate the presence of residues with the respective types described above, followed by a number for each distinct sequence
[2] Modular group see figure 8.
[3] The mature fHbp begins with a cysteine residue that is lipidated, which is followed by three invariant amino acid residues, SSG. This invariant sequence is followed by a repetitive variable sequence consisting of 1 to 6 glycine and/or serine residues and then by two invariant glycine residues

Fig. 1B: Table 7, Source strains and characteristics of unique factor H binding protein variants.

| | | | | | | | | | | | | | | | | |
|---|---|---|---|---|---|---|---|---|---|---|---|---|---|---|---|---|
| 03S-0501 (Beernink et al., 2006) | US | B | 44 | 41/44 | 19-1,26 | 1 | B | 8 | I | GQ219775 | G | A.α.2 | B.α.1 | C.α.16 | D.α. 1 | E.α.23 |
| Mali 29/07 (Beernink et al., 2009) | Mali | W-135 | 11 | 11 | 5,2 | 1 | B | 9 | I | ACI31833 | GGGSGG | A.α.2 | B.α.1 | C.α.1 | D.α.6 | E.α.16 |
| M01 240185 | UK | B | 11 | 11 | 5-1,10-8 | 1 | B | 10 | I | ACB38154 | G | A.α.3 | B.α.2 | C.α.1 | D.α.1 | E.α.3 |
| M01 240993 (Beernink et al., 2008) | UK | B | 11 | 11 | NT | 1 | B | 11 | I | EU337063 | G | A.α.3 | B.α.1 | C.α.6 | D.α.1 | E.α.7 |
| 03S-0444 (Beernink et al., 2006) | US | B | 136 | 41/44 | 17,16-3 | 1 | B | 12 | I | GQ219774 | G | A.α.1 | B.α.1 | C.α.1 | D.α.1 | E.α.6 |
| M05 240018 | UK | B | 1161 | 269 | 22,9 | 1 | B | 13 | I | ACB38141 | G | A.α.2 | B.α.2 | C.α.1 | D.α.1 | E.α.6 |
| NZ98/254 (Welsch et al., 2004) | New Zealand | B | 41 | 41/44 | 7-2,4 | 1 | B | 14 | I | AAS56918 | G | A.α.1 | B.α.1 | C.α.3 | D.α.1 | E.α.3 |
| M97 250571 (Fletcher et al., 2004) | UK | B | NA | NA | ?,16 | 1 | B | 40 | I | AAR84486 | G | A.α.2 | B.α.1 | C.α.5 | D.α.5 | E.α.9 |
| 6940 (Fletcher et al., 2004) | US | B | NA | NA | 18,25,6 | 1 | B | 54 | I | AAR84474 | G | A.α.2 | B.α.4 | C.α.2 | D.α.2 | E.α.10 |
| CDC-852 (Fletcher et al., 2004) | US | B | NA | NA | 5,2 | 1 | B | 56 | I | AAR84482 | G | A.α.2 | B.α.2 | C.α.15 | D.α.1 | E.α.24 |
| CDC-983 (Fletcher et al., 2004) | US | B | NA | NA | 5,2 | 1 | B | 57 | I | AAR84483 | G | A.α.3 | B.α.5 | C.α.7 | D.α.2 | E.α.1 |

Fig. 1C: Table 7, Source strains and characteristics of unique factor H binding protein variants.

| | | | | | | | | | | | A.α.1 | B.α.1 | C.α.19 | D.α.1 | E.α.11 |
|---|---|---|---|---|---|---|---|---|---|---|---|---|---|---|---|
| CDC-1343 (Fletcher et al., 2004) | NA | B | NA | NA | NA | 1 | B | 58 | I | AAR84484 | G | A.α.1 | B.

Fig. 1D: Table 7. Source strains and characteristics of unique factor H binding protein variants.

| Strain | Country | C | | | | | | | | | Accession | Linker | A | B | C | D | E |
|---|---|---|---|---|---|---|---|---|---|---|---|---|---|---|---|---|---|
| 053442 (Peng et al., 2008) | China | C | 4821 | 4821 | 4821 | NA | 1 | B | 80 | I | ABX72558 | GG GSG S | A.α.14 | B.α.4 | C.α.20 | D.α.3 | E.α.18 |
| SK80 (Beernink et al., 2008) | US | B | 162 | 162 | 162 | 22,14 | 1 | B | 88 | I | GQ219767 | G | A.α.15 | B.α.1 | C.α.21 | D.α.3 | E.α.25 |
| SK84 (Beernink et al., 2008) | US | B | 32 | 32 | 32 | 7,16 | 1 | B | 89 | I | GQ219768 | G | A.α.2 | B.α.1 | C.α.22 | D.α.9 | E.α.26 |
| SK141 (Beernink et al., 2008) | US | B | 213 | 213 | 213 | 22,14 | 1 | B | 90 | I | GQ219770 | G | A.α.16 | B.α.1 | C.α.6 | D.α.1 | E.α.7 |
| M1239 (Masignani et al., 2003) | US | B | 437 | 437 | 41/44 | 23,14 | 3 | A | 28 | II | ABF82029 | GG GSG G | A.β.1 | B.β.1 | C.β.9 | D.β.1 | E.β.6 |
| 03S-0669 (Beernink et al., 2006) | US | B | 5573 | 5573 | 162 | 22,14 | 3 | A | 29 | II | GQ219776 | GG GSG G | A.β.6 | B.β.1 | C.β.10 | D.β.2 | E.β.4 |
| M01 240988 | UK | B | 213 | 213 | 213 | 22,14 | 3 | A | 30 | II | ACA52541 | GG GSG G | A.β.1 | B.β.1 | C.β.11 | D.β.2 | E.β.5 |
| CDC-1135 (Fletcher et al., 2004) | US | B | NA | NA | NA | non-typable | 3 | A | 46 | II | AAR84437 | GG GSG G | A.β.1 | B.β.1 | C.β.1 | D.β.3 | E.β.4 |
| M06 240137 | UK | B | 492 | 492 | 269 | 12-1,13-1 | 3 | A | 64 | II | ACB38148 | SGG | A.β.1 | B.β.1 | C.β.5 | D.β.2 | E.β.5 |
| M01 242162 | UK | B | 283 | 283 | 269 | 19-1,15-11 | 3 | A | 72 | II | ACM44939 | GG GS | A.β.2 | B.β.1 | C.β.1 | D.α.1 | E.β.2 |

Fig. 1E: Table 7, Source strains and characteristics of unique factor H binding protein variants.

| | | | | | | | | | | | | | | | | |
|---|---|---|---|---|---|---|---|---|---|---|---|---|---|---|---|---|
| 03S-0451 (Beernink et al., 2006) | US | B | 32 | 32 | 22-1,14 | 3 | A | 76 | II | ACJ04735 | GG GS | A.β.8 | B.β.1 | C.β.1 | D.β.1 | E.β.3 |
| MD1397 (this study) | US | B | 162 | 162 | 22,14 | 2 | A | 21 | III | GQ219771 | G | A.α.1 | B.α.1 | C.α.2 | D.β.1 | E.β.3 |
| RM1090 (Beernink et al., 2008) | US | C | 11 | 11 | 5,2 | 2 | A | 22 | III | ABY26518 | GG | A.α.1 | B.α.1 | C.β.2 | D.β.1 | E.β.1 |
| BuFa 2/03 (Beernink et al., 2009) | Burkina Faso | W-135 | 11 | 11 | 5-1,2 | 2 | A | 23 | III | ACI31834 | GG | A.α.2 | B.α.1 | C.β.2 | D.β.1 | E.β.1 |
| M08 240117 | UK | B | 3496 | 213 | 22,14 | 2 | A | 24 | III | ACM44952 | GG | A.α.1 | B.α.3 | C.β.3 | D.β.1 | E.β.1 |
| 6275 | NA | B | NA | NA | NA | 2 | A | 25 | III | AAR84427 | G | A.α.4 | B.α.3 | C.β.3 | D.β.1 | E.β.1 |
| NM452 | US | B | 283 | 269 | 19-1,15-11 | 1 | B | 15 | IV | ABL14232 | GG GSG G | A.β.3 | B.α.1 | C.α.4 | D.α.1 | E.α.4 |
| CDC-1573 (Fletcher et al., 2004) | US | B | NA | NA | 7-1,1 | 1 | B | 55 | IV | AAR84481 | GG GSG G | A.β.9 | B.α.1 | C.α.8 | D.α.1 | E.α.14 |
| M06 241169 | CaNAda | B | NT | 269 | 17,19 | 1 | B | 65 | IV | ACB38149 | GG GSG G | A.β.3 | B.α.1 | C.α.4 | D.α.1 | E.α.5 |
| M08 240004 | UK | B | 5861 | 41/44 | 7-2,4 | 1 | B | 86 | IV | ACM44948 | GG GSG G | A.β.3 | B.α.1 | C.α.4 | D.α.1 | E.α.3 |
| M08 240077 | UK | B | 839 | 41/44 | 21,16 | 1 | B | 87 | IV | ACM44953 | GG GSG G | A.β.3 | B.α.1 | C.α.11 | D.α.1 | E.α.4 |

Fig. 1F: Table 7, Source strains and characteristics of unique factor H binding protein variants.

| | | | | | | | | | | | | | | | | |
|---|---|---|---|---|---|---|---|---|---|---|---|---|---|---|---|---|
| M01 240355 | UK | B | 213 | 213 | 22,14 | 3 | A | 31 | V | ACB38139 | GG GSGS | A.β.2 | B.β.1 | C.β.1 | D.α.1 | E.β.2 |
| M98 250771 (Fletcher et al., 2004) | UK | B | NA | NA | 22,14 | 3 | A | 45 | V | AAR84436 | SGS GG | A.β.5 | B.β.1 | C.β.2 | D.α.1 | E.β.3 |
| M97 252153 (Fletcher et al., 2004) | UK | B | NA | NA | 18,25,6 | 3 | A | 47 | V | AAR84438 | G | A.β.4 | B.β.1 | C.β.5 | D.α.1 | E.β.9 |
| C2120 (Madico *et al.*, 2006) | Germany | C | 11 | 11 | 5,2 | 3 | A | 59 | V | ABC59061 | GG GSGS | A.β.2 | B.β.1 | C.β.1 | D.α.8 | E.β.2 |
| M06 240138 | UK | B | 269 | 269 | 19-1,15-36 | 3 | A | 70 | V | ACM44938 | GG GSGG | A.β.7 | B.β.1 | C.β.1 | D.α.1 | E.β.2 |
| S3032 (Plested & Granoff, 2008) | US | B | 6874 | UA | 12,16 | 3 | A | 79 | V | ACH48234 | GG GSGS | A.β.2 | B.β.1 | C.β.1 | D.α.1 | E.β.4 |
| MD1475 (this study) | US | B | 162 | 162 | 7-2,4-21 | 3 | A | 82 | V | GQ219772 | G | A.β.1 | B.β.1 | C.β.8 | D.α.1 | E.β.11 |
| M08 240109 | UK | B | 2391 | 213 | 5-2,10-1 | 3 | A | 85 | V | ACM44944 | GG GSGS | A.β.2 | B.β.1 | C.β.2 | D.α.1 | E.β.3 |
| 961-5945 (Masignani et al., 2003) | Australia | B | 153 | 8 | 21,16 | 2 | A | 16 | VI | AAR84453 | GG | A.α.1 | B.α.1 | C.β.4 | D.α.1 | E.β.2 |
| C4678 | Germany | C | 11 | 11 | 5,2 | 2 | A | 17 | VI | None* | GG | A.α.1 | B.α.1 | C.β.1 | D.α.1 | E.β.2 |
| 03S-0150 (Beernink et al., 2006) | US | B | 44 | 41/44 | 7-1,1 | 2 | A | 19 | VI | GQ219773 | G | A.α.1 | B.α.1 | C.β.2 | D.α.1 | E.β.1 |

Fig. 1G: Table 7, Source strains and characteristics of unique factor H binding protein variants.

| | | | | | | | | | | | | | | | | |
|---|---|---|---|---|---|---|---|---|---|---|---|---|---|---|---|---|
| M0579 | US | B | 43 | 41/44 | 5,2 | 2 | A | 20 | VI | None* | GG | A.α.1 | B.α.1 | C.β.6 | D.α.1 | E.β.1 |
| ISS1024 | Italy | C | 1860 | 11 | 5,- | 2 | A | 27 | VI | None* | GG | A.α.2 | B.α.1 | C.β.4 | D.α.1 | E.β.2 |
| M98 250809 (Fletcher et al., 2004) | UK | B | NA | NA | 7,16 | 2 | A | 49 | VI | AAR84452 | GG | A.α.1 | B.α.1 | C.β.2 | D.α.7 | E.β.2 |
| NMB (Fletcher et al., 2004) | US | B | NA | 8 | 5-1,2-2 | 2 | A | 50 | VI | AAR84454 | GG | A.α.1 | B.α.1 | C.β.7 | D.α.1 | E.β.2 |
| M08 240014 | UK | B | 275 | 269 | 22,9 | 2 | A | 68 | VI | ACH81607 | GG | A.α.3 | B.α.2 | C.β.2 | D.α.1 | E.β.1 |
| 8047 (Beernink & Granoff, 2008) | US | B | 8 | 8 | 5-1,2-2 | 2 | A | 77 | VI | ACJ45782 | GG | A.α.5 | B.α.1 | C.β.4 | D.α.1 | E.β.2 |
| M06 241348 | Germany | B | 3476 | 269 | 10 | 2 | A | 83 | VI | ACM44936 | GG | A.α.1 | B.α.1 | C.β.2 | D.α.1 | E.β.7 |
| M08 240023 | UK | B | 6788 | 41/44 | 21,16-32 | 3 | A | 84 | VI | ACM44943 | GG GSG G | A.β.1 | B.β.1 | C.β.1 | D.α.1 | E.β.8 |

Fig. 2A: Table 8, Segment A. Unique sequences in fHbp variable segment A and number from each variant group.

| Segment ID | Sequence | SEQ ID NO: |
|---|---|---|
| A.α.1 | VAADIGAGLA DALTAPLDHK DKSLQSLTLD QSVRKNEKLK LAAQGAEKTY GNGDSLN TGKLKNDKV | 15 |
| A.α.2 | VAADIGAGLA DALTAPLDHK DKGLQSLTLD QSVRKNEKLK LAAQGAEKTY GNGDSLN TGKLKNDKV | 16 |
| A.α.3 | VAADIGAGLA DALTAPLDHK DKGLQSLMLD QSVRKNEKLK LAAQGAEKTY GNGDSLN TGKLKNDKV | 17 |
| A.α.4 | VAADIGAGLA DALTTPLDHK DKSLQSLTLD QSVRKNEKLK LAAQGAEKTY GNGDSLN TGKLKNDKV | 18 |
| A.α.5 | VAADIGARLA DALTAPLDHK DKSLQSLTLD QSVRKNEKLK LAAQGAEKTY GNGDSLN TGKLKNDKV | 19 |
| A.α.6 | VAADIGAGLA DALTALPDHK DKGLQSLTLD QSVRKNEKLK LAAQGAEETY GNGDSLD TGKLKNDKV | 20 |
| A.α.7 | VAADIGTGLA DALTAPLDHK DKGLQSLTLD QSVRKNEKLK LAAQGAEKTY GNGDSLN TGKLKNDKV | 21 |
| A.α.8 | VAADIGAGLA DALTAPLDHK DKGLQSLTLD QSVRKNEKLK LAAQGAEKTY GNGDRLN TGKLKNDKV | 22 |
| A.α.9 | VAADIGAGLA DALTAPFDHK DKGLQSLTLD QSVRKNEKLK LAAQGAEEIY GNGDSLD TGKLKNDKV | 23 |
| A.α.10 | VTADIGTGLA DALTAPLDHK DKGLQSLTLD QSVRKNEKLK LAAQGAEKTY GNGDSLN TGKLKNDKI | 24 |
| A.α.11 | VAADIGAGLA DALTAPLDHK DKGLQSLTLD QSVRKKEKLK LAAQGAEKTY GNGDSLN TGKLKNDKV | 25 |
| A.α.12 | VAADIGAGLA DALTAPLDHK DKGLRSLTLD QSVRKNEKLK LAAQGAEKTY GNGDSLN TGKLKNDKV | 26 |
| A.α.13 | VAADIGAVLA DALTAPLDHK DKSLQSLTLD QSVRKNEKLK LAAQGAEKTY GNGDSLN TGKLKNDKV | 27 |
| A.α.14 | VAADIGTGLA DALTAPLDHK DKGLRSLTLD QSVRKNEKLK LAAQGAEKTY GNGDSLN TGKLKNDKV | 28 |
| A.α.15 | VAADIGAGLA DALTAPLDHK DKGLQSLTLD QSVRKNEKLK LAAQGVEKTY GNGDSLN TGKLKNDKV | 29 |
| A.α.16 | VAVDIGTGLA DALTAPLDHK DKGLQSLTLD QSVRKNEKLK LAAQGAEKTY GNGDSLN TGKLKNDKI | 30 |
| A.α.17 | VAADIGTGLA DALTAPLDHK DKGLQSLTLD QSVRKNEKLK LAAQGAEETY GNGDSLN TGKLKNDKV | 31 |
| A.α.18 | VAADIGAGLA DALTAPLDHK DKGLQSLILD QSVRKNEKLK LAAQGAEKTY GNGDSLN TGKLKNDKV | 32 |
| A.α.19 | VAADIGAGLA DALTAPLDHK DKGLQSLTLD QSVRKNEKLK LAAQGAEKTY GNGDSLN TGKLKNDKI | 33 |
| A.α.20 | VAADIGAGLA DALTAPLDHK DKGLQSLTLD QSVRKNEKLK LAAQGAEKTY GNGDSLN TSKLKNDKV | 34 |
| A.α.21 | VAADIGAGLA DALTVPLDHK DKSLQSLTLD QSVRKNEKLK LAAQGAEKTY GNGDSLN TGKLKNDKV | 35 |
| A.α.22 | VAADIGTGLA DALTAPLDHK DKSLQSLTLD QSVRKNEKLK LAAQGAEKTY GNGDSLN TGKLKNDKV | 36 |
| A.α.23 | VAADIGAGLA DALTTPLDHK DKSLQSLTLD QSVRKNEKLK LAAQGAEKTY GNGDNLN TGKLKNDKV | 37 |
| A.α.24 | VAADIGAGLA DALTAPLDHK DKGLQSLALD QSVRKNEKLK LAAQGAEKTY GNGDSLN TGKLKNDKV | 38 |
| A.α.25 | VAADIGAGLA DALTAPLDHK DKGLQSLTLD QSVRKNEKLK LAAQGAEETY GNGDSLN TGKLKNDKV | 39 |
| A.α.26 | VTADIGAGLA DALTAPLDHK DKGLRSLMLD QSVRKNEKLK LAAQGAEKTY GNGDSLN TGKLKNDKI | 40 |
| A.α.27 | VAADIGVGLA DALTTPLDHK DKGLQSLTLD QSVRKNEKLK LAAQGAEKTY GNGDSLN TGKLKNDKV | 41 |

Fig. 2A (Con't): Table 8, Segment A. Unique sequences in fHbp variable segment A and number from each variant group.

| | | | | | | | |
|---|---|---|---|---|---|---|---|
| A.α.28 | VAADIGAGLA | DALTAPLDHK | DKGLQSLTLD | QSVRKNEKLK | LSAQGAEKTY | GNGDSLN | TGKLKNDK | 42 |
| A.α.29 | VAADIGTGLA | DALTAPLDHK | DKGLQSLTLD | QSVRKNEKLK | LAAQGAEKTY | GNGDSLN | TGKLKNDKI | 43 |
| A.α.30 | VAADIGAGLA | DALTAPLDHK | DKGLQSLTLD | QSVRKNEKLK | LSAQGAEKTY | GNGDSLN | TGKLKNDKV | 44 |
| A.α.31 | VAADIGTGLA | DALTAPLDHK | DKGLQSLMLD | QSVRKNEKLK | LSAQGAEKTY | GNGDSLN | TGKLKNDKI | 45 |
| A.α.32 | VTADIGTGLA | DALTAPLDHK | DKGLQSLTLD | QSVRKNEKLK | LAAQGAEKTY | GNGDSLN | TGKLKNDKV | 46 |
| A.α.33 | VAADIGTGLA | DALTALPDHK | DKGLQSLTLD | QSVRKNEKLK | LAAQGAEKTY | GNGDSLN | TGKLKNDKV | 47 |
| A.α.34 | VAADIGAGLA | DALTAPLDHK | DKGLQSLTLN | QSVRKKEKLK | LAAQGAEKTY | GNGDSLS | TGKLKNDKV | 48 |
| A.α.35 | VAADIGAGLA | DALTAPLDHK | DKGLQSLTLD | QSVRRNEKLK | LAAQGAEKTY | GNGDSLN | TGKLKNDKV | 49 |
| A.α.36 | VAADIGAGLA | DALTAPLDHK | DKSLQSLTLD | QSVRKNEKLK | LAAQGAEKTY | GNGDSLN | TGKLKNDKI | 50 |
| A.α.37 | VAADIGAGLA | DALTAPLDHK | DKGLQSLMLD | QSVRKNEKLK | LSAQGAEKTY | GNGDSLN | TGKLKNDKV | 51 |
| A.α.38 | VAADIGAGLA | YALTAPLDHK | DKSLQSLTLD | QSVRKNEKLK | LAAQGAEKTY | GNGDSLN | QTGKLKNDKV | 52 |
| A.α.39 | VTADIGTGLA | DALTAPLDHK | DKSLQSLMLD | QSVRKNEKLK | LAAQGAEKTY | GNGDSLN | TGKLKNDKI | 53 |
| A.α.40 | VAADIGAGLA | DALTAPLDHK | DKGLQSLMLD | QSVRKNEKLK | LAAQGAEKTY | GNGDSLN | TGKLKNDKI | 54 |
| A.α.41 | VAADIGTGLA | DALTAPLDYK | DKGLQSLMLD | QSVRKNEKLK | LSAQGAEKTY | GNGDSLN | TGKLKNDKV | 55 |
| A.α.42 | VAADIGAGLA | DALTAPLDYK | DKGLQSLTLD | QSVRKNEKLK | LAAQGAEKTY | GNGDSLN | TGKLKNDKV | 56 |
| A.α.43 | VAADIGAGLA | DALTAPLDHK | DKGLQSLTLD | QSVRKNEKLK | LAAQGAEETY | GNGDSLN | TDKLKNDKV | 57 |
| A.α.44 | VAADIGAGLA | DVLTAPLDHK | DKGLQSLTLD | QSVRKNEKLK | LAAQGAEKTY | GNGDSLN | TGKLKNDKV | 58 |
| A.α.45 | VAADIGAGLA | DALTTPLDHK | DKGLRSLMLD | QSVRKNEKLK | LSAQGAEKTY | GNGDSLN | TGKLKNDKV | 59 |
| A.α.46 | VVADIGAGLA | DALTAPLDHK | DKGLQSLMLD | QSVRKNEKLK | LAAQGAEKTY | GNGDILN | TGKLKNDKV | 60 |
| A.α.47 | VAADIGAGLA | DVLTAQLDHK | DKGLQSLTLD | QSVRKNEKLK | LAAQGAEKTF | KAGDKDN | SLNTGKLKNDKI | 61 |
| A.α.48 | IAADIGAGLA | DALTAPLDHK | DKSLQSLTLD | QSVRKNEKLK | LAAQGAEKTY | GNGDSLN | TGKLKNDKI | 62 |
| A.α.49 | VAANIGAGLA | DALTAPLDHK | DKSLQSLTLD | QSVRKNEKLK | LAAQGAEKTY | GNGDSLN | TGKLKNDKV | 63 |
| A.α.50 | VAADIGAGLT | DALTAPLDHK | DKSLQSLTLD | QSVRKNEKLK | LAAQGAEKTY | GNGDSLN | TGKLKNDKV | 64 |
| A.α.51 | VAADIGAGLA | DALTAPLDHK | DKGLQSLMLD | QSVRKNEKLK | LAAQGAEETY | GNGDSLN | TGKLKNDKV | 65 |
| A.α.52 | VAADIGAGLA | DALTAPFDHK | DKGLQSLTLD | QSVRKNEKLK | LAAQGAEKTY | GNGDSLN | TGKLKNDKI | 66 |
| A.β.1 | VAADIGTGLA | DALTAPLDHK | DKGLKSLTLE | DSIPQNGTLT | LSAQGAEKTF | KAGDKDNSLN | TGKLKNDKI | 67 |
| A.β.2 | VAADIGTGLA | DALTTPLDHK | DKGLKSLTLE | DSIPQNGTLT | LSAQGAEKTF | KAGDKDNSLN | TGKLKNDKI | 68 |
| A.β.3 | VAADIGAGLA | DALTAPLDHK | DKGLKSLTLE | DSISQNGTLT | LSAQGAERTF | KAGDKDNSLN | TGKLKNDKI | 69 |
| A.β.4 | VAADIGAGLA | DALTAPLDHK | DKGLKSLTLE | DSISQNGTLT | LSAQGAEKTF | KVGDKDNSLN | TGKLKNDKI | 70 |
| A.β.5 | VAADIGTGLA | DALTAPLDHK | DKGLKSLTLE | DSISQNGTLT | LSAQGAEKTF | KVGDKDNSLN | TGKLKNDKI | 71 |
| A.β.6 | VAADIGAGLA | DALTAPLDHK | DKGLKSLTLE | DSIPQNGTLT | LSAQGAEKTF | KAGGKDNSLN | TGKLKNDKI | 72 |
| A.β.7 | VAADIGAGLA | DALTAPLDHK | DKGLKSLTLE | DSIPQNGTLT | LSAQGAEKTF | KAGDKDNSLN | TGKLKNDKI | 73 |

Fig. 2A(Con't): Table 8, Segment A. Unique sequences in fHbp variable segment A and number from each variant group.

| | | | | | | |
|---|---|---|---|---|---|---|
| A.β.8 | IAADIGTGLA | DALTAPLDHK | DKGLKSLTLE | DSIPQNGTLT | LSAQGAEKTF | KAGDKDNSLN TGKLKNDKI | 74 |
| A.β.9 | VTADIGTGLA | DALTAPLDHK | DKGLKSLTLE | DSISQNGTLT | LSAQGAEKTY | GNGDSLN    TGKLKNDKV | 75 |
| A.β.10 | VAADIGAGLA | DALTAPLDHK | NKGLKSLTLE | DSIPQNGTLT | LSAQGAEKTY | GNGDSLN    TGKLKNDKV | 76 |
| A.β.11 | VAADIGTGLA | DALTAPLDHK | DKGLKSLTLE | DSIPQNGTLT | LSAQGAEKTF | KAGGKDN    SLNTGKLKNDKI | 77 |
| A.β.12 | VAADIGTGLA | DALTAPLDHK | DKGLKSLTLE | DSIPQNGTLT | LSAQGAEKTF | KVGDKDN    SLNTGKLKNDKI | 78 |
| A.β.13 | VAADIGAGLA | DALTTPLDHK | DKGLKSLTLE | DSIPQNGTLT | LSAQGAEKTF | KAGDKDN    SLNTGKLKNDKI | 79 |
| A.β.14 | VAADIGAGLA | DALTAPLDHK | DKGLKSLTLE | DSIPQNGTLT | LSAQGVEKTF | KAGDKDN    SLNTGKLKNDKI | 80 |
| A.β.15 | VAADIGAGLA | DALTAPLDHK | DKGLKSLTLE | DSISQNGTLT | LSAQGAERTF | KAGNKDN    SLNTGKLKNDKI | 81 |
| A.β.16 | VTADIGTGLA | DALTAPLDHK | DKGLKSLTLE | DSIPQNGTLT | LSAQGAEKTF | KAGDKDN    SLNTGKLKNDKI | 82 |
| A.β.17 | VAADIGAGLA | DALTAPLDHK | DKGLKSLTLE | DSISQNGTLT | LSAQGAERTF | KAGDKDN    SLNTGKLKNDKV | 83 |
| A.β.18 | VVADIGTGLA | DALTAPLDHK | DKGLKSLTLE | DSIPQNGTLT | LSAQGAEKTF | KAGDKDN    SLNTGKLKNDKI | 84 |

| Segment ID | Number in Variant Group | | |
|---|---|---|---|
| | Variant 1 | Variant 2 | Variant 3 |
| A.α.1 | 4 | 10 | 0 |
| A.α.2 | 12 | 2 | 0 |
| A.α.3 | 6 | 1 | 0 |
| A.α.4 | 0 | 1 | 0 |
| A.α.5 | 0 | 1 | 0 |
| A.α.6 | 1 | 0 | 0 |
| A.α.7 | 1 | 0 | 0 |
| A.α.8 | 1 | 0 | 0 |
| A.α.9 | 1 | 0 | 0 |
| A.α.10 | 1 | 0 | 0 |
| A.α.11 | 1 | 0 | 0 |
| A.α.12 | 1 | 0 | 0 |
| A.α.13 | 1 | 0 | 0 |
| A.α.14 | 1 | 0 | 0 |
| A.α.15 | 1 | 0 | 0 |
| A.α.16 | 1 | 0 | 0 |

| Segment ID | Number in Variant Group | | |
|---|---|---|---|
| | Variant 1 | Variant 2 | Variant 3 |
| A.β.1 | 0 | 0 | 6 |
| A.β.2 | 0 | 0 | 5 |
| A.β.3 | 4 | 0 | 0 |
| A.β.4 | 0 | 0 | 1 |
| A.β.5 | 0 | 0 | 1 |
| A.β.6 | 0 | 0 | 1 |
| A.β.7 | 1 | 0 | 0 |
| A.β.8 | 0 | 0 | 0 |
| A.β.9 | 0 | 0 | 0 |

Fig. 2B: Table 8, Segment B. Unique sequences in fHbp variable segment B and number from each variant group.

| Segment ID | Sequence | SEQ ID NO: | Number in variant group | | |
|---|---|---|---|---|---|
| | | | Variant 1 | Variant 2 | Variant 3 |
| B.α.1 | IRQIEVDGQL ITLES | 85 | 28 | 12 | 0 |
| B.α.2 | IRQIEVDGKL ITLES | 86 | 5 | 1 | 0 |
| B.α.3 | IRQIEVDGQT ITLAS | 87 | 0 | 2 | 0 |
| B.α.4 | IRQIEVDRQL ITLES | 88 | 2 | 0 | 0 |
| B.α.5 | IRQIEVDGQL ITLEN | 89 | 1 | 0 | 0 |
| B.α.6 | IHQIEVDGQL ITLES | 90 | 1 | 0 | 0 |
| B.α.7 | IRQIEVNGQL ITLES | 91 | 1 | 0 | 0 |
| B.α.8 | IRQIRSDGQL ITLES | 92 | | | |
| B.α.9 | IRQIEVDGQL ITLER | 93 | | | |
| B.α.10 | IRQIEVDGRL ITLES | 94 | | | |
| B.β.1 | VQKIEVDGQT ITLAS | 95 | 0 | 0 | 16 |

Fig. 2C: Table 8, Segment C, i. Unique sequences in fHbp variable segment C.

| Segment ID | Sequence | SEQ ID NO: |
|---|---|---|
| C.α.1 | VYKQSHSALT ALQTEQVQDS EDSGKMVAKR QFRIGDIAGE HTSFDKLPKG GSATYRGTAF GS | 96 |
| C.α.2 | VYKQSHSALT ALQTEQVQDS EHSGKMVAKR QFRIGDIAGE HTSFDKLPEG GRATYRGTAF GS | 97 |
| C.α.3 | VYKQSHSALT ALQTEQEQDP EHSGKMVAKR RFKIGDIAGE HTSFDKLPKD VMATYRGTAF GS | 98 |
| C.α.4 | VYKQSHSALT ALQTEQVQDS EHSGKMVAKR QFRIGDIVGE HTSFGKLPKD VMATYRGTAF GS | 99 |
| C.α.5 | VYKQSHSALT AFQTEQIQDS EHSGKMVAKR QFRIGDIAGE HTSFDKLPEG GRATYRGTAF GS | 100 |
| C.α.6 | VYKQSHSALT ALQTEQVQDS EDSGKMVAKR QFRIGDIAGE HTSFDKLPKD VMATYRGTAF GS | 101 |
| C.α.7 | VYKQSHSALT ALQTEQVQDS EHSGSMVAKR QFRIGDIAGE HTSFDKLPEG GRATYRGTAF GS | 102 |
| C.α.8 | VYKQSHSALT ALQTEQEQDP EHSEKMVAKR RFRIGDIAGE HTSFDKLPKD VMATYRGTAF GS | 103 |
| C.α.9 | VYKQSYSALT ALQTEQEQDS EHSGKMVAKR RFRIGDIAGE HTSFDKLPKG SSATYRGTAF GS | 104 |
| C.α.10 | VYKQSHSALT ALQTEQEQDL EHSGKMVAKR RFRIGDIAGE HTSFDKLREG GRATYRGTAF GS | 105 |
| C.α.11 | VYKQSHSALT ALQTEQVQDS EHSGKMVAKR QFRIGDIVGE HTSFDKLPKD VMATYRGTAF GS | 106 |
| C.α.12 | VYKQSHSALT AFQTEQIQDS EDSGKMVAKR RFRIGDIAGE HTSFDKLPKG GSATYRGTAF GS | 107 |
| C.α.13 | VYKQSHSALT ALQTEQVQDS EHSGKMVAKR RFRIGDIAGE HTSFDKLPES DRATYRGTAF SS | 108 |
| C.α.14 | VYKQSHSALT ALQTEQVQDS EHSRKMVAKR QFRIGDIAGE HTSFDKLPKG DSATYRGTAF GS | 109 |
| C.α.15 | VYKQSHSALT ALQTEQVQDS EDSGKMVAKR QFRIGDIAGE HTSFDKLPKG GSATYRGTAL GS | 110 |
| C.α.16 | VYKQSHSALT ALQTEQVQDS EDSGKMVAKR QFRIGDIAGE HTSFDKLPKG GSATYRGTAF SS | 111 |
| C.α.17 | VYKQSHSALT ALQTEQVQDS EHSGKMVAKR QFRIGDIAGE HTSFDKLPKG GSATYRGTAF GS | 112 |
| C.α.18 | VYKQSHSALT ALQTEQVQDS EHSRKMVAKR QFRIGDIAGE HTSFDKLPEG GRATYRGTAL GS | 113 |
| C.α.19 | VYKQSHSALT ALQTEQVQDS EHSGKMVAKR QFRIGDIAGE HTSFDKLPEG GRATYRGTAF SS | 114 |
| C.α.20 | VYKQSHSALT AFQTEQIQDS EHSGKMVAKR RFRIGDIAGE HTSFDKLPEG GRATYRGTAF SS | 115 |
| C.α.21 | VYKQSYSALT ALQTEQIQDS EHSGKMVAKR RFRIGDIAGE HTFFDKLPKG GSAIYRGTAF GS | 116 |
| C.α.22 | VYKQSHSALT AFQTEQIQDS EHSGKMVAKR QFRIGDIAGE HTSFDKLPEG GRATYRGTAF SS | 117 |
| C.α.23 | VYKQSHSALT AFQTEQIQDS EHSGKMVAKR RFRIGDIAGE HTSFDKLPEG GRATYRGTAF GS | 118 |
| C.α.24 | VYKQSHSALT ALQTEQIQDS EHSGKMVAKR QFRIGDIAGE HTSFDKLPEG GRATYRGTAF GS | 119 |
| C.α.25 | VYKQSHSALT ALQTEQVQDS EHSGKMVAKR QFRIGDIAGE HTSFDKLPKG GRATYRGTAF GS | 120 |
| C.α.26 | VYKQSHSALT ALQTEQVQDS EHSGKMVAKR QFRIGDIAGE HISFDKLPEG GRATYRGTAF GS | 121 |
| C.α.27 | VYKQSHSALT ALQTEQVQDS EDSGKMVAKR QFRIGDIAGE HTSFDKLPEG GRATYRGTAF GS | 122 |
| C.α.28 | VYKQSHSALT AFQTEQIQDS EHSGKMVAKR QFRIGDIAGE HTSFDKLPKG GSATYRGTAF GS | 123 |

Fig. 2C (Con't): Table 8, Segment C, i. Unique sequences in fHbp variable segment C.

| | | | | | | | |
|---|---|---|---|---|---|---|---|
| C.α.29 | VYKQSHSALT | ALQTEQVQDS | EDSGKMVAKR | QFRIGDIAGE | HTSFDKLPKG | DSATYRGTAF | SS | 124 |
| C.α.30 | VYKQSHSALT | ALQTEQVQDS | EDSGKMVAKR | QFRIGDIAGE | HTSFDKLPES | DSATYRGTAF | SS | 125 |
| C.α.31 | VYKQSHSALT | ALQTEQVQDS | EDSGKMVAKR | QFRIGDIAGE | HTSFDKLPKG | GRATYRGTAF | GS | 126 |
| C.α.32 | VYKQSHSALT | ALQTEQVQDS | EDSGKMVAKR | QFRIGDIAGE | HTSFDKLHKG | GSATYRGTAF | SS | 127 |
| C.α.33 | VYKQSHSALT | ALQTEQVQDS | EDSRKMVAKR | QFRIGDIAGE | HTSFDKLPES | DRATYRGTAF | SS | 128 |
| C.α.34 | VYKQSHSALT | ALQTEQEQDP | EHSGKMVAKR | RFKIGDIAGE | HTSFDKLPKD | VMVTYRGTAF | GS | 129 |
| C.α.35 | VYKQSHSALT | ALQTEQVQDS | EHSAKMVAKR | QFRIGDIAGE | HTSFDKLPEG | GRATYRGTAF | GS | 130 |
| C.α.36 | VYKQSHSALT | ALQTEQEQDP | EHSEKMVAKR | RFKIGDIAGE | HTSFDKLPKD | VMATYRGTAF | GS | 131 |
| C.α.37 | VYKQSHSALT | ALQTEQVQDS | EHSEKMVAKR | RFKIGDIAGE | HTSFDKLPKD | VMATYRGTAF | GS | 132 |
| C.α.38 | VYKQSHSALT | ALQTEQVQDS | EDSGKMVAKR | QFRIGDIAGE | HTSFDKLPKG | GSATYRGTAF | GS | 133 |
| C.α.39 | VYKQSYSALT | ALQTEQVQDS | EHSGKMVAKR | RFRIGDIAGE | HTSFDKLPGD | SRATYRGTAF | SS | 134 |
| C.α.40 | VYKQSHSALT | ALQTEQVQDS | EDSGKMVAKR | RFRIGDIAGE | HTSFDKLPEG | GRATYRGTAF | GS | 135 |
| C.α.41 | VYKQSHSALT | ALQTEQVQDS | EHSGKMVAKR | QFRIGDIAGE | HTSFDKLPED | VRATYRGTAF | GS | 136 |
| C.α.42 | VYKQSHSALT | ALQTEQEQDS | EHSGKMVAKR | QFRIGDIAGE | HTSFDKLPEG | VRATYRGTAF | GS | 137 |
| C.α.43 | VYKQSHSALT | AFQTEQEQDS | EHSGKMVAKR | QFRIGDIAGE | HTSFDKLPDV | VRATYRGTAF | GS | 138 |
| C.α.44 | VYKQSHSALT | ALQTEQVQDS | EHSGKMVAKR | RFKIGDIAGE | HISFDKLPES | GRATYRGTAF | GS | 139 |
| C.α.45 | VYKQSHSALT | ALQTEQEQDL | EHSGKMVAKR | RFKIGDIAGE | HTSFDKLPKD | VMATYRGTAF | GS | 140 |
| C.α.46 | VYKQSHSALT | ALQTEQEQDP | EHSGKMVAKR | QFRIGDIAGE | HTSFDKLPES | GSATYRGTAF | GS | 141 |
| C.α.47 | VYKQSHSALT | AFQTEQVQDS | EHSGRMVAKR | QFRIGDIAGE | HTSFDKLPEG | GRATYRGTAF | GS | 142 |
| C.α.48 | VYKQSHSALT | ALQTEQVQDS | EHFGKMVAKR | QFRIGDIAGE | HTSFDKLPKG | VRATYRGTAF | GS | 143 |
| C.α.49 | VYKQSHSALT | ALQTEQEQDL | EHSRKMVAKR | RFRIGDIAGE | HTSFDKLPKD | VMATYRGTAF | GS | 144 |
| C.α.50 | VYKQSHSALT | ALQTEQEQDL | EHSRKMVAKR | RFKIGDIAGE | HTSFDKLPKD | VMATYRGTAF | GS | 145 |
| C.α.51 | VYKQSHSALT | ALQTEQEQDP | EHSGKMVAKR | RFKIGDIAGE | HTSFDKLPKD | IMATYRGTAF | GS | 146 |
| C.α.52 | VYKQSHSALT | ALQTEQVQDS | EHSGRMVAKR | QFRIGDIAGE | HTSFDKLPEG | GRATYRGTAF | GS | 147 |
| C.α.53 | VYKQSHSALT | AFQTEQVQDS | EHFGKMVAKR | QFRIGDIAGE | HTSFDKLPEG | GRATYRGTAF | GS | 148 |
| C.α.54 | VYKQSHSALT | ALQTEQVQDS | EHSGKMVAKR | RFRIGDIAGE | HTSFDKLPKD | GMATYRGTAF | GS | 149 |
| C.α.55 | IYKQSHSALT | AFQTEQIQDS | EHSGKMVAKR | QFRIGDIAGE | HTSFDKLPEG | GRATYRGTAF | GS | 150 |
| C.α.56 | VYKQSHSALT | ALQTEQEQDS | EDSGKMVAKR | RFKIGDIAGE | HTSFDKLPKD | VMATYRGTAF | GS | 151 |
| C.β.1 | IYKQDHSAVV | ALQIEKINNP | DKIDSLINQR | SFLVSGLGGE | HTAFNQLP-G | GKAEYHGKAF | SS | 152 |
| C.β.2 | IYKQDHSAVV | ALQIEKINNP | DKIDSLINQR | SFLVSGLGGE | HTAFNQLP-S | GKAEYHGKAF | SS | 153 |
| C.β.3 | IYKQNHSAVV | ALQIEKINNP | DKIDSLINQR | SFLVSGLGGE | HTAFNQLP-D | GKAEYHGKAF | SS | 154 |

Fig. 2C (Con't): Table 8, Segment C, i. Unique sequences in fHbp variable segment C.

| | | | | | | | |
|---|---|---|---|---|---|---|---|
| C.β.4 | IYKQDHSAVV | ALQIEKINNP | DKIDSLINQR | SFLVSGLGGE | HTAFNQLP-D | GKAEYHGKAF | SS | 155 |
| C.β.5 | IYKQNHSAVV | ALQIEKINNP | DKIDSLINQR | SFLVSGLGGE | HTAFNQLP-G | GKAEYHGKAF | SS | 156 |
| C.β.6 | IYKQDHSAVV | ALQIEKINNP | DKIDSLINQR | SFLVSGLGGE | HTAFNQLP-S | GKAEYHGKAF | SF | 157 |
| C.β.7 | IYKQDHSAVV | ALQIEKINNP | DKIDSLINRR | SFLVSGLGGE | HTAFNQLP-D | GKAEYHGKAF | SS | 158 |
| C.β.8 | IYKQNHSAVV | ALQIEKINNP | DKIDSLINQR | SFLVSGLGGE | HTAFNQLP-V | GKAEYHGKAF | SS | 159 |
| C.β.9 | IYKQNHSAVV | ALQIEKINNP | DKTDSLINQR | SFLVSGLGGE | HTAFNQLP-G | GKAEYHGKAF | SS | 160 |
| C.β.10 | IYKQDHSAVV | ALQIEKINNP | DKTDSLINQR | SFLVSGLGGE | HTAFNQLP-G | GKAEYHGKAF | SS | 161 |
| C.β.11 | IYKQNHSAVV | ALQIEKINNP | DKIDSLINQR | SFLVSGLGGE | HTAFNQLP-G | DKAEYHGKAF | SS | 162 |
| C.β.12 | IYKQDHSAVV | ALQIEKINNP | DKIDSLINQR | SFLVSGLGGE | HTAFNQLP-V | DKAEYHGKAF | SS | 163 |
| C.β.13 | IYKQNHSAVV | ALQIEKINNP | DKIDSLINQR | SFLVSGLGGE | HTAFNQLP-S | GKAEYHGKAF | SS | 164 |
| C.β.14 | IYKQDHSAVV | ALQIEKINNP | DKIDSLINQR | SFLVSGLGGE | HTAFNQLP-S | GKAEYHGKAL | SS | 165 |
| C.β.15 | IYKQDHSAVV | ALQIEKINNP | DKIDSLINQR | SFLVSGLGGE | HTAFNQLP-G | DKAEYHGKAF | SS | 166 |
| C.β.16 | IYKQDHSAVV | ALQTEKVNNP | DKTDSLINQR | SFLVSGLGGE | HTAFNQLP-V | GKSEYHGKAF | SS | 167 |
| C.β.17 | IYKQDHSAVV | ALQIEKINNP | DKIDSLINQR | SFLVSGLGGE | HTAFNQLP-S | GKAEYHGKAF | SS | 168 |
| C.β.18 | IYKQNHSAVV | ALQIEKINNP | DKIDSLINQR | SFLVSSLGGE | HTAFNQLP-G | GKAEYHGKAF | SS | 169 |
| C.β.19 | VYKQDHSAVV | ALQIEKINNP | DKIDSLINQR | SFLVSGLGGE | HTAFNQLP-G | GKAEYHGKAF | SS | 170 |
| C.β.20 | IYKQDHSAVV | ALQTEKVNNP | DKTDSLINQR | SFLVSGLGGE | HTAFNQLP-G | GKAEYHGKAF | SS | 171 |
| C.β.21 | IYKQDHSAVV | ALQIEKINNP | DKIDSLINQR | SFLVSGLGGE | HTAFNQLS-G | GKAEYHGKAF | SS | 172 |
| C.β.22 | IYKQDHSAVV | ALQIEKINNP | DKIDSLINQR | SFLVSGLGGK | HTAFNQLP-G | GKAEYHGKAF | SS | 173 |

Fig. 2D: Table 8, Segment C, ii. Unique sequences in fHbp variable segment C and number from each variant group.

| Segment ID | Number in Variant Group | | | Segment ID | Number in Variant Group | | |
|---|---|---|---|---|---|---|---|
| | Variant 1 | Variant 2 | Variant 3 | | Variant 1 | Variant 2 | Variant 3 |
| C.α.1 | 6 | 0 | 0 | C.β.1 | 0 | 2 | 8 |
| C.α.2 | 4 | 0 | 0 | C.β.2 | 0 | 6 | 2 |
| C.α.3 | 3 | 0 | 0 | C.β.3 | 0 | 2 | 0 |
| C.α.4 | 3 | 0 | 0 | C.β.4 | 0 | 3 | 0 |
| C.α.5 | 2 | 0 | 0 | C.β.5 | 0 | 0 | 2 |
| C.α.6 | 3 | 0 | 0 | C.β.6 | 0 | 1 | 0 |
| C.α.7 | 2 | 0 | 0 | C.β.7 | 0 | 1 | 0 |
| C.α.8 | 1 | 0 | 0 | C.β.8 | 0 | 0 | 1 |
| C.α.9 | 1 | 0 | 0 | C.β.9 | 0 | 0 | 1 |
| C.α.10 | 1 | 0 | 0 | C.β.10 | 0 | 0 | 1 |
| C.α.11 | 1 | 0 | 0 | C.β.11 | 0 | 0 | 1 |
| C.α.12 | 1 | 0 | 0 | | | | |
| C.α.13 | 1 | 0 | 0 | | | | |
| C.α.14 | 1 | 0 | 0 | | | | |
| C.α.15 | 1 | 0 | 0 | | | | |
| C.α.16 | 1 | 0 | 0 | | | | |
| C.α.17 | 1 | 0 | 0 | | | | |
| C.α.18 | 1 | 0 | 0 | | | | |
| C.α.19 | 1 | 0 | 0 | | | | |
| C.α.20 | 1 | 0 | 0 | | | | |
| C.α.21 | 1 | 0 | 0 | | | | |
| C.α.22 | 1 | 0 | 0 | | | | |

Fig. 2D (Con't) : Table 8, Segment D. Unique sequences in fHbp variable segment D and number from each variant group.

| Segment ID | Sequence | | SEQ ID NO: | Number in variant group | | |
|---|---|---|---|---|---|---|
| | | | | Variant 1 | Variant 2 | Variant 3 |
| D.α.1 | AGGKLTYTID | FAAKQGHGK | 174 | 21 | 9 | 9 |
| D.α.2 | AGGKLIYTID | FAAKQGHGK | 175 | 5 | 0 | 0 |
| D.α.3 | ASGKLTYTID | FAAKQGHGK | 176 | 5 | 0 | 0 |
| D.α.4 | AGGKLTYTID | FAAKQGYGK | 177 | 2 | 0 | 0 |
| D.α.5 | AGGKLTYTID | FAAKQGNGK | 178 | 2 | 0 | 0 |
| D.α.6 | AGGKLTYTID | FAVKQGHGK | 179 | 2 | 0 | 0 |
| D.α.7 | AGGKLTYTID | FATKQGHGK | 180 | 0 | 1 | 0 |
| D.α.8 | AGGKLTYTID | FASKQGHGK | 181 | 0 | 0 | 1 |
| D.α.9 | AGGKLIYTID | FAAKQGYGK | 182 | 1 | 0 | 0 |
| D.α.10 | ARGKLTYTID | FAAKQGHGK | 183 | | | |
| D.α.11 | ASGELTYTID | FAAKQGHGK | 184 | | | |
| D.α.12 | TGGKLTYTID | FAAKQGHGK | 185 | | | |
| D.α.13 | AGGKLTYTID | FVAKQGHGK | 186 | | | |
| D.α.14 | AGGKLTYTID | FAAKQGHGR | 187 | | | |
| D.α.15 | AGGRLTYTID | FAAKQGCGK | 188 | | | |
| D.α.16 | AGEKLTYTID | FAAKQGHGK | 189 | | | |
| D.α.17 | TGGKLIYTID | FAAKQGHGK | 190 | | | |
| D.α.18 | AGGKLTYIID | FAAKQGYGK | 191 | | | |
| D.β.1 | PNGRLHYSID | FTKKQGYGR | 192 | 0 | 5 | 2 |
| D.β.2 | PNGRLHYTID | FTNKQGYGR | 193 | 0 | 0 | 3 |
| D.β.3 | PNGRLHYSID | FTKKQGYGG | 194 | 0 | 0 | 1 |

Fig. 2E: Table 8, Segment E, i. Unique sequences in fHbp variable segment E.

| Segment ID | Sequence | SEQ ID NO: |
|---|---|---|
| E.α.1 | SPELNVDLAA AYIKPDEKHH AVISGSVLYN QAEKGSYSLG IFGGKAQEVA GSAEVKTVNG IRHIGLAA | 195 |
| E.α.2 | SPELNVDLAA SDIKPDKKRH AVISGSVLYN QAEKGSYSLG IFGGQAQEVA GSAEVETANG IRHIGLAA | 196 |
| E.α.3 | SPELNVELAT AYIKPDEKHH AVISGSVLYN QDEKGSYSLG IFGGQAQEVA GSAEVETANG IHHIGLAA | 197 |
| E.α.4 | SPELNVDLAA ADIKPDEKHH AVISGSVLYN QAEKGSYSLG IFGGQAQEVA GSAEVETANG IRHIGLAA | 198 |
| E.α.5 | SPELNVDLAA ADIKPDEKRH AVISGSVLYN QAEKGSYSLG IFGGKAQEVA GSAEVKTVNG IRHIGLAA | 199 |
| E.α.6 | SPELNVELAT AYIKPDEKRH AVISGSVLYN QDEKGSYSLG IFGGQAQEVA GSAEVETANG IHHIGLAA | 200 |
| E.α.7 | SPELNVDLVS ADIKPDEKRH AVISGSVLYN QDEKGSYSLG IFGGKAQEVA GSAEVKTVNG IRHIGLAA | 201 |
| E.α.8 | SPELNVDLAA ADIKPDGKRH AVISGSVLYN QAEKGSYSLG IFGGKAQEVA GSAEVKTVNG IRHIGLAA | 202 |
| E.α.9 | SPELNVDLAA ADIKPDGKRH AVISGSVLYN QAEKSSYSLG IFGGKAQEVA GSAEVKTVNG IRHIGLAA | 203 |
| E.α.10 | SPELNVDLAA ADIKPDEKHH AVISGSVLYN QAEKGSYSLG IFGGKAQEVA GSAEVKTVNG IRHIGLAA | 204 |
| E.α.11 | SPELNVDLAA ADIKPDEKHH AVISGSVLYN QDEKGSYSLG IFGGKAQEVA GSAEVKTVNG IRHIGLAA | 205 |
| E.α.12 | SPELNVDLAA ADIKPDEKHH AVISGSVLYN QDEKGSYSLG IFGGEAQEVA GSAEVKTANG IHHIGLAA | 206 |
| E.α.13 | SPELNVDLAV AYIKPDEKHH AVISGSVLYN QDEKGSYSLG IFGEKAQEVA GSAEVKTANG IHHIGLAA | 207 |
| E.α.14 | SPELNVDLAV AYIKPDEKHH AVISGSVLYN QDEKGSYSLG IFGEKAQEVA GSAEVETANG IHHIGLAA | 208 |
| E.α.15 | SPELNVDLAA ADIKPDEKHH AVISGSVLYN QDEKGSYSLG IFGGQAQEVA GSAEVETANG IHHIGLAA | 209 |
| E.α.16 | SPELNVDLAA AYIKPDKKRH AVISGSVLYN QDEKGSYSLG IFGGQAQEVA GSAEVETANG IHHIGLAA | 210 |
| E.α.17 | SPELNVDLAA AYIKPDEKHH AVISGSVLYN QDEKGSYSLG IFGGQAQEVA GSAEVKTANG IRHIGLAA | 211 |
| E.α.18 | SPELNVELAA AYIKPDEKHH AVISGSVLYN QDEKGSYSLG IFGGQAQEVA GSAEVETANG IQHIGLAA | 212 |
| E.α.19 | SPELNVELAT ADIKPDEKHH AVISGSVLYN QDEKGSYSLG IFGGQAQEVA GSAEVETANG IHHIGLAA | 213 |
| E.α.20 | SPELNVELAT AYIKPDEKHH AVISGSVLYN QDEKGSYSLG IFGGKAQEVA GSAEVETANG IHHIGLAA | 214 |
| E.α.21 | SPELNVELAT AYIKPDEKRH AVISCSVLYN QDEKGSYSLG IFGGQAQEVA GSAEVKTVNG IRHIGLAA | 215 |
| E.α.22 | SPELNVELAT AYIKPDEKRH AVISGSVLYN QDEKGSYSLG IFGGQAQEVA GSAEVETANG IRHIGLAA | 216 |
| E.α.23 | SPELNVELAT AYIKPDEKRH AVISGSVLYN QDEKGSYSLG IFGGQAQEVA GSAEVETANG IQHIGLAA | 217 |
| E.α.24 | SPELNVELAT AYIKPDEKRH AVISGSVLYN QDEKGSYSLG IFGGQAQEVA GSAEVETVNG IHHIGLAA | 218 |
| E.α.25 | SPELNVNLAA ADIKPDEKRH AVISGSVLYN QDEKGSYSLG IFGEKFQEVA GSAEVKTANG IHHIGLAA | 219 |
| E.α.26 | SPELNVDLAA AYIKPDEKHY AVISGSVLYN QDEKGSYSLG IFGGKAQEVA GSAEVKTVNG IRHIGLAA | 220 |
| E.α.27 | SPELNVDLAA AYIKPDEKRH AVISGSVLYN QDEKGSYSLG IFGGKAQEVA GSAEVKTANG IHHIGLAA | 221 |
| E.α.28 | SPELNVDLAA SDIKPDKKRH AVISGSVLYN QAEKGSYSLG IFGGQAQEVA WQRRVETANG IRHIGLAA | 222 |
| E.α.29 | SPELNVDLAA ADIKPDEKHH AVISGSVLYN QDEKGSYSLG IFGGKAQEVA GSAEVETANG IHHIGLAA | 223 |

Fig. 2E (Con't): Table 8, Segment E, i. Unique sequences in fHbp variable segment E.

| Segment ID | Sequence | | | | | | SEQ ID NO: |
|---|---|---|---|---|---|---|---|
| E.α.30 | SPELNVDLAA | SDIKPDKKRH | AVISGSVLYN | QAEKGSYSLG | IFGRQAQEVA | GSAEVETANG | IRHIGLAA | 224 |
| E.α.31 | SPELNVDLAA | SDIKPDKKRH | AVISGSVLYN | QAEKGSYSLG | IFGGKAQEVA | GSAEVETANG | IRHIGLAA | 225 |
| E.α.32 | SPELNVDLAA | ADIKPDKKRH | AVISGSVLYN | QAEKGSYSLG | IFGGQAQEVA | GSAEVETVNG | IRHIGLAA | 226 |
| E.α.33 | SPELNVDLAA | ADIKPDEKRH | AVISGSVLYN | QDEKGSYSLG | IFGGQAQEVA | GSAEVETANG | IQHIGLAA | 227 |
| E.α.34 | SPELNVELAA | AYIKPDEKRH | AVISGSVLYN | QDEKGSYSLG | IFGGQAQEVA | GSAEVETANG | IQHIGLAA | 228 |
| E.α.35 | SPELNVELAT | AYIKPDEKHH | AVISGFVLYN | QDEKGSYSLG | IFGGQAQEVA | GSAEVETANG | IHHIGLAA | 229 |
| E.α.36 | SPELNVDLAA | AYIKPDEKRH | AVISGSVLYN | QDEKGSYSLG | IFGGKAQEVA | GSAEVKTVNG | IRHIGLAA | 230 |
| E.α.37 | SPELNVDLAA | SDIKPDKKRH | AVISGSVLYN | HAEKGSYSLG | IFGGQAQEVA | GSAEVETANG | IRHIGLAA | 231 |
| E.α.38 | SPELNVDLAA | AYIKPDEKRH | AVISGSVLYN | QDEKGSYSLG | IFGGQAQEVA | GSAEVETANG | IQHIGLAA | 232 |
| E.α.39 | SPELNVDLVA | ADIKPDKKRH | AVISGSVLYN | QAEKGSYSLG | IFSGQAQEVA | GSAEVETANG | IRHIGLAA | 233 |
| E.α.40 | SPELNVELAT | AYIKPDEKRH | AVISGSVLYN | QDEKGSYSLG | IFGGQAQEVA | GSAEVETANG | IHHIGLAA | 234 |
| E.α.41 | SPELNVELAT | AYIKPDEKRY | AVISGSVLYN | QDEKGSYSLG | IFGGQAQEVA | GSAEVETANG | IHHIGLAA | 235 |
| E.α.42 | SPELNVDLAV | AYIKPDEKHH | AVISGSVLYN | QDEKGSYSLG | IFGGQAQEVA | GSAEVETANG | IHHIGLAA | 236 |
| E.α.43 | SPELNVELAT | AYIKPDEKHH | AVISGSVLYN | QDEKGSYSLG | IFGGQAQEIA | GSAEVETANG | IHHIGLAA | 237 |
| E.α.44 | SPELNVDLAA | ANIEQDEKHH | AVISGSVLYN | QDEKGSYSLG | IFGEKAQEVA | GSAEVKTANG | IRHIGLAA | 238 |
| E.α.45 | SPELNVELAT | AYIKPDEKRH | AVISGSVLYN | QNEKGSYSLG | IFGGQAQEVA | GSAEVETANG | IHHIGLAA | 239 |
| E.α.46 | SPELNVELAA | AYIKPDEKHH | AVISGSVLYN | QDEKGSYSLG | IFGGQAQEVA | GSAEVETANG | IHHIGLAA | 240 |
| E.α.47 | SPELNVDLAV | AYIKPDEKHH | AVISGSVLYN | QDEKGSYSLG | IFGEKAQEVA | GSAEVKTVNG | IRHIGLAA | 241 |
| E.α.48 | SPELNVDLAV | AYIKPDEKHH | AVISGSVLYN | QDEKGSYSLG | IFGGKAQEVA | GSAEVETANG | IHHIGLAA | 242 |
| E.α.49 | SPELNVDLAA | AYIKPDEKHH | AVISGSVLYN | QDEKGSYSLG | IFGGQAQEVA | GSAEVETANG | IHHIGLAA | 243 |
| E.α.50 | SPELNVDLAA | ADIKPDEKRH | AVISGSVLYN | QAEKGSYSLG | IFGGQAQEVA | GSAEVKTVNG | IRHIGLAA | 244 |
| E.α.51 | SPELNVNLAA | ADIKPDEKRH | AVISGSVLYN | QAEKGSYSLG | IFGEKAQEVA | GSAEVETVNG | IHHIGLAA | 245 |
| E.α.52 | SPELNVDLAA | AYIKPDEKHH | AVISGSVLYN | QDEKGSYSLG | IFGGKAQEVA | GSAEVETANG | IRHIGLAA | 246 |
| E.α.53 | SPELNVDLAA | ADIKPDEKHH | AVISGSVLYN | QDEKGSYSLG | IFGGKAQEVA | GSAEVETANG | IQHIGLAA | 247 |
| E.α.54 | SPELNVDLAA | ADIKPDEKHH | AVISGSVLYN | QDEKGSYSLG | IFGEKAQEVA | GSAEVKTANG | IHHIGLAA | 248 |
| E.α.55 | SPELNVDLAA | AYIKPDEKHH | AVISGSVLYN | QDEKGSYSLG | IFGGKAQEVA | GSAEVKTVNG | IRHIGLAA | 249 |
| E.α.56 | SPELNVDLAA | AYIKPDEKRH | AVISGSVLYN | QDEKGSYSLG | IFGGQAQEVA | GSAEVKTVNG | IRHIGLAA | 250 |
| E.α.57 | SPELNVDLAA | AYIKPDEKHH | AVISGSVLYN | QDEKGSYSLG | IFGGQAQEVA | GSAEVETANG | IQHIGLAA | 251 |
| E.α.58 | SPELNVDLAA | AYIKPDKKRH | AVISGSVLYN | QDEKGSYSLG | IFGGKAQEVA | GSAEVETANG | IHHIGLAA | 252 |
| E.α.59 | SPELNVDLAA | AYIKPDEKHH | AVISGSVLYN | QAEKGSYSLG | IFGGQAQEVA | GSAEVETANG | IRHIGLAA | 253 |
| E.α.60 | SPELNVELAT | AYIKPDEKRH | AVISDSVLYN | QDEKGSYSLG | IFGGQAQEVA | GSAEVETANG | IHHIGLAA | 254 |

Fig. 2E (Con't) : Table 8, Segment E, i. Unique sequences in fHbp variable segment E.

| Segment ID | Sequence | SEQ ID NO: |
|---|---|---|
| E.α.61 | SPELNVDLAA AYIKPDEKHH AVISGSVLYN QDEKGSYSLG IFGGKAEEVA GSAEVKTVNG IRHIGLAA | 255 |
| E.α.62 | SPELNVDLAA ANIEQDEKHH AVISGSVLYN QAEKGSYSLG IFGEKFQEVA GSAEVKTVNG IRHIGLAA | 256 |
| E.α.63 | SPELNVDLAA AYIKPDEKHH AVISGSVLYN QAEKGSYSLG IFGGKAQEVA GSAEVKTVNG ILHIGLAA | 257 |
| E.α.64 | SPELNVELAT AYIKPDEKHH AVISGSVLYN QDEKGSYSLG IFGGQAQEVA GSAEVETANG IRHIGLAA | 258 |
| E.α.65 | SPELNVDLAA ADIKPDEKHH AVISGSVLYN QDEKGSYSLG IFGGQAQEVA GSAEVKTVNG IRHIGLAA | 259 |
| E.α.66 | SPELNVDLAA SDIKPDKKRH AVISGSVLYN QAEKGSYSLG IFGGQAQEVA GSAEVKTVNG IRHIGLAA | 260 |
| E.α.67 | SPELNVDLAA ADIKPDEKRH AVISGSVLYN QDEKGSYSLG IFGGQAQEVA GSAEVETANG IHHIGLAA | 261 |
| E.β.1 | TPEQNVELAS AELKADEKSH AVILGDTRYG GEEKGTYHLA LFGDRAQEIA GSATVKIREK VHEIGIAG | 262 |
| E.β.2 | TPEQNVELAA AELKADEKSH AVILGDTRYG SEEKGTYHLA LFGDRAQEIA GSATVKIGEK VHEIGIAG | 263 |
| E.β.3 | TPEQNVELAS AELKADEKSH AVILGDTRYG SEEKGTYHLA LFGDRAQEIA GSATVKIREK VHEIGIAG | 264 |
| E.β.4 | TPEQNVELAS AELKADEKSH AVILGDTRYG SEEKGTYHLA LFGDRAQEIA GSATVKIGEK VHEIGIAG | 265 |
| E.β.5 | TPELNVDLAS AELKADEKSH AVILGDTRYG SEEKGTYHLA LFGDRAQEIA GSATVKIGEK VHEIGIAG | 266 |
| E.β.6 | TLEQNVELAA AELKADEKSH AVILGDTRYG SEEKGTYHLA LFGDRAQEIA GSATVKIGEK VHEIGIAG | 267 |
| E.β.7 | TPEQNVELAA AELKADEKSH AVILGDTRYG GEEKGTYHLA LFGDRAQEIA GSATVKIREK VHEIGIAG | 268 |
| E.β.8 | TPEQNVELAA AELKADEKSH AVILGDTRYD SEEKGTYHLA LFGDRAQEIA GSATVKIGEK VHEISIAG | 269 |
| E.β.9 | TPEQNVELAA AELKADEKSH AVILGDTRYG SEEKGTYHLA LFGDRAQEIA GSATVKIGEK VHEISIAG | 270 |
| E.β.10 | SPELNVELAT AELKADEKSH AVILGDTRYG SEEKGTYHLA LFGDRAQEIA GSATVKIREK VHEIGIAG | 271 |
| E.β.11 | TPEQNVELAS AELKADEKSH AVILGDTRYG GEEKGTYHLA LFGDRAQEIA GSATVKIREK VHEIDIAG | 272 |
| E.β.12 | TPEQNVELAA AELKADEKSH AVILGDTHYG SEEKGTYHLA LFGDRAQEIA GSATVKIGEK VHEISIAG | 273 |
| E.β.13 | TPEQNVELAA AELKADEKSH AVILGDTRYG SEEKGTYHLA LFGDRAQEIA GSATVKIREK VHEIGIAG | 274 |
| E.β.14 | TPEQNVELAS AELKADEKSH AVILGDTRYG GEEKGTYHLA LFGDRAQEIA GSATVKIGEK VHEIGIAG | 275 |
| E.β.15 | TPEQNVELAS AELKADEKSH AVILGDTRYG SEEKDTYHLA LFGDRAQEIA GSATVKIREK VHEIGIAG | 276 |
| E.β.16 | TPELNVDLAS AELKADEKSH AVILGDTRYG GEEKGTYHLA LFGDRAQEIA GSATVKIREK VHEIGIAG | 277 |

A.

B.

| Invariant segment | Amino acid residues |
|---|---|
| $I_1$ | CSSG (SEQ ID NO: 2) |
| $I_2$ | GG |
| $I_3$ | SRFDF (SEQ ID NO: 3) |
| $I_4$ | GEFQ (SEQ ID NO: 4) |
| $I_5$ | DD |
| $I_6$ | IEHLK (SEQ ID NO: 5) or IEHLE (SEQ ID NO: 6) |
| $I_7$ | KQ |

Fig. 5
A.
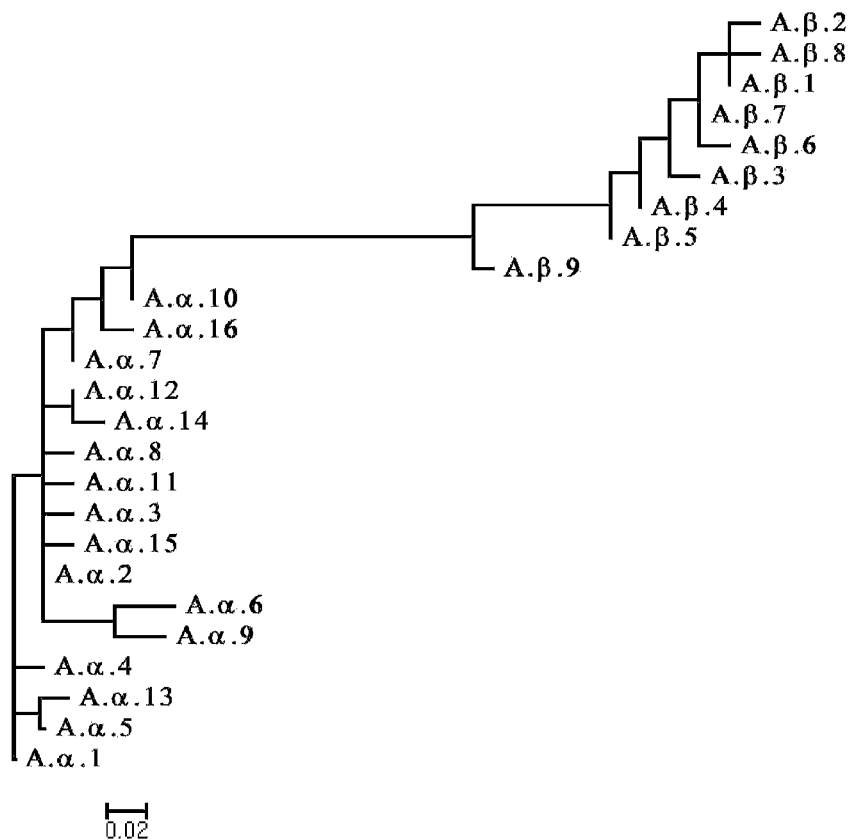
B.
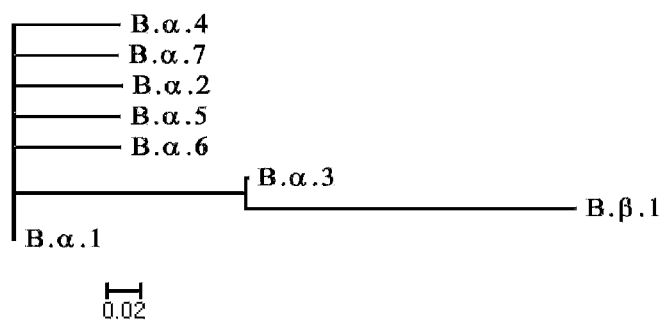

Fig. 6
A.
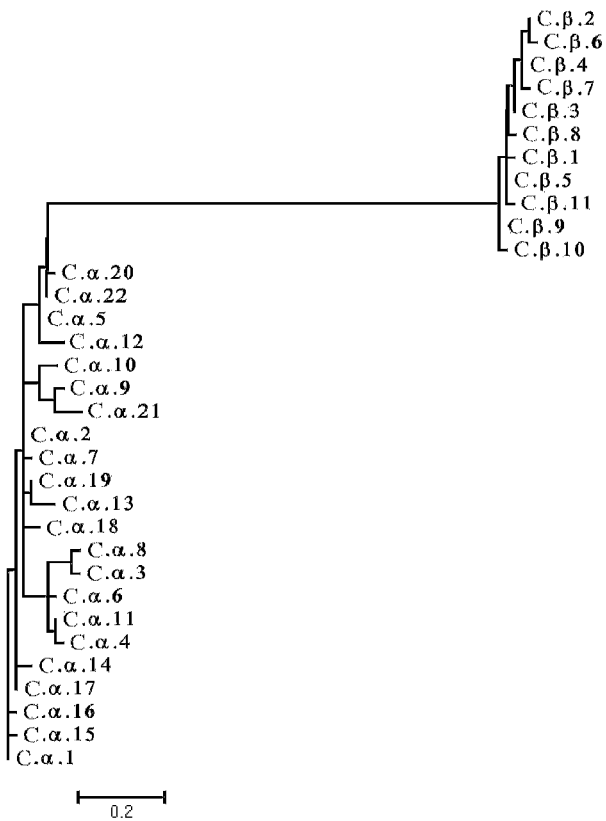
B.
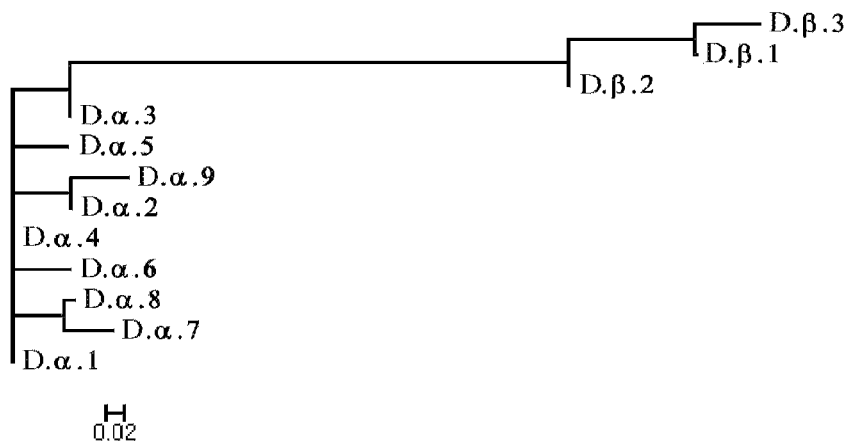

A.

B.

Peptide ID 55
Peptide ID 24
Peptide ID 82

C.

| Variable segment | Conserved junction point within the variable segment | Amino acid residue(s) |
|---|---|---|
| A | $J_1$ | AQGAE (starting at 50) (SEQ ID NO: 278) |
| B | $J_2$ | IEV (starting at 82) |
| E | $J_3$ | A (196) |

Fig. 9
A.
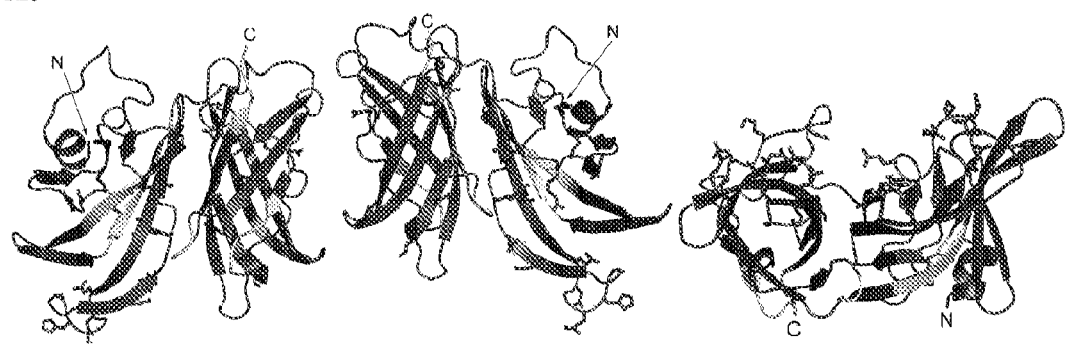
B.
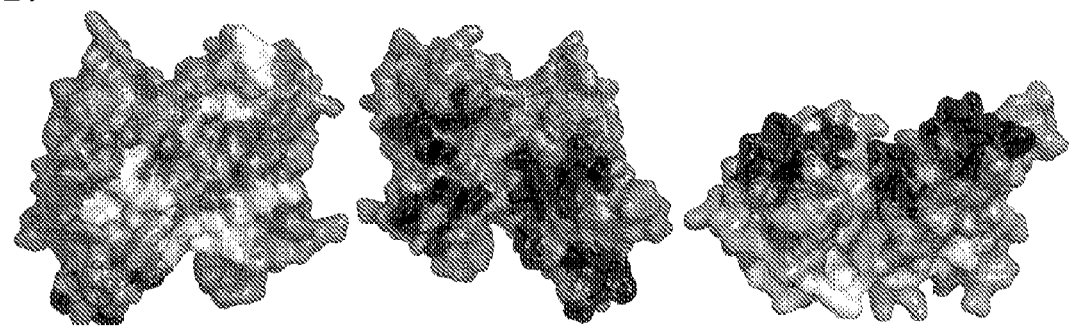

Fig. 9 (Con't)

Fig. 10A: Table 9. Characteristics of unique factor H binding protein variants.

| fHbp Protein ID[1] | Novartis Variant Group[2] | Wyeth Sub-Family[3] | fHbp Modular Group[4] | N-terminal Variable sequence[4] | Modular Variable Segment Allele[5] | | | | | C-terminal[6] |
|---|---|---|---|---|---|---|---|---|---|---|
| | | | | | A | B | C | D | E | |
| 1 | 1 | B | I | G | Aα2 | Bα1 | Cα5 | Dα5 | Eα8 | |
| 2 | 1 | B | I | G | Aα3 | Bα1 | Cα1 | Dα2 | Eα1 | |
| 3 | 1 | B | I | G | Aα3 | Bα1 | Cα6 | Dα1 | Eα1 | |
| 4 | 1 | B | I | G | Aα1 | Bα1 | Cα1 | Dα3 | Eα2 | |
| 5 | 1 | B | I | G | Aα13 | Bα7 | Cα1 | Dα3 | Eα2 | |
| 6 | 1 | B | I | G | Aα2 | Bα1 | Cα14 | Dα4 | Eα17 | |
| 7 | 1 | B | I | G | Aα12 | Bα1 | Cα10 | Dα4 | Eα12 | |
| 8 | 1 | B | I | G | Aα2 | Bα1 | Cα16 | Dα1 | Eα23 | |
| 9 | 1 | B | I | GGGSGG | Aα2 | Bα1 | Cα6 | Dα6 | Eα16 | |
| 10 | 1 | B | I | G | Aα3 | Bα2 | Cα2 | Dα1 | Eα3 | |
| 11 | 1 | B | I | G | Aα3 | Bα1 | Cα6 | Dα1 | Eα18 | |
| 12 | 1 | B | I | G | Aα1 | Bα1 | Cα2 | Dα1 | Eα6 | |
| 13 | 1 | B | I | G | Aα2 | Bα2 | Cα2 | Dα1 | Eα6 | |
| 14 | 1 | B | I | G | Aα1 | Bα1 | Cα3 | Dα1 | Eα3 | |
| 15 | 1 | B | IV | GGGSGG | Aβ3 | Bα1 | Cα4 | Dα1 | Eα4 | |
| 16 | 2 | A | VI | GG | Aα1 | Bα1 | Cβ4 | Dα1 | Eβ2 | |
| 17 | 2 | A | VI | GG | Aα1 | Bα1 | Cβ1 | Dα1 | Eβ2 | |
| 18 | 2 | A | VI | G | Aα36 | Bα10 | Cβ4 | Dα1 | Eβ13 | |
| 19 | 2 | A | VI | G | Aα1 | Bα1 | Cβ2 | Dα1 | Eβ1 | |
| 20 | 2 | A | VI | GG | Aα2 | Bα1 | Cβ6 | Dα1 | Eβ1 | |
| 21 | 2 | A | III | G | Aα1 | Bα1 | Cβ1 | Dβ1 | Eβ3 | |
| 22 | 2 | A | III | GG | Aα1 | Bα1 | Cβ2 | Dβ1 | Eβ1 | |
| 23 | 2 | A | III | GG | Aα2 | Bα1 | Cβ2 | Dβ1 | Eβ1 | |
| 24 | 2 | A | III | GG | Aα1 | Bα3 | Cβ3 | Dβ1 | Eβ1 | |
| 25 | 2 | A | III | G | Aα4 | Bα3 | Cβ3 | Dβ1 | Eβ1 | |
| 26 | 2 | A | III | G | Aα27 | Bα3 | Cβ3 | Dβ1 | Eβ14 | |
| 27 | 2 | A | VI | GG | Aα2 | Bα1 | Cβ4 | Dα1 | Eβ2 | |

Fig. 10B: Table 9, Characteristics of unique factor H binding protein variants.

| # | | | | Linker | | | | | | |
|---|---|---|---|---|---|---|---|---|---|---|
| 28 | A | 3 | II | GGGSGG | Aβ1 | Bβ1 | Cβ9 | Dβ1 | Eβ6 | |
| 29 | A | 3 | II | | Aβ6 | Bβ1 | Cβ10 | Dβ2 | Eβ4 | |
| 30 | A | 3 | II | GGGSGG | Aβ1 | Bβ1 | Cβ11 | Dβ2 | Eβ5 | |
| 31 | A | 3 | V | GGGSGS | Aβ2 | Bβ1 | Cβ1 | Dα1 | Eβ2 | |
| 32 | A | 2 | VI | G | Aα7 | Bα1 | Cβ2 | Dα1 | Eβ1 | |
| 33 | A | 2 | VI | G | Aα3 | Bα1 | Cβ19 | Dα1 | Eβ2 | |
| 34 | A | 2 | III | SGG | Aα38 | Bα1 | Cβ1 | Dβ1 | Eβ1 | |
| 35 | B | 1 | I | G | Aα2 | Bα1 | Cα45 | Dα1 | Eα13 | |
| 36 | B | 1 | I | G | Aα13 | Bα7 | Cα1 | Dα3 | Eα2 | |
| 37 | B | 1 | I | G | Aα40 | Bα1 | Cα33 | Dα1 | Eα56 | EPL |
| 38 | B | 1 | I | G | Aα44 | Bα1 | Cα50 | Dα1 | Eα13 | |
| 39 | B | 1 | I | G | Aα2 | Bα1 | Cα50 | Dα1 | Eα13 | |
| 40 | B | 1 | I | G | Aα2 | Bα1 | Cα5 | Dα5 | Eα9 | |
| 45 | A | 3 | V | SGSGG | Aβ5 | Bβ1 | Cβ2 | Dα1 | Eβ3 | |
| 46 | A | 3 | II | GGGSGG | Aβ1 | Bβ1 | Cβ1 | Dβ3 | Eβ4 | |
| 47 | A | 3 | V | G | Aβ4 | Bβ1 | Cβ5 | Dα1 | Eβ9 | |
| 49 | A | 2 | VI | GG | Aα1 | Bα1 | Cβ2 | Dα7 | Eβ2 | |
| 50 | A | 2 | VI | GG | Aα1 | Bα1 | Cβ7 | Dα1 | Eβ2 | |
| 54 | B | 1 | I | G | Aα2 | Bα4 | Cα1 | Dα2 | Eα10 | |
| 55 | B | 1 | IV | GGGSGG | Aβ9 | Bα1 | Cα8 | Dα1 | Eα14 | |
| 56 | B | 1 | I | G | Aα2 | Bα2 | Cα15 | Dα1 | Eα24 | |
| 57 | B | 1 | I | G | Aα3 | Bα5 | Cα7 | Dα2 | Eα1 | |
| 58 | B | 1 | I | G | Aα1 | Bα1 | Cα19 | Dα1 | Eα11 | |
| 59 | A | 3 | V | GGGSGS | Aβ2 | Bβ1 | Cβ1 | Dα8 | Eβ2 | |
| 60 | B | 1 | I | G | Aα2 | Bα2 | Cα2 | Dα2 | Eα22 | |
| 61 | B | 1 | I | G | Aα9 | Bα1 | Cα18 | Dα2 | Eα1 | |
| 62 | B | 1 | I | G | Aα10 | Bα1 | Cα17 | Dα1 | Eα21 | |
| 63 | B | 1 | I | G | Aα2 | Bα2 | Cα2 | Dα1 | Eα4 | |
| 64 | A | 3 | II | SGG | Aβ1 | Bβ1 | Cβ5 | Dβ2 | Eβ5 | |
| 65 | B | 1 | IV | GGGSGG | Aβ3 | Bα1 | Cα4 | Dα1 | Eα5 | |
| 66 | B | 1 | I | G | Aα11 | Bα1 | Cα9 | Dα4 | Eα5 | |

Fig. 10C: Table 9. Characteristics of unique factor H binding protein variants.

| | | | | | | | | | | |
|---|---|---|---|---|---|---|---|---|---|---|
| 67 | 3 | A | VIII | GGGSGG | Aβ3 | Bα1 | Cβ2 | Dβ1 | Eβ1 | |
| 68 | 2 | A | VI | GG | Aα3 | Bα2 | Cβ2 | Dα1 | Eβ1 | |
| 69 | 1 | B | I | GGGSGG | Aα7 | Bα6 | Cα3 | Dα1 | Eα20 | |
| 70 | 3 | A | V | GGGSGG | Aβ7 | Bβ1 | Cβ1 | Dα1 | Eβ2 | |
| 71 | 1 | B | I | G | Aα8 | Bα1 | Cα12 | Dα6 | Eα19 | |
| 72 | 3 | A | V | GGGS | Aβ2 | Bβ1 | Cβ1 | Dα1 | Eβ2 | |
| 73 | 1 | B | I | G | Aα6 | Bα1 | Cα13 | Dα1 | Eα15 | |
| 74 | 1 | B | I | G | Aα2 | Bα1 | Cα3 | Dα1 | Eα13 | |
| 76 | 3 | A | II | GGGS | Aβ8 | Bβ1 | Cβ1 | Dβ1 | Eβ3 | |
| 77 | 2 | A | VI | GG | Aα5 | Bα1 | Cβ4 | Dα1 | Eβ2 | |
| 78 | 1 | B | I | G | Aα3 | Bα1 | Cα7 | Dα2 | Eα1 | |
| 79 | 3 | A | V | GGGSGS | Aβ2 | Bβ1 | Cβ1 | Dα1 | Eβ4 | |
| 80 | 1 | B | I | GGGSGS | Aα14 | Bα4 | Cα20 | Dα4 | Eα7 | |
| 82 | 3 | A | V | | Aβ1 | Bβ1 | Cβ8 | Dα1 | Eβ10 | |
| 83 | 2 | A | VI | GG | Aα1 | Bα1 | Cβ2 | Dα1 | Eβ7 | |
| 84 | 3 | A | V | GGGSGG | Aβ1 | Bβ1 | Cβ1 | Dα1 | Eβ8 | |
| 85 | 3 | A | V | GGGSGS | Aβ2 | Bβ1 | Cβ2 | Dβ2 | Fβ3 | |
| 86 | 1 | B | IV | GGGSGG | Aβ3 | Bα1 | Cα4 | Dβ1 | Fα3 | |
| 87 | 1 | B | IV | GGGSGG | Aβ3 | Bα3 | Cα11 | Dβ1 | Eα4 | |
| 88 | 1 | B | I | | Aα15 | Bα1 | Cα21 | Dα4 | Eα25 | |
| 89 | 1 | B | I | G | Aα2 | Bα1 | Cα22 | Dα9 | Eα26 | |
| 90 | 1 | B | I | GGGSGG | Aα16 | Bα1 | Cα6 | Dα1 | Eα18 | |
| 94 | 3 | A | V | G | Aβ7 | Bβ1 | Cβ1 | Dβ1 | Eβ9 | |
| 95 | 2 | A | III | G | Aα3 | Bα3 | Cβ3 | Dβ1 | Eβ1 | |
| 96 | 3 | A | II | GGGSGG | Aβ16 | Bβ1 | Cβ11 | Dβ2 | Eβ5 | |
| 97 | 2 | A | III | G | Aα27 | Bα3 | Cβ3 | Dβ1 | Eβ1 | |
| 98 | 3 | A | III | GGGS | Aβ8 | Bβ1 | Cβ1 | Dβ1 | Eβ2 | |
| 99 | 3 | A | II | GGGSGG | Aβ1 | Bβ1 | Cβ1 | Dα1 | Eβ4 | |
| 100 | 1 | B | I | G | Aα2 | Bα1 | Cα42 | Dα1 | Eα11 | |
| 101 | 2 | A | III | G | Aα1 | Bα1 | Cβ1 | Dβ1 | Eβ1 | |
| 102 | 2 | A | III | G | Aα1 | Bα1 | Cβ10 | Dβ1 | Eβ2 | |

Fig. 10D: Table 9, Characteristics of unique factor H binding protein variants.

| 103 | 2 | A | III | G | Aα4 | Bα3 | Cβ9 | Dβ1 | Eβ2 |
|-----|---|---|-----|---|-----|-----|-----|-----|-----|
| 104 | 2 | A | III | G | Aα4 | Bα1 | Cβ17 | Dβ1 | Eβ1 |
| 105 | 2 | A | III | G | Aα2 | Bα2 | Cβ1 | Dβ1 | Eβ3 |
| 106 | 2 | A | VI | G | Aα1 | Bα1 | Cβ4 | Dα1 | Eβ9 |
| 107 | 1 | B | I | GGGSGG | Aα41 | Bα1 | Cα2 | Dα1 | Eα34 |
| 108 | 1 | B | I | G | Aα2 | Bα1 | Cα23 | Dα1 | Eα29 |
| 109 | 2 | A | VI | G | Aα2 | Bα1 | Cβ2 | Dα1 | Eβ1 |
| 110 | 1 | B | I | G | Aα2 | Bα1 | Cα23 | Dα1 | Eα11 |
| 118 | 2 | A | VI | GG | Aα3 | Bα1 | Cβ2 | Dα1 | Eβ1 |
| 119 | 2 | A | VI | G | Aα1 | Bα1 | Cβ4 | Dα1 | Fβ13 |
| 120 | 1 | B | I | GGGSGS | Aα11 | Bα1 | Cα9 | Dα4 | Eα44 |
| 121 | 1 | B | I | G | Aα3 | Bα1 | Cα3 | Dα1 | Eα3 |
| 122 | 1 | B | I | G | Aα1 | Bα1 | Cα51 | Dα1 | Eα3 |
| 123 | 1 | B | I | G | Aα1 | Bα1 | Cα3 | Dα1 | Eα35 |
| 124 | 1 | B | I | G | Aα1 | Bα1 | Cα3 | Dα16 | Fα3 |
| 125 | 1 | B | I | G | Aα2 | Bα1 | Cα2 | Dα1 | Eα6 |
| 126 | 1 | B | I | G | Aα7 | Bα1 | Cα2 | Dα6 | Eα58 |
| 127 | 1 | B | I | GGGSGG | Aα3 | Bα1 | Cα2 | Dα1 | Eα38 |
| 128 | 1 | B | I | G | Aα3 | Bα1 | Cα2 | Dα1 | Eα34 |
| 129 | 1 | B | I | G | Aα3 | Bα1 | Cα52 | Dα2 | Eα1 |
| 130 | 1 | B | I | G | Aα1 | Bα1 | Cα53 | Dα2 | Eα1 |
| 131 | 1 | B | I | G | Aα2 | Bα1 | Cα1 | Dα3 | Eα59 |
| 132 | 1 | B | I | GSGG | Aα17 | Bα5 | Cα1 | Dα12 | Eα23 |
| 133 | 2 | A | VI | G | Aα1 | Bα3 | Cβ17 | Dα1 | Eβ1 |
| 138 | 2 | A | VI | GG | Aα3 | Bα1 | Cβ4 | Dα2 | Eβ2 |
| 139 | 1 | B | I | G | Aα3 | Bα1 | Cα26 | Dα2 | Eα1 |
| 144 | 1 | B | I | G | Aα1 | Bα1 | Cα5 | Dα5 | Eα8 |
| 145 | 1 | B | I | G | Aα37 | Bα2 | Cα2 | Dα1 | Eα34 |
| 150 | 1 | B | I | G | Aα3 | Bα1 | Cα2 | Dα1 | Eα6 |
| 151 | 2 | A | VI | GG | Aα1 | Bα1 | Cβ12 | Dα1 | Fβ4 |
| 152 | 3 | A | V | GGGSGG | Aβ1 | Bβ1 | Cβ2 | Dα1 | Eβ1 |

Fig. 10E: Table 9, Characteristics of unique factor II binding protein variants.

| | | | | | | | | | | |
|---|---|---|---|---|---|---|---|---|---|---|
| 153 | 3 | A | II | GGGSGG | Aβ1 | Bβ1 | Cβ20 | Dβ1 | Fβ3 | |
| 154 | 1 | B | I | G | Aα36 | Bα1 | Cα46 | Dα6 | Fα3 | |
| 155 | 1 | B | I | GGGSGG | Aα7 | Bα1 | Cα1 | Dα3 | Eα2 | |
| 156 | 1 | B | I | G | Aα42 | Bα1 | Cα47 | Dα2 | Eα1 | |
| 157 | 1 | B | I | G | Aα43 | Bα1 | Cα1 | Dα17 | Eα55 | |
| 158 | 1 | B | I | G | Aα2 | Bα1 | Cα2 | Dα1 | Lα38 | |
| 159 | 1 | B | I | G | Aα7 | Bα1 | Cα48 | Dα1 | Eα11 | |
| 160 | 3 | A | V | GGGSGG | Aβ1 | Bβ1 | Cβ1 | Dα1 | Fβ9 | |
| 161 | 2 | A | VI | G | Aα1 | Bα1 | Cβ4 | Dα1 | Eβ1 | |
| 162 | 3 | A | II | GGGSGGG G | Aβ11 | Bβ1 | Cβ21 | Dβ2 | Eβ4 | |
| 163 | 1 | B | I | GGSGG | Aα29 | Bα1 | Cα2 | Dα1 | Eα57 | |
| 164 | 1 | B | I | G | Aα7 | Bα1 | Cα6 | Dα4 | Eα12 | |
| 165 | 3 | A | II | G | Aβ15 | Bβ1 | Cβ18 | Dβ1 | Eβ2 | |
| 166 | 3 | A | II | GGGSGG | Aβ7 | Bβ1 | Cβ20 | Dβ1 | Eβ2 | |
| 167 | 3 | A | II | SGSGG | Aβ5 | Bβ1 | Cβ10 | Dβ1 | Eβ4 | |
| 168 | 3 | A | II | G | Aβ1 | Bβ1 | Cβ1 | Dβ1 | Eβ3 | |
| 169 | 3 | A | II | GGGSGG | Aβ1 | Bβ1 | Cβ1 | Dβ1 | Eβ2 | |
| 170 | 3 | A | II | GGGSGG | Aβ2 | Bβ1 | Cβ1 | Dβ1 | Lβ2 | |
| 171 | 3 | A | II | GGGSGG | Aβ2 | Bβ1 | Cβ1 | Dβ1 | Eβ3 | |
| 172 | 3 | A | II | GGGSGG | Aβ7 | Bβ1 | Cβ15 | Dβ2 | Eβ4 | |
| 173 | 3 | A | II | GGGSGG | Aβ1 | Bβ1 | Cβ10 | Dβ2 | Eβ4 | |
| 174 | 3 | A | II | GGGSGG | Aβ6 | Bβ1 | Cβ9 | Dβ2 | Eβ4 | |
| 175 | 3 | A | IX | GGGSGG | Aβ3 | Bα1 | Cβ4 | Dα1 | Eβ2 | |
| 176 | 3 | A | V | GGGSGG | Aβ7 | Bβ1 | Cβ16 | Dα1 | Eβ9 | |
| 177 | 3 | A | V | G | Aβ4 | Bβ1 | Cβ5 | Dα1 | Eβ12 | |
| 178 | 3 | A | V | G | Aβ4 | Bβ1 | Cβ5 | Dα1 | Fβ2 | |
| 179 | 3 | A | V | G | Aβ14 | Bβ1 | Cβ17 | Dα7 | Eβ13 | |
| 180 | 3 | A | V | GGGS | Aβ1 | Bβ1 | Cβ15 | Dα1 | Eβ2 | |
| 181 | 3 | A | V | GGGSGGG SGG | Aβ8 | Bβ1 | Cβ1 | Dα1 | Eβ2 | |

Fig. 10F: Table 9, Characteristics of unique factor H binding protein variants.

| | | | | | | | | | | |
|---|---|---|---|---|---|---|---|---|---|---|
| 182 | 3 | A | V | GGGS | Aβ11 | Bβ1 | Cβ1 | Dα14 | Eβ4 | |
| 183 | 3 | A | V | G | Aβ13 | Bβ1 | Cβ1 | Dα1 | Eβ13 | |
| 184 | 3 | A | V | G | Aβ7 | Bβ1 | Cβ1 | Dα1 | Eβ13 | |
| 185 | 3 | A | V | GGGSGS | Aβ3 | Bβ1 | Cβ2 | Dα1 | Eβ3 | |
| 186 | 3 | A | V | GGGSGS | Aβ2 | Bβ1 | Cβ2 | Dα1 | Eβ1 | |
| 187 | 3 | A | V | SGSGG | Aβ4 | Bβ1 | Cβ2 | Dα1 | Eβ3 | |
| 188 | 3 | A | V | G | Aβ8 | Bβ1 | Cβ2 | Dα1 | Eβ3 | |
| 189 | 3 | A | V | GGGSGG | Aβ1 | Bβ1 | Cβ1 | Dα1 | Eβ3 | |
| 190 | 3 | A | V | GGGSGS | Aβ12 | Bβ1 | Cβ2 | Dα1 | Eβ3 | |
| 191 | 3 | A | V | G | Aβ1 | Bβ1 | Cβ2 | Dα1 | Eβ3 | |
| 192 | 2 | A | VI | G | Aα21 | Bα1 | Cβ2 | Dα1 | Eβ1 | |
| 193 | 2 | A | VI | G | Aα1 | Bα1 | Cβ13 | Dα1 | Eβ1 | |
| 194 | 2 | A | VI | G | Aα1 | Bα1 | Cβ14 | Dα1 | Eβ1 | |
| 195 | 2 | A | VI | GG | Aα1 | Bα2 | Cβ4 | Dα1 | Eβ2 | |
| 196 | 2 | A | III | GG | Aα9 | Bα1 | Cβ2 | Dβ1 | Eβ1 | |
| 197 | 2 | A | III | G | Aα23 | Bα3 | Cβ3 | Dβ1 | Eβ1 | |
| 198 | 2 | A | III | G | Aα4 | Bα3 | Cβ3 | Dβ1 | Eβ7 | |
| 199 | 2 | A | III | GGGSGG | Aα39 | Bα1 | Cβ19 | Dβ1 | Eβ1 | |
| 200 | 2 | A | III | GG | Aα1 | Bα1 | Cβ4 | Dβ1 | Eβ14 | |
| 201 | 2 | A | III | GG | Aα1 | Bα1 | Cβ2 | Dβ1 | Eβ11 | |
| 202 | 2 | A | III | G | Aα27 | Bα1 | Cβ1 | Dβ1 | Eβ3 | |
| 203 | 2 | A | III | G | Aα2 | Bα1 | Cβ1 | Dβ1 | Eβ3 | |
| 204 | 2 | A | III | G | Aα36 | Bα1 | Cβ1 | Dβ1 | Eβ1 | |
| 205 | 2 | A | III | G | Aα22 | Bα1 | Cβ1 | Dβ1 | Eβ3 | |
| 206 | 2 | A | III | GGGSGG | Aα22 | Bα1 | Cβ1 | Dβ1 | Eβ1 | |
| 207 | 1 | B | VII | G | Aα2 | Bα2 | Cα2 | Dα1 | Eβ1 | |
| 208 | 1 | B | I | G | Aα45 | Bα1 | Cα29 | Dα1 | Eα6 | |
| 209 | 1 | B | IV | GGGSGG | Aβ3 | Bα1 | Cα11 | Dα1 | Eα50 | |
| 210 | 1 | B | IV | G | Aβ3 | Bα1 | Cα4 | Dα1 | Eα4 | |
| 211 | 1 | B | IV | GGGSGGG G | Aβ3 | Bα1 | Cα4 | Dα1 | Eα4 | |

Fig. 10G: Table 9, Characteristics of unique factor H binding protein variants.

| | | | | | | | | |
|---|---|---|---|---|---|---|---|---|
| 212 | 1 | B | IV | GGGSGG | Aβ4 | Bα1 | Cα38 | Dα1 | Eα49 |
| 213 | 1 | B | IV | GGGSGG | Aβ9 | Bα2 | Cα6 | Dα1 | Eα43 |
| 214 | 1 | B | IV | GGGSGG | Aβ9 | Bα2 | Cα2 | Dα1 | Eα3 |
| 215 | 1 | B | I | G | Aα11 | Bα1 | Cα9 | Dα4 | Eα44 |
| 216 | 1 | B | I | G | Aα12 | Bα1 | Cα39 | Dα15 | Eα51 |
| 217 | 1 | B | IV | GGGSGG | Aβ10 | Bα1 | Cα36 | Dα1 | Eα13 |
| 218 | 1 | B | I | G | Aα31 | Bα6 | Cα37 | Dα1 | Eα46 |
| 219 | 1 | B | I | G | Aα31 | Bα1 | Cα34 | Dα1 | Eα42 |
| 220 | 1 | B | I | GGGSGG | Aα29 | Bα1 | Cα3 | Dα1 | Eα45 |
| 221 | 1 | B | I | GGGSGG | Aα32 | Bα1 | Cα3 | Dα1 | Eα3 |
| 222 | 1 | B | I | G | Aα2 | Bα1 | Cα3 | Dα1 | Eα48 |
| 223 | 1 | B | I | G | Aα2 | Bα1 | Cα36 | Dα1 | Eα47 |
| 224 | 1 | B | I | GGGSGG | Aα32 | Bα1 | Cα36 | Dα1 | Eα13 |
| 225 | 1 | B | I | G | Aα2 | Bα1 | Cα36 | Dα1 | Eα13 |
| 226 | 1 | B | I | GGGSGG | Aα33 | Bα6 | Cα3 | Dα1 | Eα20 |
| 227 | 1 | B | I | GGGSGG | Aα3 | Bα6 | Cα3 | Dα1 | Eα20 |
| 228 | 1 | B | I | GGGSGG | Aα27 | Bα9 | Cα1 | Dα1 | Eα39 |
| 229 | 1 | B | I | G | Aα1 | Bα1 | Cα1 | Dα11 | Eα37 |
| 230 | 1 | B | I | G | Aα1 | Bα2 | Cα27 | Dα3 | Eα2 |
| 231 | 1 | B | I | G | Aα1 | Bα1 | Cα1 | Dα10 | Eα2 |
| 232 | 1 | B | I | G | Aα1 | Bα1 | Cα1 | Dα3 | Eα30 |
| 233 | 1 | B | I | G | Aα1 | Bα1 | Cα1 | Dα3 | Eα31 |
| 234 | 1 | B | I | G | Aα36 | Bα1 | Cα33 | Dα1 | Eα56 |
| 235 | 1 | B | I | G | Aα34 | Bα1 | Cα40 | Dα2 | Eα52 |
| 236 | 1 | B | I | G | Aα24 | Bα1 | Cα19 | Dα2 | Eα36 |
| 237 | 1 | B | I | G | Aα2 | Bα7 | Cα19 | Dα2 | Eα32 |
| 238 | 1 | B | I | G | Aα1 | Bα1 | Cα23 | Dα1 | Eα11 |
| 239 | 1 | B | I | G | Aα2 | Bα1 | Cα2 | Dα5 | Eα8 |
| 240 | 1 | B | I | G | Aα2 | Bα1 | Cα25 | Dα5 | Fα5 |
| 241 | 1 | B | I | G | Aα2 | Bα8 | Cα5 | Dα5 | Eα8 |
| 242 | 1 | B | I | G | Aα3 | Bα1 | Cα24 | Dα5 | Eα8 |

Fig. 10H: Table 9, Characteristics of unique factor H binding protein variants.

| | | | | | | | | | |
|---|---|---|---|---|---|---|---|---|---|
| 243 | 1 | B | I | G | Aα7 | Bα1 | Cα5 | Dα5 | Eα8 | |
| 244 | 1 | B | I | GGGSGG | Aα2 | Bα4 | Cα5 | Dα5 | Eα8 | |
| 245 | 1 | B | I | G | Aα8 | Bα1 | Cα5 | Dα5 | Eα5 | |
| 246 | 1 | B | I | G | Aα2 | Bα1 | Cα5 | Dα5 | Hα5 | |
| 247 | 1 | B | I | G | Aα35 | Bα1 | Cα42 | Dα1 | Eα11 | |
| 248 | 1 | B | I | G | Aα2 | Bα1 | Cα1 | Dα1 | Hα55 | |
| 249 | 1 | B | I | G | Aα2 | Bα1 | Cα44 | Dα1 | Eα65 | |
| 250 | 1 | B | I | G | Aα2 | Bα1 | Cα5 | Dα2 | Hα1 | |
| 251 | 1 | B | I | G | Aα2 | Bα4 | Cα35 | Dα2 | Eα10 | |
| 252 | 1 | B | I | G | Aα18 | Bα1 | Cα19 | Dα2 | Hα10 | |
| 253 | 1 | B | I | G | Aα12 | Bα1 | Cα43 | Dα4 | Eα54 | |
| 254 | 1 | B | I | G | Aα2 | Bα1 | Cα10 | Dα4 | Eα33 | |
| 255 | 1 | B | I | GGGSGG | Aα2 | Bα1 | Cα28 | Dα6 | Eα16 | |
| 256 | 1 | B | I | GGGSGG | Aα19 | Bα1 | Cα41 | Dα2 | Eα53 | |
| 257 | 1 | B | I | G | Aα25 | Bα5 | Cα1 | Dα12 | Eα23 | |
| 258 | 1 | B | I | G | Aα19 | Bα1 | Cα6 | Dα1 | Eα18 | |
| 259 | 1 | B | I | G | Aα2 | Bα2 | Cα27 | Dα2 | Eα6 | |
| 260 | 1 | B | I | G | Aα1 | Bα2 | Cα2 | Dα1 | Eα6 | |
| 261 | 1 | B | I | G | Aα2 | Bα2 | Cα2 | Dα1 | Eα3 | |
| 262 | 1 | B | I | G | Aα20 | Bα2 | Cα2 | Dα1 | Eα6 | |
| 263 | 1 | B | I | GGGSGG | Aα7 | Bα1 | Cα31 | Dα13 | Eα38 | |
| 264 | 1 | B | I | G | Aα29 | Bα1 | Cα33 | Dα1 | Eα3 | |
| 265 | 1 | B | I | GGGSGG | Aα26 | Bα1 | Cα32 | Dα1 | Eα6 | |
| 266 | 1 | B | I | GGGSGG | Aα28 | Bα1 | Cα2 | Dα1 | Eα40 | |
| 267 | 1 | B | I | GGGSGG | Aα2 | Bα1 | Cα30 | Dα1 | Eα6 | EPL |
| 268 | 1 | B | I | G | Aα30 | Bα1 | Cα29 | Dα1 | Eα6 | |
| 269 | 1 | B | I | G | Aα3 | Bα1 | Cα29 | Dα1 | Eα6 | |
| 270 | 1 | B | I | G | Aα3 | Bα1 | Cα29 | Dα1 | Eα41 | |
| 271 | 3 | A | V | G | Aβ7 | Bβ1 | Cβ22 | Dα1 | Eβ9 | |
| 272 | 1 | B | I | G | Aα2 | Bα1 | Cα2 | Dα1 | Eα1 | |
| 273 | 1 | B | I | G | Aα2 | Bα2 | Cα2 | Dα1 | Eα60 | |

Fig. 10I: Table 9, Characteristics of unique factor H binding protein variants.

| | | | III | G | Aα1 | Bα1 | Cβ1 | Dβ1 | Eβ15 |
|---|---|---|---|---|---|---|---|---|---|
| 274 | 2 | A | | | Aα7 | Bα1 | | | |
| 275 | 1 | B | I | GGGSGG | | | Cα6 | Dα1 | Eα46 |

[1]Protein IDs were obtained from the Neisseria.org fHbp peptide database.
[2]Variant groups as described by Masignani et al (2003) *J Exp Med* 197(6):789-99.
[3]Sub-family A or B as described by Fletcher et al (2004) *Infect Immun* 72(4):2088-100 and Murphy et al (2009) *J Infect Dis*
[4]Modular classification according to the present disclosure.
[5]Segment alleles as described by Beernink and Granoff (2009) *Microbiology* 155(Pt 9):2873-83. See also Table 5
[6]Two protein variants had three additional amino acids at their C-termini (See text)
[7]NA, not available

SEQUENCE LISTING

<160> NUMBER OF SEQ ID NOS: 280

<210> SEQ ID NO 1
<211> LENGTH: 255
<212> TYPE: PRT
<213> ORGANISM: Neisseria meningitidis

<400> SEQUENCE: 1

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

```
Thr Gly Lys Leu Lys Asn Asp Lys Val Ser Arg Phe Asp Phe Ile Arg
 65                  70                  75                  80

Gln Ile Glu Val Asp Gly Gln Leu Ile Thr Leu Glu Ser Gly Glu Phe
                 85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide

<400> SEQUENCE: 2

Cys Ser Ser Gly
1

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide

<400> SEQUENCE: 3

Ser Arg Phe Asp Phe
1               5

<210> SEQ ID NO 4
<211> LENGTH: 4
<212> TYPE: PRT
<213> ORGANISM: Artificial Sequence
<220> FEATURE:
<223> OTHER INFORMATION: Synthetic peptide

<400> SEQUENCE: 4

Gly Glu Phe Gln
1

<210> SEQ ID NO 5
<211> LENGTH: 5
```

```
<212> TYPE: PRT
<213> ORGANISM: Artificial Sequence
<220> FEATURE:
<223> OTHER INFORMATION: Synthetic peptide

<400> SEQUENCE: 5

Ile Glu His Leu Lys
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic peptide

<400> SEQUENCE: 6

Ile Glu His Leu Glu
1               5

<210> SEQ ID NO 7
<211> LENGTH: 4
<212> TYPE: PRT
<213> ORGANISM: Artificial Sequence
<220> FEATURE:
<223> OTHER INFORMATION: Synthetic peptide

<400> SEQUENCE: 7

Gly Gly Gly Ser
1

<210> SEQ ID NO 8
<211> LENGTH: 5
<212> TYPE: PRT
<213> ORGANISM: Artificial Sequence
<220> FEATURE:
<223> OTHER INFORMATION: Synthetic peptide

<400> SEQUENCE: 8

Ser Gly Ser Gly Gly
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic peptide

<400> SEQUENCE: 9

Gly Gly Gly Ser Gly Gly
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic peptide

<400> SEQUENCE: 10

Gly Gly Gly Ser Gly Ser
1               5

<210> SEQ ID NO 11
<211> LENGTH: 4
<212> TYPE: PRT
```

```
<213> ORGANISM: Artificial Sequence
<220> FEATURE:
<223> OTHER INFORMATION: Synthetic peptide

<400> SEQUENCE: 11

Gly Ser Gly Gly
1

<210> SEQ ID NO 12
<211> LENGTH: 8
<212> TYPE: PRT
<213> ORGANISM: Artificial Sequence
<220> FEATURE:
<223> OTHER INFORMATION: Synthetic peptide

<400> SEQUENCE: 12

Gly Gly Gly Ser Gly Gly Gly Gly
1               5

<210> SEQ ID NO 13
<211> LENGTH: 10
<212> TYPE: PRT
<213> ORGANISM: Artificial Sequence
<220> FEATURE:
<223> OTHER INFORMATION: Synthetic peptide

<400> SEQUENCE: 13

Gly Gly Gly Ser Gly Gly Gly Ser Gly Gly
1               5                   10

<210> SEQ ID NO 14
<211> LENGTH: 5
<212> TYPE: PRT
<213> ORGANISM: Artificial Sequence
<220> FEATURE:
<223> OTHER INFORMATION: Synthetic peptide

<400> SEQUENCE: 14

Gly Gly Ser Gly Gly
1               5

<210> SEQ ID NO 15
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 15

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val
65

<210> SEQ ID NO 16
<211> LENGTH: 66
<212> TYPE: PRT
<213> ORGANISM: Artificial Sequence
<220> FEATURE:
```

<223> OTHER INFORMATION: fHbp sequence variant

<400> SEQUENCE: 16

Val Ala Ala Asp Ile Gly Ala Gly Leu Ala Asp Ala Leu Thr Ala Pro
1

Val Ala Asp Ile Gly Ala Arg Leu Ala Asp Ala Leu Thr Ala Pro
1               5                   10                  15

Leu Asp His Lys Asp Lys Ser Leu Gln Ser Leu Thr Leu Asp Gln Ser
            20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
        50                  55                  60

Lys Val
65

<210> SEQ ID NO 20
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 20

Val Ala Ala Asp Ile Gly Ala Gly Leu Ala Asp Ala Leu Thr Ala Leu
1               5                   10                  15

Pro Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Glu
            35                  40                  45

Thr Tyr Gly Asn Gly Asp Ser Leu Asp Thr Gly Lys Leu Lys Asn Asp
        50                  55                  60

Lys Val
65

<210> SEQ ID NO 21
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 21

Val Ala Ala Asp Ile Gly Thr Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
        50                  55                  60

Lys Val
65

<210> SEQ ID NO 22
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 22

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser

```
                 20                  25                  30

Val Arg Lys Asn Glu Lys Leu Lys Leu Ala Ala Gln Gly Ala Glu Lys
         35                  40                  45

Thr Tyr Gly Asn Gly Asp Arg Leu Asn Thr Gly Lys Leu Lys Asn Asp
     50                  55                  60

Lys Val
65

<210> SEQ ID NO 23
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 23

Val Ala Ala Asp Ile Gly Ala Gly Leu Ala Asp Ala Leu Thr Ala Pro
1               5                   10                  15

Phe Asp His Lys Asp Lys Gly Leu Gln Ser Leu Thr Leu Asp Gln Ser
                20                  25                  30

Val Arg Lys Asn Glu Lys Leu Lys Leu Ala Ala Gln Gly Ala Glu Glu
         35                  40                  45

Ile Tyr Gly Asn Gly Asp Ser Leu Asp Thr Gly Lys Leu Lys Asn Asp
     50                  55                  60

Lys Val
65

<210> SEQ ID NO 24
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 24

Val Th

Thr Tyr Gly Asn Gly Asp Ser Leu Asn Thr Gly Lys Leu Lys Asn Asp
         50                  55                  60

Lys Val
65

<210> SEQ ID NO 26
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 26

Val Ala Ala Asp Ile Gly Ala Gly Leu Ala Asp Ala Leu Thr Ala Pro
1               5                   10                  15

Leu Asp His Lys Asp Lys Gly Leu Arg Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val
65

<210> SEQ ID NO 27
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 27

Val Ala Ala Asp Ile Gly Ala Val Leu Ala Asp Ala Leu Thr Ala Pro
1               5                   10                  15

Leu Asp His Lys Asp Lys Ser Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val
65

<210> SEQ ID NO 28
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 28

Val Ala Ala Asp Ile Gly Thr Gly Leu Ala Asp Ala Leu Thr Ala Pro
1               5                   10                  15

Leu Asp His Lys Asp Lys Gly Leu Arg Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val
65

<210> SEQ ID NO 29
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 29

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Val Glu Lys
        35                  40                  45

Thr Tyr Gly Asn Gly Asp Ser Leu Asn Thr Gly Lys Leu Lys Asn Asp
    50                  55                  60

Lys Val
65

<210> SEQ ID NO 30
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 30

Val Ala Val Asp Ile Gly Thr Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Ile
65

<210> SEQ ID NO 31
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 31

Val Ala Ala Asp Ile Gly Thr Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Glu
        35                  40                  45

Thr Tyr Gly Asn Gly Asp Ser Leu Asn Thr Gly Lys Leu Lys Asn Asp
    50                  55                  60

Lys Val
65

```
<210> SEQ ID NO 32
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 32

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Ile Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val
65

<210> SEQ ID NO 33
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 33

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Ile
65

<210> SEQ ID NO 34
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 34

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Ser Lys Leu Lys Asn Asp
    50                  55                  60

Lys Val
65

<210> SEQ ID NO 35
<211> LENGTH: 66
<212> TYPE: PRT
<213> ORGANISM: Artificial Sequence
```

```
<220> FEATURE:
<223> OTHER INFORMATION: fHbp sequence variant

<400> SEQUENCE: 35

Val Ala Ala Asp Ile Gly Ala Gly Leu Ala Asp Ala Leu Thr Val Pro
1               5                   10                  15

Leu Asp His Lys Asp Lys Ser Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val
65

<210> SEQ ID NO 36
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 36

Val Ala Ala Asp Ile Gly Thr Gly Leu Ala Asp Ala Leu Thr Ala Pro
1               5                   10                  15

Leu Asp His Lys Asp Lys Ser Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val
65

<210> SEQ ID NO 37
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 37

Val Ala Ala Asp Ile Gly Ala Gly Leu Ala Asp Ala Leu Thr Thr Pro
1               5                   10                  15

Leu Asp His Lys Asp Lys Ser Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Asn Leu Asn Thr Gly Lys Leu Lys Asn Asp
    50                  55                  60

Lys Val
65

<210> SEQ ID NO 38
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 38
```

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Ala Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val
65

<210> SEQ ID NO 39
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 39

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Glu
        35                  40                  45

Thr Tyr Gly Asn Gly Asp Ser Leu Asn Thr Gly Lys Leu Lys Asn Asp
    50                  55                  60

Lys Val
65

<210> SEQ ID NO 40
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 40

Val Thr Ala Asp Ile Gly Ala Gly Leu Ala Asp Ala Leu Thr Ala Pro
1               5                   10                  15

Leu Asp His Lys Asp Lys Gly Leu Arg Ser Leu Met Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Ile
65

<210> SEQ ID NO 41
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 41

Val Ala Ala Asp Ile Gly Val Gly Leu Ala Asp Ala Leu Thr Thr Pro
1               5                   10                  15

```
Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val
65

<210> SEQ ID NO 42
<211> LENGTH: 65
<212> TYPE: PRT
<213> ORGANISM: Artificial Sequence
<220> FEATURE:
<223> OTHER INFORMATION: fHbp sequence variant

<400> SEQUENCE: 42

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ser Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys
65

<210> SEQ ID NO 43
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 43

Val Ala Ala Asp Ile Gly Thr Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Ile
65

<210> SEQ ID NO 44
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 44

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ser Ala Gln Gly Ala Glu Lys
```

```
                35                  40                  45
Thr Tyr Gly Asn Gly Asp Ser Leu Asn Thr Gly Lys Leu Lys Asn Asp
         50                  55                  60

Lys Val
65

<210> SEQ ID NO 45
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 45

Val Ala Ala Asp Ile Gly Thr Gly Leu Ala Asp Ala Leu Thr Ala Pro
1               5                   10                  15

Leu Asp His Lys Asp Lys Gly Leu Gln Ser Leu Met Leu Asp Gln Ser
             20                  25                  30

Val Arg Lys Asn Glu Lys Leu Lys Leu Ser Ala Gln Gly Ala Glu Lys
         35                  40                  45

Thr Tyr Gly Asn Gly Asp Ser Leu Asn Thr Gly Lys Leu Lys Asn Asp
     50                  55                  60

Lys Ile
65

<210> SEQ ID NO 46
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 46

Val Thr Ala Asp Ile Gly Thr Gly Leu Ala Asp Ala Leu Thr Ala Pro
1               5                   10                  15

Leu Asp His Lys Asp Lys Gly Leu Gln Ser Leu Thr Leu Asp Gln Ser
             20                  25                  30

Val Arg Lys Asn Glu Lys Leu Lys Leu Ala Ala Gln Gly Ala Glu Lys
         35                  40                  45

Thr Tyr Gly Asn Gly Asp Ser Leu Asn Thr Gly Lys Leu Lys Asn Asp
     50                  55                  60

Lys Val
65

<210> SEQ ID NO 47
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 47

Val Ala Ala Asp Ile Gly Thr Gly Leu Ala Asp Ala Leu Thr Ala Leu
1               5                   10                  15

Pro Asp His Lys Asp Lys Gly Leu Gln Ser Leu Thr Leu Asp Gln Ser
             20                  25                  30

Val Arg Lys Asn Glu Lys Leu Lys Leu Ala Ala Gln Gly Ala Glu Lys
         35                  40                  45

Thr Tyr Gly Asn Gly Asp Ser Leu Asn Thr Gly Lys Leu Lys Asn Asp
     50                  55                  60
```

```
<210> SEQ ID NO 48
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 48

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asn Gln Ser
                20                  25                  30

Val Arg Lys Lys Glu Lys Leu Lys Leu Ala Ala Gln Gly Ala Glu Lys
            35                  40                  45

Thr Tyr Gly Asn Gly Asp Ser Leu Ser Thr Gly Lys Leu Lys Asn Asp
    50                  55                  60

Lys Val
65

<210> SEQ ID NO 49
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 49

Val Ala Ala Asp Ile Gly Ala Gly

<210> SEQ ID NO 51
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 51

```
Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Met Leu Asp Gln Ser
            20                  25                  30

Val Arg Lys Asn Glu Lys Leu Lys Leu Ser Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val
65
```

<210> SEQ ID NO 52
<211> LENGTH: 67
<212> TYPE: PRT
<213> ORGANISM: Artificial Sequence
<220> FEATURE:
<223> OTHER INFORMATION: fHbp sequence variant

<400> SEQUENCE: 52

```
Val Ala Ala Asp Ile Gly Thr Gly Leu Ala Tyr Ala Leu Thr Ala Pro
1               5                   10                  15

Leu Asp His Lys Asp Lys Ser Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Gln Thr Gly Lys Leu Lys Asn
    50                  55                  60

Asp Lys Val
65
```

<210> SEQ ID NO 53
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 53

```
Val Thr Ala Asp Ile Gly Thr Gly Leu Ala Asp Ala Leu Thr Ala Pro
1               5                   10                  15

Leu Asp His Lys Asp Lys Gly Leu Gln Ser Leu Met Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Ile
65
```

<210> SEQ ID NO 54
<211> LENGTH: 66
<212> TYPE: PRT

```
<213> ORGANISM: Artificial Sequence
<220> FEATURE:
<223> OTHER INFORMATION: fHbp sequence variant

<400> SEQUENCE: 54

Val Ala Ala Asp Ile Gly Ala Gly Leu Ala Asp Ala Leu Thr Ala Pro
1               5                   10                  15

Leu Asp His Lys Asp Lys Gly Leu

```
<400> SEQUENCE: 57

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Glu
        35                  40                  45

Thr Tyr Gly Asn Gly Asp Ser Leu Asn Thr Asp Lys Leu Lys Asn Asp
    50                  55                  60

Lys Val
65

<210> SEQ ID NO 58
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 58

Val Ala Ala Asp Ile Gly Ala Gly Leu Ala Asp Val Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val
65

<210> SEQ ID NO 59
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 59

Val Ala Ala Asp Ile Gly Ala Gly Leu Ala Asp Ala Leu Thr Thr Pro
1               5                   10                  15

Leu Asp His Lys Asp Lys Gly Leu Arg Ser Leu Met Leu Asp Gln Ser
            20                  25                  30

Val Arg Lys Asn Glu Lys Leu Lys Leu Ser Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val
65

<210> SEQ ID NO 60
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 60

Val Val Ala Asp Ile Gly Ala Gly Leu Ala Asp Ala Leu Thr Ala Pro
1               5                   10                  15
```

```
Leu Asp His Lys Asp Lys Gly Leu Gln Ser Leu Met Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ile Leu Asn Thr Gly Lys Leu Lys Asn Asp
    50                  55                  60

Lys Val
65

<210> SEQ ID NO 61
<211> LENGTH: 69
<212> TYPE: PRT
<213> ORGANISM: Artificial Sequence
<220> FEATURE:
<223> OTHER INFORMATION: fHbp sequence variant

<400> SEQUENCE: 61

Val Ala Ala Asp Ile Gly Ala Gly Leu Ala Asp Val Leu Thr Ala Gln
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Phe Lys Ala Gly Asp Lys Asp Asn Ser Leu Asn Thr Gly Lys Leu
    50                  55                  60

Lys Asn Asp Lys Ile
65

<210> SEQ ID NO 62
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 62

Ile Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val
65

<210> SEQ ID NO 63
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 63

Val Ala Ala Asn Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Ser
            20                  25                  30
```

```
Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
 50                  55                  60

Lys Val
 65

<210> SEQ ID NO 64
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 64

Val Ala Ala Asp Ile Gly Ala Gly Leu Thr Asp Ala Leu Thr Ala Pro
 1               5                  10                  15

Leu Asp His Lys Asp Lys Ser Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
 50                  55                  60

Lys Val
 65

<210> SEQ ID NO 65
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 65

Val Ala Ala Asp Ile Gly Ala Gly Leu Ala Asp Ala Leu Thr Ala Pro
 1               5                  10                  15

Leu Asp His Lys Asp Lys Gly Leu Gln Ser Leu Met Leu Asp Gln Ser
                20                  25                  30

Val Arg Lys Asn Glu Lys Leu Lys Leu Ala Ala Gln Gly Ala Glu Glu
            35                  40                  45

Thr Tyr Gly Asn Gly Asp Ser Leu Asn Thr Gly Lys Leu Lys Asn Asp
 50                  55                  60

Lys Val
 65

<210> SEQ ID NO 66
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 66

Val Ala Ala Asp Ile Gly Ala Gly Leu Ala Asp Ala Leu Thr Ala Pro
 1               5                  10                  15

Phe Asp His Lys Asp Lys Gly Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
```

```
                50                  55                  60

Lys Ile
 65

<210> SEQ ID NO 67
<211> LENGTH: 69
<212> TYPE: PRT
<213> ORGANISM: Artificial Sequence
<220> FEATURE:
<223> OTHER INFORMATION: fHbp sequence variant

<400> SEQUENCE: 67

Val Ala Ala Asp Ile Gly Thr Gly Leu Ala Asp Ala Leu Thr Ala Pro
 1               5                  10                  15

Leu Asp His Lys Asp Lys Gly Leu Lys Ser Leu Thr Leu Glu Asp Ser
                20                  25                  30

Ile Pro Gln Asn Gly Thr Leu Thr Leu Ser Ala Gln Gly Ala Glu Lys
            35                  40                  45

Thr Phe Lys Ala Gly Asp Lys Asp Asn Ser Leu Asn Thr Gly Lys Leu
        50                  55                  60

Lys Asn Asp Lys Ile
 65

<210> SEQ ID NO 68
<211> LENGTH: 69
<212> TYPE: PRT
<213> ORGANISM: Artificial Sequence
<220> FEATURE:
<223> OTHER INFORMATION: fHbp sequence variant

<400> SEQUENCE: 68

Val Ala Ala Asp Ile Gly Thr Gly Leu Ala Asp Ala Leu Thr Thr Pro
 1               5                  10                  15

Leu Asp His Lys Asp Lys Gly Leu Lys Ser Leu Thr Leu Glu Asp Ser
                20                  25                  30

Ile Pro Gln Asn Gly Thr Leu Thr Leu Ser Ala Gln Gly Ala Glu Lys
            35                  40                  45

Thr Phe Lys Ala Gly Asp Lys Asp Asn Ser Leu Asn Thr Gly Lys Leu
        50                  55                  60

Lys Asn Asp Lys Ile
 65

<210> SEQ ID NO 69
<211> LENGTH: 69
<212> TYPE: PRT
<213> ORGANISM: Artificial Sequence
<220> FEATURE:
<223> OTHER INFORMATION: fHbp sequence variant

<400> SEQUENCE: 69

Val Ala Ala Asp Ile Gly Ala Gly Leu Ala Asp Ala Leu Thr Ala Pro
 1               5                  10                  15

Leu Asp His Lys Asp Lys Gly Leu Lys Ser Leu Thr Leu Glu Asp Ser
                20                  25                  30

Ile Ser Gln Asn Gly Thr Leu Thr Leu Ser Ala Gln Gly Ala Glu Arg
            35                  40                  45

Thr Phe Lys Ala Gly Asp Lys Asp Asn Ser Leu Asn Thr Gly Lys Leu
        50                  55                  60

Lys Asn Asp Lys Ile
 65
```

<210> SEQ ID NO 70
<211> LENGTH: 69
<212> TYPE: PRT
<213> ORGANISM: Artificial Sequence
<220> FEATURE:
<223> OTHER INFORMATION: fHbp sequence variant

<400> SEQUENCE: 70

Val Ala Ala Asp Ile Gly Ala Gly Leu Ala Asp Ala Leu Thr Ala Pro
1               5                   10                  15

Leu Asp His Lys Asp Lys Gly Leu Lys Ser Leu Thr Leu Glu Asp Ser
                20                  25                  30

Ile Ser Gln Asn Gly Thr Leu Thr Leu Ser Ala Gln Gly Ala Glu Lys
            35                  40                  45

Thr Phe Lys Val Gly Asp Lys Asp Asn Ser Leu Asn Thr Gly Lys Leu
        50                  55                  60

Lys Asn Asp Lys Ile
65

<210> SEQ ID NO 71
<211> LENGTH: 69
<212> TYPE: PRT
<213> ORGANISM: Artificial Sequence
<220> FEATURE:
<223> OTHER INFORMATION: fHbp sequence variant

<400> SEQUENCE: 71

Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Ser
                20                  25                  30

Ile Ser Gln Asn Gly Thr Leu Thr Leu Ser Ala Gln Gly Ala Glu Lys
            35                  40                  45

Thr Phe Lys Val Gly Asp Lys Asp Asn Ser Leu Asn Thr Gly Lys Leu
        50                  55                  60

Lys Asn Asp Lys Ile
65

<210> SEQ ID NO 72
<211> LENGTH: 69
<212> TYPE: PRT
<213> ORGANISM: Artificial Sequence
<220> FEATURE:
<223> OTHER INFORMATION: fHbp sequence variant

<400> SEQUENCE: 72

Val Ala Ala Asp Ile Gly Ala Gly Leu Ala Asp Ala Leu Thr Ala Pro
1               5                   10                  15

Leu Asp His Lys Asp Lys Gly Leu Lys Ser Leu Thr Leu Glu Asp Ser
                20                  25                  30

Ile Pro Gln Asn Gly Thr Leu Thr Leu Ser Ala Gln Gly Ala Glu Lys
            35                  40                  45

Thr Phe Lys Ala Gly Gly Lys Asp Asn Ser Leu Asn Thr Gly Lys Leu
        50                  55                  60

Lys Asn Asp Lys Ile
65

<210> SEQ ID NO 73
<211> LENGTH: 69

<212> TYPE: PRT
<213> ORGANISM: Artificial Sequence
<220> FEATURE:
<223> OTHER INFORMATION: fHbp sequence variant

<400> SEQUENCE: 73

Val Ala Ala Asp Ile Gly Ala Gly Leu Ala Asp Ala Leu Thr Ala Pro
1               5                   10                  15
Leu Asp His Lys Asp Lys Gly Leu Lys Ser Leu Thr Leu Glu Asp Ser
                20                  25                  30
Ile Pro Gln Asn Gly Thr Leu Thr Leu Ser Ala Gln Gly Ala Glu Lys
            35                  40                  45
Thr Phe Lys Ala Gly Asp Lys Asp Asn Ser Leu Asn Thr Gly Lys Leu
    50                  55                  60
Lys Asn Asp Lys Ile
65

<210> SEQ ID NO 74
<211> LENGTH: 69
<212> TYPE: PRT
<213> ORGANISM: Artificial Sequence
<220> FEATURE:
<223> OTHER INFORMATION: fHbp sequence variant

<400> SEQUENCE: 74

Ile Ala Ala Asp Ile Gly Thr Gly Leu Ala Asp Ala Leu Thr Ala Pro
1               5                   10                  15
Leu Asp His Lys Asp Lys Gly Leu Lys Ser Leu Thr Leu Glu Asp Ser
                20                  25                  30
Ile Pro Gln Asn Gly Thr Leu Thr Leu Ser Ala Gln Gly Ala Glu Lys
            35                  40                  45
Thr Phe Lys Ala Gly Asp Lys Asp Asn Ser Leu Asn Thr Gly Lys Leu
    50                  55                  60
Lys Asn Asp Lys Ile
65

<210> SEQ ID NO 75
<211> LENGTH: 66
<212> TYPE: PRT
<213> ORGANISM: Artificial Sequence
<220> FEATURE:
<223> OTHER INFORMATION: fHbp sequence variant

<400> SEQUENCE: 75

Val Thr Ala Asp Ile Gly Thr Gly Leu Ala Asp Ala Leu Thr Ala Pro
1               5                   10                  15
Leu Asp His Lys Asp Lys Gly Leu Lys Ser Leu Thr Leu Glu Asp Ser
                20                  25                  30
Ile Ser Gln Asn Gly Thr Leu Thr Leu Ser Ala Gln Gly Ala Glu Lys
            35                  40                  45
Thr Tyr Gly Asn Gly Asp Ser Leu Asn Thr Gly Lys Leu Lys Asn Asp
    50                  55                  60
Lys Val
65

<210> SEQ ID NO 76
<211> LENGTH: 66
<212> TYPE: PRT
<213> ORGANISM: Artificial Sequence
<220> FEATURE:
<223> OTHER INFORMATION: fHbp sequence variant -continued

<400> SEQUENCE: 76

Val Ala Ala Asp Ile Gly Ala Gly Leu Ala Asp Ala Leu Thr Ala Pro
1               5                   10                  15

Leu Asp His Lys Asn Lys Gly Leu Lys Ser Leu Thr Leu Glu Asp Ser
            20                  25                  30

Ile Pro Gln Asn Gly Thr Leu Thr Leu Ser Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val
65

<210> SEQ ID NO 77
<211> LENGTH: 69
<212> TYPE: PRT
<213> ORGANISM: Artificial Sequence
<220> FEATURE:
<223> OTHER INFORMATION: fHbp sequence variant

<400> SEQUENCE: 77

Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Pro Gln Asn Gly Thr Leu Thr Leu Ser Ala Gln Gly Ala Glu Lys
        35                  40                  45

Thr Phe Lys Ala Gly Gly Lys Asp Asn Ser Leu Asn Thr Gly Lys Leu
    50                  55                  60

Lys Asn Asp Lys Ile
65

<210> SEQ ID NO 78
<211> LENGTH: 69
<212> TYPE: PRT
<213> ORGANISM: Artificial Sequence
<220> FEATURE:
<223> OTHER INFORMATION: fHbp sequence variant

<400> SEQUENCE: 78

Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Pro Gln Asn Gly Thr Leu Thr Leu Ser Ala Gln Gly Ala Glu Lys
        35                  40                  45

Thr Phe Lys Val Gly Asp Lys Asp Asn Ser Leu Asn Thr Gly Lys Leu
    50                  55                  60

Lys Asn Asp Lys Ile
65

<210> SEQ ID NO 79
<211> LENGTH: 69
<212> TYPE: PRT
<213> ORGANISM: Artificial Sequence
<220> FEATURE:
<223> OTHER INFORMATION: fHbp sequence variant

<400> SEQUENCE: 79

Val Ala Ala Asp Ile Gly Ala Gly Leu Ala Asp Ala Leu Thr Thr Pro

```
1               5                  10                 15
Leu Asp His Lys Asp Lys Gly Leu Lys Ser Leu Thr Leu Glu Asp Ser
            20                  25                 30

Ile Pro Gln Asn Gly Thr Leu Thr Leu Ser Ala Gln Gly Ala Glu Lys
            35                  40                 45

Thr Phe Lys Ala Gly Asp Lys Asp Asn Ser Leu Asn Thr Gly Lys Leu
        50                  55                 60

Lys Asn Asp Lys Ile
65
```

<210> SEQ ID NO 80
<211> LENGTH: 69
<212> TYPE: PRT
<213> ORGANISM: Artificial Sequence
<220> FEATURE:
<223> OTHER INFORMATION: fHbp sequence variant

<400> SEQUENCE: 80

```
Val Ala Ala Asp Ile Gly Ala Gly Leu Ala Asp Ala Leu Thr Ala Pro
1               5                  10                 15

Leu Asp His Lys Asp Lys Gly Leu Lys Ser Leu Thr Leu Glu Asp Ser
            20                  25                 30

Ile Pro Gln Asn Gly Thr Leu Thr Leu Ser Ala Gln Gly Val Glu Lys
            35                  40                 45

Thr Phe Lys Ala Gly Asp Lys Asp Asn Ser Leu Asn Thr Gly Lys Leu
        50                  55                 60

Lys Asn Asp Lys Ile
65
```

<210> SEQ ID NO 81
<211> LENGTH: 69
<212> TYPE: PRT
<213> ORGANISM: Artificial Sequence
<220> FEATURE:
<223> OTHER INFORMATION: fHbp sequence variant

<400> SEQUENCE: 81

```
Val Ala Ala Asp Ile Gly Ala Gly Leu Ala Asp Ala Leu Thr Ala Pro
1               5                  10                 15

Leu Asp His Lys Asp Lys Gly Leu Lys Ser Leu Thr Leu Glu Asp Ser
            20                  25                 30

Ile Ser Gln Asn Gly Thr Leu Thr Leu Ser Ala Gln Gly Ala Glu Arg
            35                  40                 45

Thr Phe Lys Ala Gly Asn Lys Asp Asn Ser Leu Asn Thr Gly Lys Leu
        50                  55                 60

Lys Asn Asp Lys Ile
65
```

<210> SEQ ID NO 82
<211> LENGTH: 69
<212> TYPE: PRT
<213> ORGANISM: Artificial Sequence
<220> FEATURE:
<223> OTHER INFORMATION: fHbp sequence variant

<400> SEQUENCE: 82

```
Val Thr Ala Asp Ile Gly Thr Gly Leu Ala Asp Ala Leu Thr Ala Pro
1               5                  10                 15

Leu Asp His Lys Asp Lys Gly Leu Lys Ser Leu Thr Leu Glu Asp Ser
            20                  25                 30
```

```
Ile Pro Gln Asn Gly Thr Leu Thr Leu Ser Ala Gln Gly Ala Glu Lys
            35                  40                  45

Thr Phe Lys Ala Gly Asp Lys Asp Asn Ser Leu Asn Thr Gly Lys Leu
 50                  55                  60

Lys Asn Asp Lys Ile
 65
```

<210> SEQ ID NO 83
<211> LENGTH: 69
<212> TYPE: PRT
<213> ORGANISM: Artificial Sequence
<220> FEATURE:
<223> OTHER INFORMATION: fHbp sequence variant

<400> SEQUENCE: 83

```
Val Ala Ala Asp Ile Gly Ala Gly Leu Ala Asp Ala Leu Thr Ala Pro
 1               5                  10                  15

Leu Asp His Lys Asp Lys Gly Leu Lys Ser Leu Thr Leu Glu Asp Ser
            20                  25                  30

Ile Ser Gln Asn Gly Thr Leu Thr Leu Ser Ala Gln Gly Ala Glu Arg
            35                  40                  45

Thr Phe Lys Ala Gly Asp Lys Asp Asn Ser Leu Asn Thr Gly Lys Leu
 50                  55                  60

Lys Asn Asp Lys Val
 65
```

<210> SEQ ID NO 84
<211> LENGTH: 69
<212> TYPE: PRT
<213> ORGANISM: Artificial Sequence
<220> FEATURE:
<223> OTHER INFORMATION: fHbp sequence variant

<400> SEQUENCE: 84

```
Val Val Ala Asp Ile Gly Thr Gly Leu Ala Asp Ala Leu Thr Ala Pro
 1               5                  10                  15

Leu Asp His Lys Asp Lys Gly Leu Lys Ser Leu Thr Leu Glu Asp Ser
            20                  25                  30

Ile Pro Gln Asn Gly Thr Leu Thr Leu Ser Ala Gln Gly Ala Glu Lys
            35                  40                  45

Thr Phe Lys Ala Gly Asp Lys Asp Asn Ser Leu Asn Thr Gly Lys Leu
 50                  55                  60

Lys Asn Asp Lys Ile
 65
```

<210> SEQ ID NO 85
<211> LENGTH: 15
<212> TYPE: PRT
<213> ORGANISM: Artificial Sequence
<220> FEATURE:
<223> OTHER INFORMATION: fHbp sequence variant

<400> SEQUENCE: 85

```
Ile Arg Gln Ile Glu Val Asp Gly Gln Leu Ile Thr Leu Glu Ser
 1               5                  10                  15
```

<210> SEQ ID NO 86
<211> LENGTH: 15
<212> TYPE: PRT
<213> ORGANISM: Artificial Sequence
<220> FEATURE:

```
<223> OTHER INFORMATION: fHbp sequence variant

<400> SEQUENCE: 86

Ile Arg Gln Ile Glu Val Asp Gly Lys Leu Ile Thr Leu Glu Ser
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: fHbp sequence variant

<400> SEQUENCE: 87

Ile Arg Gln Ile Glu Val Asp Gly Gln Thr Ile Thr Leu Ala Ser
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: fHbp sequence variant

<400> SEQUENCE: 88

Ile Arg Gln Ile Glu Val Asp Arg Gln Leu Ile Thr Leu Glu Ser
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: fHbp sequence variant

<400> SEQUENCE: 89

Ile Arg Gln Ile Glu Val Asp Gly Gln Leu Ile Thr Leu Glu Asn
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: fHbp sequence variant

<400> SEQUENCE: 90

Ile His Gln Ile Glu Val Asp Gly Gln Leu Ile Thr Leu Glu Ser
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: fHbp sequence variant

<400> SEQUENCE: 91

Ile Arg Gln Ile Glu Val Asn Gly Gln Leu Ile Thr Leu Glu Ser
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: fHbp sequence variant
```

```
<400> SEQUENCE: 92

Ile Arg Gln Ile Arg Ser Asp Gly Gln Leu Ile Thr Leu Glu Ser
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: fHbp sequence variant

<400> SEQUENCE: 93

Ile Arg Gln Ile Glu Val Asp Gly Gln Leu Ile Thr Leu Glu Arg
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: fHbp sequence variant

<400> SEQUENCE: 94

Ile Arg Gln Ile Glu Val Asp Gly Arg Leu Ile Thr Leu Glu Ser
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: fHbp sequence variant

<400> SEQUENCE: 95

Val Gln Lys Ile Glu Val Asp Gly Gln Thr Ile Thr Leu Ala Ser
1               5                   10                  15

<210> SEQ ID NO 96
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 96

Val Tyr Lys Gln Ser His Ser Ala Leu Thr Ala Leu Gln Thr Glu Gln
1               5                   10                  15

Val Gln Asp Ser Glu Asp Ser Gly Lys Met Val Ala Lys Arg Gln Phe
            20                  25                  30

Arg Ile Gly Asp Ile Ala Gly Glu His Thr Ser Phe Asp Lys Leu Pro
        35                  40                  45

Lys Gly Gly Ser Ala Thr Tyr Arg Gly Thr Ala Phe Gly Ser
    50                  55                  60

<210> SEQ ID NO 97
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 97

Val Tyr Lys Gln Ser His Ser Ala Leu Thr Ala Leu Gln Thr Glu Gln
1               5                   10                  15
```

```
Val Gln Asp Ser Glu His Ser Gly Lys Met Val Ala Lys Arg Gln Phe
            20                  25                  30

Arg Ile Gly Asp Ile Ala Gly Glu His Thr Ser Phe Asp Lys Leu Pro
        35                  40                  45

Glu Gly Gly Arg Ala Thr Tyr Arg Gly Thr Ala Phe Gly Ser
    50                  55                  60

<210> SEQ ID NO 98
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 98

Val Tyr Lys Gln Ser His Ser Ala Leu Thr Ala Leu Gln Thr Glu Gln
1               5                   10                  15

Glu Gln Asp Pro Glu His Ser Gly Lys Met Val Ala Lys Arg Arg Phe
            20                  25                  30

Lys Ile Gly Asp Ile Ala Gly Glu His Thr Ser Phe Asp Lys Leu Pro
        35                  40                  45

Lys Asp Val Met Ala Thr Tyr Arg Gly Thr Ala Phe Gly Ser
    50                  55                  60

<210> SEQ ID NO 99
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 99

Val Tyr Lys Gln Ser His Ser Ala Leu Thr Ala Leu Gln Thr Glu Gln
1               5                   10                  15

Val Gln Asp Ser Glu His Ser Gly Lys Met Val Ala Lys Arg Gln Phe
            20                  25                  30

Arg Ile Gly Asp Ile Val Gly Glu His Thr Ser Phe Gly Lys Leu Pro
        35                  40                  45

Lys Asp Val Met Ala Thr Tyr Arg Gly Thr Ala Phe Gly Ser
    50                  55                  60

<210> SEQ ID NO 100
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 100

Val Tyr Lys Gln Ser His Ser Ala Leu Thr Ala Phe Gln Thr Glu Gln
1               5                   10                  15

Ile Gln Asp Ser Glu His Ser Gly Lys Met Val Ala Lys Arg Gln Phe
            20                  25                  30

Arg Ile Gly Asp Ile Ala Gly Glu His Thr Ser Phe Asp Lys Leu Pro
        35                  40                  45

Glu Gly Gly Arg Ala Thr Tyr Arg Gly Thr Ala Phe Gly Ser
    50                  55                  60

<210> SEQ ID NO 101
<211> LENGTH: 62
```

```
<212> TYPE: PRT
<213> ORGANISM: Artificial Sequence
<220> FEATURE:
<223> OTHER INFORMATION: fHbp sequence variant

<400> SEQUENCE: 101

Val Tyr Lys Gln Ser His Ser Ala Leu Thr Ala Leu Gln Thr Glu Gln
1               5                   10                  15

Val Gln Asp Ser Glu Asp Ser Gly Lys Met Val Ala Lys Arg Gln Phe
            20                  25                  30

Arg Ile Gly Asp Ile Ala Gly Glu His Thr Ser Phe Asp Lys Leu Pro
        35                  40                  45

Lys Asp Val Met Ala Thr Tyr Arg Gly Thr Ala Phe Gly Ser
    50                  55                  60

<210> SEQ ID NO 102
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 102

Val Tyr Lys Gln Ser His Ser Ala Leu Thr Ala Leu Gln Thr Glu Gln
1               5                   10                  15

Val Gln Asp Ser Glu His Ser Gly Ser Met Val Ala Lys Arg Gln Phe
            20                  25                  30

Arg Ile Gly Asp Ile Ala Gly Glu His Thr Ser Phe Asp Lys Leu Pro
        35                  40                  45

Glu Gly Gly Arg Ala Thr Tyr Arg Gly Thr Ala Phe Gly Ser
    50                  55                  60

<210> SEQ ID NO 103
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 103

Val Tyr Lys Gln Ser His Ser Ala Leu Thr Ala Leu Gln Thr Glu Gln
1               5                   10                  15

Glu Gln Asp Pro Glu His Ser Glu Lys Met Val Ala Lys Arg Arg Phe
            20                  25                  30

Arg Ile Gly Asp Ile Ala Gly Glu His Thr Ser Phe Asp Lys Leu Pro
        35                  40                  45

Lys Asp Val Met Ala Thr Tyr Arg Gly Thr Ala Phe Gly Ser
    50                  55                  60

<210> SEQ ID NO 104
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 104

Val Tyr Lys Gln Ser Tyr Ser Ala Leu Thr Ala Leu Gln Thr Glu Gln
1               5                   10                  15

Glu Gln Asp Ser Glu His Ser Gly Lys Met Val Ala Lys Arg Arg Phe
            20                  25                  30
```

-continued

```
Arg Ile Gly Asp Ile Ala Gly Glu His Thr Ser Phe Asp Lys Leu Pro
            35                  40                  45

Lys Gly Ser Ser Ala Thr Tyr Arg Gly Thr Ala Phe Gly Ser
    50                  55                  60

<210> SEQ ID NO 105
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 105

Val Tyr Lys Gln Ser His Ser Ala Leu Thr Ala Leu Gln Thr Glu Gln
1               5                   10                  15

Glu Gln Asp Leu Glu His Ser Gly Lys Met Val Ala Lys Arg Arg Phe
            20                  25                  30

Arg Ile Gly Asp Ile Ala Gly Glu His Thr Ser Phe Asp Lys Leu Arg
            35                  40                  45

Glu Gly Gly Arg Ala Thr Tyr Arg Gly Thr Ala Phe Gly Ser
    50                  55                  60

<210> SEQ ID NO 106
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 106

Val Tyr Lys Gln Ser His Ser Ala Leu Thr Ala Leu Gln Thr Glu Gln
1               5                   10                  15

Val Gln Asp Ser Glu His Ser Gly Lys Met Val Ala Lys Arg Gln Phe
            20                  25                  30

Arg Ile Gly Asp Ile Val Gly Glu His Thr Ser Phe Asp Lys Leu Pro
            35                  40                  45

Lys Asp Val Met Ala Thr Tyr Arg Gly Thr Ala Phe Gly Ser
    50                  55                  60

<210> SEQ ID NO 107
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 107

Val Tyr Lys Gln Ser His Ser Ala Leu Thr Ala Phe Gln Thr Glu Gln
1               5                   10                  15

Ile Gln Asp Ser Glu Asp Ser Gly Lys Met Val Ala Lys Arg Arg Phe
            20                  25                  30

Arg Ile Gly Asp Ile Ala Gly Glu His Thr Ser Phe Asp Lys Leu Pro
            35                  40                  45

Lys Gly Gly Ser Ala Thr Tyr Arg Gly Thr Ala Phe Gly Ser
    50                  55                  60

<210> SEQ ID NO 108
<211> LENGTH: 62
<212> TYPE: PRT
<213> ORGANISM: Artificial Sequence
<220> FEATURE:
<223> OTHER INFORMATION: fHbp sequence variant
```

<400> SEQUENCE: 108

Val Tyr Lys Gln Ser His Ser Ala Leu Thr Ala Leu Gln Thr Glu Gln
1               5                   10                  15

Val Gln Asp Ser Glu His Ser Gly Lys Met Val Ala Lys Arg Arg Phe
            20                  25                  30

Arg Ile Gly Asp Ile Ala Gly Glu His Thr Ser Phe Asp Lys Leu Pro
        35                  40                  45

Glu Ser Asp Arg Ala Thr Tyr Arg Gly Thr Ala Phe Ser Ser
    50                  55                  60

<210> SEQ ID NO 109
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 109

Val Tyr Lys Gln Ser His Ser Ala Leu Thr Ala Leu Gln Thr Glu Gln
1               5                   10                  15

Val Gln Asp Ser Glu His Ser Arg Lys Met Val Ala Lys Arg Gln Phe
            20                  25                  30

Arg Ile Gly Asp Ile Ala Gly Glu His Thr Ser Phe Asp Lys Leu Pro
        35                  40                  45

Lys Gly Asp Ser Ala Thr Tyr Arg Gly Thr Ala Phe Gly Ser
    50                  55                  60

<210> SEQ ID NO 110
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 110

Val Tyr Lys Gln Ser His Ser Ala Leu Thr Ala Leu Gln Thr Glu Gln
1               5                   10                  15

Val Gln Asp Ser Glu Asp Ser Gly Lys Met Val Ala Lys Arg Gln Phe
            20                  25                  30

Arg Ile Gly Asp Ile Ala Gly Glu His Thr Ser Phe Asp Lys Leu Pro
        35                  40                  45

Lys Gly Gly Ser Ala Thr Tyr Arg Gly Thr Ala Leu Gly Ser
    50                  55                  60

<210> SEQ ID NO 111
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 111

Val Tyr Lys Gln Ser His Ser Ala Leu Thr Ala Leu Gln Thr Glu Gln
1               5                   10                  15

Val Gln Asp Ser Glu Asp Ser Gly Lys Met Val Ala Lys Arg Gln Phe
            20                  25                  30

Arg Ile Gly Asp Ile Ala Gly Glu His Thr Ser Phe Asp Lys Leu Pro
        35                  40                  45

Lys Gly Gly Ser Ala Thr Tyr Arg Gly Thr Ala Phe Ser Ser

```
                50              55              60

<210> SEQ ID NO 112
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 112

Val Tyr Lys Gln Ser His Ser Ala Leu Thr Ala Leu Gln Thr Glu Gln
  1               5                  10                  15

Val Gln Asp Ser Glu His Ser Gly Lys Met Val Ala Lys Arg Gln Phe
                 20                  25                  30

Arg Ile Gly Asp Ile Ala Gly Glu His Thr Ser Phe Asp Lys Leu Pro
             35                  40                  45

Lys Gly Gly Ser Ala Thr Tyr Arg Gly Thr Ala Phe Gly Ser
         50                  55                  60

<210> SEQ ID NO 113
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 113

Val Tyr Lys Gln Ser His Ser Ala Leu Thr Ala Leu Gln Thr Glu Gln
  1               5                  10                  15

Val Gln Asp Ser Glu His Ser Arg Lys Met Val Ala Lys Arg Gln Phe
                 20                  25                  30

Arg Ile Gly Asp Ile Ala Gly Glu His Thr Ser Phe Asp Lys Leu Pro
             35                  40                  45

Glu Gly Gly Arg Ala Thr Tyr Arg Gly Thr Ala Leu Gly Ser
         50                  55                  60

<210> SEQ ID NO 114
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 114

Val Tyr Lys Gln Ser His Ser Ala Leu Thr Ala Leu Gln Thr Glu Gln
  1               5                  10                  15

Val Gln Asp Ser Glu His Ser Gly Lys Met Val Ala Lys Arg Gln Phe
                 20                  25                  30

Arg Ile Gly Asp Ile Ala Gly Glu His Thr Ser Phe Asp Lys Leu Pro
             35                  40                  45

Glu Gly Gly Arg Ala Thr Tyr Arg Gly Thr Ala Phe Ser Ser
         50                  55                  60

<210> SEQ ID NO 115
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 115

Val Tyr Lys Gln Ser His Ser Ala Leu Thr Ala Phe Gln Thr Glu Gln
  1               5                  10                  15
```

-continued

```
               1               5                  10                 15
Ile Gln Asp Ser Glu His Ser Gly Lys Met Val Ala Lys Arg Arg Phe
               20                 25                 30

Arg Ile Gly Asp Ile Ala Gly Glu His Thr Ser Phe Asp Lys Leu Pro
       35                 40                 45

Glu Gly Gly Arg Ala Thr Tyr Arg Gly Thr Ala Phe Ser Ser
       50                 55                 60

<210> SEQ ID NO 116
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 116

Val Tyr Lys Gln Ser Tyr Ser Ala Leu Thr Ala Leu Gln Thr Glu Gln
1               5                  10                 15

Ile Gln Asp Ser Glu His Ser Gly Lys Met Val Ala Lys Arg Arg Phe
               20                 25                 30

Arg Ile Gly Asp Ile Ala Gly Glu His Thr Phe Phe Asp Lys Leu Pro
       35                 40                 45

Lys Gly Gly Ser Ala Ile Tyr Arg Gly Thr Ala Phe Gly Ser
       50                 55                 60

<210> SEQ ID NO 117
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 117

Val Tyr Lys Gln Ser His Ser Ala Leu Thr Ala Phe Gln Thr Glu Gln
1               5                  10                 15

Ile Gln Asp Ser Glu His Ser Gly Lys Met Val Ala Lys Arg Gln Phe
               20                 25                 30

Arg Ile Gly Asp Ile Ala Gly Glu His Thr Ser Phe Asp Lys Leu Pro
       35                 40                 45

Glu Gly Gly Arg Ala Thr Tyr Arg Gly Thr Ala Phe Ser Ser
       50                 55                 60

<210> SEQ ID NO 118
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 118

Val Tyr Lys Gln Ser His Ser Ala Leu Thr Ala Phe Gln Thr Glu Gln
1               5                  10                 15

Ile Gln Asp Ser Glu His Ser Gly Lys Met Val Ala Lys Arg Arg Phe
               20                 25                 30

Arg Ile Gly Asp Ile Ala Gly Glu His Thr Ser Phe Asp Lys Leu Pro
       35                 40                 45

Glu Gly Gly Arg Ala Thr Tyr Arg Gly Thr Ala Phe Gly Ser
       50                 55                 60

<210> SEQ ID NO 119
```

```
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 119

Val Tyr Lys Gln Ser His Ser Ala Leu Thr Ala Leu Gln Thr Glu Gln
1               5                   10                  15

Ile Gln Asp Ser Glu His Ser Gly Lys Met Val Ala Lys Arg Gln Phe
            20                  25                  30

Arg Ile Gly Asp Ile Ala Gly Glu His Thr Ser Phe Asp Lys Leu Pro
        35                  40                  45

Glu Gly Gly Arg Ala Thr Tyr Arg Gly Thr Ala Phe Gly Ser
    50                  55                  60

<210> SEQ ID NO 120
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 120

Val Tyr Lys Gln Ser His Ser Ala Leu Thr Ala Leu Gln Thr Glu Gln
1               5                   10                  15

Val Gln Asp Ser Glu His Ser Gly Lys Met Val Ala Lys Arg Gln Phe
            20                  25                  30

Arg Ile Gly Asp Ile Ala Gly Glu His Thr Ser Phe Asp Lys Leu Pro
        35                  40                  45

Lys Gly Gly Arg Ala Thr Tyr Arg Gly Thr Ala Phe Gly Ser
    50                  55                  60

<210> SEQ ID NO 121
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 121

Val Tyr Lys Gln Ser His Ser Ala Leu Thr Ala Leu Gln Thr Glu Gln
1               5                   10                  15

Val Gln Asp Ser Glu His Ser Gly Lys Met Val Ala Lys Arg Gln Phe
            20                  25                  30

Arg Ile Gly Asp Ile Ala Gly Glu His Ile Ser Phe Asp Lys Leu Pro
        35                  40                  45

Glu Gly Gly Arg Ala Thr Tyr Arg Gly Thr Ala Phe Gly Ser
    50                  55                  60

<210> SEQ ID NO 122
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 122

Val Tyr Lys Gln Ser His Ser Ala Leu Thr Ala Leu Gln Thr Glu Gln
1               5                   10                  15

Val Gln Asp Ser Glu Asp Ser Gly Lys Met Val Ala Lys Arg Gln Phe
            20                  25                  30
```

```
Arg Ile Gly Asp Ile Ala Gly Glu His Thr Ser Phe Asp Lys Leu Pro
        35                  40                  45

Glu Gly Gly Arg Ala Thr Tyr Arg Gly Thr Ala Phe Gly Ser
    50                  55                  60

<210> SEQ ID NO 123
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 123

Val Tyr Lys Gln Ser His Ser Ala Leu Thr Ala Phe Gln Thr Glu Gln
1               5                   10                  15

Ile Gln Asp Ser Glu His Ser Gly Lys Met Val Ala Lys Arg Gln Phe
            20                  25                  30

Arg Ile Gly Asp Ile Ala Gly Glu His Thr Ser Phe Asp Lys Leu Pro
        35                  40                  45

Lys Gly Gly Ser Ala Thr Tyr Arg Gly Thr Ala Phe Gly Ser
    50                  55                  60

<210> SEQ ID NO 124
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 124

Val Tyr Lys Gln Ser His Ser Ala Leu Thr Ala Leu Gln Thr Glu Gln
1               5                   10                  15

Val Gln Asp Ser Glu Asp Ser Gly Lys Met Val Ala Lys Arg Gln Phe
            20                  25                  30

Arg Ile Gly Asp Ile Ala Gly Glu His Thr Ser Phe Asp Lys Leu Pro
        35                  40                  45

Lys Gly Asp Ser Ala Thr Tyr Arg Gly Thr Ala Phe Ser Ser
    50                  55                  60

<210> SEQ ID NO 125
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 125

Val Tyr Lys Gln Ser His Ser Ala Leu Thr Ala Leu Gln Thr Glu Gln
1               5                   10                  15

Val Gln Asp Ser Glu Asp Ser Gly Lys Met Val Ala Lys Arg Gln Phe
            20                  25                  30

Arg Ile Gly Asp Ile Ala Gly Glu His Thr Ser Phe Asp Lys Leu Pro
        35                  40                  45

Glu Ser Asp Ser Ala Thr Tyr Arg Gly Thr Ala Phe Ser Ser
    50                  55                  60

<210> SEQ ID NO 126
<211> LENGTH: 62
<212> TYPE: PRT
<213> ORGANISM: Artificial Sequence
<220> FEATURE:
```

<223> OTHER INFORMATION: fHbp sequence variant

<400> SEQUENCE: 126

Val Tyr Lys Gln Ser His Ser Ala Leu Thr Ala Leu Gln Thr Glu Gln
1               5                   10                  15

Val Gln Asp Ser Glu Asp Ser Gly Lys Met Val Ala Lys Arg Gln Phe
            20                  25                  30

Arg Ile Gly Asp Ile Ala Gly Glu His Thr Ser Phe Asp Lys Leu Pro
        35                  40                  45

Lys Gly Gly Arg Ala Thr Tyr Arg Gly Thr Ala Phe Gly Ser
    50                  55                  60

<210> SEQ ID NO 127
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 127

Val Tyr Lys Gln Ser His Ser Ala Leu Thr Ala Leu Gln Thr Glu Gln
1               5                   10                  15

Val Gln Asp Ser Glu Asp Ser Gly Lys Met Val Ala Lys Arg Gln Phe
            20                  25                  30

Arg Ile Gly Asp Ile Ala Gly Glu His Thr Ser Phe Asp Lys Leu His
        35                  40                  45

Lys Gly Gly Ser Ala Thr Tyr Arg Gly Thr Ala Phe Ser Ser
    50                  55                  60

<210> SEQ ID NO 128
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 128

Val Tyr Lys Gln Ser His Ser Ala Leu

```
Lys Asp Val Met Val Thr Tyr Arg Gly Thr Ala Phe Gly Ser
    50                  55                  60
```

<210> SEQ ID NO 130
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 130

```
Val Tyr Lys Gln Ser His Ser Ala Leu Thr Ala Leu Gln Thr Glu Gln
1               5                   10                  15

Val Gln Asp Ser Glu His Ser Ala Lys Met Val Ala Lys Arg Gln Phe
            20                  25                  30

Arg Ile Gly Asp Ile Ala Gly Glu His Thr Ser Phe Asp Lys Leu Pro
        35                  40                  45

Glu Gly Gly Arg Ala Thr Tyr Arg Gly Thr Ala Phe Gly Ser
    50                  55                  60
```

<210> SEQ ID NO 131
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 131

```
Val Tyr Lys Gln Ser His Ser Ala Leu Thr Ala Leu Gln Thr Glu Gln
1               5                   10                  15

Glu Gln Asp Pro Glu His Ser Glu Lys Met Val Ala Lys Arg Arg Phe
            20                  25                  30

Lys Ile Gly Asp Ile Ala Gly Glu His Thr Ser Phe Asp Lys Leu Pro
        35                  40                  45

Lys Asp Val Met Ala Thr Tyr Arg Gly Thr Ala Phe Gly Ser
    50                  55                  60
```

<210> SEQ ID NO 132
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 132

```
Val Tyr Lys Gln Ser His Ser Ala Leu Thr Ala Leu Gln Thr Glu Gln
1               5                   10                  15

Val Gln Asp Ser Glu His Ser Glu Lys Met Val Ala Lys Arg Arg Phe
            20                  25                  30

Lys Ile Gly Asp Ile Ala Gly Glu His Thr Ser Phe Asp Lys Leu Pro
        35                  40                  45

Lys Asp Val Met Ala Thr Tyr Arg Gly Thr Ala Phe Gly Ser
    50                  55                  60
```

<210> SEQ ID NO 133
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 133

```
Val Tyr Lys Gln Ser Tyr Ser Ala Leu Thr Ala Leu Gln Thr Glu Gln
1               5                   10                  15

Val Gln Asp Ser Glu Asp Ser Gly Lys Met Val Ala Arg Gln Phe
            20                  25                  30

Arg Ile Gly Asp Ile Ala Gly Glu His Thr Ser Phe Asp Lys Leu Pro
            35                  40                  45

Lys Gly Gly Ser Ala Thr Tyr Arg Gly Thr Ala Phe Gly Ser
        50                  55                  60
```

<210> SEQ ID NO 134
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 134

```
Val Tyr Lys Gln Ser Tyr Ser Ala Leu Thr Ala Leu Gln Thr Glu Gln
1               5                   10                  15

Val Gln Asp Ser Glu His Ser Gly Lys Met Val Ala Lys Arg Phe
            20                  25                  30

Arg Ile Gly Asp Ile Ala Gly Glu His Thr Ser Phe Asp Lys Leu Pro
            35                  40                  45

Gly Asp Ser Arg Ala Thr Tyr Arg Gly Thr Ala Phe Gly Ser
        50                  55                  60
```

<210> SEQ ID NO 135
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 135

```
Val Tyr Lys Gln Ser His Ser Ala Leu Thr Ala Leu Gln Thr Glu Gln
1               5                   10                  15

Val Gln Asp Ser Glu His Ser Gly Lys Met Val Ala Lys Arg Arg Phe
            20                  25                  30

Arg Ile Gly Asp Ile Ala Gly Glu His Thr Ser Phe Asp Lys Leu Pro
            35                  40                  45

Glu Gly Gly Arg Ala Thr Tyr Arg Gly Thr Ala Phe Ser Ser
        50                  55                  60
```

<210> SEQ ID NO 136
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 136

```
Val Tyr Lys Gln Ser His Ser Ala Leu Thr Ala Leu Gln Thr Glu Gln
1               5                   10                  15

Val Gln Asp Ser Glu Asp Ser Gly Lys Met Val Ala Lys Arg Gln Phe
            20                  25                  30

Arg Ile Gly Asp Ile Ala Gly Glu His Thr Ser Phe Asp Lys Leu Pro
            35                  40                  45

Glu Asp Val Arg Ala Thr Tyr Arg Gly Thr Ala Phe Gly Ser
        50                  55                  60
```

-continued

```
<210> SEQ ID NO 137
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 137

Val Tyr Lys Gln Ser His Ser Ala Leu Thr Ala Leu Gln Thr Glu Gln
1               5                   10                  15

Val Gln Asp Ser Glu His Ser Gly Lys Met Val Ala Lys Arg Gln Phe
            20                  25                  30

Arg Ile Gly Asp Ile Ala Gly Glu His Thr Ser Phe Asp Lys Leu Pro
        35                  40                  45

Glu Gly Val Arg Ala Thr Tyr Arg Gly Thr Ala Phe Gly Ser
    50                  55                  60

<210> SEQ ID NO 138
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 138

Val Tyr Lys Gln Ser His Ser Ala Leu Thr Ala Phe Gln Thr Glu Gln
1               5                   10                  15

Glu Gln Asp Ser Glu His Ser Gly Lys Met Val Ala Lys Arg Gln Phe
            20                  25                  30

Arg Ile Gly Asp Ile Ala Gly Glu His Thr Ser Phe Asp Lys Leu Pro
        35                  40                  45

Asp Val Val Arg Ala Thr Tyr Arg Gly Thr Ala Phe Gly Ser
    50                  55                  60

<210> SEQ ID NO 139
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 139

Val Tyr Lys Gln Ser His Ser Ala Leu Thr Ala Leu Gln Thr Glu Gln
1               5                   10                  15

Val Gln Asp Ser Glu His Ser Gly Lys Met Val Ala Lys Arg Gln Phe
            20                  25                  30

Arg Ile Gly Asp Ile Ala Gly Glu His Thr Ser Phe Asp Lys Leu Pro
        35                  40                  45

Glu Ser Gly Arg Ala Thr Tyr Arg Gly Thr Ala Phe Gly Ser
    50                  55                  60

<210> SEQ ID NO 140
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 140

Val Tyr Lys Gln Ser His Ser Ala Leu Thr Ala Leu Gln Thr Glu Gln
1               5                   10                  15

Glu Gln Asp Leu Glu His Ser Gly Lys Met Val Ala Lys Arg Arg Phe
```

```
                    20                  25                  30

Lys Ile Gly Asp Ile Ala Gly Glu His Thr Ser Phe Asp Lys Leu Pro
            35                  40                  45

Lys Asp Val Met Ala Thr Tyr Arg Gly Thr Ala Phe Gly Ser
        50                  55                  60

<210> SEQ ID NO 141
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 141

Val Tyr Lys Gln Ser His Ser Ala Leu Thr Ala Leu Gln Thr Glu Gln
1               5                   10                  15

Val Gln Asp Ser Glu His Ser Glu Lys Met Val Ala Lys Arg Gln Phe
                20                  25                  30

Arg Ile Gly Asp Ile Ala Gly Glu His Thr Ser Phe Asp Lys Leu Pro
            35                  40                  45

Glu Ser Gly Ser Ala Thr Tyr Arg Gly Thr Ala Phe Gly Ser
        50                  55                  60

<210> SEQ ID NO 142
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 142

Val Tyr Lys Gln Ser His Ser Ala Leu Thr Ala Phe Gln Thr Glu Gln
1               5                   10                  15

Val Gln Asp Ser Glu His Ser Gly Lys Met Val Ala Lys Arg Gln Phe
                20                  25                  30

Arg Ile Gly Asp Ile Ala Gly Glu His Thr Ser Phe Asp Lys Leu Pro
            35                  40                  45

Glu Gly Gly Arg Ala Thr Tyr Arg Gly Thr Ala Phe Gly Ser
        50                  55                  60

<210> SEQ ID NO 143
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 143

Val Tyr Lys Gln Ser His Ser Ala Leu Thr Ala Leu Gln Thr Glu Gln
1               5                   10                  15

Val Gln Asp Ser Glu His Ser Gly Lys Met Val Ala Lys Arg Gln Phe
                20                  25                  30

Arg Ile Gly Asp Ile Ala Gly Glu His Thr Ser Phe Asp Lys Leu Pro
            35                  40                  45

Lys Gly Val Arg Ala Thr Tyr Arg Gly Thr Ala Phe Gly Ser
        50                  55                  60

<210> SEQ ID NO 144
<211> LENGTH: 62
<212> TYPE: PRT
<213> ORGANISM: Artificial Sequence
```

```
<220> FEATURE:
<223> OTHER INFORMATION: fHbp sequence variant

<400> SEQUENCE: 144

Val Tyr Lys Gln Ser His Ser Ala Leu Thr Ala Leu Gln Thr Glu Gln
1               5                   10                  15

Glu Gln Asp Leu Glu His Ser Arg Lys Met Val Ala Lys Arg Arg Phe
            20                  25                  30

Lys Ile Gly Asp Ile Ala Gly Glu His Thr Ser Phe Asp Lys Leu Pro
        35                  40                  45

Lys Asp Val Met Ala Thr Tyr Arg Gly Thr Ala Phe Gly Ser
    50                  55                  60

<210> SEQ ID NO 145
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 145

Val Tyr Lys Gln Ser His Ser Ala Leu Thr Ala Leu Gln Thr Glu Gln
1               5                   10                  15

Glu Gln Asp Leu Glu His Ser Arg Lys Met Val Ala Lys Arg Arg Phe
            20                  25                  30

Lys Ile Gly Asp Ile Ala Gly Glu His Thr Ser Phe Asp Lys Leu Pro
        35                  40                  45

Lys Asp Val Met Ala Thr Tyr Arg Gly Thr Ala Phe Gly Ser
    50                  55                  60

<210> SEQ ID NO 146
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 146

Val Tyr Lys Gln Ser His Ser Ala Leu Thr Ala Leu Gln Thr Glu Gln
1               5                   10                  15

Glu Gln Asp Pro Glu His Ser Gly Lys Met Val Ala Lys Arg Arg Phe
            20                  25                  30

Lys Ile Gly Asp Ile Ala Gly Glu His Thr Ser Phe Asp Lys Leu Pro
        35                  40                  45

Lys Asp Ile Met Ala Thr Tyr Arg Gly Thr Ala Phe Gly Ser
    50                  55                  60

<210> SEQ ID NO 147
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 147

Val Tyr Lys Gln Ser His Ser Ala Leu Thr Ala Leu Gln Thr Glu Gln
1               5                   10                  15

Val Gln Asp Ser Glu His Ser Gly Arg Met Val Ala Lys Arg Gln Phe
            20                  25                  30

Arg Ile Gly Asp Ile Ala Gly Glu His Thr Ser Phe Asp Lys Leu Pro
        35                  40                  45
```

```
Glu Gly Gly Arg Ala Thr Tyr Arg Gly Thr Ala Phe Gly Ser
     50                  55                  60
```

<210> SEQ ID NO 148
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 148

```
Val Tyr Lys Gln Ser His Ser Ala Leu Thr Ala Leu Gln Thr Glu Gln
1               5                   10                  15

Val Gln Asp Ser Glu His Phe Gly Lys Met Val Ala Lys Arg Gln Phe
            20                  25                  30

Arg Ile Gly Asp Ile Ala Gly Glu His Thr Ser Phe Asp Lys Leu Pro
        35                  40                  45

Glu Gly Gly Arg Ala Thr Tyr Arg Gly Thr Ala Phe Gly Ser
     50                  55                  60
```

<210> SEQ ID NO 149
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 149

```
Val Tyr Lys Gln Ser His Ser Ala Leu Thr Ala Leu Gln Thr Glu Gln
1               5                   10                  15

Val Gln Asp Ser Glu His Ser Gly Lys Met Val Ala Lys Arg Arg Phe
            20                  25                  30

Arg Ile Gly Asp Ile Ala Gly Glu His Thr Ser Phe Asp Lys Leu Pro
        35                  40                  45

Lys Asp Gly Met Ala Thr Tyr Arg Gly Thr Ala Phe Gly Ser
     50                  55                  60
```

<210> SEQ ID NO 150
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 150

```
Ile Tyr Lys Gln Ser His Ser Ala Leu Thr Ala Phe Gln Thr Glu Gln
1               5                   10                  15

Ile Gln Asp Ser Glu His Ser Gly Lys Met Val Ala Lys Arg Gln Phe
            20                  25                  30

Arg Ile Gly Asp Ile Ala Gly Glu His Thr Ser Phe Asp Lys Leu Pro
        35                  40                  45

Glu Gly Gly Arg Ala Thr Tyr Arg Gly Thr Ala Phe Gly Ser
     50                  55                  60
```

<210> SEQ ID NO 151
<211> LENGTH: 62
<212> TYPE: PRT
<213> ORGANISM: Artificial Sequence
<220> FEATURE:
<223> OTHER INFORMATION: fHbp sequence variant

<400> SEQUENCE: 151

-continued

```
Val Tyr Lys Gln Ser His Ser Ala Leu Thr Ala Leu Gln Thr Glu Gln
1               5                   10                  15

Val Gln Asp Ser Glu Asp Ser Gly Lys Met Val Ala Lys Arg Arg Phe
            20                  25                  30

Lys Ile Gly Asp Ile Ala Gly Glu His Thr Ser Phe Asp Lys Leu Pro
        35                  40                  45

Lys Asp Val Met Ala Thr Tyr Arg Gly Thr Ala Phe Gly Ser
    50                  55                  60
```

<210> SEQ ID NO 152
<211> LENGTH: 61
<212> TYPE: PRT
<213> ORGANISM: Artificial Sequence
<220> FEATURE:
<223> OTHER INFORMATION: fHbp sequence variant

<400> SEQUENCE: 152

```
Ile Tyr Lys Gln Asp His Ser Ala Val Val Ala Leu Gln Ile Glu Lys
1               5                   10                  15

Ile Asn Asn Pro Asp Lys Ile Asp Ser Leu Ile Asn Gln Arg Ser Phe
            20                  25                  30

Leu Val Ser Gly Leu Gly Gly Glu His Thr Ala Phe Asn Gln Leu Pro
        35                  40                  45

Gly Gly Lys Ala Glu Tyr His Gly Lys Ala Phe Ser Ser
    50                  55                  60
```

<210> SEQ ID NO 153
<211> LENGTH: 61
<212> TYPE: PRT
<213> ORGANISM: Artificial Sequence
<220> FEATURE:
<223> OTHER INFORMATION: fHbp sequence variant

<400> SEQUENCE: 153

```
Ile Tyr Lys Gln Asp His Ser Ala Val Val Ala Leu Gln Ile Glu Lys
1               5                   10                  15

Ile Asn Asn Pro Asp Lys Ile Asp Ser Leu Ile Asn Gln Arg Ser Phe
            20                  25                  30

Leu Val Ser Gly Leu Gly Gly Glu His Thr Ala Phe Asn Gln Leu Pro
        35                  40                  45

Ser Gly Lys Ala Glu Tyr His Gly Lys Ala Phe Ser Ser
    50                  55                  60
```

<210> SEQ ID NO 154
<211> LENGTH: 61
<212> TYPE: PRT
<213> ORGANISM: Artificial Sequence
<220> FEATURE:
<223> OTHER INFORMATION: fHbp sequence variant

<400> SEQUENCE: 154

```
Ile Tyr Lys Gln Asn His Ser Ala Val Val Ala Leu Gln Ile Glu Lys
1               5                   10                  15

Ile Asn Asn Pro Asp Lys Ile Asp Ser Leu Ile Asn Gln Arg Ser Phe
            20                  25                  30

Leu Val Ser Gly Leu Gly Gly Glu His Thr Ala Phe Asn Gln Leu Pro
        35                  40                  45

Asp Gly Lys Ala Glu Tyr His Gly Lys Ala Phe Ser Ser
    50                  55                  60
```

<210> SEQ ID NO 155
<211> LENGTH: 61
<212> TYPE: PRT
<213> ORGANISM: Artificial Sequence
<220> FEATURE:
<223> OTHER INFORMATION: fHbp sequence variant

<400> SEQUENCE: 155

Ile Tyr Lys Gln Asp His Ser Ala Val Val Ala Leu Gln Ile Glu Lys
1               5                   10                  15

Ile Asn Asn Pro Asp Lys Ile Asp Ser Leu Ile Asn Gln Arg Ser Phe
            20                  25                  30

Leu Val Ser Gly Leu Gly Gly Glu His Thr Ala Phe Asn Gln Leu Pro
        35                  40                  45

Asp Gly Lys Ala Glu Tyr His Gly Lys Ala Phe Ser Ser
    50                  55                  60

<210> SEQ ID NO 156
<211> LENGTH: 61
<212> TYPE: PRT
<213> ORGANISM: Artificial Sequence
<220> FEATURE:
<223> OTHER INFORMATION: fHbp sequence variant

<400> SEQUENCE: 156

Ile Tyr Lys Gln Asn His Ser Ala Val Val Ala Leu Gln Ile Glu Lys
1               5                   10                  15

Ile Asn Asn Pro Asp Lys Ile Asp Ser Leu Ile Asn Gln Arg Ser Phe
            20                  25                  30

Leu Val Ser Gly Leu Gly Gly Glu His Thr Ala Phe Asn Gln Leu Pro
        35                  40                  45

Gly Gly Lys Ala Glu Tyr His Gly Lys Ala Phe Ser Ser
    50                  55                  60

<210> SEQ ID NO 157
<211> LENGTH: 61
<212> TYPE: PRT
<213> ORGANISM: Artificial Sequence
<220> FEATURE:
<223> OTHER INFORMATION: fHbp sequence variant

<400> SEQUENCE: 157

Ile Tyr Lys Gln Asp His Ser Ala Val Val Ala Leu Gln Ile Glu Lys
1               5                   10                  15

Ile Asn Asn Pro Asp Lys Ile Asp Ser Leu Ile Asn Gln Arg Ser Phe
            20                  25                  30

Leu Val Ser Gly Leu Gly Gly Glu His Thr Ala Phe Asn Gln Leu Pro
        35                  40                  45

Ser Gly Lys Ala Glu Tyr His Gly Lys Ala Phe Ser Phe
    50                  55                  60

<210> SEQ ID NO 158
<211> LENGTH: 61
<212> TYPE: PRT
<213> ORGANISM: Artificial Sequence
<220> FEATURE:
<223> OTHER INFORMATION: fHbp sequence variant

<400> SEQUENCE: 158

Ile Tyr Lys Gln Asp His Ser Ala Val Val Ala Leu Gln Ile Glu Lys
1               5                   10                  15

Ile Asn Asn Pro Asp Lys Ile Asp Ser Leu Ile Asn Arg Ser Phe
            20                  25                  30

Leu Val Ser Gly Leu Gly Gly Glu His Thr Ala Phe Asn Gln Leu Pro
        35                  40                  45

Asp Gly Lys Ala Glu Tyr His Gly Lys Ala Phe Ser Ser
    50                  55                  60

<210> SEQ ID NO 159
<211> LENGTH: 61
<212> TYPE: PRT
<213> ORGANISM: Artificial Sequence
<220> FEATURE:
<223> OTHER INFORMATION: fHbp sequence variant

<400> SEQUENCE: 159

Ile Tyr Lys Gln Asn His Ser Ala Val Val Ala Leu Gln Ile Glu Lys
1               5                   10                  15

Ile Asn Asn Pro Asp Lys Ile Asp Ser Leu Ile Asn Gln Arg Ser Phe
            20                  25                  30

Leu Val Ser Gly Leu Gly Gly Glu His Thr Ala Phe Asn Gln Leu Pro
        35                  40                  45

Val Gly Lys Ala Glu Tyr His Gly Lys Ala Phe Ser Ser
    50                  55                  60

<210> SEQ ID NO 160
<211> LENGTH: 61
<212> TYPE: PRT
<213> ORGANISM: Artificial Sequence
<220> FEATURE:
<223> OTHER INFORMATION: fHbp sequence variant

<400> SEQUENCE: 160

Ile Tyr Lys Gln Asn His Ser Ala Val Val Ala Leu Gln Ile Glu Lys
1               5                   10                  15

Ile Asn Asn Pro Asp Lys Thr Asp Ser Leu Ile Asn Gln Arg Ser Phe
            20                  25                  30

Leu Val Ser Gly Leu Gly Gly Glu His Thr Ala Phe Asn Gln Leu Pro
        35                  40                  45

Gly Gly Lys Ala Glu Tyr His Gly Lys Ala Phe Ser Ser
    50                  55                  60

<210> SEQ ID NO 161
<211> LENGTH: 61
<212> TYPE: PRT
<213> ORGANISM: Artificial Sequence
<220> FEATURE:
<223> OTHER INFORMATION: fHbp sequence variant

<400> SEQUENCE: 161

Ile Tyr Lys Gln Asp His Ser Ala Val Val Ala Leu Gln Ile Glu Lys
1               5                   10                  15

Ile Asn Asn Pro Asp Lys Thr Asp Ser Leu Ile Asn Gln Arg Ser Phe
            20                  25                  30

Leu Val Ser Gly Leu Gly Gly Glu His Thr Ala Phe Asn Gln Leu Pro
        35                  40                  45

Gly Gly Lys Ala Glu Tyr His Gly Lys Ala Phe Ser Ser
    50                  55                  60

<210> SEQ ID NO 162
<211> LENGTH: 61
<212> TYPE: PRT

```
<213> ORGANISM: Artificial Sequence
<220> FEATURE:
<223> OTHER INFORMATION: fHbp sequence variant

<400> SEQUENCE: 162

Ile Tyr Lys Gln Asn His Ser Ala Val Ala Leu Gln Ile Glu Lys
1               5                   10                  15

Ile Asn Asn Pro Asp Lys Ile Asp Ser Leu Ile Asn Gln Arg Ser Phe
            20                  25                  30

Leu Val Ser Gly Leu Gly Gly Glu His Thr Ala Phe Asn Gln Leu Pro
        35                  40                  45

Gly Asp Lys Ala Glu Tyr His Gly Lys Ala Phe Ser Ser
    50                  55                  60

<210> SEQ ID NO 163
<211> LENGTH: 61
<212> TYPE: PRT
<213> ORGANISM: Artificial Sequence
<220> FEATURE:
<223> OTHER INFORMATION: fHbp sequence variant

<400> SEQUENCE: 163

Ile Tyr Lys Gln Asp His Ser Ala Val Ala Leu Gln Ile Glu Lys
1               5                   10                  15

Ile Asn Asn Pro Asp Lys Ile Asp Ser Leu Ile Asn Gln Arg Ser Phe
            20                  25                  30

Leu Val Ser Gly Leu Gly Gly Glu His Thr Ala Phe Asn Gln Leu Pro
        35                  40                  45

Val Asp Lys Ala Glu Tyr His Gly Lys Ala Phe Ser Ser
    50                  55                  60

<210> SEQ ID NO 164
<211> LENGTH: 61
<212> TYPE: PRT
<213> ORGANISM: Artificial Sequence
<220> FEATURE:
<223> OTHER INFORMATION: fHbp sequence variant

<400> SEQUENCE: 164

Ile Tyr Lys Gln Gly His Ser Ala Val Ala Leu Gln Ile Glu Lys
1               5                   10                  15

Ile Asn Asn Pro Asp Lys Ile Asp Ser Leu Ile Asn Gln Arg Ser Phe
            20                  25                  30

Leu Val Ser Gly Leu Gly Gly Glu His Thr Ala Phe Asn Gln Leu Pro
        35                  40                  45

Ser Gly Lys Ala Glu Tyr His Gly Lys Ala Phe Ser Ser
    50                  55                  60

<210> SEQ ID NO 165
<211> LENGTH: 61
<212> TYPE: PRT
<213> ORGANISM: Artificial Sequence
<220> FEATURE:
<223> OTHER INFORMATION: fHbp sequence variant

<400> SEQUENCE: 165

Ile Tyr Lys Gln Asp His Ser Ala Val Ala Leu Gln Ile Glu Lys
1               5                   10                  15

Ile Asn Asn Pro Asp Lys Ile Asp Ser Leu Ile Asn Gln Arg Ser Phe
            20                  25                  30

Leu Val Ser Gly Leu Gly Gly Glu His Thr Ala Phe Asn Gln Leu Pro
```

```
                    35                  40                  45

Ser Gly Lys Ala Glu Tyr His Gly Lys Ala Leu Ser Ser
     50                  55                  60

<210> SEQ ID NO 166
<211> LENGTH: 61
<212> TYPE: PRT
<213> ORGANISM: Artificial Sequence
<220> FEATURE:
<223> OTHER INFORMATION: fHbp sequence variant

<400> SEQUENCE: 166

Ile Tyr Lys Gln Asp His Ser Ala Val Val Ala Leu Gln Ile Glu Lys
1               5                   10                  15

Ile Asn Asn Pro Asp Lys Ile Asp Ser Leu Ile Asn Gln Arg Ser Phe
            20                  25                  30

Leu Val Ser Gly Leu Gly Gly Glu His Thr Ala Phe Asn Gln Leu Pro
        35                  40                  45

Gly Asp Lys Ala Glu Tyr His Gly Lys Ala Phe Ser Ser
     50                  55                  60

<210> SEQ ID NO 167
<211> LENGTH: 61
<212> TYPE: PRT
<213> ORGANISM: Artificial Sequence
<220> FEATURE:
<223> OTHER INFORMATION: fHbp sequence variant

<400> SEQUENCE: 167

Ile Tyr Lys Gln Asp His Ser Ala Val Val Ala Leu Gln Thr Glu Lys
1               5                   10                  15

Val Asn Asn Pro Asp Lys Thr Asp Ser Leu Ile Asn Gln Arg Ser Phe
            20                  25                  30

Leu Val Ser Gly Leu Gly Gly Glu His Thr Ala Phe Asn Gln Leu Pro
        35                  40                  45

Val Gly Lys Ser Glu Tyr His Gly Lys Ala Phe Ser Ser
     50                  55                  60

<210> SEQ ID NO 168
<211> LENGTH: 61
<212> TYPE: PRT
<213> ORGANISM: Artificial Sequence
<220> FEATURE:
<223> OTHER INFORMATION: fHbp sequence variant

<400> SEQUENCE: 168

Ile Tyr Lys Gln Asn His Ser Ala Val Val Ala Leu Gln Ile Glu Lys
1               5                   10                  15

Ile Asn Asn Pro Asp Lys Ile Asp Ser Leu Ile Asn Gln Arg Ser Phe
            20                  25                  30

Leu Val Ser Gly Leu Gly Gly Glu His Thr Ala Phe Asn Gln Leu Pro
        35                  40                  45

Ser Gly Lys Ala Glu Tyr His Gly Lys Ala Phe Ser Ser
     50                  55                  60

<210> SEQ ID NO 169
<211> LENGTH: 61
<212> TYPE: PRT
<213> ORGANISM: Artificial Sequence
<220> FEATURE:
<223> OTHER INFORMATION: fHbp sequence variant
```

<400> SEQUENCE: 169

Ile Tyr Lys Gln Asn His Ser Ala Val Ala Leu Gln Ile Glu Lys
1               5                   10                  15

Ile Asn Asn Pro Asp Lys Ile Asp Ser Leu Ile Asn Gln Arg Ser Phe
            20                  25                  30

Leu Val Ser Ser Leu Gly Gly Glu His Thr Ala Phe Asn Gln Leu Pro
        35                  40                  45

Gly Gly Lys Ala Glu Tyr His Gly Lys Ala Phe Ser Ser
    50                  55                  60

<210> SEQ ID NO 170
<211> LENGTH: 61
<212> TYPE: PRT
<213> ORGANISM: Artificial Sequence
<220> FEATURE:
<223> OTHER INFORMATION: fHbp sequence variant

<400> SEQUENCE: 170

Val Tyr Lys Gln Asp His Ser Ala Val Ala Leu Gln Ile Glu Lys
1               5                   10                  15

Ile Asn Asn Pro Asp Lys Ile Asp Ser Leu Ile Asn Gln Arg Ser Phe
            20                  25                  30

Leu Val Ser Gly Leu Gly Gly Glu His Thr Ala Phe Asn Gln Leu Pro
        35                  40                  45

Gly Gly Lys Ala Glu Tyr His Gly Lys Ala Phe Ser Ser
    50                  55                  60

<210> SEQ ID NO 171
<211> LENGTH: 61
<212> TYPE: PRT
<213> ORGANISM: Artificial Sequence
<220> FEATURE:
<223> OTHER INFORMATION: fHbp sequence variant

<400> SEQUENCE: 171

Ile Tyr Lys Gln Asp His Ser Ala Val Ala Leu Gln Thr Glu Lys
1               5                   10                  15

Val Asn Asn Pro Asp Lys Thr Asp Ser Leu Ile Asn Gln Arg Ser Phe
            20                  25                  30

Leu Val Ser Gly Leu Gly Gly Glu His Thr Ala Phe Asn Gln Leu Pro
        35                  40                  45

Gly Gly Lys Ala Glu Tyr His Gly Lys Ala Phe Ser Ser
    50                  55                  60

<210> SEQ ID NO 172
<211> LENGTH: 61
<212> TYPE: PRT
<213> ORGANISM: Artificial Sequence
<220> FEATURE:
<223> OTHER INFORMATION: fHbp sequence variant

<400> SEQUENCE: 172

Ile Tyr Lys Gln Asp His Ser Ala Val Ala Leu Gln Ile Glu Lys
1               5                   10                  15

Ile Asn Asn Pro Asp Lys Ile Asp Ser Leu Ile Asn Gln Arg Ser Phe
            20                  25                  30

Leu Val Ser Gly Leu Gly Gly Glu His Thr Ala Phe Asn Gln Leu Ser
        35                  40                  45

Gly Gly Lys Ala Glu Tyr His Gly Lys Ala Phe Ser Ser
    50                  55                  60

```
<210> SEQ ID NO 173
<211> LENGTH: 61
<212> TYPE: PRT
<213> ORGANISM: Artificial Sequence
<220> FEATURE:
<223> OTHER INFORMATION: fHbp sequence variant

<400> SEQUENCE: 173

Ile Tyr Lys Gln Asp His Ser Ala Val Val Ala Leu Gln Ile Glu Lys
1               5                   10                  15

Ile Asn Asn Pro Asp Lys Ile Asp Ser Leu Ile Asn Gln Arg Ser Phe
            20                  25                  30

Leu Val Ser Gly Leu Gly Gly Lys His Thr Ala Phe Asn Gln Leu Pro
        35                  40                  45

Gly Gly Lys Ala Glu Tyr His Gly Lys Ala Phe Ser Ser
    50                  55                  60

<210> SEQ ID NO 174
<211> LENGTH: 19
<212> TYPE: PRT
<213> ORGANISM: Artificial Sequence
<220> FEATURE:
<223> OTHER INFORMATION: fHbp sequence variant

<400> SEQUENCE: 174

Ala Gly Gly Lys Leu Thr Tyr Thr Ile Asp Phe Ala Ala Lys Gln Gly
1               5                   10                  15

His Gly Lys

<210> SEQ ID NO 175
<211> LENGTH: 19
<212> TYPE: PRT
<213> ORGANISM: Artificial Sequence
<220> FEATURE:
<223> OTHER INFORMATION: fHbp sequence variant

<400> SEQUENCE: 175

Ala Gly Gly Lys Leu Ile Tyr Thr Ile Asp Phe Ala Ala Lys Gln Gly
1               5                   10                  15

His Gly Lys

<210> SEQ ID NO 176
<211> LENGTH: 19
<212> TYPE: PRT
<213> ORGANISM: Artificial Sequence
<220> FEATURE:
<223> OTHER INFORMATION: fHbp sequence variant

<400> SEQUENCE: 176

Ala Ser Gly Lys Leu Thr Tyr Thr Ile Asp Phe Ala Ala Lys Gln Gly
1               5                   10                  15

His Gly Lys

<210> SEQ ID NO 177
<211> LENGTH: 19
<212> TYPE: PRT
<213> ORGANISM: Artificial Sequence
<220> FEATURE:
<223> OTHER INFORMATION: fHbp sequence variant

<400> SEQUENCE: 177

Ala Gly Gly Lys Leu Thr Tyr Thr Ile Asp Phe Ala Ala Lys Gln Gly
```

-continued

```
1               5                   10                  15

Tyr Gly Lys

<210> SEQ ID NO 178
<211> LENGTH: 19
<212> TYPE: PRT
<213> ORGANISM: Artificial Sequence
<220> FEATURE:
<223> OTHER INFORMATION: fHbp sequence variant

<400> SEQUENCE: 178

Ala Gly Gly Lys Leu Thr Tyr Thr Ile Asp Phe Ala Ala Lys Gln Gly
1               5                   10                  15

Asn Gly Lys

<210> SEQ ID NO 179
<211> LENGTH: 19
<212> TYPE: PRT
<213> ORGANISM: Artificial Sequence
<220> FEATURE:
<223> OTHER INFORMATION: fHbp sequence variant

<400> SEQUENCE: 179

Ala Gly Gly Lys Leu Thr Tyr Thr Ile Asp Phe Ala Val Lys Gln Gly
1               5                   10                  15

His Gly Lys

<210> SEQ ID NO 180
<211> LENGTH: 19
<212> TYPE: PRT
<213> ORGANISM: Artificial Sequence
<220> FEATURE:
<223> OTHER INFORMATION: fHbp sequence variant

<400> SEQUENCE: 180

Ala Gly Gly Lys Leu Thr Tyr Thr Ile Asp Phe Ala Thr Lys Gln Gly
1               5                   10                  15

His Gly Lys

<210> SEQ ID NO 181
<211> LENGTH: 19
<212> TYPE: PRT
<213> ORGANISM: Artificial Sequence
<220> FEATURE:
<223> OTHER INFORMATION: fHbp sequence variant

<400> SEQUENCE: 181

Ala Gly Gly Lys Leu Thr Tyr Thr Ile Asp Phe Ala Ser Lys Gln Gly
1               5                   10                  15

His Gly Lys

<210> SEQ ID NO 182
<211> LENGTH: 19
<212> TYPE: PRT
<213> ORGANISM: Artificial Sequence
<220> FEATURE:
<223> OTHER INFORMATION: fHbp sequence variant

<400> SEQUENCE: 182

Ala Gly Gly Lys Leu Ile Tyr Thr Ile Asp Phe Ala Ala Lys Gln Gly
1               5                   10                  15

Tyr Gly Lys
```

<210> SEQ ID NO 183
<211> LENGTH: 19
<212> TYPE: PRT
<213> ORGANISM: Artificial Sequence
<220> FEATURE:
<223> OTHER INFORMATION: fHbp sequence variant

<400> SEQUENCE: 183

Ala Arg Gly Lys Leu Thr Tyr Thr Ile Asp Phe Ala Ala Lys Gln Gly
1               5                   10                  15

His Gly Lys

<210> SEQ ID NO 184
<211> LENGTH: 19
<212> TYPE: PRT
<213> ORGANISM: Artificial Sequence
<220> FEATURE:
<223> OTHER INFORMATION: fHbp sequence variant

<400> SEQUENCE: 184

Ala Ser Gly Glu Leu Thr Tyr Thr Ile Asp Phe Ala Ala Lys Gln Gly
1               5                   10                  15

His Gly Lys

<210> SEQ ID NO 185
<211> LENGTH: 19
<212> TYPE: PRT
<213> ORGANISM: Artificial Sequence
<220> FEATURE:
<223> OTHER INFORMATION: fHbp sequence variant

<400> SEQUENCE: 185

Thr Gly Gly Lys Leu Thr Tyr Thr Ile Asp Phe Ala Ala Lys Gln Gly
1               5                   10                  15

His Gly Lys

<210> SEQ ID NO 186
<211> LENGTH: 19
<212> TYPE: PRT
<213> ORGANISM: Artificial Sequence
<220> FEATURE:
<223> OTHER INFORMATION: fHbp sequence variant

<400> SEQUENCE: 186

Ala Gly Gly Lys Leu Thr Tyr Thr Ile Asp Phe Val Ala Lys Gln Gly
1               5                   10                  15

His Gly Lys

<210> SEQ ID NO 187
<211> LENGTH: 19
<212> TYPE: PRT
<213> ORGANISM: Artificial Sequence
<220> FEATURE:
<223> OTHER INFORMATION: fHbp sequence variant

<400> SEQUENCE: 187

Ala Gly Gly Lys Leu Thr Tyr Thr Ile Asp Phe Ala Ala Lys Gln Gly
1               5                   10                  15

His Gly Arg

<210> SEQ ID NO 188
<211> LENGTH: 19
<212> TYPE: PRT

```
<213> ORGANISM: Artificial Sequence
<220> FEATURE:
<223> OTHER INFORMATION: fHbp sequence variant

<400> SEQUENCE: 188

Ala Gly Gly Arg Leu Thr Tyr Thr Ile Asp Phe Ala Ala Lys Gln Gly
 1               5                  10                  15

Cys Gly Lys

<210> SEQ ID NO 189
<211> LENGTH: 19
<212> TYPE: PRT
<213> ORGANISM: Artificial Sequence
<220> FEATURE:
<223> OTHER INFORMATION: fHbp sequence variant

<400> SEQUENCE: 189

Ala Gly Glu Lys Leu Thr Tyr Thr Ile Asp Phe Ala Ala Lys Gln Gly
 1               5                  10                  15

His Gly Lys

<210> SEQ ID NO 190
<211> LENGTH: 19
<212> TYPE: PRT
<213> ORGANISM: Artificial Sequence
<220> FEATURE:
<223> OTHER INFORMATION: fHbp sequence variant

<400> SEQUENCE: 190

Thr Gly Gly Lys Leu Ile Tyr Thr Ile Asp Phe Ala Ala Lys Gln Gly
 1               5                  10                  15

His Gly Lys

<210> SEQ ID NO 191
<211> LENGTH: 19
<212> TYPE: PRT
<213> ORGANISM: Artificial Sequence
<220> FEATURE:
<223> OTHER INFORMATION: fHbp sequence variant

<400> SEQUENCE: 191

Ala Gly Gly Lys Leu Thr Tyr Ile Ile Asp Phe Ala Ala Lys Gln Gly
 1               5                  10                  15

Tyr Gly Lys

<210> SEQ ID NO 192
<211> LENGTH: 19
<212> TYPE: PRT
<213> ORGANISM: Artificial Sequence
<220> FEATURE:
<223> OTHER INFORMATION: fHbp sequence variant

<400> SEQUENCE: 192

Pro Asn Gly Arg Leu His Tyr Ser Ile Asp Phe Thr Lys Lys Gln Gly
 1               5                  10                  15

Tyr Gly Arg

<210> SEQ ID NO 193
<211> LENGTH: 19
<212> TYPE: PRT
<213> ORGANISM: Artificial Sequence
<220> FEATURE:
<223> OTHER INFORMATION: fHbp sequence variant
```

```
<400> SEQUENCE: 193

Pro Asn Gly Arg Leu His Tyr Thr Ile Asp Phe Thr Asn Lys Gln Gly
1               5                   10                  15

Tyr Gly Arg

<210> SEQ ID NO 194
<211> LENGTH: 19
<212> TYPE: PRT
<213> ORGANISM: Artificial Sequence
<220> FEATURE:
<223> OTHER INFORMATION: fHbp sequence variant

<400> SEQUENCE: 194

Pro Asn Gly Arg Leu His Tyr Ser Ile Asp Phe Thr Lys Lys Gln Gly
1               5                   10                  15

Tyr Gly Gly

<210> SEQ ID NO 195
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 195

Ser Pro Glu Leu Asn Val Asp Leu Ala Ala Ala Tyr Ile Lys Pro Asp
1               5                   10                  15

Glu Lys His His Ala Val Ile Ser Gly Ser Val Leu Tyr Asn Gln Ala
            20                  25                  30

Glu Lys Gly Ser Tyr Ser Leu Gly Ile Phe Gly Gly Lys Ala Gln Glu
        35                  40                  45

Val Ala Gly Ser Ala Glu Val Lys Thr Val Asn Gly Ile Arg His Ile
    50                  55                  60

Gly Leu Ala Ala
65

<210> SEQ ID NO 196
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 196

Ser Pro Glu Leu Asn Val Asp Leu Ala Ala Ser Asp Ile Lys Pro Asp
1               5                   10                  15

Lys Lys Arg His Ala Val Ile Ser Gly Ser Val Leu Tyr Asn Gln Ala
            20                  25                  30

Glu Lys Gly Ser Tyr Ser Leu Gly Ile Phe Gly Gly Gln Ala Gln Glu
        35                  40                  45

Val Ala Gly Ser Ala Glu Val Glu Thr Ala Asn Gly Ile Arg His Ile
    50                  55                  60

Gly Leu Ala Ala
65

<210> SEQ ID NO 197
<211> LENGTH: 68
<212> TYPE: PRT
<213> ORGANISM: Artificial Sequence
<220> FEATURE:
<223> OTHER INFORMATION: fHbp sequence variant
```

```
<400> SEQUENCE: 197

Ser Pro Glu Leu Asn Val Glu Leu Ala Thr Ala Tyr Ile Lys Pro Asp
1               5                   10                  15

Glu Lys His His Ala Val Ile Ser Gly Ser Val Leu Tyr Asn Gln Asp
            20                  25                  30

Glu Lys Gly Ser Tyr Ser Leu Gly Ile Phe Gly Gly Gln Ala Gln Glu
        35                  40                  45

Val Ala Gly Ser Ala Glu Val Glu Thr Ala Asn Gly Ile His His Ile
    50                  55                  60

Gly Leu Ala Ala
65

<210> SEQ ID NO 198
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 198

Ser Pro Glu Leu Asn Val Asp Leu Ala Ala Asp Ile Lys Pro Asp
1               5                   10                  15

Glu Lys His His Ala Val Ile Ser Gly Ser Val Leu Tyr Asn Gln Ala
            20                  25                  30

Glu Lys Gly Ser Tyr Ser Leu Gly Ile Phe Gly Gly Gln Ala Gln Glu
        35                  40                  45

Val Ala Gly Ser Ala Glu Val Glu Thr Ala Asn Gly Ile Arg His Ile
    50                  55                  60

Gly Leu Ala Ala
65

<210> SEQ ID NO 199
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 199

Ser Pro Glu Leu Asn Val Asp Leu Ala Ala Asp Ile Lys Pro Asp
1               5                   10                  15

Glu Lys Arg His Ala Val Ile Ser Gly Ser Val Leu Tyr Asn Gln Ala
            20                  25                  30

Glu Lys Gly Ser Tyr Ser Leu Gly Ile Phe Gly Gly Lys Ala Gln Glu
        35                  40                  45

Val Ala Gly Ser Ala Glu Val Lys Thr Val Asn Gly Ile Arg His Ile
    50                  55                  60

Gly Leu Ala Ala
65

<210> SEQ ID NO 200
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 200

Ser Pro Glu Leu Asn Val Glu Leu Ala Thr Ala Tyr Ile Lys Pro Asp
```

```
                1               5                  10                  15
            Glu Lys Arg His Ala Val Ile Ser Gly Ser Val Leu Tyr Asn Gln Asp
                        20                  25                  30

Glu Lys Gly Ser Tyr Ser Leu Gly Ile Phe Gly Gly Gln Ala Gln Glu
                    35                  40                  45

Val Ala Gly Ser Ala Glu Val Glu Thr Ala Asn Gly Ile His His Ile
                50                  55                  60

Gly Leu Ala Ala
            65

<210> SEQ ID NO 201
            <211> LENGTH: 68
            <212> TYPE: PRT
            <213> ORGANISM: Artificial Sequence
            <220> FEATURE:
            <223> OTHER INFORMATION: fHbp sequence variant

<400> SEQUENCE: 201

Ser Pro Glu Leu Asn Val Asp Leu Val Ser Ala Asp Ile Lys Pro Asp
            1               5                  10                  15

Glu Lys Arg His Ala Val Ile Ser Gly Ser Val Leu Tyr Asn Gln Asp
                        20                  25                  30

Glu Lys Gly Ser Tyr Ser Leu Gly Ile Phe Gly Gly Lys Ala Gln Glu
                    35                  40                  45

Val Ala Gly Ser Ala Glu Val Lys Thr Val Asn Gly Ile Arg His Ile
                50                  55                  60

Gly Leu Ala Ala
            65

<210> SEQ ID NO 202
            <211> LENGTH: 68
            <212> TYPE: PRT
            <213> ORGANISM: Artificial Sequence
            <220> FEATURE:
            <223> OTHER INFORMATION: fHbp sequence variant

<400> SEQUENCE: 202

Ser Pro Glu Leu Asn Val Asp Leu Ala Ala Ala Asp Ile Lys Pro Asp
            1               5                  10                  15

Gly Lys Arg His Ala Val Ile Ser Gly Ser Val Leu Tyr Asn Gln Ala
                        20                  25                  30

Glu Lys Gly Ser Tyr Ser Leu Gly Ile Phe Gly Gly Lys Ala Gln Glu
                    35                  40                  45

Val Ala Gly Ser Ala Glu Val Lys Thr Val Asn Gly Ile Arg His Ile
                50                  55                  60

Gly Leu Ala Ala
            65

<210> SEQ ID NO 203
            <211> LENGTH: 68
            <212> TYPE: PRT
            <213> ORGANISM: Artificial Sequence
            <220> FEATURE:
            <223> OTHER INFORMATION: fHbp sequence variant

<400> SEQUENCE: 203

Ser Pro Glu Leu Asn Val Asp Leu Ala Ala Ala Asp Ile Lys Pro Asp
            1               5                  10                  15

Gly Lys Arg His Ala Val Ile Ser Gly Ser Val Leu Tyr Asn Gln Ala
                        20                  25                  30
```

Glu Lys Ser Ser Tyr Ser Leu Gly Ile Phe Gly Gly Lys Ala Gln Glu
            35                  40                  45

Val Ala Gly Ser Ala Glu Val Lys Thr Val Asn Gly Ile Arg His Ile
        50                  55                  60

Gly Leu Ala Ala
65

<210> SEQ ID NO 204
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 204

Ser Pro Glu Leu Asn Val Asp Leu Ala Ala Ala Asp Ile Lys Pro Asp
1               5                   10                  15

Glu Lys His His Ala Val Ile Ser Gly Ser Val Leu Tyr Asn Gln Ala
            20                  25                  30

Glu Lys Gly Ser Tyr Ser Leu Gly Ile Phe Gly Gly Lys Ala Gln Glu
            35                  40                  45

Val Ala Gly Ser Ala Glu Val Lys Thr Val Asn Gly Ile Arg His Ile
        50                  55                  60

Gly Leu Ala Ala
65

<210> SEQ ID NO 205
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 205

Ser Pro Glu Leu Asn Val Asp Leu Ala Ala Ala Asp Ile Lys Pro Asp
1               5                   10                  15

Glu Lys His His Ala Val Ile Ser Gly Ser Val Leu Tyr Asn Gln Asp
            20                  25                  30

Glu Lys Gly Ser Tyr Ser Leu Gly Ile Phe Gly Gly Lys Ala Gln Glu
            35                  40                  45

Val Ala Gly Ser Ala Glu Val Lys Thr Val Asn Gly Ile Arg His Ile
        50                  55                  60

Gly Leu Ala Ala
65

<210> SEQ ID NO 206
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 206

Ser Pro Glu Leu Asn Val Asp Leu Ala Ala Ala Asp Ile Lys Pro Asp
1               5                   10                  15

Glu Lys His His Ala Val Ile Ser Gly Ser Val Leu Tyr Asn Gln Asp
            20                  25                  30

Glu Lys Gly Ser Tyr Ser Leu Gly Ile Phe Gly Gly Glu Ala Gln Glu
            35                  40                  45

Val Ala Gly Ser Ala Glu Val Lys Thr Ala Asn Gly Ile His His Ile
    50                  55                  60

Gly Leu Ala Ala
65

<210> SEQ ID NO 207
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 207

Ser Pro Glu Leu Asn Val Asp Leu Ala Val Ala Tyr Ile Lys Pro Asp
1               5                   10                  15

Glu Lys His His Ala Val Ile Ser Gly Ser Val Leu Tyr Asn Gln Asp
                20                  25                  30

Glu Lys Gly Ser Tyr Ser Leu Gly Ile Phe Gly Glu Lys Ala Gln Glu
            35                  40                  45

Val Ala Gly Ser Ala Glu Val Lys Thr Ala Asn Gly Ile His His Ile
    50                  55                  60

Gly Leu Ala Ala
65

<210> SEQ ID NO 208
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 208

Ser Pro Glu Leu Asn Val Asp Leu Ala Val Ala Tyr Ile Lys Pro Asp
1               5                   10                  15

Glu Lys His His Ala Val Ile Ser Gly Ser Val Leu Tyr Asn Gln Asp
                20                  25                  30

Glu Lys Gly Ser Tyr Ser Leu Gly Ile Phe Gly Glu Lys Ala Gln Glu
            35                  40                  45

Val Ala Gly Ser Ala Glu Val Glu Thr Ala Asn Gly Ile His His Ile
    50                  55                  60

Gly Leu Ala Ala
65

<210> SEQ ID NO 209
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 209

Ser Pro Glu Leu Asn Val Asp Leu Ala Ala Asp Ile Lys Pro Asp
1               5                   10                  15

Glu Lys His His Ala Val Ile Ser Gly Ser Val Leu Tyr Asn Gln Asp
                20                  25                  30

Glu Lys Gly Ser Tyr Ser Leu Gly Ile Phe Gly Gly Gln Ala Gln Glu
            35                  40                  45

Val Ala Gly Ser Ala Glu Val Glu Thr Ala Asn Gly Ile His His Ile
    50                  55                  60

Gly Leu Ala Ala

<210> SEQ ID NO 210
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 210

Ser Pro Glu Leu Asn Val Asp Leu Ala Ala Ala Tyr Ile Lys Pro Asp
1               5                   10                  15

Lys Lys Arg His Ala Val Ile Ser Gly Ser Val Leu Tyr Asn Gln Asp
            20                  25                  30

Glu Lys Gly Ser Tyr Ser Leu Gly Ile Phe Gly Gly Gln Ala Gln Glu
        35                  40                  45

Val Ala Gly Ser Ala Glu Val Glu Thr Ala Asn Gly Ile His His Ile
    50                  55                  60

Gly Leu Ala Ala
65

<210> SEQ ID NO 211
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 211

Ser Pro Glu Leu Asn Val Asp Leu Ala Ala Ala Tyr Ile Lys Pro Asp
1               5                   10                  15

Glu Lys His His Ala Val Ile Ser Gly Ser Val Leu Tyr Asn Gln Asp
            20                  25                  30

Glu Lys Gly Ser Tyr Ser Leu Gly Ile Phe Gly Gly Gln Ala Gln Glu
        35                  40                  45

Val Ala Gly Ser Ala Glu Val Lys Thr Ala Asn Gly Ile Arg His Ile
    50                  55                  60

Gly Leu Ala Ala
65

<210> SEQ ID NO 212
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 212

Ser Pro Glu Leu Asn Val Glu Leu Ala Ala Ala Tyr Ile Lys Pro Asp
1               5                   10                  15

Glu Lys His His Ala Val Ile Ser Gly Ser Val Leu Tyr Asn Gln Asp
            20                  25                  30

Glu Lys Gly Ser Tyr Ser Leu Gly Ile Phe Gly Gly Gln Ala Gln Glu
        35                  40                  45

Val Ala Gly Ser Ala Glu Val Glu Thr Ala Asn Gly Ile Gln His Ile
    50                  55                  60

Gly Leu Ala Ala
65

<210> SEQ ID NO 213

```
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 213

Ser Pro Glu Leu Asn Val Glu Leu Ala Thr Ala Asp Ile Lys Pro Asp
1               5                   10                  15

Glu Lys His His Ala Val Ile Ser Gly Ser Val Leu Tyr Asn Gln Asp
            20                  25                  30

Glu Lys Gly Ser Tyr Ser Leu Gly Ile Phe Gly Gly Gln Ala Gln Glu
        35                  40                  45

Val Ala Gly Ser Ala Glu Val Glu Thr Ala Asn Gly Ile His His Ile
    50                  55                  60

Gly Leu Ala Ala
65

<210> SEQ ID NO 214
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 214

Ser Pro Glu Leu Asn Val Glu Leu Ala Thr Ala Tyr Ile Lys Pro Asp
1               5                   10                  15

Glu Lys His His Ala Val Ile Ser Gly Ser Val Leu Tyr Asn Gln Asp
            20                  25                  30

Glu Lys Gly Ser Tyr Ser Leu Gly Ile Phe Gly Gly Lys Ala Gln Glu
        35                  40                  45

Val Ala Gly Ser Ala Glu Val Glu Thr Ala Asn Gly Ile His His Ile
    50                  55                  60

Gly Leu Ala Ala
65

<210> SEQ ID NO 215
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 215

Ser Pro Glu Leu Asn Val Glu Leu Ala Thr Ala Tyr Ile Lys Pro Asp
1               5                   10                  15

Glu Lys Arg His Ala Val Ile Ser Gly Ser Val Leu Tyr Asn Gln Asp
            20                  25                  30

Glu Lys Gly Ser Tyr Ser Leu Gly Ile Phe Gly Gly Gln Ala Gln Glu
        35                  40                  45

Val Ala Gly Ser Ala Glu Val Lys Thr Val Asn Gly Ile Arg His Ile
    50                  55                  60

Gly Leu Ala Ala
65

<210> SEQ ID NO 216
<211> LENGTH: 68
<212> TYPE: PRT
<213> ORGANISM: Artificial Sequence
<220> FEATURE:
```

<223> OTHER INFORMATION: fHbp sequence variant

<400> SEQUENCE: 216

Ser Pro Glu Leu Asn Val Glu Leu Ala Thr Ala Tyr Ile Lys Pro Asp
1               5                   10                  15

Glu Lys Arg His Ala Val Ile Ser Gly Ser Val Leu Tyr Asn Gln Asp
            20                  25                  30

Glu Lys Gly Ser Tyr Ser Leu Gly Ile Phe Gly Gly Gln Ala Gln Glu
        35                  40                  45

Val Ala Gly Ser Ala Glu Val Glu Thr Ala Asn Gly Ile Arg His Ile
    50                  55                  60

Gly Leu Ala Ala
65

<210> SEQ ID NO 217
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 217

Ser Pro Glu Leu Asn Val Glu Leu Ala Thr Ala Tyr Ile Lys Pro Asp
1               5                   10                  15

Glu Lys Arg His Ala Val Ile Ser Gly Ser Val Leu Tyr Asn Gln Asp
            20                  25                  30

Glu Lys Gly Ser Tyr Ser Leu Gly Ile Phe Gly Gly Gln Ala Gln Glu
        35                  40                  45

Val Ala Gly Ser Ala Glu Val Glu Thr Ala Asn Gly Ile Gln His Ile
    50                  55                  60

Gly Leu Ala Ala
65

<210> SEQ ID NO 218
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 218

Ser Pro Glu Leu Asn Val Glu Leu Ala Thr Ala Tyr Ile Lys Pro Asp
1               5                   10                  15

Glu Lys Arg His Ala Val Ile Ser Gly Ser Val Leu Tyr Asn Gln Asp
            20                  25                  30

Glu Lys Gly Ser Tyr Ser Leu Gly Ile Phe Gly Gly Gln Ala Gln Glu
        35                  40                  45

Val Ala Gly Ser Ala Glu Val Glu Thr Val Asn Gly Ile His His Ile
    50                  55                  60

Gly Leu Ala Ala
65

<210> SEQ ID NO 219
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 219

```
Ser Pro Glu Leu Asn Val Asn Leu Ala Ala Asp Ile Lys Pro Asp
1               5                   10                  15

Glu Lys Arg His Ala Val Ile Ser Gly Ser Val Leu Tyr Asn Gln Asp
            20                  25                  30

Glu Lys Gly Ser Tyr Ser Leu Gly Ile Phe Gly Glu Lys Phe Gln Glu
        35                  40                  45

Val Ala Gly Ser Ala Glu Val Lys Thr Ala Asn Gly Ile His His Ile
    50                  55                  60

Gly Leu Ala Ala
65

<210> SEQ ID NO 220
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 220

Ser Pro Glu Leu Asn Val Asp Leu Ala Ala Ala Tyr Ile Lys Pro Asp
1               5                   10                  15

Glu Lys His Tyr Ala Val Ile Ser Gly Ser Val Leu Tyr Asn Gln Asp
            20                  25                  30

Glu Lys Gly Ser Tyr Ser Leu Gly Ile Phe Gly Gly Lys Ala Gln Glu
        35                  40                  45

Val Ala Gly Ser Ala Glu Val Lys Thr Val Asn Gly Ile Arg His Ile
    50                  55                  60

Gly Leu Ala Ala
65

<210> SEQ ID NO 221
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 221

Ser Pro Glu Leu Asn Val Asp Leu Ala Ala Ala Tyr Ile Lys Pro Asp
1               5                   10                  15

Glu Lys Arg His Ala Val Ile Ser Gly Ser Val Leu Tyr Asn Gln Asp
            20                  25                  30

Glu Lys Gly Ser Tyr Ser Leu Gly Ile Phe Gly Gly Lys Ala Gln Glu
        35                  40                  45

Val Ala Gly Ser Ala Glu Val Lys Thr Ala Asn Gly Ile His His Ile
    50                  55                  60

Gly Leu Ala Ala
65

<210> SEQ ID NO 222
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 222

Ser Pro Glu Leu Asn Val Asp Leu Ala Ala Ser Asp Ile Lys Pro Asp
1               5                   10                  15

Lys Lys Arg His Ala Val Ile Ser Gly Ser Val Leu Tyr Asn Gln Ala
```

```
                20                  25                  30

Glu Lys Gly Ser Tyr Ser Leu Gly Ile Phe Gly Gly Gln Ala Gln Glu
        35                  40                  45

Val Ala Trp Gln Arg Arg Val Glu Thr Ala Asn Gly Ile Arg His Ile
    50                  55                  60

Gly Leu Ala Ala
65

<210> SEQ ID NO 223
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 223

Ser Pro Glu Leu Asn Val Asp Leu Ala Ala Ala Asp Ile Lys Pro Asp
1               5                   10                  15

Glu Lys His His Ala Val Ile Ser Gly Ser Val Leu Tyr Asn Gln Asp
                20                  25                  30

Glu Lys Gly Ser Tyr Ser Leu Gly Ile Phe Gly Gly Lys Ala Gln Glu
        35                  40                  45

Val Ala Gly Ser Ala Glu Val Glu Thr Ala Asn Gly Ile His His Ile
    50                  55                  60

Gly Leu Ala Ala
65

<210> SEQ ID NO 224
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 224

Ser Pro Glu Leu Asn Val Asp Leu Ala Ala Ser Asp Ile Lys Pro Asp
1               5                   10                  15

Lys Lys Arg His Ala Val Ile Ser Gly Ser Val Leu Tyr Asn Gln Ala
                20                  25                  30

Glu Lys Gly Ser Tyr Ser Leu Gly Ile Phe Gly Arg Gln Ala Gln Glu
        35                  40                  45

Val Ala Gly Ser Ala Glu Val Glu Thr Ala Asn Gly Ile Arg His Ile
    50                  55                  60

Gly Leu Ala Ala
65

<210> SEQ ID NO 225
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 225

Ser Pro Glu Leu Asn Val Asp Leu Ala Ala Ser Asp Ile Lys Pro Asp
1               5                   10                  15

Lys Lys Arg His Ala Val Ile Ser Gly Ser Val Leu Tyr Asn Gln Ala
                20                  25                  30

Glu Lys Gly Ser Tyr Ser Leu Gly Ile Phe Gly Gly Lys Ala Gln Glu
        35                  40                  45
```

Val Ala Gly Ser Ala Glu Val Glu Thr Ala Asn Gly Ile Arg His Ile
    50                    55                  60

Gly Leu Ala Ala
65

<210> SEQ ID NO 226
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 226

Ser Pro Glu Leu Asn Val Asp Leu Ala Ala Ala Asp Ile Lys Pro Asp
1                5                    10                15

Lys Lys Arg His Ala Val Ile Ser Gly Ser Val Leu Tyr Asn Gln Ala
                20                  25                30

Glu Lys Gly Ser Tyr Ser Leu Gly Ile Phe Gly Gly Gln Ala Gln Glu
                35                  40                45

Val Ala Gly Ser Ala Glu Val Glu Thr Val Asn Gly Ile Arg His Ile
    50                    55                  60

Gly Leu Ala Ala
65

<210> SEQ ID NO 227
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 227

Ser Pro Glu Leu Asn Val Asp Leu Ala Ala Ala Asp Ile Lys Pro Asp
1                5                    10                15

Glu Lys Arg His Ala Val Ile Ser Gly Ser Val Leu Tyr Asn Gln Asp
                20                  25                30

Glu Lys Gly Ser Tyr Ser Leu Gly Ile Phe Gly Gly Gln Ala Gln Glu
                35                  40                45

Val Ala Gly Ser Ala Glu Val Glu Thr Ala Asn Gly Ile Gln His Ile
    50                    55                  60

Gly Leu Ala Ala
65

<210> SEQ ID NO 228
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 228

Ser Pro Glu Leu Asn Val Glu Leu Ala Ala Ala Tyr Ile Lys Pro Asp
1                5                    10                15

Glu Lys Arg His Ala Val Ile Ser Gly Ser Val Leu Tyr Asn Gln Asp
                20                  25                30

Glu Lys Gly Ser Tyr Ser Leu Gly Ile Phe Gly Gly Gln Ala Gln Glu
                35                  40                45

Val Ala Gly Ser Ala Glu Val Glu Thr Ala Asn Gly Ile Gln His Ile
    50                    55                  60

Gly Leu Ala Ala
65

<210> SEQ ID NO 229
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 229

Ser Pro Glu Leu Asn Val Glu Leu Ala Thr Ala Tyr Ile Lys Pro Asp
1               5                   10                  15

Glu Lys His His Ala Val Ile Ser Gly Phe Val Leu Tyr Asn Gln Asp
            20                  25                  30

Glu Lys Gly Ser Tyr Ser Leu Gly Ile Phe Gly Gly Gln Ala Gln Glu
        35                  40                  45

Val Ala Gly Ser Ala Glu Val Glu Thr Ala Asn Gly Ile His His Ile
    50                  55                  60

Gly Leu Ala Ala
65

<210> SEQ ID NO 230
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 230

Ser Pro Glu Leu Asn Val Asp Leu Ala Ala Ala Tyr Ile Lys Pro Asp
1               5                   10                  15

Glu Lys Arg His Ala Val Ile Ser Gly Ser Val Leu Tyr Asn Gln Asp
            20                  25                  30

Glu Lys Gly Ser Tyr Ser Leu Gly Ile Phe Gly Gly Lys Ala Gln Glu
        35                  40                  45

Val Ala Gly Ser Ala Glu Val Lys Thr Val Asn Gly Ile Arg His Ile
    50                  55                  60

Gly Leu Ala Ala
65

<210> SEQ ID NO 231
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 231

Ser Pro Glu Leu Asn Val Asp Leu Ala Ala Ser Asp Ile Lys Pro Asp
1               5                   10                  15

Lys Lys Arg His Ala Val Ile Ser Gly Ser Val Leu Tyr Asn His Ala
            20                  25                  30

Glu Lys Gly Ser Tyr Ser Leu Gly Ile Phe Gly Gly Gln Ala Gln Glu
        35                  40                  45

Val Ala Gly Ser Ala Glu Val Glu Thr Ala Asn Gly Ile Arg His Ile
    50                  55                  60

Gly Leu Ala Ala
65

<210> SEQ ID NO 232
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 232

```
Ser Pro Glu Leu Asn Val Asp Leu Ala Ala Ala Tyr Ile Lys Pro Asp
1               5                   10                  15

Glu Lys Arg His Ala Val Ile Ser Gly Ser Val Leu Tyr Asn Gln Asp
            20                  25                  30

Glu Lys Gly Ser Tyr Ser Leu Gly Ile Phe Gly Gly Gln Ala Gln Glu
        35                  40                  45

Val Ala Gly Ser Ala Glu Val Glu Thr Ala Asn Gly Ile Gln His Ile
    50                  55                  60

Gly Leu Ala Ala
65
```

<210> SEQ ID NO 233
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 233

```
Ser Pro Glu Leu Asn Val Asp Leu Val Ala Asp Ile Lys Pro Asp
1               5                   10                  15

Lys Lys Arg His Ala Val Ile Ser Gly Ser Val Leu Tyr Asn Gln Ala
            20                  25                  30

Glu Lys Gly Ser Tyr Ser Leu Gly Ile Phe Gly Gly Gln Ala Gln Glu
        35                  40                  45

Val Ala Gly Ser Ala Glu Val Glu Thr Ala Asn Gly Ile Arg His Ile
    50                  55                  60

Gly Leu Ala Ala
65
```

<210> SEQ ID NO 234
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 234

```
Ser Pro Glu Leu Asn Val Glu Leu Ala Thr Ala Tyr Ile Lys Pro Asp
1               5                   10                  15

Glu Lys Arg His Ala Val Ile Ser Gly Ser Val Leu Tyr Asn Gln Asp
            20                  25                  30

Glu Lys Gly Ser Tyr Ser Leu Gly Ile Phe Ser Gly Gln Ala Gln Glu
        35                  40                  45

Val Ala Gly Ser Ala Glu Val Glu Thr Ala Asn Gly Ile His His Ile
    50                  55                  60

Gly Leu Ala Ala
65
```

<210> SEQ ID NO 235
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 235

Ser Pro Glu Leu Asn Val Glu Leu Ala Thr Ala Tyr Ile Lys Pro Asp
1               5                   10                  15

Glu Lys Arg Tyr Ala Val Ile Ser Gly Ser Val Leu Tyr Asn Gln Asp
            20                  25                  30

Glu Lys Gly Ser Tyr Ser Leu Gly Ile Phe Gly Gly Gln Ala Gln Glu
        35                  40                  45

Val Ala Gly Ser Ala Glu Val Glu Thr Ala Asn Gly Ile His His Ile
    50                  55                  60

Gly Leu Ala Ala
65

<210> SEQ ID NO 236
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 236

Ser Pro Glu Leu Asn Val Asp Leu Ala Val Ala Tyr Ile Lys Pro Asp
1               5                   10                  15

Glu Lys His His Ala Val Ile Ser Gly Ser Val Leu Tyr Asn Gln Asp
            20                  25                  30

Glu Lys Gly Ser Tyr Ser Leu Gly Ile Phe Gly Gly Gln Ala Gln Glu
        35                  40                  45

Val Ala Gly Ser Ala Glu Val Glu Thr Ala Asn Gly Ile His His Ile
    50                  55                  60

Gly Leu Ala Ala
65

<210> SEQ ID NO 237
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 237

Ser Pro Glu Leu Asn Val Glu Leu Ala Thr Ala Tyr Ile Lys Pro Asp
1               5                   10                  15

Glu Lys His His Ala Val Ile Ser Gly Ser Val Leu Tyr Asn Gln Asp
            20                  25                  30

Glu Lys Gly Ser Tyr Ser Leu Gly Ile Phe Gly Gly Gln Ala Gln Glu
        35                  40                  45

Ile Ala Gly Ser Ala Glu Val Glu Thr Ala Asn Gly Ile His His Ile
    50                  55                  60

Gly Leu Ala Ala
65

<210> SEQ ID NO 238
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 238

-continued

Ser Pro Glu Leu Asn Val Asp Leu Ala Ala Ala Asn Ile Glu Gln Asp
1               5                   10                  15

Glu Lys His His Ala Val Ile Ser Gly Ser Val Leu Tyr Asn Gln Asp
            20                  25                  30

Glu Lys Gly Ser Tyr Ser Leu Gly Ile Phe Gly Glu Lys Ala Gln Glu
        35                  40                  45

Val Ala Gly Ser Ala Glu Val Lys Thr Ala Asn Gly Ile Arg His Ile
    50                  55                  60

Gly Leu Ala Ala
65

<210> SEQ ID NO 239
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 239

Ser Pro Glu Leu Asn Val Glu Leu Ala Thr Ala Tyr Ile Lys Pro Asp
1               5                   10                  15

Glu Lys Arg His Ala Val Ile Ser Gly Ser Val Leu Tyr Asn Gln Asn
            20                  25                  30

Glu Lys Gly Ser Tyr Ser Leu Gly Ile Phe Gly Gly Gln Ala Gln Glu
        35                  40                  45

Val Ala Gly Ser Ala Glu Val Glu Thr Ala Asn Gly Ile His His Ile
    50                  55                  60

Gly Leu Ala Ala
65

<210> SEQ ID NO 240
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 240

Ser Pro Glu Leu Asn Val Glu Leu Ala Ala Ala Tyr Ile Lys Pro Asp
1               5                   10                  15

Glu Lys Arg His Ala Val Ile Ser Gly Ser Val Leu Tyr Asn Gln Asp
            20                  25                  30

Glu Lys Gly Ser Tyr Ser Leu Gly Ile Phe Gly Gly Gln Ala Gln Glu
        35                  40                  45

Val Ala Gly Ser Ala Glu Val Glu Thr Ala Asn Gly Ile His His Ile
    50                  55                  60

Gly Leu Ala Ala
65

<210> SEQ ID NO 241
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 241

Ser Pro Glu Leu Asn Val Asp Leu Ala Val Ala Tyr Ile Lys Pro Asp
1               5                   10                  15

```
Glu Lys His His Ala Val Ile Ser Gly Ser Val Leu Tyr Asn Gln Asp
            20                  25                  30

Glu Lys Gly Ser Tyr Ser Leu Gly Ile Phe Gly Glu Lys Ala Gln Glu
        35                  40                  45

Val Ala Gly Ser Ala Glu Val Lys Thr Val Asn Gly Ile Arg His Ile
    50                  55                  60

Gly Leu Ala Ala
65

<210> SEQ ID NO 242
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 242

Ser Pro Glu Leu Asn Val Asp Leu Ala Val Ala Tyr Ile Lys Pro Asp
1               5                   10                  15

Glu Lys His His Ala Val Ile Ser Gly Ser Val Leu Tyr Asn Gln Asp
            20                  25                  30

Glu Lys Gly Ser Tyr Ser Leu Gly Ile Phe Gly Gly Lys Ala Gln Glu
        35                  40                  45

Val Ala Gly Ser Ala Glu Val Glu Thr Ala Asn Gly Ile His His Ile
    50                  55                  60

Gly Leu Ala Ala
65

<210> SEQ ID NO 243
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 243

Ser Pro Glu Leu Asn Val Asp Leu Ala Ala Ala Tyr Ile Lys Pro Asp
1               5                   10                  15

Glu Lys His His Ala Val Ile Ser

```
            35                  40                  45

Val Ala Gly Ser Ala Glu Val Lys Thr Val Asn Gly Ile Arg His Ile
    50                  55                  60

Gly Leu Ala Ala
65

<210> SEQ ID NO 245
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 245

Ser Pro Glu Leu Asn Val Asn Leu Ala Ala Ala Asp Ile Lys Pro Asp
1               5                   10                  15

Glu Lys Arg His Ala Val Ile Ser Gly Ser Val Leu Tyr Asn Gln Ala
            20                  25                  30

Glu Lys Gly Ser Tyr Ser Leu Gly Ile Phe Gly Glu Lys Ala Gln Glu
        35                  40                  45

Val Ala Gly Ser Ala Glu Val Lys Thr Ala Asn Gly Ile His His Ile
    50                  55                  60

Gly Leu Ala Ala
65

<210> SEQ ID NO 246
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 246

Ser Pro Glu Leu Asn Val Asp Leu Ala Ala Ala Tyr Ile Lys Pro Asp
1               5                   10                  15

Glu Lys His His Ala Val Ile Ser Gly Ser Val Leu Tyr Asn Gln Asp
            20                  25                  30

Glu Lys Gly Ser Tyr Ser Leu Gly Ile Phe Gly Gly Lys Ala Gln Glu
        35                  40                  45

Val Ala Gly Ser Ala Glu Val Glu Thr Val Asn Gly Ile Arg His Ile
    50                  55                  60

Gly Leu Ala Ala
65

<210> SEQ ID NO 247
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 247

Ser Pro Glu Leu Asn Val Asp Leu Ala Ala Ala Asp Ile Lys Pro Asp
1               5                   10                  15

Glu Lys Arg His Ala Val Ile Ser Gly Ser Val Leu Tyr Asn Gln Asp
            20                  25                  30

Glu Lys Gly Ser Tyr Ser Leu Gly Ile Phe Gly Gly Lys Ala Gln Glu
        35                  40                  45

Val Ala Gly Ser Ala Glu Val Glu Thr Ala Asn Gly Ile Gln His Ile
    50                  55                  60
```

```
Gly Leu Ala Ala
65

<210> SEQ ID NO 248
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 248

Ser Pro Glu Leu Asn Val Asp Leu Ala Ala Ala Asp Ile Lys Pro Asp
1               5                   10                  15

Glu Lys His His Ala Val Ile Ser Gly Ser Val Leu Tyr Asn Gln Asp
            20                  25                  30

Glu Lys Gly Ser Tyr Ser Leu Gly Ile Phe Gly Glu Lys Ala Gln Glu
        35                  40                  45

Val Ala Gly Ser Ala Glu Val Lys Thr Ala Asn Gly Ile His His Ile
    50                  55                  60

Gly Leu Ala Ala
65

<210> SEQ ID NO 249
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 249

Ser Pro Glu Leu Asn Val Asp Leu Ala Ala Ala Tyr Ile Lys Pro Asp
1               5                   10                  15

Glu Lys His His Ala Val Ile Ser Gly Ser Val Leu Tyr Asn Gln Asp
            20                  25                  30

Glu Lys Gly Ser Tyr Ser Leu Gly Ile Phe Gly Gly Lys Ala Gln Glu
        35                  40                  45

Val Ala Gly Ser Ala Glu Val Lys Thr Val Asn Gly Ile Arg His Ile
    50                  55                  60

Gly Leu Ala Ala
65

<210> SEQ ID NO 250
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 250

Ser Pro Glu Leu Asn Val Asp Leu Ala Ala Ala Asp Ile Lys Pro Asp
1               5                   10                  15

Glu Lys Arg His Ala Val Ile Ser Gly Ser Val Leu Tyr Asn Gln Asp
            20                  25                  30

Glu Lys Gly Ser Tyr Ser Leu Gly Ile Phe Gly Gly Gln Ala Gln Glu
        35                  40                  45

Val Ala Gly Ser Ala Glu Val Lys Thr Val Asn Gly Ile Arg His Ile
    50                  55                  60

Gly Leu Ala Ala
65
```

<210> SEQ ID NO 251
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 251

Ser Pro Glu Leu Asn Val Asp Leu Ala Ala Ala Tyr Ile Lys Pro Asp
1               5                   10                  15

Glu Lys His His Ala Val Ile Ser Gly Ser Val Leu Tyr Asn Gln Asp
            20                  25                  30

Glu Lys Gly Ser Tyr Ser Leu Gly Ile Phe Gly Gly Gln Ala Gln Glu
        35                  40                  45

Val Ala Gly Ser Ala Glu Val Glu Thr Ala Asn Gly Ile Gln His Ile
    50                  55                  60

Gly Leu Ala Ala
65

<210> SEQ ID NO 252
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 252

Ser Pro Glu Leu Asn Val Asp Leu Ala Ala Ala Tyr Ile Lys Pro Asp
1               5                   10                  15

Lys Lys Arg His Ala Val Ile Ser Gly Ser Val Leu Tyr Asn Gln Asp
            20                  25                  30

Glu Lys Gly Ser Tyr Ser Leu Gly Ile Phe Gly Gly Lys Ala Gln Glu
        35                  40                  45

Val Ala Gly Ser Ala Glu Val Glu Thr Ala Asn Gly Ile His His Ile
    50                  55                  60

Gly Leu Ala Ala
65

<210> SEQ ID NO 253
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 253

Ser Pro Glu Leu Asn Val Asp Leu Ala Ala Ala Tyr Ile Lys Pro Asp
1               5                   10                  15

Glu Lys His His Ala Val Ile Ser Gly Ser Val Leu Tyr Asn Gln Ala
            20                  25                  30

Glu Lys Gly Ser Tyr Ser Leu Gly Ile Phe Gly Gly Gln Ala Gln Glu
        35                  40                  45

Val Ala Gly Ser Ala Glu Val Glu Thr Ala Asn Gly Ile Arg His Ile
    50                  55                  60

Gly Leu Ala Ala
65

<210> SEQ ID NO 254
<211> LENGTH: 68
<212> TYPE: PRT

<213> ORGANISM: Artificial Sequence
<220> FEATURE:
<223> OTHER INFORMATION: fHbp sequence variant

<400> SEQUENCE: 254

```
Ser Pro Glu Leu Asn Val Glu Leu Ala Thr Ala Tyr Ile Lys Pro Asp
1               5                   10                  15

Glu Lys Arg His Ala Val Ile Ser Asp Ser Val Leu Tyr Asn Gln Asp
                20                  25                  30

Glu Lys Gly Ser Tyr Ser Leu Gly Ile Phe Gly Gly Gln Ala Gln Glu
            35                  40                  45

Val Ala Gly Ser Ala Glu Val Glu Thr Ala Asn Gly Ile His His Ile
    50                  55                  60

Gly Leu Ala Ala
65
```

<210> SEQ ID NO 255
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 255

```
Ser Pro Glu Leu Asn Val Asp Leu Ala Ala Ala Tyr Ile Lys Pro Asp
1               5                   10                  15

Glu Lys His His Ala Val Ile Ser Gly Ser Val Leu Tyr Asn Gln Asp
                20                  25                  30

Glu Lys Gly Ser Tyr Ser Leu Gly Ile Phe Gly Gly Lys Ala Glu Glu
            35                  40                  45

Val Ala Gly Ser Ala Glu Val Lys Thr Val Asn Gly Ile Arg His Ile
    50                  55                  60

Gly Leu Ala Ala
65
```

<210> SEQ ID NO 256
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 256

```
Ser Pro Glu Leu Asn Val Asp Leu Ala Ala Ala Asn Ile Glu Gln Asp
1               5                   10                  15

Glu Lys His His Ala Val Ile Ser Gly Ser Val Leu Tyr Asn Gln Ala
                20                  25                  30

Glu Lys Gly Ser Tyr Ser Leu Gly Ile Phe Gly Glu Lys Phe Gln Glu
            35                  40                  45

Val Ala Gly Ser Ala Glu Val Lys Thr Val Asn Gly Ile Arg His Ile
    50                  55                  60

Gly Leu Ala Ala
65
```

<210> SEQ ID NO 257
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 257

```
Ser Pro Glu Leu Asn Val Asp Leu Ala Ala Tyr Ile Lys Pro Asp
1               5                   10                  15

Glu Lys His His Ala Val Ile Ser Gly Ser Val Leu Tyr Asn Gln Ala
                20                  25                  30

Glu Lys Gly Ser Tyr Ser Leu Gly Ile Phe Gly Gly Lys Ala Gln Glu
            35                  40                  45

Val Ala Gly Ser Ala Glu Val Lys Thr Val Asn Gly Ile Leu His Ile
    50                  55                  60

Gly Leu Ala Ala
65
```

<210> SEQ ID NO 258
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 258

```
Ser Pro Glu Leu Asn Val Glu Leu Ala Thr Ala Tyr Ile Lys Pro Asp
1               5                   10                  15

Glu Lys His His Ala Val Ile Ser Gly Ser Val Leu Tyr Asn Gln Asp
                20                  25                  30

Glu Lys Gly Ser Tyr Ser Leu Gly Ile Phe Gly Gly Gln Ala Gln Glu
            35                  40                  45

Val Ala Gly Ser Ala Glu Val Glu Thr Ala Asn Gly Ile Arg His Ile
    50                  55                  60

Gly Leu Ala Ala
65
```

<210> SEQ ID NO 259
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 259

```
Ser Pro Glu Leu Asn Val Asp Leu Ala Ala Ala Asp Ile Lys Pro Asp
1               5                   10                  15

Glu Lys His His Ala Val Ile Ser Gly Ser Val Leu Tyr Asn Gln Asp
                20                  25                  30

Glu Lys Gly Ser Tyr Ser Leu Gly Ile Phe Gly Gly Gln Ala Gln Glu
            35                  40                  45

Val Ala Gly Ser Ala Glu Val Lys Thr Val Asn Gly Ile Arg His Ile
    50                  55                  60

Gly Leu Ala Ala
65
```

<210> SEQ ID NO 260
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 260

```
Ser Pro Glu Leu Asn Val Asp Leu Ala Ala Ser Asp Ile Lys Pro Asp
1               5                   10                  15
```

```
Lys Lys Arg His Ala Val Ile Ser Gly Ser Val Leu Tyr Asn Gln Ala
                20                  25                  30

Glu Lys Gly Ser Tyr Ser Leu Gly Ile Phe Gly Gly Gln Ala Gln Glu
            35                  40                  45

Val Ala Gly Ser Ala Glu Val Lys Thr Val Asn Gly Ile Arg His Ile
 50                  55                  60

Gly Leu Ala Ala
 65
```

<210> SEQ ID NO 261
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 261

```
Ser Pro Glu Leu Asn Val Asp Leu Ala Ala Asp Ile Lys Pro Asp
 1               5                  10                  15

Glu Lys Arg His Ala Val Ile Ser Gly Ser Val Leu Tyr Asn Gln Asp
                20                  25                  30

Glu Lys Gly Ser Tyr Ser Leu Gly Ile Phe Gly Gly Gln Ala Gln Glu
            35                  40                  45

Val Ala Gly Ser Ala Glu Val Glu Thr Ala Asn Gly Ile His His Ile
 50                  55                  60

Gly Leu Ala Ala
 65
```

<210> SEQ ID NO 262
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 262

```
Thr Pro Glu Gln Asn Val Glu Leu Ala Ser Ala Glu Leu Lys Ala Asp
 1               5                  10                  15

Glu Lys Ser His Ala Val Ile Leu Gly Asp Thr Arg Tyr Gly Gly Glu
                20                  25                  30

Glu Lys Gly Thr Tyr His Leu Ala Leu Phe Gly Asp Arg Ala Gln Glu
            35                  40                  45

Ile Ala Gly Ser Ala Thr Val Lys Ile Arg Glu Lys Val His Glu Ile
 50                  55                  60

Gly Ile Ala Gly
 65
```

<210> SEQ ID NO 263
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 263

```
Thr Pro Glu Gln Asn Val Glu Leu Ala Ala Ala Glu Leu Lys Ala Asp
 1               5                  10                  15

Glu Lys Ser His Ala Val Ile Leu Gly Asp Thr Arg Tyr Gly Ser Glu
                20                  25                  30
```

Glu Lys Gly Thr Tyr His Leu Ala Leu Phe Gly Asp Arg Ala Gln Glu
            35                  40                  45

Ile Ala Gly Ser Ala Thr Val Lys Ile Gly Glu Lys Val His Glu Ile
 50                  55                  60

Gly Ile Ala Gly
65

<210> SEQ ID NO 264
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 264

Thr Pro Glu Gln Asn Val Glu Leu Ala Ser Ala Glu Leu Lys Ala Asp
1               5                   10                  15

Glu Lys Ser His Ala Val Ile Leu Gly Asp Thr Arg Tyr Gly Ser Glu
            20                  25                  30

Glu Lys Gly Thr Tyr His Leu Ala Leu Phe Gly Asp Arg Ala Gln Glu
            35                  40                  45

Ile Ala Gly Ser Ala Thr Val Lys Ile Arg Glu Lys Val His Glu Ile
 50                  55                  60

Gly Ile Ala Gly
65

<210> SEQ ID NO 265
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 265

Thr Pro Glu Gln Asn Val Glu Leu Ala Ser Ala Glu Leu Lys Ala Asp
1               5                   10                  15

Glu Lys Ser His Ala Val Ile Leu Gly Asp Thr Arg Tyr Gly Ser Glu
            20                  25                  30

Glu Lys Gly Thr Tyr His Leu Ala Leu Phe Gly Asp Arg Ala Gln Glu
            35                  40                  45

Ile Ala Gly Ser Ala Thr Val Lys Ile Gly Glu Lys Val His Glu Ile
 50                  55                  60

Gly Ile Ala Gly
65

<210> SEQ ID NO 266
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 266

Thr Pro Glu Leu Asn Val Asp Leu Ala Ser Ala Glu Leu Lys Ala Asp
1               5                   10                  15

Glu Lys Ser His Ala Val Ile Leu Gly Asp Thr Arg Tyr Gly Ser Glu
            20                  25                  30

Glu Lys Gly Thr Tyr His Leu Ala Leu Phe Gly Asp Arg Ala Gln Glu
            35                  40                  45

Ile Ala Gly Ser Ala Thr Val Lys Ile Gly Glu Lys Val His Glu Ile

<210> SEQ ID NO 267
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 267

Thr Leu Glu Gln Asn Val Glu Leu Ala Ala Ala Glu Leu Lys Ala Asp
1               5                   10                  15

Glu Lys Ser His Ala Val Ile Leu Gly Asp Thr Arg Tyr Gly Ser Glu
            20                  25                  30

Glu Lys Gly Thr Tyr His Leu Ala Leu Phe Gly Asp Arg Ala Gln Glu
        35                  40                  45

Ile Ala Gly Ser Ala Thr Val Lys Ile Gly Glu Lys Val His Glu Ile
    50                  55                  60

Gly Ile Ala Gly
65

<210> SEQ ID NO 268
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 268

Thr Pro Glu Gln Asn Val Glu Leu Ala Ala Ala Glu Leu Lys Ala Asp
1               5                   10                  15

Glu Lys Ser His Ala Val Ile Leu Gly Asp Thr Arg Tyr Gly Gly Glu
            20                  25                  30

Glu Lys Gly Thr Tyr His Leu Ala Leu Phe Gly Asp Arg Ala Gln Glu
        35                  40                  45

Ile Ala Gly Ser Ala Thr Val Lys Ile Arg Glu Lys Val His Glu Ile
    50                  55                  60

Gly Ile Ala Gly
65

<210> SEQ ID NO 269
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 269

Thr Pro Glu Gln Asn Val Glu Leu Ala Ala Ala Glu Leu Lys Ala Asp
1               5                   10                  15

Glu Lys Ser His Ala Val Ile Leu Gly Asp Thr Arg Tyr Asp Ser Glu
            20                  25                  30

Glu Lys Gly Thr Tyr His Leu Ala Leu Phe Gly Asp Arg Ala Gln Glu
        35                  40                  45

Ile Ala Gly Ser Ala Thr Val Lys Ile Gly Glu Lys Val His Glu Ile
    50                  55                  60

Ser Ile Ala Gly
65

<210> SEQ ID NO 270
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 270

Thr Pro Glu Gln Asn Val Glu Leu Ala Ala Ala Glu Leu Lys Ala Asp
1               5                   10                  15

Glu Lys Ser His Ala Val Ile Leu Gly Asp Thr Arg Tyr Gly Ser Glu
            20                  25                  30

Glu Lys Gly Thr Tyr His Leu Ala Leu Phe Gly Asp Arg Ala Gln Glu
        35                  40                  45

Ile Ala Gly Ser Ala Thr Val Lys Ile Gly Glu Lys Val His Glu Ile
    50                  55                  60

Ser Ile Ala Gly
65

<210> SEQ ID NO 271
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 271

Ser Pro Glu Leu Asn Val Glu Leu Ala Thr Ala Glu Leu Lys Ala Asp
1               5                   10                  15

Glu Lys Ser His Ala Val Ile Leu Gly Asp Thr Arg Tyr Gly Ser Glu
            20                  25                  30

Glu Lys Gly Thr Tyr His Leu Ala Leu Phe Gly Asp Arg Ala Gln Glu
        35                  40                  45

Ile Ala Gly Ser Ala Thr Val Lys Ile Arg Glu Lys Val His Glu Ile
    50                  55                  60

Gly Ile Ala Gly
65

<210> SEQ ID NO 272
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 272

Thr Pro Glu Gln Asn Val Glu Leu Ala Ser Ala Glu Leu Lys Ala Asp
1               5                   10                  15

Glu Lys Ser His Ala Val Ile Leu Gly Asp Thr Arg Tyr Gly Gly Glu
            20                  25                  30

Glu Lys Gly Thr Tyr His Leu Ala Leu Phe Gly Asp Arg Ala Gln Glu
        35                  40                  45

Ile Ala Gly Ser Ala Thr Val Lys Ile Arg Glu Lys Val His Glu Ile
    50                  55                  60

Asp Ile Ala Gly
65

<210> SEQ ID NO 273
<211> LENGTH: 68

```
<212> TYPE: PRT
<213> ORGANISM: Artificial Sequence
<220> FEATURE:
<223> OTHER INFORMATION: fHbp sequence variant

<400> SEQUENCE: 273

Thr Pro Glu Gln Asn Val Glu Leu Ala Ala Ala Glu Leu Lys Ala Asp
1               5                   10                  15

Glu Lys Ser His Ala Val Ile Leu Gly Asp Thr His Tyr Gly Ser Glu
            20                  25                  30

Glu Lys Gly Thr Tyr His Leu Ala Leu Phe Gly Asp Arg Ala Gln Glu
        35                  40                  45

Ile Ala Gly Ser Ala Thr Val Lys Ile Gly Glu Lys Val His Glu Ile
    50                  55                  60

Ser Ile Ala Gly
65

<210> SEQ ID NO 274
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 274

Thr Pro Glu Gln Asn Val Glu Leu Ala Ala Ala Glu Leu Lys Ala Asp
1               5                   10                  15

Glu Lys Ser His Ala Val Ile Leu Gly Asp Thr Arg Tyr Gly Ser Glu
            20                  25                  30

Glu Lys Gly Thr Tyr His Leu Ala Leu Phe Gly Asp Arg Ala Gln Glu
        35                  40                  45

Ile Ala Gly Ser Ala Thr Val Lys Ile Arg Glu Lys Val His Glu Ile
    50                  55                  60

Gly Ile Ala Gly
65

<210> SEQ ID NO 275
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 275

Thr Pro Glu Gln Asn Val Glu Leu Ala Ser Ala Glu Leu Lys Ala Asp
1               5                   10                  15

Glu Lys Ser His Ala Val Ile Leu Gly Asp Thr Arg Tyr Gly Gly Glu
            20                  25                  30

Glu Lys Gly Thr Tyr His Leu Ala Leu Phe Gly Asp Arg Ala Gln Glu
        35                  40                  45

Ile Ala Gly Ser Ala Thr Val Lys Ile Gly Glu Lys Val His Glu Ile
    50                  55                  60

Gly Ile Ala Gly
65

<210> SEQ ID NO 276
<211> LENGTH: 68
<212> TYPE: PRT
<213> ORGANISM: Artificial Sequence
<220> FEATURE:
<223> OTHER INFORMATION: fHbp sequence variant
```

<400> SEQUENCE: 276

Thr Pro Glu Gln Asn Val Glu Leu Ala Ser Ala Glu Leu Lys Ala Asp
1               5                   10                  15

Glu Lys Ser His Ala Val Ile Leu Gly Asp Thr Arg Tyr Gly Ser Glu
            20                  25                  30

Glu Lys Asp Thr Tyr His Leu Ala Leu Phe Gly Asp Arg Ala Gln Glu
        35                  40                  45

Ile Ala Gly Ser Ala Thr Val Lys Ile Arg Glu Lys Val His Glu Ile
    50                  55                  60

Gly Ile Ala Gly
65

<210> SEQ ID NO 277
<211> LENGTH: 68
<212> TYPE: PRT
<213> ORGANISM: Artificial Sequence
<220> FEATURE:
<223> OTHER INFORMATION: fHbp sequence variant

<400> SEQUENCE: 277

Thr Pro Glu Leu Asn Val Asp Leu Ala Ser Ala Glu Leu Lys Ala Asp
1               5                   10                  15

Glu Lys Ser His Ala Val Ile Leu Gly Asp Thr Arg Tyr Gly Gly Glu
            20                  25                  30

Glu Lys Gly Thr Tyr His Leu Ala Leu Phe Gly Asp Arg Ala Gln Glu
        35                  40                  45

Ile Ala Gly Ser Ala Thr Val Lys Ile Arg Glu Lys Val His Glu Ile
    50                  55                  60

Gly Ile Ala Gly
65

<210> SEQ ID NO 278
<211> LENGTH: 5
<212> TYPE: PRT
<213> ORGANISM: Artificial Sequence
<220> FEATURE:
<223> OTHER INFORMATION: Synthetic peptide

<400> SEQUENCE: 278

Ala Gln Gly Ala Glu
1               5

<210> SEQ ID NO 279
<211> LENGTH: 5
<212> TYPE: PRT
<213> ORGANISM: Artificial Sequence
<220> FEATURE:
<223> OTHER INFORMATION: Synthetic peptide

<400> SEQUENCE: 279

Ser His Phe Asp Phe
1               5

<210> SEQ ID NO 280
<211> LENGTH: 4
<212> TYPE: PRT
<213> ORGANISM: Artificial sequence
<220> FEATURE:
<223> OTHER INFORMATION: Synthetic peptide

```
<400> SEQUENCE: 280

His Leu Ala Leu
1
```

US 9,266,942 B2

CHIMERIC FACTOR H BINDING PROTEINS (FHBP) AND METHODS OF USE

CROSS REFERENCED TO RELATED APPLICATION

This application claims priority to U.S. Provisional Application No. 61/174,424 filed Apr. 30, 2009, which is incorporated herein by reference in its entirety and for all purposes.

STATEMENT REGARDING FEDERALLY SPONSORED RESEARCH

This invention was made with government support under National Institutes of Health grant nos. R01 AI46464 and C06 RR16226. The government has certain rights in this invention.

FIELD OF THE INVENTION

This invention relates to vaccines for diseases caused by *Neisseria meningitidis*.

INTRODUCTION

*Neisseria meningitidis* is a Gram-negative bacterium which colonizes the human upper respiratory tract and is responsible for worldwide sporadic and cyclical epidemic outbreaks of, most notably, meningitis and sepsis. The attack and morbidity rates are highest in children under 2 years of age. Like other Gram-negative bacteria, *Neisseria meningitidis* typically possess a cytoplasmic membrane, a peptidoglycan layer, an outer membrane which together with the capsular polysaccharide constitute the bacterial wall, and pili, which project into the outside environment. Encapsulated strains of *Neisseria meningitidis* are a major cause of bacterial meningitis and septicemia in children and young adults. The prevalence and economic importance of invasive *Neisseria meningitidis* infections have driven the search for effective vaccines that can confer immunity across different strains, and particularly across genetically diverse group B strains with different serotypes or serosubtypes.

Factor H Binding Protein (fHbp, also referred to in the art as lipoprotein 2086 (Fletcher et al, Infect Immun 2004; 72:2088-2100), Genome-derived *Neisserial* antigen (GNA) 1870 (Masignani et al. J Exp Med 2003; 197:789-99) or "741") is an *N. meningitidis* protein which is expressed in the bacterium as a surface-exposed lipoprotein. An important function of fHbp is to bind human complement fH, which down-regulates complement activation. Binding of fH to the bacterial surface is an important mechanism by which the pathogen survives in non-immune human serum or blood and evades innate host defenses.

From analysis of 71 *N. meningitidis* strains in the first study, and more than 200 strains in the second study, representative of its genetic and geographic diversity, *N. meningitidis* strains have been sub-divided into three fHbp variant groups (referred to as variant 1 (v.1), variant 2 (v.2), and variant 3 (v.3)) based on amino acid sequence variability and immunologic cross-reactivity (Masignani et al. J Exp Med 2003; 197:789-99). Other workers (Fletcher et al, 2004) have subdivided the protein into two sub-families designated A (which includes v.2 and v.3 of Masignani) and B (v.1). Variant 1 strains account for about 60% of disease-producing group B isolates (Masignani et al. 2003, supra). Within each variant group, there is on the order of about 92% or greater conservation of amino acid sequence. Specifically, conservation within each variant group ranges between 89 and 100%, while between the variant groups (e.g., between v.1 and v.2) the conservation can be as low as 59%. The protein is expressed by all known strains of *N. meningitidis*.

There remains a need for a single fHbp polypeptide that can elicit bactericidal antibody responses that are effective against a broad spectrum of strains expressing different fHbp variants.

SUMMARY

Chimeric fHbps that can elicit antibodies that are bactericidal for different fHbp variant strains of *N. meningitidis*, and methods of use, are provided.

BRIEF DESCRIPTION OF THE DRAWINGS

FIG. 1A-1G is Table 7 that lists the source strains and characteristics of about 69 unique factor H binding proteins.

FIG. 2A-2E is Table 8 that lists unique sequences in fHbp variable segment A through E and number of unique peptides from each variant group containing the segment ID. Segment ID is an identifier for each variable segment. Distinct sequence variants were assigned a unique identifier beginning with a letter, A through E, to represent the segment; followed by an α or β to indicate homology of the segment with either the corresponding fHbp segment from peptide ID 1 (fHbp v.1) or peptide ID 28 (fHbp v.3), respectively, followed by a number for each distinct sequence. Numbers in variant groups 1, 2, and 3 are provided for some segment IDs of each segment (A through E) in subtables.

FIG. 5 is a phylogram of unique fHbp amino acid sequences in variable segments A (residues 8-73) (panel A) and B (residues 79-93) (panel B).

FIG. 6 is a phylogram of unique fHbp amino acid sequences in variable segments C (residues 98-159) (panel A) and D (residues 162-180) (panel B).

FIG. 9 presents structural models of factor H binding protein based on the coordinates of fHbp in a complex with a fragment of human factor H (Schneider et al. (2009) *Nature* 458:890-3). Left models in each of the following panels show fHbps facing membrane side; center models are facing exposed side; and the right models depict membrane side of the fHbp down. Panel A, Cartoon representation depicting the two structural domains. B, Space-filling model with factor H-binding residues depicted in black and the amino acid residues of the invariant segments in white. C, Space-filling model with the amino acid residues of the invariant segments depicted in white as in panel B, and the residues affecting the epitopes of anti-fHbp mAbs shown in black.

Figure 3:
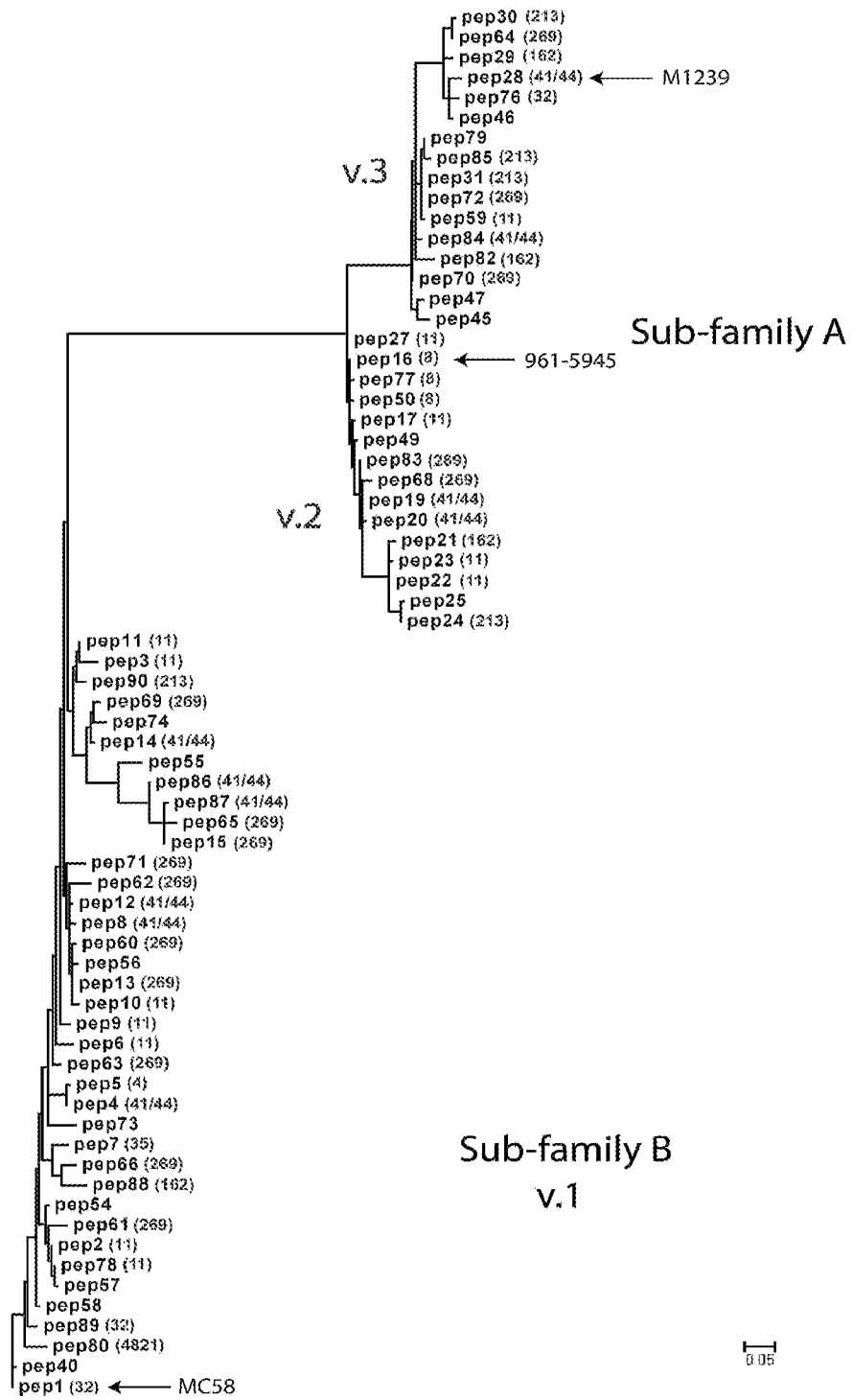
FIG. 3 is a phylogram of fHbp based on 69 unique amino acid sequences.

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "an antigen" includes a plurality of such antigens and reference to "the protein" includes reference to one or more proteins, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF EXEMPLARY EMBODIMENTS OF THE INVENTION

The present disclosure provides chimeric fHbps that can elicit antibodies that are bactericidal for different fHBP variant strains of *N. meningitidis*, and methods of use.

DEFINITIONS

"Factor H Binding Protein" (fHbp), which is also known in the literature as GNA1870, GNA 1870, ORF2086, LP2086 (lipoprotein 2086), and "741" refers to a polypeptide of *N. meningitidis* that is a lipoprotein presented on the surface of the bacterium. *N. meningitidis* strains have been sub-divided into three fHbp variant groups (referred to as variant 1 (v.1), variant 2 (v.2), and variant 3 (v.3) in some reports (Masignani et al. 2003, supra) and Family A and B in other reports (see, e.g., Fletcher et al. 2004 Infect Immun 2088-2100)) based on amino acid sequence variability and immunologic cross-reactivity (Masignani et al. J Exp Med 2003; 197:789-99). Each unique fHbp found in *N. meningitidis* is also assigned a peptide ID according to neisseria.org, as shown in FIGS. 1A-1G (Table 7) and FIGS. 10A-10I (Table 9). For clarity, the present disclosure uses the v.1, v.2 and v.3 terminology. Because the length of variant 2 (v.2) fHbp protein (from strain 8047, peptide ID 77) and variant 3 (v.3) fHBP (from strain M1239, peptide ID 28) differ by −1 and +7 amino acid residues, respectively, from that of MC58 (peptide ID 1), the numbering used to refer to residues for v.2 and v.3 fHbp proteins differs from numbering based on the actual amino acid sequences of these proteins. Thus, for example, reference to a leucine residue (L) at position 166 of the v.2 or v.3 fHBP sequence refers to the residue at position 165 of the v.2 protein and at position 173 in the v.3 protein.

The term "heterologous" or "chimeric" refers to two components that are defined by structures derived from different sources. For example, where "heterologous" is used in the context of a chimeric polypeptide, the chimeric polypeptide includes operably linked amino acid sequences that can be derived from different polypeptides of different phylogenic groupings (e.g., a first component from an α and a second component from a β progenitor amino acid sequences). Similarly, "heterologous" in the context of a polynucleotide encoding a chimeric polypeptide includes operably linked nucleic acid sequence that can be derived from different genes (e.g., a first component from a nucleic acid encoding a fHbp v.1 polypeptide and a second component from a nucleic acid encoding a fHbp v.2 polypeptide). Such chimeric polypeptides as described herein provide for presentation of epitopes in a single polypeptide that are normally found in different polypeptides. Other exemplary "heterologous" nucleic acids include expression constructs in which a nucleic acid comprising a coding sequence is operably linked to a regulatory element (e.g., a promoter) that is from a genetic origin different from that of the coding sequence (e.g., to provide for expression in a host cell of interest, which may be of different genetic origin relative to the promoter, the coding sequence or both). For example, a T7 promoter operably linked to a polynucleotide encoding an fHbp polypeptide or domain thereof is said to be a heterologous nucleic acid. "Heterologous" in the context of recombinant cells can refer to the presence of a nucleic acid (or gene product, such as a polypeptide) that is of a different genetic origin than the host cell in which it is present. For example, a Neisserial amino acid or nucleic acid sequence of one strain is heterologous to a Neisserial host of another strain.

"Derived from" in the context of an amino acid sequence or polynucleotide sequence (e.g., an amino acid sequence "derived from" a v.1 fHbp) is meant to indicate that the polypeptide or nucleic acid has a sequence that is based on that of a reference polypeptide or nucleic acid (e.g., a naturally occurring fHbp protein or encoding nucleic acid), and is not meant to be limiting as to the source or method in which the protein or nucleic acid is made. "Derived from" in the context of bacterial strains is meant to indicate that a strain was obtained through passage in vivo, or in in vitro culture, of a parental strain and/or is a recombinant cell obtained by modification of a parental strain.

"Conservative amino acid substitution" refers to a substitution of one amino acid residue for another sharing chemical and physical properties of the amino acid side chain (e.g., charge, size, hydrophobicity/hydrophilicity). "Conservative substitutions" are intended to include substitution within the following groups of amino acid residues: gly, ala; val, ile, leu; asp, glu; asn, gln; ser, thr; lys, arg; and phe, tyr. Conservative amino acid substitutions in the context of a chimeric fHBP disclosed herein are selected so as to preserve presentation of an epitope of interest. Guidance for such substitutions can be drawn from alignments of amino acid sequences of polypeptides presenting the epitope of interest.

The term "protective immunity" means that a vaccine or immunization schedule that is administered to a mammal induces an immune response that prevents, retards the development of, or reduces the severity of a disease that is caused by Neisseria meningitidis, or diminishes or altogether eliminates the symptoms of the disease. Protective immunity can be accompanied by production of bactericidal antibodies. It should be noted that production of bactericidal antibodies against Neisseria meningitidis is accepted in the field as predictive of a vaccine's protective effect in humans. (Goldschneider et al., 1969, J. Exp. Med. 129:1307; Borrow et al. 2001 Infect Immun. 69:1568).

The phrase "a disease caused by a strain of capsular group B of Neisseria meningitidis" encompasses any clinical symptom or combination of clinical symptoms that are present in an infection of a human with a member of capsular group B of Neisseria meningitidis. These symptoms include but are not limited to: colonization of the upper respiratory tract (e.g. mucosa of the nasopharynx and tonsils) by a pathogenic strain of capsular group B of Neisseria meningitidis, penetration of the bacteria into the mucosa and the submucosal vascular bed, septicemia, septic shock, inflammation, haemmorrhagic skin lesions, activation of fibrinolysis and of blood coagulation, organ dysfunction such as kidney, lung, and cardiac failure, adrenal hemorrhaging and muscular infarction, capillary leakage, edema, peripheral limb ischaemia, respiratory distress syndrome, pericarditis and meningitis.

The phrase "broad spectrum protective immunity" means that a vaccine or immunization schedule elicits "protective immunity" against at least more than one strain (and can be against at least two, at least three, at least four, at least five, against at least eight, or more strains) of Neisseria meningitidis, wherein each of the strains expresses a different fHbp subvariant or fHbp variant. The present disclosure specifically contemplates and encompasses a vaccine or vaccination regimen that confers protection against a disease caused by a member of any capsular group (e.g., A, B, or C), with protection against disease caused by a capsular group B strain of Neisseria meningitidis being of interest due to the epidemiological prevalence of strains causing disease with this capsular group and lack of broadly effective group B vaccines.

The phrase "specifically binds to an antibody" or "specifically immunoreactive with", in the context of an antigen (e.g., a polypeptide antigen) refers to a binding reaction which is based on and/or is probative of the presence of the antigen in a sample which may also include a heterogeneous population of other molecules. Thus, under designated conditions, the specified antibody or antibodies bind(s) to a particular antigen or antigens in a sample and do not bind in a significant amount to other molecules present in the sample. "Specifically binds to an antibody" or "specifically immunoreactive with" in the context of an epitope of an antigen (e.g., an epitope of a polypeptide) refers to a binding reaction which is based on and/or is probative of the presence of the epitope in an antigen (e.g., polypeptide) which may also include a heterogeneous population of other epitopes, as well as a heterogeneous population of antigens. Thus, under designated conditions, the specified antibody or antibodies bind(s) to a particular epitope of an antigen and do not bind in a significant amount to other epitopes present in the antigen and/or in the sample.

The phrase "in a sufficient amount to elicit an immune response" means that there is a detectable difference between an immune response indicator measured before and after administration of a particular antigen preparation. Immune response indicators include but are not limited to: antibody titer or specificity, as detected by an assay such as enzyme-linked immunoassay (ELISA), bactericidal assay, flow cytometry, immunoprecipitation, Ouchter-Lowny immunodiffusion; binding detection assays of, for example, spot, Western blot or antigen arrays; cytotoxicity assays, etc.

A "surface antigen" is an antigen that is present in a surface structure of Neisseria meningitidis (e.g. the outer membrane, capsule, pili, etc.).

"Isolated" refers to an entity of interest that is in an environment different from that in which the compound may naturally occur. "Isolated" is meant to include compounds that are within samples that are substantially enriched for the compound of interest and/or in which the compound of interest is partially or substantially purified."

"Enriched" means that a sample is non-naturally manipulated (e.g., by an experimentalist or a clinician) so that a compound of interest is present in a greater concentration (e.g., at least a three-fold greater, at least 4-fold greater, at least 8-fold greater, at least 64-fold greater, or more) than the concentration of the compound in the starting sample, such as a biological sample (e.g., a sample in which the compound naturally occurs or in which it is present after administration), or in which the compound was made (e.g., as in a bacterial polypeptide, antibody, chimeric polypeptide, and the like)

A "knock-out" or "knockout" of a target gene refers to an alteration in the sequence of the gene that results in a decrease of function of the target gene, e.g., such that target gene expression is undetectable or insignificant, and/or the gene product is not functional or not significantly functional. For example, a "knockout" of a gene involved in LPS synthesis indicates means that function of the gene has been substantially decreased so that the expression of the gene is not detectable or only present at insignificant levels and/or a biological activity of the gene product (e.g., an enzymatic activity) is significantly reduced relative to prior to the modification or is not detectable. "Knock-outs" encompass conditional knock-outs, where alteration of the target gene can occur upon, for example, exposure to a predefined set of conditions (e.g., temperature, osmolarity, exposure to substance that promotes target gene alteration, and the like. A "knock-in" or "knockin" of a target gene refers to a genetic alteration in a host cell genome that that results in an increase in a function provided by the target gene.

"Non-naturally occurring", as used herein, refers to a protein (e.g. fHbp) that is not normally found in nature and is instead artificially produced and/or modified by a human. A non-naturally occurring subject fHbp can be made via chemical synthesis or recombinant methods. For example, "non-naturally occurring chimeras" refers to "man-made chimeras" and encompass fHbp with heterologous components that are not found in nature.

fHbp and fHbp-Encoding Nucleic Acids

Before describing further exemplary chimeric fHbps contemplated by the present disclosure, it is helpful to describe naturally-occurring fHbps.

For convenience and clarity, the native amino acid sequence of the v.1 fHBP of the *N. meningitidis* strain MC58 (peptide ID 1) was arbitrarily selected as a reference sequence for all native v.1, v.2, and v.3 fHbp amino acid sequences, as well as for the chimeric fHbps described herein. Unless otherwise noted, amino acid residue positions are also referred herein with reference to peptide ID 1. The sequence of peptide ID 1 is presented below:

sequences (I) and the variable segments are designated as the N-terminal element, $V_A$, $V_B$, $V_C$, $V_D$, or $V_E$ segments. The amino acid sequence of the conserved sequences are listed in FIG. 4, panel B.

As such, naturally occurring fHbps can be defined by the formula: $I_1$-Nte-$I_2$-$V_A$-$I_3$-$V_B$-$I_4$-$V_C$-$I_5$-$V_D$-$I_6$-$V_E$-$I_7$, wherein "Nte" refers to the N-terminal element, "I" refers to an "invariant" segment, and "V" refers to a variable segment of either an α or a β progenitor type.

As disclosed below in more detail, the non-naturally occurring chimeric fHbps of the present disclosure can be constructed by various combinations of the V segments which are flanked by I segments. The invariant and variable segments which can be used in construction of such chimeric fHbps are described from N-terminus to C-terminus in more detail below. This modular classification can also be found on the Neisseria.org website (neisseria.org/perl/agdbnet/agdbnet.pl?file=nm_fhbp.xml). On the website the progenitor groups α and β as described below are referred to 1 and 2, respectively. For example, $V_A\alpha2$-$V_B\alpha1$-$V_C\beta5$-$V_D\alpha5$-$V_E\alpha8$ becomes A1.2-B1.1-C2.5-D1.5-E1.8.

Invariant Segments fHbps contain amino acid sequences that are conserved among all fHbp amino acid sequences analyzed herein. The conserved sequences flank variable segments that are derived from either the α or β progenitor amino acid sequences. These conserved sequences are referred to herein as "invariant sequences" or "invariant segments", and may serve as sites of recombination in naturally-occurring fHbps. Where these invariant segments are flanked by variable segments, the invariant segments may be referred to as "linker" sequences. While these sequences exhibit amino acid sequence identity between the fHbps disclosed herein, such amino acid sequences may still tolerate certain conservative amino acid substitutions. As such, the term "invariant segment" as used herein should not be construed to be limited to the specific amino acid sequences described herein, and may at least contain one or more conservative amino acid substitutions.

(SEQ ID NO: 1)

CSSGGGGVAADIGAGLADALTAPLDHKDKGLQSLTLDQSVRKNEKLKLAAQGAEKT

YGNGDSLNTGKLKNDKVSRFDFIRQIEVDGQLITLESGEFQVYKQSHSALTAFQTEQIQDSEHSGKMVA

KRQFRIGDIAGEHTSFDKLPEGGRATYRGTAFGSDDAGGKLTYTIDFAAKQGNGKIEHLKSPELNVDLA

AADIKPDGKRHAVISGSVLYNQAEKGSYSLGIFGGKAQEVAGSAEVKTVNGIRHIGLAAKQ

Despite the diversity of variant groups and other classification schemes for the sequences listed in FIGS. 1A-1G (Table 7) and FIGS. 10A-10I (Table 9), a first analysis of 69 unique fHbp sequences and a second analysis of all 275 peptide IDs, as described in the Examples below revealed that several different stretches of amino acid sequences within the fHbps are conserved among all the fHbps analyzed. As shown by the phylogenic studies presented in the Examples section below, these conserved amino acid sequences separate fHbp into modular segments of amino acid sequences that cluster in the phylogram to define two progenitor sequences from which each variable segment may be derived. As illustrated in FIGS. 5-7, each of the variable segments in fHbps can be classified as being of one of the two progenitor amino acid sequences: designated for convenience, α or β.

The nomenclature architecture used to characterize fHbp based on modular segments is illustrated in FIG. 4, panel A. The rectangles in FIG. 4, panel A represent the conserved As illustrated in FIG. 4, the most N-terminal invariant segment found in naturally-occurring fHbps starts at residue 1 and is of the amino acid sequence CSSG (SEQ ID NO:1). Immediately C-terminal to the first invariant segment CSSG (SEQ ID NO:2) ($I_1$) is a variable N-terminal element of about 1 to about 6 glycine or serine residues. The various N-terminal elements are listed in FIG. 1A-1G (Table 7) and FIGS. 10A-10I (Table 9). The second invariant segment ($I_2$) is of the amino acid sequence GG, which is positioned C-terminal to the N-terminal element and starts at residue 6, 7, or 11, depending on the length of the N-terminal element (e.g., in peptide ID 28 of variant 3, $I_2$ starts at residue 11). The next invariant segment, $I_3$, is defined by the amino acid sequence of SRFDF (SEQ ID NO:3) and is positioned at residue 74, C-terminal to $I_2$ and a variable segment. $I_4$, which is C-terminal to $I_3$, is defined by the amino acid sequence GEFQ (SEQ ID NO:4) and is positioned at residue 94. $I_5$ is defined by the amino acid sequence DD and is C-terminal to $I_4$ at residue 159. I₆, positioned C-terminal to I₅, is defined by IEHLK (SEQ ID NO:5) or IEHLE (SEQ ID NO: 6) and starts at residue 180. Lastly, I₇, the most C-terminal invariant segment in naturally-occurring fHbps, starts at residue 252 and is defined by the amino acid sequence of KQ.

The residue position listed above at which each invariant segment starts may be shifted from 1 to 8 residues depending on the length of the N-terminal element and the amino acid sequence of the variable segments. As noted above, for convenience and clarity residue numbering used in reference to non-naturally occurring chimeric fHbps throughout the present disclosure is based on the amino acid sequence numbering of the fHbp of MC58 (peptide ID 1), which is a variant 1 strain.

Based on the sequences analyzed herein, the length of the invariant segments ranges from about 2 amino acid residues to about 5 amino acid residues.

Variable Segments

As noted above, variable segments (V) are flanked by linkers, also referred herein as invariant segments (I). In addition to a variable N-terminal element, there are five variable segments in an fHbp and they are designated from N-terminus to C-terminus as $V_A$, $V_B$, $V_C$, $V_D$, and $V_E$, each flanked by the invariant segments discussed above. As mentioned previously, each of the variable segments may be classified as being of one of the two progenitor amino acid sequences: α or β. For example, $V_A\alpha$ indicates that variable segment A is derived from an α progenitor amino acid sequence while $V_A\beta$ refers to a variable segment A derived from a β progenitor amino acid sequence. In a more specific example, $V_A\alpha1$ denotes that the variable segment A is of the amino acid sequence set forth as Segment ID A.α.1 in FIG. 2A (Table 8, segment A), which is one allele of the α progenitor sequences of variable segment A. As described below, the chimeric fHbp of the present disclosure contain a non-naturally occurring combination of variable segments in which each segment may be independently selected from either an α and a β progenitor type and/or a non-naturally occurring combination of any alleles of the corresponding segment shown in FIGS. 2A-2E, Table 8.

The α and β progenitor variable segments are each defined by certain signature amino acid residues. In addition, the α progenitor variable segments exhibit sequence similarity to fHbp of variant 1 group (e.g. peptide ID 1), while the β progenitor variable segments exhibit sequence similarity to fHbp of variant 3 group (e.g. peptide ID 28). Signature amino acid residues of α or β progenitors for each variable segment are be discussed below.

In addition to being defined by their corresponding amino acid signature sequence, variable segments of the same progenitor type share amino acid sequence identity of at least 80%, at least 85%, at least 90%, at least 95%, and can be 100%. When amino acid sequences of the same variable segments of different progenitor types are compared, the amino acid sequence identity drops by at least 10% to 40%.

See Table 4 in Example section below for amino acid identities within and between sequence groups by segment.

Various alleles for each variable segment and their sequences are presented in FIG. 2A-2E (Table 8) and are described in detail below.

Figure 4:
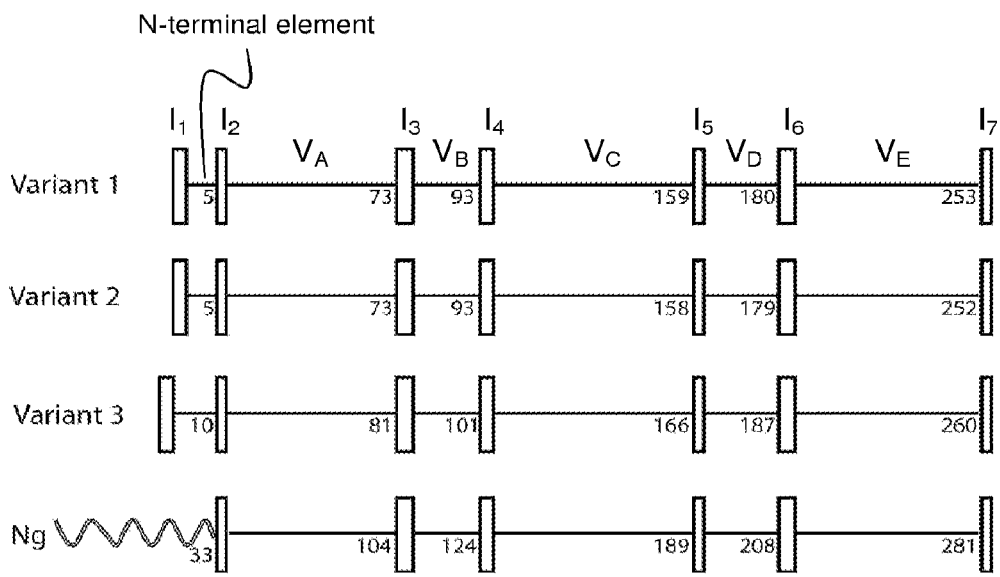
FIG. 4, panel A is a schematic representation of fHbp showing positions of linkers, which are also referred herein as invariant segment (I), shown as vertical rectangles, together with variable segments (V). Panel B is a table listing the amino acid sequence for each invariant segment.

The most N-terminal variable segment is referred to herein as the N-terminal element (Nte) (FIG. 4). The various N-terminal elements found in the fHbps analyzed are listed in FIGS. 1A-1G (Table 7) and also in FIGS. 10A-10I (Table 9). They range in length from 1 to 6 residues of glycine or a combination of glycine and serine.

The variable segment $V_A$ starts at residue 7, C-terminal to I₂, and ends at residue 73, N-terminal to I₃. $V_A$ of an α progenitor ($V_A\alpha$) comprises an amino acid sequence that is about 89 to 100% identical to Segment ID A.α.1 as presented in FIG. 2A (Table 8): V<u>A</u>ADIG<u>AGL</u>A DAL<u>T</u>APLDHK DK SLQSLTLD QSVRK<u>NEKL</u>K L<u>AA</u>QGAEK<u>TY</u> GNGD<u>SLN</u> TGKLKNDK<u>V</u> (SEQ ID NO:15). $V_A\alpha$ is further characterized by signature amino acid residues QSV, bolded in sequence. Certain residues that may have alternative amino acid residues among $V_A\alpha$ of different fHbps are underlined.

$V_A$ of a β progenitor ($V_A\beta$) comprises an amino acid sequence that is about 89 to 100% identical to Segment ID A.β.1 as set forth in FIG. 2A (Table 8): VAADIG<u>T</u>GLA DALTAPLDHK DKGLKSLTLE DSI<u>PQ</u>NGTLT LSAQ-GAEKT<u>F</u> <u>KAGDKDNSLN</u> TGKLKNDK<u>I</u> (SEQ ID NO:67). $V_A\beta$ is further characterized by signature amino acid residues DSI and/or KDN, bolded in sequence. Certain residues that have alternative or deleted amino acid residues among $V_A\beta$ of different fHbps are underlined.

The variable segment $V_B$ starts at residue 79, and ends N-terminal to where I₄ is located, at residue 93. $V_B$ of an α progenitor ($V_B\alpha$) comprises an amino acid sequence that is about 80% to 100% identical to Segment ID B.α.1 as set forth in FIG. 2B (Table 8): <u>IRQ</u>IEV<u>DGQL</u> <u>ITLES</u> (SEQ ID NO:85). $V_B\alpha$ is further characterized by signature amino acid residues IRQ, bolded in the sequence. Certain residues that have alternative or deleted amino acid residues among $V_B\alpha$ of different fHbps are underlined.

$V_B$ of a β progenitor ($V_B\beta$) comprises an amino acid sequence that is about 100% identical to Segment ID B.β.1 as set forth in FIG. 2B (Table 8): VQKIEVDGQT ITLAS (SEQ ID NO:95). $V_B\beta$ is further characterized by signature amino acid residues VQK, bolded in the sequence.

The variable segment $V_C$ starts around residue 98, C-terminal to I₄ and ends at residue 158, N-terminal to I₅. $V_C$ of an α progenitor ($V_C\alpha$) comprises an amino acid sequence that is about 85 to 100% identical to Segment ID C.α.1 as presented in FIG. 2C (Table 8): VYKQS<u>H</u>SALT A<u>L</u>QTEQVQDS E<u>H</u>S GKMVAKR QFRIGDI<u>A</u>GE HTSFDKL<u>P</u>EG GRATYRGTAF <u>G</u>S (SEQ ID NO:96). $V_C\alpha$ is further characterized by signature amino acid residues QDS, bolded in the sequence. Certain residues that have alternative or deleted amino acid residues among $V_C\alpha$ of different fHbps are underlined.

$V_C$ of a β progenitor ($V_C\beta$) comprises an amino acid sequence that is about 93 to 100% identical to Segment ID C.β.1 as presented in FIG. 2C (Table 8): IYKQ<u>D</u>HSAVV ALQIEKINNP DK<u>I</u>DSLINQR SFLVSGLGGE HTAFN-QLPG <u>G</u>KAEYHGKAF S<u>S</u> (SEQ ID NO:152). $V_C\beta$ is further characterized by signature amino acid residues NNP, bolded in sequence. This signature is found in all of $V_C\beta$ amino acid sequences. Certain residues that have alternative or deleted amino acid residues among $V_C\beta$ of different fHbps are underlined.

The variable segment $V_D$ starts at residue 161, C-terminal to I₅ and ends at residue 179, N-terminal to I₆. $V_D$ of an α progenitor ($V_D\alpha$) comprises an amino acid sequence that is about 89 to 100% identical to Segment ID D.α.1 as presented in FIG. 2D (Table 8): A<u>G</u>GKL<u>TY</u>TID FA<u>A</u>KQG<u>H</u>GK (SEQ ID NO:174). $V_D\alpha$ is further characterized by signature amino acid residues AG or AS, of which AG is bolded in sequence. Certain residues that have alternative or deleted amino acid residues among $V_D\alpha$ of different fHbps are underlined.

$V_D$ of a β progenitor ($V_D\beta$) comprises an amino acid sequence that is about 84 to 100% identical to Segment ID D.β.1 as presented in FIG. 2D (Table 8): PNGRLHY<u>S</u>ID FTKKQGYG<u>R</u> (SEQ ID NO:192). $V_D\beta$ is further characterized by signature amino acid residues PN, bolded in sequence. Certain residues that have alternative or deleted amino acid residues among $V_D\beta$ of different fHbps are underlined.

The variable segment $V_E$ starts around residue 185, C-terminal to $I_6$ and ends at residue 253, N-terminal to $I_7$. $V_E$ of an α progenitor ($V_E\alpha$) comprises an amino acid sequence that is about 86 to 100% identical to Segment ID E.α.1 as presented in FIG. 2E (Table 8): SPELNV<u>D</u>LA<u>A</u> <u>A</u>YIKPDE<u>KHH</u> AVISGSVLYN Q<u>A</u>EKGSYSLG IFG<u>GKA</u>QEVA <u>GSAEV</u> <u>KT</u>V<u>N</u>G <u>IR</u>HIGLAA (SEQ ID NO:195). $V_E\alpha$ is further characterized by signature amino acid residues SLGI (SEQ ID NO: 281), bolded in sequence. Certain residues that have alternative or deleted amino acid residues among $V_E\alpha$ of different fHbps are underlined.

$V_E$ of a β progenitor ($V_E\beta$) comprises an amino acid sequence that is about 94 to 100% identical to Segment ID E.β.1 as set forth in FIG. 2E (Table 8): <u>T</u>PEQNV<u>ELAS</u> AELKADEKSH AVILGDTRY<u>G</u> <u>GEEKGTYHLA</u> LFGDRAQEIA GSATVKI<u>REK</u> V<u>H</u>EI<u>G</u>IAG (SEQ ID NO:262). $V_E\beta$ is further characterized by signature amino acid residues HLAL, bolded in sequence. Certain residues that have alternative or deleted amino acid residues among $V_E\beta$ of different fHbps are underlined.

As noted above, for convenience and clarity residue numbering used in reference to non-naturally occurring chimeric fHbps throughout the present disclosure is based on the amino acid sequence numbering of the fHbp of MC58 (peptide ID 1). In addition, the residue position listed above at which each variable segment starts and ends may be shifted from 1 to 8 residues depending on the length of the N-terminal element and the amino acid sequence of the variable segments.

fHbp Modular Groups

Figure 8:
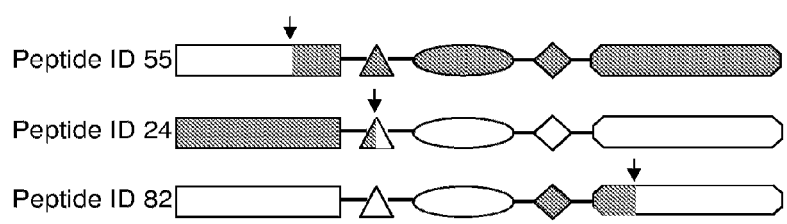
FIG. 8, panel A is a schematic representation of 9 fHbp modular architectures deduced from phylogenic analysis, including the more common 6 modular group types. Gray segments represent α progenitor sequences homologous to peptide ID 1 while white segments represent β progenitor sequences homologous to peptide 28. About 94% of the unique fHbp amino acid sequences analyzed herein belong to one of the first six modular group types (I, II, III, IV, V, and VI). Panel B, Four of the analyzed fHbps are classified as one of three modular architectures shown. The architectures contain junction points within a variable segment, designated by arrows. Panel C is a table listing the amino acid residues at which an α progenitor sequence switches to a β or vice versa ($J_1$, $J_2$, and $J_3$) within a variable segment.
Figure 10:
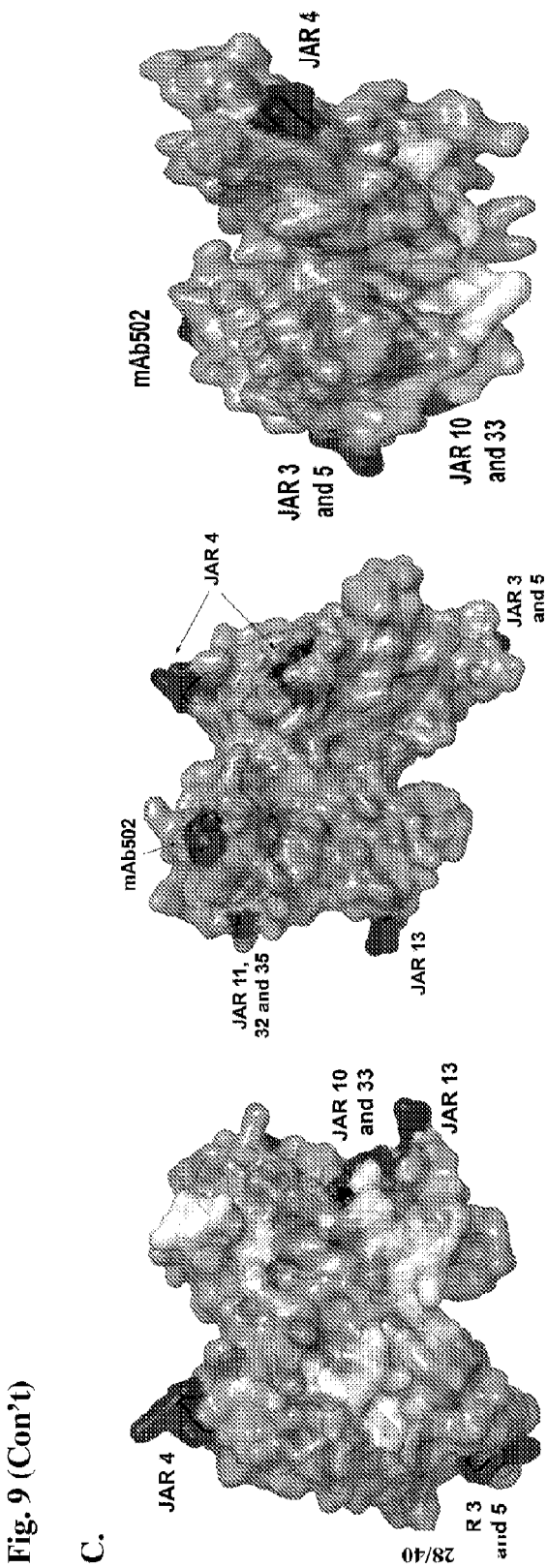
FIG. 10A-10I is Table 9 that lists certain characteristics of unique factor H binding protein variants use in an analysis that include 275 peptide IDs. Sequence identifiers for N-terminal variable sequences are as follows: GGGS (SEQ ID NO: 7), SGSGG (SEQ ID NO: 8), GGGSGG (SEQ ID NO:9), GGGSGS (SEQ ID NO:10), GSGG (SEQ ID NO:11), GGGSGGGG (SEQ ID NO:12), GGGSGGGSGG (SEQ ID NO:13), and GGSGG (SEQ ID NO:14).

Naturally occurring fHbp amino acid sequences can be described according to a modular architecture based on a combination of α or β progenitor segments flanked by invariable segments, as shown in FIG. 1A-1G (Table 7) and FIGS. 10A-10I (Table 9). As described in the Examples below, naturally occurring fHbps exhibit particular combinations of modular segments, and can be classified accordingly into nine modular group types as shown in FIG. 8, where gray variable segments correspond to the α progenitor sequences and white segments correspond to the β progenitor sequences.

The Type I modular group is characterized by variable segments, all of which are derived from the α progenitor amino acid sequences. FHbps classified as belonging to the Type I modular group may be represented by the following formula: $I_1$-Nte-$I_2$-$V_A\alpha$-$I_3$-$V_B\alpha$-$I_4$-$V_C\alpha$-$I_5$-$V_D\alpha$-$I_6$-$V_E\alpha$-$I_7$. An example of a fHbp that is of the Type I modular group is peptide ID 1 from strain MC58. As noted above, peptide ID is from the factor H-binding protein database at Neisseria.org.

The Type II modular group is characterized by variable segments, all of which are derived from the β progenitor. FHbps classified as belonging to the Type II modular group may be represented by the following formula: $I_1$-Nte-$I_2$-$V_A\beta$-$I_3$-$V_B\beta$-$I_4$-$V_C\beta$-$I_5$-$V_D\beta$-$I_6$-$V_E\beta$-$I_7$. An example of a fHbp that is of the Type II modular group is peptide ID 28 from strain M1239. Nearly 60% of the fHbps in FIG. 1A-1G (Table 7) belong in either Type I or II modular group.

Some fHbp, however, have variable segments from both α and β progenitors. One modular group defined by variable segments derived from both progenitors is Type III, in which variable segments $V_A$ and $V_B$ are derived from the α progenitor and the rest of the variable segments from the β progenitor. FHbps classified as belonging to the Type III modular group may be represented by the following formula: $I_1$-Nte-$I_2$-$V_A\alpha$-$I_3$-$V_B\alpha$-$I_4$-$V_C\beta$-$I_5$-$V_D\beta$-$I_6$-$V_E\beta$-$I_7$. One example of a fHbp that belongs to the Type III modular group is peptide ID 22 from strain RM1090.

Another modular group defined by variable segments derived from both progenitors is Type IV. Type IV is a modular group that has a variable segment $V_A$ derived from the β progenitor and the rest of the variable segments from the α progenitor. FHbps classified as belonging to the Type IV modular group may be represented by the following formula: $I_1$-Nte-$I_2$-$V_A\beta$-$I_3$-$V_B\alpha$-$I_4$-$V_C\alpha$-$I_5$-$V_D\alpha$-$I_6$-$V_E\alpha$-$I_7$. One example of a fHbp that belongs to the Type IV modular group is peptide ID 15 from strain NM452.

An additional modular group is Type V, in which the variable segment $V_D$ is derived from the α progenitor and the rest of the variable segments from the β progenitor. FHbps classified as belonging to the Type V modular group may be represented by the following formula: $I_1$-Nte-$I_2$-$V_A\beta$-$I_3$-$V_B\beta$-$I_4$-$V_C\beta$-$I_5$-$V_D\alpha$-$I_6$-$V_E\beta$-$I_7$. One example of a fHbp that belongs to the Type V modular group is peptide ID 79 from strain S3032.

Another modular group set forth in FIG. 8 is Type VI, in which variable segments $V_C$ and $V_E$ are derived from the β progenitor and the rest of the variable segments from the α progenitor. FHbps classified as belonging to the Type VI modular group may be represented by the following formula: $I_1$-Nte-$I_2$-$V_A\alpha$-$I_3$-$V_B\alpha$-$I_4$-$V_C\beta$-$I_5$-$V_D\alpha$-$I_6$-$V_E\beta$-$I_7$. One example of a fHbp that belongs to the Type VI modular group is peptide ID 16 from strain 961-5945.

Another modular group set forth in FIG. 8 is Type VII, in which variable segment $V_E$ are derived from the β progenitor and the rest of the variable segments from the α progenitor. FHbps classified as belonging to the Type VI modular group may be represented by the following formula: $I_1$-Nte-$I_2$-$V_A\alpha$-$I_3$-$V_B\alpha$-$I_4$-$V_C\alpha$-$I_5$-$V_D\alpha$-$I_6$-$V_E\beta$-$I_7$. One fHbp found to have the Type VI modular group is peptide ID 207 from strain 0167/03.

Another modular group set forth in FIG. 8 is Type VIII, in which variable segments $V_B$ is derived from the α progenitor and the rest of the variable segments from the β progenitor. FHbps classified as belonging to the Type VI modular group may be represented by the following formula: $I_1$-Nte-$I_2$-$V_A\beta$-$I_3$-$V_B\alpha$-$I_4$-$V_C\beta$-$I_5$-$V_D\beta$-$I_6$-$V_E\beta$-$I_7$. One fHbp found to have the Type VIII modular group is peptide ID 67 from strain MA-5756.

The last modular group set forth in FIG. 8 is Type IX, in which variable segments $V_B$ and $V_D$ are derived from the α progenitor and the rest of the variable segments from the β progenitor. FHbps classified as belonging to the Type VI modular group may be represented by the following formula: $I_1$-Nte-$I_2$-$V_A\beta$-$I_3$-$V_B\alpha$-$I_4$-$V_C\beta$-$I_5$-$V_D\alpha$-$I_6$-$V_E\beta$-$I_7$. One Example of a fHbp that belongs to the Type IX modular group is peptide ID 175 from strain 19498.

More than 98% of the unique fHbp amino acid sequences analyzed herein belong to one of the first six types of modular groups (I, II, III, IV, V, and VI) described above and schematically presented in FIG. 8. The numbers of unique fHbp that belong to each of the modular groups are also listed on the right of the schematic in FIG. 8.

Four naturally occurring fHbps vary at least slightly from this nomenclature, and do not precisely fit into the first six modular group types set forth in FIG. 8, panel A. These four fHbps "switch" from one progenitor amino acid sequence to another at a residue position that is within a canonical variable segment as described above. As a result, they each contain a heterologous variable segments and their junction points deviate from junction points of the rest of the fHbps found to be at $I_3$, $I_4$, $I_5$, or $I_6$ defined above. See FIG. 8, panel B for the modular architecture of these four fHbps along with the arrow pointing at the junction point for each. However, the junction points of these four naturally occurring fHbps still reside at conserved residue(s) found within the variable segment. See table in FIG. 8, panel C.

One such fHbp is a naturally occurring fHbp derived from strain CDC-1573 (peptide ID 55), in which the junction point where $V_A\beta$ switches to $V_A\alpha$ resides in the middle of $V_A$. The heterologous $V_A$ of peptide ID 55 may be represented as $V_A(\beta \rightarrow \alpha)$, signifying that the variable segment A comprises a β progenitor amino acid sequence starting at the N-terminus and switches to an α progenitor amino acid sequence toward the C-terminus. The junction point ($J_1$) of peptide ID 55 resides at a sequence of AQGAE (SEQ ID NO:278) conserved among all the $V_A$ sequences, which starts at residue position 50. Two other fHbps, which contain junction points that are not in the residue position of $I_3$, $I_4$, $I_5$, or $I_6$, are peptide ID 24 and peptide ID 25, derived from strain M08 240117 and strain 6275, respectively. Their junction points ($J_2$) at which $V_B\alpha$ switches to $V_B\beta$ reside in the middle of $V_B$ (residue 82), at which there is an amino acid sequence of IEV) conserved among all $V_B$s. The $V_B$ of peptide ID 24 and 25 may be represented as $V_B(\alpha\rightarrow\beta)$. Lastly, peptide ID 82 from strain MD1475 switches from $V_E\alpha$ to $V_E\beta$ at residue A196 ($J_3$), which is conserved among all $V_E$. The variable segment E of peptide ID 82 may be represented as $V_E(\alpha\rightarrow\beta)$.

As will be discussed in detail below, chimeric fHbps can be constructed using the invariant and variable segments of this modular architecture to produce amino acid sequences not found in nature.

Nucleic Acids Encoding fHbp Segments fHbp polypeptides, and encoding nucleic acids, from which segments of the chimeric fHbps of the present disclosure can be derived may be from any suitable *N. meningitidis* strain. As is known in the art, *N. meningitidis* strains are divided into serologic groups (capsular groups), serotypes (PorB phenotypes) and subtypes (PorA phenotypes) on the basis of reactions with polyclonal (Frasch, C. E. and Chapman, 1973*, J. Infect. Dis.* 127: 149-154) or monoclonal antibodies that interact with different surface antigens. Capsular grouping traditionally has been based on immunologically detectable variations in the capsular polysaccharide but is being replaced by PCR of genes encoding specific enzymes responsible for the biosynthesis of the structurally different capsular polysaccharides. About 12 capsular groups (including A, B, C, X, Y, Z, 29-E, and W-135) are known. Strains of the capsular groups A, B, C, Y and W-135 account for nearly all meningococcal disease. Serotyping traditionally has been based on monoclonal antibody defined antigenic differences in an outer membrane protein called Porin B (PorB). Antibodies defining about 21 serotypes are currently known (Sacchi et al., 1998*, Clin. Diag. Lab. Immunol.* 5:348). Serosubtyping has been based on antibody defined antigenic variations on an outer membrane protein called Porin A (PorA). Both serotyping and serosubtyping are being replaced by PCR and/or DNA sequencing for identification of genes encoding the variable regions of PorB and PorA, respectively that are associated with mAb reactivity (e.g. Sacchi, Lemos et al., supra; Urwin et al., 1998*, Epidem. and Infect.* 120:257).

While *N. meningitidis* strains of any capsular group may be used, *N. meningitidis* strains of capsular group B are of particular interest as sources from which nucleic acid encoding fHbp and domains thereof are derived.

While the specification provides the amino acid sequence of examples of fHbps from which the chimeric fHbp can be derived, this is not intended to be limiting. For example, the chimeric fHbp can contain amino acid sequences that are at least 80%, at least 85%, at least 90%, or at least 95% identical to an amino acid sequence of a naturally occurring fHbp.

Nucleic acids encoding fHbp polypeptides for use in construction of chimeric fHbps contemplated herein are known in the art. Examples of fHbp polypeptides are described in, for example, WO 2004/048404; Masignani et al. 2003 J Exp Med 197:789-799; Fletcher et al. Infect Immun 2004 2088-2100; Welsch et al. J Immunol 2004 172:5606-5615; and WO 99/57280. Nucleic acid (and amino acid sequences) for fHbp variants and subvariants are also provided in GenBank as accession nos.: NC_003112, GeneID: 904318 (NCBI Ref. NP_274866), peptide ID 1 from *N. meningitidis* strain MC58; AY548371 (AAT01290.1) (from *N. meningitidis* strain CU385); AY548370 (AAT01289.1) (from *N. meningitidis* strain H44/76); AY548377 (AAS56920.1) peptide ID 4 from *N. meningitidis* strain M4105; AY548376 (AAS56919.1) (from *N. meningitidis* strain M1390); AY548375 (AAS56918.1) (from *N. meningitidis* strain NZ98/254); AY548374 (AAS56917.1) (from *N. meningitidis* strain M6190); AY548373 (AAS56916.1) (from *N. meningitidis* strain 4243); and AY548372 (AAS56915.1) (from *N. meningitidis* strain BZ83).

For purposes of identifying relevant amino acid sequences contemplated for use in the chimeric fHbps disclosed herein, it should be noted that the immature fHbp protein includes a leader sequence of about 19 residues. Furthermore, when provided an amino acid sequence the ordinarily skilled person can readily envision the sequences of nucleic acid that can encode for, and provide for expression of, a polypeptide having such an amino acid sequence.

In addition to the specific amino acid sequences and nucleic acid sequences provided herein, the disclosure also contemplates polypeptides and nucleic acids having sequences that are at least 80%, at least 85%, at least 90%, or at least 95% identical in sequence to the amino acid and nucleic acids. The terms "identical" or percent "identity," in the context of two or more polynucleotide sequences, or two or more amino acid sequences, refers to two or more sequences or subsequences that are the same or have a specified percentage of amino acid residues or nucleotides that are the same (e.g., at least 80%, at least 85%, at least 90%, or at least 95% identical over a specified region), when compared and aligned for maximum correspondence over a designated region, e.g., a $V_E$ or a region at least about 40, 45, 50, 55, 60, 65 or more amino acids or nucleotides in length, and can be up to the full-length of the reference amino acid or nucleotide sequence (e.g., a full-length fHbp). The disclosure specifically contemplates both naturally-occurring polymorphisms and synthetically produced amino acid sequences and their encoding nucleic acids.

For sequence comparison, typically one sequence acts as a reference sequence (e.g., a naturally-occurring fHbp polypeptide sequence), to which test sequences are compared. When using a sequence comparison algorithm, test and reference sequences are input into a computer program, sequence coordinates are designated, if necessary, and sequence algorithm program parameters are designated. The sequence comparison algorithm then calculates the percent sequence identity for the test sequence(s) relative to the reference sequence, based on the designated program parameters.

Examples of algorithms that are suitable for determining percent sequence identity are the BLAST and BLAST 2.0 algorithms, which are described in Altschul et al. (1990) J. Mol. Biol. 215: 403-410 and Altschul et al. (1977) Nucleic Acids Res. 25: 3389-3402, respectively. Software for performing BLAST analyses is publicly available through the National Center for Biotechnology Information ("www" followed by ".ncbi.nlm.nih" followed by ".gov"). Further exemplary algorithms include ClustalW (Higgins D., et al. (1994) Nucleic Acids Res 22: 4673-4680), available at "www" followed by ".ebi.ac.uk/Tools/clustalw/index" followed by ".html".

In one embodiment, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine.

Sequence identity between two nucleic acids can also be described in terms of hybridization of two molecules to each other under stringent conditions. The hybridization conditions are selected following standard methods in the art (see, for example, Sambrook, et al., Molecular Cloning: A Laboratory Manual, Second Edition, (1989) Cold Spring Harbor, N.Y.). An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5×Denhardt's solution, 10% dextran sulfate, and 20 mg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, typically at least 90% as stringent as the above specific stringent conditions.

The chimeric fHbps of the present disclosure are described in more detail below in the context of modular architecture described above.

Chimeric Factor H Binding Proteins

The chimeric fHbp of the present disclosure refers to non-naturally occurring chimeric fHbp, including fHbps that may be described by a modular architecture as those set forth in FIG. 8, panels A and B and a modular architecture not shown in FIG. 8, panels A and B. The term "chimeric factor H binding protein" or "chimeric fHbp" refers to a polypeptide comprising, from N-terminus to C-terminus, a group of five variable segments represented by $V_A$, $V_B$, $V_C$, $V_D$, and $V_E$, in which the combination of α/β progenitor segments and/or combination of alleles of which is not found in nature. One example of the chimeric fHbps of the present disclosure can contain at least one or more of the variable segments derived from a different progenitor than at least one other variable segment in the chimeric fHbp. In other words, the chimeric fHbp contains at least one variable segment of an α progenitor amino acid sequences and at least one variable segment of a β progenitor, such that the combination is not found in nature. In another example, the fHbp may also be of a modular architecture shown in FIG. 8, panel A (e.g. modular I or II in which all variable segments are α or β, respectively), in which each segment is of an allele such that the combination of the alleles is not found in nature.

The variable segments may be flanked by invariant segments ($I_2$, $I_3$, $I_4$, $I_5$, $I_6$, $I_7$), which can act as linkers for the variable segments. Accordingly, the chimeric fHbps of the present disclosure can be described by the formula:

$$V_A\text{-}I_3\text{-}V_B\text{-}I_4\text{-}V_C\text{-}I_5\text{-}V_D\text{-}I_6\text{-}V_E$$

wherein each of the variable segments ($V_A$, $V_B$, $V_C$, $V_D$, and $V_E$) can be derived from either an α or a β progenitor amino acid sequence.

Chimeric fHbp can optionally include a leader sequence, e.g., to provide for expression of the chimeric fHbp on a cell surface of a bacterial host cell. Chimeric fHbp may also include about 1, 5, 10, or more residues as an N-terminal element (Nte) and/or C-terminal element (Cte). For example, the Nte may comprise 1, 2, or 6 glycine residues, or about 6 residues of a mixture of glycines and serines following the N-terminal most invariant segment ($I_1$).

In addition, chimeric fHbps of the present disclosure can optionally include an N-terminal element, one or both of invariant segments that flank the N-terminal element, and/or most C-terminal invariant segment ($I_7$). A chimeric fHbp comprising one or more of these optional features can be described by the following formula:

$$I_2\text{-}V_A\text{-}I_3\text{-}V_B\text{-}I_4\text{-}V_C\text{-}I_5\text{-}V_D\text{-}I_6\text{-}V_E;$$

$$Nte\text{-}I_2\text{-}V_A\text{-}I_3\text{-}V_B\text{-}I_4\text{-}V_C\text{-}I_5\text{-}V_D\text{-}I_6\text{-}V_E;$$

$$I_1\text{-}Nte\text{-}I_2\text{-}V_A\text{-}I_3\text{-}V_B\text{-}I_4\text{-}V_C\text{-}I_5\text{-}V_D\text{-}I_6\text{-}V_E;$$

$$V_A\text{-}I_3\text{-}V_B\text{-}I_4\text{-}V_C\text{-}I_5\text{-}V_D\text{-}I_6\text{-}V_E\text{-}I_7;$$

$$I_2\text{-}V_A\text{-}I_3\text{-}V_B\text{-}I_4\text{-}V_C\text{-}I_5\text{-}V_D\text{-}I_6\text{-}V_E\text{-}I_7;$$

$$Nte\text{-}I_2\text{-}V_A\text{-}I_3\text{-}V_B\text{-}I_4\text{-}V_C\text{-}I_5\text{-}V_D\text{-}I_6\text{-}V_E\text{-}I_7;\ \text{and}$$

$$I_1\text{-}Nte\text{-}I_2\text{-}V_A\text{-}I_3\text{-}V_B\text{-}I_4\text{-}V_C\text{-}I_5\text{-}V_D\text{-}I_6\text{-}V_E\text{-}I_7.$$

in which the variable segments ($V_A$, $V_B$, $V_C$, $V_D$, and $V_E$) can be derived from either an α or β progenitor amino acid sequence.

In addition to having various combinations of variable segments, each derived from either an α or β progenitor amino acid sequence, chimeric fHbp of the present disclosure may also contain one or more variable segments that are heterologous with respect to α and β progenitor amino acid sequences. A heterologous variable segment refers to a variable segment that comprises both a contiguous α and a contiguous β progenitor amino acid sequences, with the point at which the amino acid sequence "switches" to the other progenitor sequence referred to herein as a "junction point". E.g. See $V_A$ of peptide ID 55, $V_B$ of peptide ID 24 and ID 25, and $V_E$ of peptide ID 82. Particularly, one or more of the junction points ($J_1$, $J_2$, or $J_3$) within a variable segment described above for peptide ID 55, 24, 25, and 82 may be used to construct a chimeric fHbp having a heterologous variable segment. See table in FIG. 8, panel C for the conserved residues in each variable segment that serve as junction points.

Variable segments of the non-naturally occurring chimeric fHbps of the present disclosure may have an amino acid sequence of at least 80%, at least 85%, at least 90%, at least 95% identical to a corresponding segment in a naturally occurring fHbp, and can be 100% identical in amino acid sequence.

Examples of chimeric fHbps include those containing one or more of the following variable segments. Each segment can be independently selected from any alleles in the corresponding segment shown in FIGS. 2A-2E, Table 8. The variable segments are described in more detail below using certain alleles as examples.

$V_A$ contains a contiguous amino acid sequence that is at least 85%, at least 90%, or at least 95% identical to Segment ID A.α.1 or A.β.1 (SEQ ID NO:15 or NO:67) shown in FIG. 2A (Table 8), e.g., at least 85%, at least 90%, or at least 95% identical to one of the amino acid sequences shown in FIG. 2A (Table 8) for Segment A.

$V_B$ contains a contiguous amino acid sequence that is at least 75%, at least 80%, at least 90%, or at least 95% identical to Segment ID B.α.1 or B.β.1 (SEQ ID NO:85 or NO:95) shown in FIG. 2B (Table 8), e.g., at least 75%, at least 80%, at least 90%, or at least 95% identical to one of the amino acid sequences shown in FIG. 2B (Table 8) for Segment B.

$V_C$ contains s a contiguous amino acid sequence that is at least 80%, at least 85%, at least 90%, or at least 95% identical to Segment ID C.α.1 or C.β.1 (SEQ ID NO:96 or NO:152) shown in FIG. 2C (Table 8), e.g., at least 80%, at least 85%, at least 90%, or at least 95% identical to one of the amino acid sequences shown in FIG. 2C (Table 8) for Segment C.

$V_D$ contains a contiguous amino acid sequence that is at least 80%, at least 85%, at least 90%, or at least 95% identical to Segment ID D.α.1 or D.β.1 (SEQ ID NO:174 or NO:192) shown in FIG. 2D (Table 8), e.g., at least 80%, at least 85%, at least 90%, or at least 95% identical to one of the amino acid sequences shown in FIG. 2D (Table 8) for Segment D.

$V_E$ contains a contiguous amino acid sequence that is at least 80%, at least 85%, at least 90%, or at least 95% identical to Segment ID E.α.1 or E.β.1 (SEQ ID NO:195 or NO:262) shown in FIG. 2E (Table 8), e.g., at least 80%, at least 85%, at least 90%, or at least 95% identical to one of the amino acid sequences shown in FIG. 2E (Table 8) for Segment E.

The variable segments in the chimeric fHbp of the present disclosure may also be of the similar length as the corresponding segments listed in FIG. 2A-2E (Table 8). For example, a variable segment may be no more than about 50, 30, 20, 10, 5, or 1 amino acid residues less or more than one of the corresponding amino acid sequences shown in FIG. 2A-2E (Table 8).

The chimeric fHbps of the present disclosure have a full length amino acid sequence that is not found in a naturally occurring fHbp. Most of the naturally occurring fHbps which contain only α or only β progenitor sequences or combinations thereof fall into one of the following modular groups: I, II, III, IV, V, VI, VII, VIII, or IX (see FIG. 8). Non-naturally occurring fHbps of the present disclosure can also be of a modular group other than I, II, III, IV, V, VI, VII, VIII, or IX. The non-naturally occurring fHbps of the present disclosure can be described by new modular groups encompassing non-naturally occurring amino acid sequences that are built based on the modular architecture described herein. Some examples of chimeric fHbps of the present disclosure are presented below.

Examples of Chimeric fHbps

The chimeric fHbps of the present disclosure encompass those that can be described in terms of one or more of, for example, the invariant and variable segments and their progenitor type, the presence or absence of an epitope(s) specifically bound by a mAb, or any combination of such features that may be present in the chimeric fHbps.

Many combinations may be generated by switching α or β segments in and out of various segments for a different type of modular group. Any alleles of α or β segments can also be independently chosen from those shown FIG. 2A-2E (Table 8). Modular group may also be designed to maintain or include certain antibody epitopes. Certain antibodies are found to be bactericidal against a specific variant of N. meningitidis but not a different variant. If a chimeric fHbp of a modular group contains variable segments that present multiple epitopes, each specific for an antibody bactericidal against a different variant, the chimeric fHbp may be useful to elicit antibodies or immune response effective against a broad spectrum of N. meningitidis. For example, in a case where epitopes for JAR4, JAR3, and JAR32 antibodies are known and are desirable to be incorporated into an fHbp, a chimeric fHbp may be made to comprise $V_A\alpha$, $V_C\alpha$, and $V_D\beta$, where epitopes of JAR4, JAR3, and JAR32 reside, respectively.

For example, a chimeric fHbp may have $V_D$ that is derived from β progenitor sequences while the rest of the variable segments remain as derivations from α progenitor sequences. Such chimeric fHbp comprises variable segments represented as $V_A\alpha$, $V_B\alpha$, $V_C\alpha$, $V_D\beta$, and $V_E\alpha$; and its first and second junction points are at $I_5$ and $I_6$, respectively. In a different example, an fHbp belonging to another modular group encompassing non-naturally occurring chimeric fHbp may contain $V_A\alpha$, $V_B\alpha$, $V_C\alpha$, $V_D\beta$, and $V_E\beta$; and its junction point resides at $I_5$. An additional example of a modular group encompasses non-naturally occurring fHbp that comprises $V_A\alpha$, $V_B\alpha$, $V_C\alpha$, $V_D\alpha$, and $V_E\beta$ as the invariable segments.

Accordingly, examples of non-naturally occurring chimeric fHbps including those described above may be of modular groups represented by the following formula but not limited to:

$$V_A\alpha\text{-}I_3\text{-}V_B\alpha\text{-}I_4\text{-}V_C\alpha\text{-}I_5\text{-}V_D\beta\text{-}I_6\text{-}V_E\alpha;$$

$$V_A\alpha\text{-}I_3\text{-}V_B\alpha\text{-}I_4\text{-}V_C\alpha\text{-}I_5\text{-}V_D\beta\text{-}I_6\text{-}V_E\beta;$$

$$V_A\alpha\text{-}I_3\text{-}V_B\alpha\text{-}I_4\text{-}V_C\alpha\text{-}I_5\text{-}V_D\alpha\text{-}I_6\text{-}V_E\beta;$$

$$V_A\alpha\text{-}I_3\text{-}V_B\alpha\text{-}I_4\text{-}V_C\beta\text{-}I_5\text{-}V_D\text{-}I_6\text{-}V_E\alpha;$$

$$V_A\alpha\text{-}I_3\text{-}V_B\beta\text{-}I_4\text{-}V_C\text{-}I_5\text{-}V_D\text{-}I_6\text{-}V_E;$$

$$V_A\beta\text{-}I_3\text{-}V_B\alpha\text{-}I_4\text{-}V_C\alpha\text{-}I_5\text{-}V_D\alpha\text{-}I_6\text{-}V_E\beta;$$

$$V_A\beta\text{-}I_3\text{-}V_B\alpha\text{-}I_4\text{-}V_C\alpha\text{-}I_5\text{-}V_D\beta\text{-}I_6\text{-}V_E\alpha;$$

$$V_A\beta\text{-}I_3\text{-}V_B\alpha\text{-}I_4\text{-}V_C\beta\text{-}I_5\text{-}V_D\text{-}I_6\text{-}V_E;$$

$$V_A\beta\text{-}I_3\text{-}V_B\beta\text{-}I_4\text{-}V_C\beta\text{-}I_5\text{-}V_D\alpha\text{-}I_6\text{-}V_E\alpha; \text{ or}$$

$$V_A\beta\text{-}I_3\text{-}V_B\beta\text{-}I_4\text{-}V_C\beta\text{-}I_5\text{-}V_D\beta\text{-}I_6\text{-}V_E\alpha;$$

In any group shown above in which a variable segment ($V_A$, $V_B$, $V_C$, $V_D$, or $V_E$) is not followed by an α or a β (e.g. $V_C$, $V_D$, and $V_E$ in the fifth modular group from the top) represents a variable segment that can be derived from either an α or a β progenitor amino acid sequence. The formula may also include a variable N-terminal element, its flanking invariable sequences ($I_1$ and $I_2$), or the most C-terminal invariable segment ($I_7$), omitted in the formula above. As noted above for fHbp of the present disclosure, each variable segment of the fHbps described by the formulas above can be of any allele.

In another example, the chimeric fHbp of the present disclosure also encompass those that contain all α or all β segments, in which each of the segments is of an allele such that the combination of all α or all β allelic segments is not found in nature.

Chimeric fHbp Comprising Heterologous Variable Segment

In certain cases, non-naturally occurring fHbp of the present disclosure may comprise one or more heterologous variable segments. These heterologous variable segment-containing fHbps may also be described by modular architectures other than those set forth in FIG. 8, panel A. Thus, for example, non-naturally occurring fHbp of the present disclosure include those having: a heterologous $V_A(\beta \rightarrow \alpha)$, but do not have α progenitor sequence for all of $V_B$, $V_C$, $V_D$, and $V_E$; a heterologous $V_B(\alpha \rightarrow \beta)$, but do not have a $V_A$ of α progenitor sequence together with $V_C$, $V_D$, and $V_E$ of β progenitor sequence; and a heterologous $V_E(\alpha \rightarrow \beta)$, but do not have β progenitor sequence for all of $V_A$, $V_B$, and $V_C$ together with α progenitor sequence for $V_D$. Exemplary non-naturally occurring fHbps are presented by several examples below, each containing one heterologous variable segment. However, non-naturally occurring fHbps are not limited to the examples, e.g. an fHbp may comprise more than one heterologous variable segment.

For example, a heterologous variable segment-containing fHbp may be one comprising a heterologous $V_A$, such as $V_A(\beta \rightarrow \alpha)$ as exemplified by peptide ID 55, in which not all of $V_B$, $V_C$, $V_D$, and $V_E$ are of the α progenitor amino acid sequences. A non-naturally occurring fHbp may also comprise $V_A(\alpha \rightarrow \beta)$, and in which $V_B$, $V_C$, $V_D$, and $V_E$ are independently selected from α and β. Another exemplary non-naturally occurring fHbp may comprise $V_B(\alpha \rightarrow \beta)$ as exemplified by peptide ID 24, in which $V_A$ is of a α progenitor and not all of $V_C$, $V_D$, and $V_E$ are of the β progenitor amino acid sequences. A non-naturally occurring fHbp may comprise $V_B(\alpha \rightarrow \beta)$, in which $V_A$ is of a β progenitor. A non-naturally occurring fHbp may comprise $V_B(\beta \rightarrow \alpha)$ in which $V_A$, $V_C$, $V_D$, and $V_E$ are independently selected from α and β. Additionally, a non-naturally occurring fHbp may comprise a heterologous $V_E$, such as $V_E(\alpha \rightarrow \beta)$ seen in peptide ID 82, together with $V_D\alpha$, in which not all of $V_A$, $V_B$, $V_C$ are of the β progenitor origin. A non-naturally occurring fHbp may comprise $V_E(\alpha \rightarrow \beta)$ together with $V_D\beta$, in which $V_A$, $V_B$, and $V_C$ are independently selected from α and β. Another example of a non-naturally occurring fHbp that contains a heterologous variable segment is one that comprises $V_E(\beta \rightarrow \alpha)$, in which $V_A$, $V_B$, $V_C$, and $V_D$ are independently selected from α and β.

Chimeric fHbp Having Modified Epitope(s)

The chimeric fHbp of the present disclosure may comprise one or more variable segments in which one or more residues may be mutated relative to the amino acid sequence found in the naturally occurring fHbp so as to introduce an epitope of interest. These epitopes are referred to herein "heterologous epitopes" since they are heterologous to the variable segment in which they reside. Site-directed mutagenesis may be used to introduce one or more heterologous epitopes for a specific antibody of interest into a variable segment that naturally does not contain such epitope. As such, mutations to insert, delete, or substitute one or more amino acid residues may be used to create chimeric fHbp of the present disclosure. Various mutations may be also screened for an fHbp that is effective as vaccines or may be immunogenic to elicit bactericidal antibodies.

For example, an fHbp may comprise an epitope that binds to an antibody JAR13, normally found in $V_E$ of a β progenitor sequence and not in an α progenitor sequence. To generate a fHbp that includes $V_E\alpha$ while at the same time contains the JAR13 epitope, the epitope may be introduced into a $V_E\alpha$ sequence. Selective mutation allows the amino acid sequence of $V_E$ to be derived from the α progenitor type except for a specific site for the JAR13 epitope. As such, regardless of the amino acid sequence used to derive the sequences of the variable segments of the chimeric fHbp, epitopes may be introduced into the corresponding variable segment to include or maintain regions of desired antigenicity.

Chimeric fHbps also encompass chimeric fHbp that contain two or more epitopes that elicit antibodies that, when both are bound to their respective epitopes, exhibit enhanced bactericidal activity against *N. meningitidis* than when either one is bound alone. For example, the combination of JAR 4 and JAR 5 mAbs exhibit higher level of bactericidal activity against *N. meningitidis* than when each is used alone in a human-complement-mediated assay. Chimeric fHbp can be designed so as to ensure that such epitopes are maintained or to introduce such combination of epitopes. Chimeric fHbps can also be designed to include an epitope(s) that elicits antibodies that, when bound to fHbp, inhibit fH binding. For example, when the epitopes bound by the monoclonal antibodies JAR3, JAR 5, JAR11, or JAR32/35 are bound by antibody, binding of fHbp to fH is inhibited. Thus, the presence of such fH-binding epitopes in the chimeric fHbp polypeptides can provide for production of antibodies that can facilitate protection through this pathway.

The antibodies that bind epitopes that may be of interest to introduce or maintain in the segments of a chimeric fHbp are disclosed in WO 09/114,485, the disclosure of which is incorporated in its entirety by reference. Certain epitopes of interest with a corresponding JAR mAbs are presented in the table 1 below and pointed out in FIG. 9, panel C.

TABLE 1

Antibodies and their corresponding epitopes.

| (Immunogen) Antibody | Reactive Residue(s) | fHbp variant bound |
|---|---|---|
| mAb 502 | R204 | 1 |
| JAR 3 | G121 and K122 | 1 |
| JAR 4 | DHK (starting at 25); YGN (starting at 57) | v.1, v.2 (high reactivity) and v.3 (lower reactivity) |
| JAR 5 | G121 and K122 | v.1 |
| JAR 10 | K180 and E192 | v.1 (subset), v.2 (subset) and v. 3 (subset) |
| JAR 11 | A174 | v.2 (subset) and v.3 (subset) |
| JAR 13 | S216 | v. 2 (subset) and v.3 (all) |
| JAR 32 | K174 | v. 3 and v.2 (subset) |
| JAR 33 | E180 and R192 | v. 3 and v.2 (subset) |
| JAR 35 | K174 | v. 3 and v.2 (subset) |

Other Features of Interest

Chimeric polypeptides described herein can include additional heterologous amino acid sequences, e.g., to provide an N-terminal methionine or derivative thereof (e.g., pyroglutamate) as a result of expression in a bacterial host cell (e.g., *E. coli*) and/or to provide a chimeric polypeptide having a fusion partner at its N-terminus or C-terminus. Fusion partners of interest include, for example, glutathione-S-transferase (GST), maltose binding protein (MBP), $His_6$-tag, and the like, as well as leader peptides from other proteins, particularly lipoproteins. Fusion partners can provide for additional features, such as in facilitating isolation and purification of the chimeric polypeptide.

Native fHbp usually contains an N-terminal cysteine to which a lipid moiety can be covalently attached. This cysteine residue is usually lipidated in the naturally-occurring protein, and can be lipidated in the chimeric fHbps disclosed herein. Thus, in the amino acid sequences described herein (including those presented in any Sequence Listing), reference to "cysteine" or "C" at this position specifically includes reference to both an unmodified cysteine as well as to a cysteine that is lipidated (e.g., due to post-translational modification). Thus, the chimeric fHbp can be lipidated or non-lipidated. Methods for production of lipidated proteins in vitro, (see, e.g., Andersson et al., 2001 J. Immunological Methods 255

(1-2):135-48) or in vivo are known in the art. For example, lipidated fHbp previously has been purified from the membrane fraction of *E. coli* protein by detergent extraction (Fletcher et al., 2004 Infection and Immunity 72(4):2088-100), which method may be adapted for the production of lipidated chimeric fHbp. Lipidated proteins may be of interest as such can be more immunogenic than soluble protein (see, e.g., Fletcher et al., 2004 Infection and Immunity 72(4):2088-100).

Nucleic Acid Encoding Chimeric fHBP

The chimeric fHbp can be generated using recombinant techniques to manipulate nucleic acids of different fHbps known in the art to provide constructs encoding a chimeric fHbp of interest. As noted above, nucleic acids encoding a variety of different v.1, v.2, and v.3 fHbps of *N. meningitidis* are available in the art, and their nucleotide sequences are known.

Amino acid and nucleic acid sequences of the naturally occurring fHbps are provided in FIG. 2A-2E (Table 5) and available in the art. It will be appreciated that the nucleotide sequences encoding the chimeric fHbps can be modified so as to optimize the codon usage to facilitate expression in a host cell of interest (e.g., *E. coli, N. meningitidis*, human (as in the case of a DNA-based vaccine), and the like). Methods for production of codon optimized sequences are known in the art.

Methods of Screening

The present disclosure also features methods of screening for an immunogenic composition comprising a chimeric fHbp, vaccine against bacterial pathogens, antibodies and nucleic acid encoding the same. The methods may involve evaluating the ability of a specific chimeric fHbp to elicit bactericidal antibodies and/or to provide a broad spectrum immunity against bacterial pathogens. The methods can involve assessing the ability of antibodies elicited by immunization with a chimeric fHbp of the present disclosure to inhibit fH binding to fHbp of *N. meningitidis* of diverse variant groups and/or to elicit bactericidal activity. The antibody may be elicited in a host animal immunized with an immunogenic composition comprising a chimeric fHbp of the present disclosure or screened in a phage display library for its specific affinity to a candidate chimeric fHbp. Among other aspects, the methods find particular use in identifying and/or evaluating antibody having bactericidal and/or anti-neoplastic activity.

In one embodiment, a method of evaluating binding of an antibody to a bacterial cell is provided. The method comprises: (a) immunizing a host animal with a composition comprising a chimeric fHbp of the present disclosure, (b) isolating antibodies from the host animal that have binding affinity to the chimeric fHbp, (c) contacting a bacterial cell with the isolated antibodies; and (d) assessing binding of the antibody to the bacterial cell. Additional steps may include assessing the competitive binding of the antibody to fHbp with human factor H; assessing the bactericidal activity against a bacterial pathogen when incubated in vitro with complement; or assessing the ability of the antibody administered to an animal to confer passive protection against infection. In some embodiments, the antibody is in an antibody population, and the method further comprises: (c) isolating one or more antibodies of the antibody population that bind the bacterial cell. A featured aspect is isolated antibody that is bactericidal against the bacterial cell, which may include, for example, complement-mediated bactericidal activity and/or opsonophagocytic activity capable of decreasing the viability of the bacteria in human blood. The subject method may also include assessing the susceptibility of a host animal administered with a vaccine comprising a chimeric fHbp to a bacterial pathogen.

Bacterial pathogen of particular interest are *N. meningitidis* of any or all fHbp variant groups, of diverse capsular groups, such as *N. meningitidis* Serogroup B, *N. meningitidis* Serogroup C, *N. meningitidis* Serogroup X, *N. meningitidis* Serogroup Y, *N. meningitidis* Serogroup W-135, and the like.

Methods of Production

Chimeric fHbps can be produced by any suitable method, including recombinant and non-recombinant methods (e.g., chemical synthesis). Where the chimeric fHbp is produced using recombinant techniques, the methods can involve any suitable construct and any suitable host cell, which can be a prokaryotic or eukaryotic cell, usually a bacterial or yeast host cell, more usually a bacterial cell. Methods for introduction of genetic material into host cells include, for example, transformation, electroporation, conjugation, calcium phosphate methods and the like. The method for transfer can be selected so as to provide for stable expression of the introduced chimeric fHbp-encoding nucleic acid. The chimeric fHbp-encoding nucleic acid can be provided as an inheritable episomal element (e.g., plasmid) or can be genomically integrated.

Suitable vectors for transferring chimeric fHbp-encoding nucleic acid can vary in composition. Integrative vectors can be conditionally replicative or suicide plasmids, bacteriophages, and the like. The constructs can include various elements, including for example, promoters, selectable genetic markers (e.g., genes conferring resistance to antibiotics (for instance kanamycin, erythromycin, chloramphenicol, or gentamycin)), origin of replication (to promote replication in a host cell, e.g., a bacterial host cell), and the like. The choice of vector will depend upon a variety of factors such as the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal. The choice of appropriate vector is well within the skill of the art. Many such vectors are available commercially.

The vector can be an expression vector based on episomal plasmids containing selectable drug resistance markers and elements that provide for autonomous replication in different host cells (e.g., in both *E. coli* and *N. meningitidis*). One example of such a "shuttle vector" is the plasmid pFP10 (Pagotto et al. Gene 2000 244:13-19).

Constructs can be prepared by, for example, inserting a polynucleotide of interest into a construct backbone, typically by means of DNA ligase attachment to a cleaved restriction enzyme site in the vector. Alternatively, the desired nucleotide sequence can be inserted by homologous recombination or site-specific recombination. Typically homologous recombination is accomplished by attaching regions of homology to the vector on the flanks of the desired nucleotide sequence, while site-specific recombination can be accomplished through use of sequences that facilitate site-specific recombination (e.g., cre-lox, att sites, etc.). Nucleic acid containing such sequences can be added by, for example, ligation of oligonucleotides, or by polymerase chain reaction using primers comprising both the region of homology and a portion of the desired nucleotide sequence.

Vectors can provide for extrachromosomal maintenance in a host cell or can provide for integration into the host cell genome. Vectors are amply described in numerous publications well known to those in the art, including, e.g., Short Protocols in Molecular Biology, (1999) F. Ausubel, et al., eds., Wiley & Sons. Vectors may provide for expression of the nucleic acids encoding a chimeric fHBP, may provide for propagating the subject nucleic acids, or both.

Examples of vectors that may be used include but are not limited to those derived from recombinant bacteriophage DNA, plasmid DNA or cosmid DNA. For example, plasmid vectors such as pBR322, pUC 19/18, pUC 118, 119 and the M13 mp series of vectors may be used. pET21 is also an expression vector that may be used. Bacteriophage vectors may include λgt10, λgt11, λgt18-23, λZAP/R and the EMBL series of bacteriophage vectors. Further vectors that may be utilized include, but are not limited to, pJB8, pCV 103, pCV 107, pCV 108, pTM, pMCS, pNNL, pHSG274, COS202, COS203, pWE15, pWE16 and the charomid 9 series of vectors.

For expression of a chimeric fHbp of interest, an expression cassette may be employed. Thus, the present disclosure provides a recombinant expression vector comprising a subject nucleic acid. The expression vector provides transcriptional and translational regulatory sequences, and may provide for inducible or constitutive expression, where the coding region is operably linked under the transcriptional control of the transcriptional initiation region, and a transcriptional and translational termination region. These control regions may be native to an fHbp from which the chimeric fHbp is derived, or may be derived from exogenous sources. In general, the transcriptional and translational regulatory sequences may include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7, and the like).

Expression vectors generally have convenient restriction sites located near the promoter sequence to provide for the insertion of nucleic acid sequences encoding proteins of interest. A selectable marker operative in the expression host may be present to facilitate selection of cells containing the vector. In addition, the expression construct may include additional elements. For example, the expression vector may have one or two replication systems, thus allowing it to be maintained in organisms, for example in mammalian or insect cells for expression and in a prokaryotic host for cloning and amplification. In addition the expression construct may contain a selectable marker gene to allow the selection of transformed host cells. Selection genes are well known in the art and will vary with the host cell used.

It should be noted that chimeric fHbp of the present disclosure may comprise additional elements, such as a detectable label, e.g., a radioactive label, a fluorescent label, a biotin label, an immunologically detectable label (e.g., an HA tag, a poly-Histidine tag) and the like. Additional elements of chimeric fHbp can be provided to facilitate isolation (e.g., biotin tag, immunologically detectable tag) through various methods (e.g., affinity capture, etc.). Chimeric fHbp can optionally be immobilized on a support through covalent or non-covalent attachment.

Isolation and purification of chimeric fHbp can be accomplished according to methods known in the art. For example, chimeric fHbp can be isolated from a lysate of cells genetically modified to express a chimeric fHbp, or from a synthetic reaction mix, by immunoaffinity purification, which generally involves contacting the sample with an anti-chimeric fHbp antibody (e.g., an anti-chimeric fHBP mAb, such as a JAR 5 mAb or other appropriate JAR mAb described herein), washing to remove non-specifically bound material, and eluting specifically bound chimeric fHbp. Isolated chimeric fHbp can be further purified by dialysis and other methods normally employed in protein purification methods. In one embodiment, the chimeric fHbp can be isolated using metal chelate chromatography methods.

Host Cells

Any of a number of suitable host cells can be used in the production of chimeric fHbp. In general, the chimeric fHbp described herein may be expressed in prokaryotes or eukaryotes, usually bacteria, more usually *E. coli* or *Neisseria* (e.g., *N. meningitidis*) in accordance with conventional techniques. Thus, the present disclosure further provides a genetically modified host cell, which contains a nucleic acid encoding a chimeric fHBP. Host cells for production (including large scale production) of a chimeric fHBP can be selected from any of a variety of available host cells. Exemplary host cells for expression include those of a prokaryotic or eukaryotic unicellular organism, such as bacteria (e.g., *Escherichia coli* strains), yeast (e.g., *S. cerevisiae, Pichia* spp., and the like), and may include host cells originally derived from a higher organism such as insects, vertebrates, particularly mammals, (e.g. CHO, HEK, and the like). Generally bacterial host cells and yeast are of particular interest for chimeric fHBP production.

Chimeric fHbps can be prepared in substantially pure or substantially isolated form (i.e., substantially free from other *Neisserial* or host cell polypeptides) or substantially isolated form. In certain embodiments, the chimeric fHbp is present in a composition that is enriched for the polypeptide relative to other components that may be present (e.g., other polypeptides or other host cell components). Purified chimeric fHbp can be provided such that the polypeptide is present in a composition that is substantially free of other expressed polypeptides, e.g., less than 90%, usually less than 60% and more usually less than 50% of the composition is made up of other expressed polypeptides.

Host Cells for Vesicle Production

Where a chimeric fHbp is to be provided in a membrane vesicle (as discussed in more detail below), a *Neisserial* host cell is genetically modified to express a chimeric fHbp. Any of a variety of *Neisseria* spp. strains can be modified to produce a chimeric fHbp, and, optionally, which produce or can be modified to produce other antigens of interest, such as PorA, can be used in the methods disclosed herein.

Methods and vectors to provide for genetic modification of *Neisserial* strains and expression of a desired polypeptide are known in the art. Examples of vectors and methods are provided in WO 02/09746 and O'Dwyer et al. Infect Immun 2004; 72:6511-80. Strong promoters, particularly constitutive strong promoters are of particular interest. Exemplary promoters include the promoters of porA, porB, lbpB, tbpB, p110, hpuAB, lgtF, opa, p110, 1st, hpuAB. and rmp.

Pathogenic *Neisseria* spp. or strains derived from pathogenic *Neisseria* spp., particularly strains pathogenic for humans or derived from strains pathogenic or commensal for humans, are of particular interest for use in membrane vesicle production. Examples of *Neisserial* spp. include *N. meningitidis, N. flavescens, N. gonorrhoeae, N. lactamica, N. polysaccharea, N. cinerea, N. mucosa, N. subflava, N. sicca, N. elongata*, and the like.

*N. meningitidis* strains are of particular interest for genetic modification to express a chimeric fHbp and for use in vesicle production. The strain used for vesicle production can be selected according to a number of different characteristics that may be desired. For example, the strain may be selected according to: a desired PorA type (a "serosubtype", as described above), capsular group, serotype, and the like;

decreased capsular polysaccharide production; and the like. For example, the production strain can produce any desired PorA polypeptide, and may express one or more PorA polypeptides (either naturally or due to genetic engineering). Examples of strains include those that produce a PorA polypeptide which confers a serosubtype of P1.7,16; P1.19, 15; P1.7,1; P1.5,2; P1.22a,14; P1.14; P1.5,10; P1.7,4; P1.12, 13; as well as variants of such PorA polypeptides which may or may not retain reactivity with conventional serologic reagents used in serosubtyping. Also of interest are PorA polypeptides characterized according to PorA variable region (VR) typing (see, e.g., Russell et al. Emerging Infect Dis 2004 10:674-678; Sacchi C T, et al, Clin Diagn Lab Immunol 1998; 5:845-55; Sacchi et al, J. Infect Dis 2000; 182:1169-1176). A substantial number of distinct VR types have been identified, which can be classified into VR1 and VR2 family "prototypes". A web-accessible database describing this nomenclature and its relationship to previous typing schemes is found at neisseria.org/nm/typing/pora. Alignments of exemplary PorA VR1 and VR2 types are provided in Russell et al. Emerging Infect Dis 2004 10:674-678.

Alternatively or in addition, the production strain can be a capsule deficient strain. Capsule deficient strains can provide vesicle-based vaccines that provide for a reduced risk of eliciting a significant autoantibody response in a subject to whom the vaccine is administered (e.g., due to production of antibodies that cross-react with sialic acid on host cell surfaces). "Capsule deficient" or "deficient in capsular polysaccharide" as used herein refers to a level of capsular polysaccharide on the bacterial surface that is lower than that of a naturally-occurring strain or, where the strain is genetically modified, is lower than that of a parental strain from which the capsule deficient strain is derived. A capsule deficient strain includes strains that are decreased in surface capsular polysaccharide production by at least 10%, 20%, 25%, 30%, 40%, 50%, 60%, 75%, 80%, 85%, 90% or more, and includes strains in which capsular polysaccharide is not detectable on the bacterial surface (e.g., by whole cell ELISA using an anti-capsular polysaccharide antibody).

Capsule deficient strains include those that are capsule deficient due to a naturally-occurring or recombinantly-generated genetic modification. Naturally-occurring capsule deficient strains (see, e.g., Dolan-Livengood et al. J. Infect. Dis. (2003) 187(10):1616-28), as well as methods of identifying and/or generating capsule-deficient strains (see, e.g., Fisseha et al. (2005) Infect. Immun. 73(7):4070-4080; Stephens et al. (1991) Infect Immun 59(11):4097-102; Frosch et al. (1990) Mol. Microbiol. 1990 4(7):1215-1218) are known in the art.

Modification of a *Neisserial* host cell to provide for decreased production of capsular polysaccharide may include modification of one or more genes involved in capsule synthesis, where the modification provides for, for example, decreased levels of capsular polysaccharide relative to a parent cell prior to modification. Such genetic modifications can include changes in nucleotide and/or amino acid sequences in one or more capsule biosynthesis genes rendering the strain capsule deficient (e.g., due to one or more insertions, deletions, substitutions, and the like in one or more capsule biosynthesis genes). Capsule deficient strains can lack or be non-functional for one or more capsule genes.

Of particular interest are strains that are deficient in sialic acid biosynthesis. Such strains can provide for production of vesicles that have reduced risk of eliciting anti-sialic acid antibodies that cross-react with human sialic acid antigens, and can further provide for improved manufacturing safety. Strains having a defect in sialic acid biosynthesis (due to either a naturally occurring modification or an engineered modification) can be defective in any of a number of different genes in the sialic acid biosynthetic pathway. Of particular interest are strains that are defective in a gene product encoded by the N-acetylglucosamine-6-phosphate 2-epimerase gene (known as synX AAF40537.1 or siaA AAA20475), with strains having this gene inactivated being of especial interest. For example, in one embodiment, a capsule deficient strain is generated by disrupting production of a functional synX gene product (see, e.g., Swartley et al. (1994) J. Bacteriol. 176(5):1530-4).

Capsule-deficient strains can also be generated from naturally-occurring strains using non-recombinant techniques, e.g., by use of bactericidal anti-capsular antibodies to select for strains that reduced in capsular polysaccharide.

Where the disclosure involves use of two or more strains (e.g., to produce antigenic compositions containing a chimeric fHbp-presenting vesicles from different strains), the strains can be selected so as to differ in one or more strain characteristics, e.g., to provide for vesicles that differ in the chimeric fHbp used, PorA, and the like.

Preparation of Vesicles

The antigenic compositions contemplated by the present disclosure generally include vesicles prepared from *Neisserial* cells that express a chimeric fHbp. As referred to herein "vesicles" is meant to encompass outer membrane vesicles as well as microvesicles (which are also referred to as blebs).

The antigenic composition can contain outer membrane vesicles (OMV) prepared from the outer membrane of a cultured strain of *Neisseria meningitidis* spp. genetically modified to express a chimeric fHbp. OMVs may be obtained from *Neisseria meningitidis* grown in broth or solid medium culture, preferably by separating the bacterial cells from the culture medium (e.g. by filtration or by a low-speed centrifugation that pellets the cells, or the like), lysing the cells (e.g. by addition of detergent, osmotic shock, sonication, cavitation, homogenization, or the like) and separating an outer membrane fraction from cytoplasmic molecules (e.g. by filtration; or by differential precipitation or aggregation of outer membranes and/or outer membrane vesicles, or by affinity separation methods using ligands that specifically recognize outer membrane molecules; or by a high-speed centrifugation that pellets outer membranes and/or outer membrane vesicles, or the like); outer membrane fractions may be used to produce OMVs.

The antigenic composition can contain microvesicles (MV) (or "blebs") containing chimeric fHbp, where the MV or blebs are released during culture of a *Neisseria meningitidis* strain genetically modified to express a chimeric fHbp. For example, MVs may be obtained by culturing a strain of *Neisseria meningitidis* in broth culture medium, separating whole cells from the broth culture medium (e.g. by filtration, or by a low-speed centrifugation that pellets only the cells and not the smaller blebs, or the like), and then collecting the MVs that are present in the cell-free culture medium (e.g. by filtration, differential precipitation or aggregation of MVs, or by a high-speed centrifugation that pellets the blebs, or the like). Strains for use in production of MVs can generally be selected on the basis of the amount of blebs produced in culture (e.g., bacteria can be cultured in a reasonable number to provide for production of blebs suitable for isolation and administration in the methods described herein). An example of a strain that produces high levels of blebs is described in PCT Publication No. WO 01/34642. In addition to bleb production, strains for use in MV production may also be selected on the basis of NspA production, where strains that produce higher levels of NspA may be of particular interest (for

*ingitidis* strains having different NspA production levels, see, e.g., Moe et al. (1999 Infect. Immun. 67: 5664). Other strains of interest for use in production of blebs include strains having an inactivated GN33 gene, which encodes a lipoprotein required for cell separation, membrane architecture and virulence (see, e.g., Adu-Bobie et al. Infect Immun 2004; 72:1914-1919).

The antigenic compositions of the present disclosure can contain vesicles from one strain, or from 2, 3, 4, 5 or more strains, which strains may be homologous or heterologous, usually heterologous, to one another. For example, the strains may be homologous or heterologous with respect to PorA. The vesicles can also be prepared from strains that express more than one chimeric fHbp (e.g., 1, 2, 3, or more chimeric fHbp) which may be composed of fHbp amino acid sequences from different variants (v.1, v.2, or v.3) or subvariants (e.g., a subvariant of v.1, v.2, or v.3).

The antigenic compositions can contain a mixture of OMVs and MVs presenting the same or different chimeric fHbps, where the chimeric fHbps may optionally present epitopes from different combinations of fHbp variants and/or subvariants and where the OMVs and/or MVs may be from the same or different strains. Vesicles from different strains can be administered as a mixture, or can be administered serially. The antigenic composition may contain vesicles containing one or more different chimeric fHbp, in which the vesicles and the fHbp are both derived from the same host cells. The composition can also be made from vesicles and fHbp that are derived from different host cells so that the vesicles and fHbp are admixed after their separate purification.

Where desired (e.g., where the strains used to produce vesicles are associated with endotoxin or particular high levels of endotoxin), the vesicles are optionally treated to reduce endotoxin, e.g., to reduce toxicity following administration. Although less desirable as discussed below, reduction of endotoxin can be accomplished by extraction with a suitable detergent (for example, BRIJ-96, sodium deoxycholate, sodium lauroylsarcosinate, EMPIGEN BB, TRITON X-100, TWEEN 20 (sorbitan monolaurate polyoxyethylene), TWEEN 80, at a concentration of 0.1-10%, preferably 0.5-2%, and SDS). Where detergent extraction is used, it is preferable to use a detergent other than deoxycholate.

The vesicles of the antigenic compositions can be prepared without detergent, e.g., without use of deoxycholate. Although detergent treatment is useful to remove endotoxin activity, it may deplete the native fHbp lipoprotein and/or chimeric fHbp (including lipidated chimeric fHbp) by extraction during vesicle production. Thus it may be particularly desirable to decrease endotoxin activity using technology that does not require a detergent. In one approach, strains that are relatively low producers of endotoxin (lipopolysaccharide, LPS) are used so as to avoid the need to remove endotoxin from the final preparation prior to use in humans. For example, the vesicles can be prepared from *Neisseria* mutants in which lipooligosaccharide or other antigens that may be undesirable in a vaccine (e.g. Rmp) is reduced or eliminated.

Vesicles can be prepared from *N. meningitidis* strains that contain genetic modifications that result in decreased or no detectable toxic activity of lipid A. For example, such strain can be genetically modified in lipid A biosynthesis (Steeghs et al. Infect Immun 1999; 67:4988-93; van der Ley et al. Infect Immun 2001; 69:5981-90; Steeghs et al. J Endotoxin Res 2004; 10:113-9; Fissha et al, Infect Immun 73:4070, 2005). The immunogenic compositions may be detoxified by modification of LPS, such as downregulation and/or inactivation of the enzymes encoded by 1pxL1 or 1pxL2, respectively. Production of a penta-acylated lipid A made in 1pxL1 mutants indicates that the enzyme encoded by 1pxL1 adds the C12 to the N-linked 3-OH C14 at the 2' position of GlcN II. The major lipid A species found in 1pxL2 mutants is tetra-acylated, indicating the enzyme encoded by 1pxL2 adds the other C12, i.e., to the N-linked 3-OH C14 at the 2 position of GlcN I. Mutations resulting in a decreased (or no) expression of these genes (or decreased or no activity of the products of these genes) result in altered toxic activity of lipid A (van der Ley et al. 2001; 69:5981-90). Tetra-acylated (1pxL2 mutant) and penta acylated (1pxL1 mutant) lipid A are less toxic than the wild-type lipid A. Mutations in the lipid A 4'-kinase encoding gene (1pxK) also decrease the toxic activity of lipid A. Of particular interest for use in production of vesicles (e.g., MV or OMV) are *N. meningitidis* strains genetically modified so as to provide for decreased or no detectable functional LpxL1-encoded protein. Such vesicles provide for reduced toxicity as compared to *N. meningitidis* strains that are wild-type for LPS production, while retaining immunogenicity of chimeric fHbp.

LPS toxic activity can also be altered by introducing mutations in genes/loci involved in polymyxin B resistance (such resistance has been correlated with addition of aminoarabinose on the 4' phosphate of lipid A). These genes/loci could be pmrE that encodes a UDP-glucose dehydrogenase, or a region of antimicrobial peptide-resistance genes common to many enterobacteriaciae which could be involved in aminoarabinose synthesis and transfer. The gene pmrF that is present in this region encodes a dolicol-phosphate manosyl transferase (Gunn J. S., Kheng, B. L., Krueger J., Kim K., Guo L., Hackett M., Miller S. I. 1998. Mol. Microbiol. 27: 1171-1182).

Mutations in the PhoP-PhoQ regulatory system, which is a phospho-relay two component regulatory system (e.g., PhoP constitutive phenotype, PhoPc), or low Mg++ environmental or culture conditions (that activate the PhoP-PhoQ regulatory system) lead to the addition of aminoarabinose on the 4'-phosphate and 2-hydroxymyristate replacing myristate (hydroxylation of myristate). This modified lipid A displays reduced ability to stimulate E-selectin expression by human endothelial cells and TNF secretion from human monocytes.

Polymyxin B resistant strains are also suitable for use, as such strains have been shown to have reduced LPS toxicity (see, e.g., van der Ley et al. 1994. In: Proceedings of the ninth international pathogenic *Neisseria* conference. The Guildhall, Winchester, England). Alternatively, synthetic peptides that mimic the binding activity of polymyxin B may be added to the antigenic compositions to reduce LPS toxic activity (see, e.g., Rustici et al. 1993, Science 259:361-365; Porro et al. Prog Clin Biol Res. 1998; 397:315-25).

Endotoxin can also be reduced through selection of culture conditions. For example, culturing the strain in a growth medium containing 0.1 mg-100 mg of aminoarabinose per liter medium provides for reduced lipid toxicity (see, e.g., WO 02/097646).

Formulations

"Antigen composition", "antigenic composition" or "immunogenic composition" is used herein as a matter of convenience to refer generically to compositions comprising a chimeric fHbp as disclosed herein, which chimeric fHbp may be optionally conjugated to further enhance immunogenicity. Compositions useful for eliciting antibodies, particularly antibodies against *Neisseria meningitidis* group B (NmB), in a human are specifically contemplated by the present disclosure. Antigenic compositions can contain 2 or more different chimeric fHbps, where the chimeric fHbps may present epitopes from different combinations of fHbp variants and/or subvariants.

Antigenic compositions generally comprise an immunologically effective amount of chimeric fHbp, and may further include other compatible components, as needed. By "immunologically effective amount" is meant that the administration of that amount to an individual, either in a single dose, as part of a series of the same or different antigenic compositions, is effective to elicit an antibody response effective for treatment or prevention of a symptom of, or disease caused by, for example, infection by *Neisseria*, particularly *N. meningitidis*, more particularly Group B *N. meningitidis*. This amount varies depending upon the health and physical condition of the individual to be treated, age, the capacity of the individual's immune system to produce antibodies, the degree of protection desired, the formulation of the vaccine, the treating clinician's assessment of the medical situation, and other relevant factors. It is expected that the amount will fall in a relatively broad range that can be determined through routine trials.

Dosage regimen may be a single dose schedule or a multiple dose schedule (e.g., including booster doses) with a unit dosage form of the antigenic composition administered at different times. The term "unit dosage form," as used herein, refers to physically discrete units suitable as unitary dosages for human and animal subjects, each unit containing a predetermined quantity of the antigenic compositions of the present disclosure in an amount sufficient to produce the desired effect, which compositions are provided in association with a pharmaceutically acceptable excipient (e.g., pharmaceutically acceptable diluent, carrier or vehicle). The antigenic composition may be administered in conjunction with other immunoregulatory agents.

Antigenic compositions can be provided in a pharmaceutically acceptable excipient, which can be a solution such as a sterile aqueous solution, often a saline solution, or they can be provided in powder form. Such excipients can be substantially inert, if desired.

The antigenic compositions can further comprise an adjuvant. Examples of known suitable adjuvants that can be used in humans include, but are not necessarily limited to, alum, aluminum phosphate, aluminum hydroxide, MF59 (4.3% w/v squalene, 0.5% w/v TWEEN 80™, 0.5% w/v SPAN 85), CpG-containing nucleic acid (where the cytosine is unmethylated), QS21, MPL, 3DMPL, extracts from Aquilla, ISCOMS, LT/CT mutants, poly(D,L-lactide-co-glycolide) (PLG) microparticles, Quil A, interleukins, and the like. For experimental animals, one can use Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dip-almitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/TWEEN 80 emulsion. The effectiveness of an adjuvant may be determined by measuring the amount of antibodies directed against the immunogenic antigen or antigenic epitope thereof.

Further exemplary adjuvants to enhance effectiveness of the composition include, but are not limited to: (1) oil-in-water emulsion formulations (with or without other specific immunostimulating agents such as muramyl peptides (see below) or bacterial cell wall components), such as for example (a) MF59™ (WO 90/14837; Chapter 10 in Vaccine design: the subunit and adjuvant approach, eds. Powell & Newman, Plenum Press 1995), containing 5% Squalene, 0.5% TWEEN 80, and 0.5% SPAN 85 (optionally containing MTP-PE) formulated into submicron particles using a microfluidizer, (b) SAF, containing 10% Squalane, 0.4% TWEEN 80, 5% PLURONIC-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% TWEEN 80, and one or more bacterial cell wall components such as monophosphorylipid A (MPL), trehalose dimycolate (TDM), and cell wall skeleton (CWS), preferably MPL+CWS (DETOX™); (2) saponin adjuvants, such as QS21 or STIMULON™ (Cambridge Bioscience, Worcester, Mass.) may be used or particles generated therefrom such as ISCOMs (immunostimulating complexes), which ISCOMS may be devoid of additional detergent e.g. WO 00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3dMPL) e.g. GB-2220221, EP-A-0689454, optionally in the substantial absence of alum when used with pneumococcal saccharides e.g. WO 00/56358; (6) combinations of 3dMPL with, for example, QS21 and/or oil-in-water emulsions e.g. EP-A-0835318, EP-A-0735898, EP-A-0761231; (7) oligonucleotides comprising CpG motifs (Krieg Vaccine 2000, 19, 618-622; Krieg Curr opin Mol Ther2001 3:15-24; Roman et al., Nat. Med, 1997, 3, 849-854; Weiner et al., PNAS USA, 1997, 94, 10833-10837; Davis et al, J. Immunol, 1998, 160, 810-876; Chu et al., J. Exp. Med, 1997, 186, 1623-1631; Lipford et al, Ear. J. Immunol., 1997, 27, 2340-2344; Moldoveami e/ al., Vaccine, 1988, 16, 1216-1224, Krieg et al., Nature, 1995, 374, 546-549; Klinman et al., PNAS USA, 1996, 93, 2879-2883; Ballas et al, J. Immunol, 1996, 157, 1840-1845; Cowdery et al, J. Immunol, 1996, 156, 4570-4575; Halpern et al, Cell Immunol, 1996, 167, 72-78; Yamamoto et al, Jpn. J. Cancer Res., 1988, 79, 866-873; Stacey et al, J. Immunol., 1996, 157, 2116-2122; Messina et al, J. Immunol, 1991, 147, 1759-1764; Yi et al, J. Immunol, 1996, 157, 4918-4925; Yi et al, J. Immunol, 1996, 157, 5394-5402; Yi et al, J. Immunol, 1998, 160, 4755-4761; and Yi et al, J. Immunol, 1998, 160, 5898-5906; International patent applications WO 96/02555, WO 98/16247, WO 98/18810, WO 98/40100, WO 98/55495, WO 98/37919 and WO 98/52581, i.e. containing at least one CG dinucleotide, where the cytosine is unmethylated; (8) a polyoxyethylene ether or a polyoxyethylene ester e.g. WO 99/52549; (9) a polyoxyethylene sorbitan ester surfactant in combination with an octoxynol (WO 01/21207) or a polyoxyethylene alkyl ether or ester surfactant in combination with at least one additional non-ionic surfactant such as an octoxynol (WO 01/21152); (10) a saponin and an immunostimulatory oligonucleotide (e.g. a CpG oligonucleotide) (WO 00/62800); (11) an immunostimulant and a particle of metal salt e.g. WO 00/23105; (12) a saponin and an oil-in-water emulsion e.g. WO 99/11241; (13) a saponin (e.g. QS21)+3dMPL+IM2 (optionally+a sterol) e.g. WO 98/57659; (14) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)- ethylamine MTP-PE), etc. Adjuvants suitable for administration to a human are of particular interest.

The antigen compositions may comprise other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of chimeric fHbp in a formulation can vary widely (e.g., from less than about 0.1%, usually at or at least about 2% to as much as 20% to 50% or more by weight) and will usually be selected primarily based on fluid volumes, viscosities, and patient-based factors in accordance with the particular mode of administration selected and the patient's needs.

Chimeric fHBP-containing formulations can be provided in the form of a solution, suspension, tablet, pill, capsule, powder, gel, cream, lotion, ointment, aerosol or the like. It is recognized that oral administration can require protection of the compositions from digestion. This is typically accomplished either by association of the composition with an agent that renders it resistant to acidic and enzymatic hydrolysis or by packaging the composition in an appropriately resistant carrier. Means of protecting from digestion are well known in the art.

Chimeric fHbp-containing formulations can also be provided so as to enhance serum half-life of chimeric fHBP following administration. For example, where isolated chimeric fHbp are formulated for injection, the chimeric fHbp may be provided in a liposome formulation, prepared as a colloid, or other conventional techniques for extending serum half-life. A variety of methods are available for preparing liposomes, as described in, e.g., Szoka et al., Ann Rev. Biophys. Bioeng. 9:467 (1980), U.S. Pat. Nos. 4,235,871, 4,501, 728 and 4,837,028. The preparations may also be provided in controlled release or slow-release forms.

Immunization

The chimeric fHbp-containing antigenic compositions are generally administered to a human subject that is at risk of acquiring a Neisserial disease so as to prevent or at least partially arrest the development of disease and its complications. An amount adequate to accomplish this is defined as a "therapeutically effective dose." Amounts effective for therapeutic use will depend on, e.g., the antigenic composition, the manner of administration, the weight and general state of health of the patient, and the judgment of the prescribing physician. Single or multiple doses of the antigenic compositions may be administered depending on the dosage and frequency required and tolerated by the patient, and route of administration.

The chimeric fHbp-containing antigenic compositions are generally administered in an amount effective to elicit an immune response, particularly a humoral immune response, in the host. As noted above, amounts for immunization will vary, and can generally range from about 1 µg to 100 µg per 70 kg patient, usually 5 µg to 50 µg/70 kg. Substantially higher dosages (e.g. 10 mg to 100 mg or more) may be suitable in oral, nasal, or topical administration routes. The initial administration can be followed by booster immunization of the same of different chimeric fHbp-containing antigenic composition. Usually vaccination involves at least one booster, more usually two boosters.

In general immunization can be accomplished by administration by any suitable route, including administration of the composition orally, nasally, nasopharyngeally, parenterally, enterically, gastrically, topically, transdermally, subcutaneously, intramuscularly, in tablet, solid, powdered, liquid, aerosol form, locally or systemically, with or without added excipients. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

An anti-chimeric fHbp immune response can be assessed by known methods (e.g. by obtaining serum from the individual before and after the initial immunization, and demonstrating a change in the individual's immune status, for example an immunoprecipitation assay, or an ELISA, or a bactericidal assay, or a Western blot, or flow cytometric assay, or the like).

The antigenic compositions can be administered to a human subject that is immunologically naive with respect to Neisseria meningitidis. In a particular embodiment, the subject is a human child about five years or younger, and preferably about two years old or younger, and the antigenic compositions are administered at any one or more of the following times: two weeks, one month, 2, 3, 4, 5, 6, 7, 8, 9, 10, or 11 months, or one year or 15, 18, or 21 months after birth, or at 2, 3, 4, or 5 years of age.

It may be generally desirable to initiate immunization prior to the first sign of disease symptoms, or at the first sign of possible or actual exposure to infection or disease (e.g., due to exposure or infection by Neisseria).

ATCC Deposit

Hybridomas producing the JAR 4, JAR 5, JAR 11, and JAR 32 monoclonal antibodies were deposited under the terms of the Budapest Treaty with the American Type Culture Collection, 10801 University Blvd., Manassas, Va. 20110-2209, USA (ATCC) on the date indicated in the table below, and were assigned the designations set out in the table below.

| ATCC Deposit No. (Deposit Date) | Material Deposited |
|---|---|
| PTA-8943 (Feb. 7, 2008) | Hybridoma producing JAR 4 Monoclonal Antibody |
| PTA-8941 (Feb. 7, 2008) | Hybridoma producing JAR 5 Monoclonal Antibody |
| PTA-8940 (Feb. 7, 2008) | Hybridoma producing JAR 10 Monoclonal Antibody |
| PTA-8938 (Feb. 7, 2008) | Hybridoma producing JAR 11 Monoclonal Antibody |
| PTA-8942 (Feb. 7, 2008) | Hybridoma producing JAR 32 Monoclonal Antibody |
| PTA-8939 (Feb. 7, 2008) | Hybridoma producing JAR 33 Monoclonal Antibody |

It should be noted that JAR 5 mAb specifically binds to an epitope that at least overlaps with the epitope specifically bound by JAR 3 mAb, and that JAR 32 mAb specifically binds to an epitope that at least overlaps with the epitope specifically bounds by JAR 35 mAb.

These deposits were made under the provisions of the Budapest Treaty on the International Recognition of the Deposit of Microorganisms for the Purpose of Patent Procedure and the Regulations there under (Budapest Treaty). This assures maintenance of a viable culture of the deposit for 30 years from the date of deposit and for at least five (5) years after the most recent request for the furnishing of a sample of the deposit received by the depository. The deposits will be made available by ATCC under the terms of the Budapest Treaty, and subject to an agreement between Children's Hospital & Research Center at Oakland and the ATCC (the assignee of the present application) which assures that all restrictions imposed by the depositor on the availability to the public of the deposited material will be irrevocably removed upon the granting of the pertinent U.S. patent, assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 C.F.R. §1.14 with particular reference to 886 OG 638).

The assignee(s) of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Materials and Methods

The following methods and materials were used in the Examples below.

fHbp Sequencing.

The fHbp gene was amplified from genomic DNA prepared with the DNeasy Tissue kit (Qiagen, Valencia, Calif.) by polymerase chain reaction using primers A1 and B2 and cycling parameters described previously (Masignani et al. *J Exp Med* 2003, 197:789-99). The PCR products were purified using QiaQuick PCR purification kit (Qiagen) and were eluted in 30 μl of sterile deionized H$_2$O. The fHbp DNA sequences were determined by a commercial sequencing facility using the primers A1 and 22 described previously (Masignani et al., 2003).

Source of Data.

Protein sequences analyzed in the first study were encoded by 69 fHbp genes from *Neisseria meningitidis* case isolates from the United States (Beernink et al. *J Infect Dis* 2007, 195:1472-9), Europe (Beernink and Granoff *Infect Immun* 2008, 76:2568-2575; Beernink et al. *Infect Immun* 2008, 76:4232-4240) and Africa (Beernink et al., *J Infect Dis* 2009, doi:10.1086/597806). This data set included 48 sequences determined as part of our previous studies and 21 new sequences performed for the present study. 95 additional fHbp gene sequences were obtained from Genbank ("www" followed by ".ncbi.nlm.nih" followed by ".gov") by performing translated BLAST (tblastn) searches with fHbp amino acid sequences from strains MC58 (variant 1/sub-family B) and M1239 (variant 3/sub-family A). Among these 164 nucleotide sequences from our collection and Genbank, which included three genome sequences (Parkhill et al. *Nature* 2000, 404:502-506; Peng et al. *Genomics* 2008, 91:78-87; Tettelin et al. *Science* 2000, 287:1809-1815), fHbp genes that encoded 63 unique protein sequences were identified. These 63, plus 6 additional unique fHbp amino acid sequences obtained from the Neisseria.org fHbp peptide database (neisseria.org), were used for the analysis of 69 unique fHbp peptides. The respective Genbank accession numbers and/or peptide identification numbers and the characteristics of the source strains are listed in FIG. 1A-1G (Table 7).

Thirty-eight (55%) of the 69 peptides were classified in the variant 1 group of Masignani et al. 2003, 15 (22%) in the variant 2 group, and 16 (23%) in the variant 3 group. Of the 69 source strains, one was capsular group A, 57 were group B, seven were group C, two were group W-135, and two were group X. Multi-locus sequence type (MLST) information was available for 58 of the strains of which 15 were from the ST-269 clonal complex, 12 each were from the ST-11, 10 were from the ST-41/44 complexes, four were from the ST-162, five were from the ST-213 complexes, three each were from the ST-8 and ST-32 complexes. Six strains were from other clonal complexes and had sequence types ST-4, ST-35, ST-751, ST-4821, ST-5403 and ST-6874. The 11 strains without MLST information were not available for testing.

In a second study, the dataset further included 172 additional distinctive sequences that were subsequently added to the Neisseria.org database ("http" followed by "://neisseria.org/perl/agdbnet/agdbnet.pl?file=nm_fhbp" followed by ".xml") as of November 2009. In describing the 242 unique proteins (FIGS. 10A-10I, Table 9), the protein identification (ID) numbers from the peptide database at the Neisseria.org website were employed.

A combination of approaches for analysis of complete or partial protein sequences was used. Sequences were aligned with MUSCLE (EBI, v3.7, "ebi.ac" followed by ".uk/Tools/muscle/index" followed by ".html") (Edgar R C. (2004) *Nucleic Acids Res.* 32:1792-7; Edgar R C (2004) *BMC Bioinform.* 5:113) configured for highest accuracy. The accuracy of the alignments was confirmed by visual inspection and using the program JALVIEW (Water house A M et al. (2009) *Bioinformatics* 25:1189-91). Alignments also were performed on the individual modular variable segments between the blocks of invariant residues. Networks were generated using SplitsTree, version 4.0 (Huson D H et al., (2006) *Mol Biol Evol* 23:254-67), with default parameters. Statistical tests for branch support were performed using the bootstrapping method (1000 replicates).

Phylogenic Analysis.

The analysis of complete or partial protein sequences was performed on the platform at "www" followed by ".phylogeny" followed by ".fr" (Dereeper et al. *Nucleic Acids Res* 2008, 36:W465-469) and comprised the following steps. Sequences were aligned with MUSCLE (v3.7) (Edgar *Nucleic Acids Res* 2004, 32:1792-1797) configured for highest accuracy. The respective alignments, which contained up to three sites of insertions or deletions, were inspected and verified by adjacent invariant sequences. The phylogenic tree was reconstructed using the maximum likelihood method implemented in the PhyML program (v3.0 aLRT). Reliability for internal branch was assessed using the bootstrapping method (100 bootstrap replicates). Phylograms were displayed with MEGA 4.0 (Tamura et al. *Mol Biol Evol* 2007, 24:1596-1599). The phylograms were rooted on peptide 1 for consistency. The percent sequence identities within and between variable segment types of sequences were determined using ClustalW (Larkin et al. *Bioinformatics* 2007, 23:2947-2948).

Cloning, Expression and Purification of Recombinant Proteins.

Expression plasmids were constructed by PCR amplification of fHbp genes from genomic DNA as described previously (Masignani et al. (2003) *J Exp Med* 197:789-99). The genes encoded fHbp ID 1 (Modular group I), 28 (group II), 22 (group III), 15 (group IV), 79 (group V) and 77 (group VI). C-terminal hexahistidine-tagged recombinant fHbps were expressed in *Escherichia coli* BL21(DE3) (Novagen, Madison, Wis., US), and purified as described elsewhere (Beernink P T et al. (2008) *Infect Immun* 76:2568-75).

Mouse Antisera.

Groups of five-week-old CD-1 female mice (10 mice per group) were obtained from Charles River (Wilmington, Md., US). The mice were immunized via the intraperitoneal route (IP) with three doses of vaccine given at 3-week intervals. Each 100-µl dose contained 20 µg of recombinant protein mixed with Freund's adjuvant (FA) (Sigma-Aldrich, St. Louis, Mo., US). (Complete FA for the first dose and incomplete for subsequent doses). Terminal blood samples were obtained three weeks after the last dose. The animal procedures were performed under a protocol approved by the Institutional Animal Care and Use Committee of the Children's Hospital Oakland Research Institute.

Bacterial Strains.

Characteristics of the *N. meningitidis* strains used to measure serum bactericidal activity are summarized in Tables 7 and 9. Two isolates each was selected from modular groups I to VI. For five of the modular groups, one strain from each pair was a low expresser of fHbp and the other a higher expresser as measured as described below. For modular group V, only strains that expressed intermediate quantities of fHbp were identified and, therefore, used for the assays.

Complement-Dependent Serum Bactericidal Antibody Activity.

The bactericidal assay was performed as described elsewhere, using early log phase bacteria grown for approximately 2 h in Mueller-Hinton broth (BD Biosciences, Franklin Lakes, N.J., US) supplemented with 0.25% glucose (w/v) and 0.02 mM cytidine 5'-monophospho-N-acetylneuraminic acid (Sigma-Aldrich, St, Louis, Mo., US) [11]. The complement source was serum from a non-immune healthy adult with normal hemolytic complement activity. The serum was passed over a protein G SEPHAROSE column (HI-TRAP Protein G HP, GE Healthcare, Piscataway, N.J., US) to remove IgG antibodies (Beernink P T et al. (2009) *J Infect Dis* 199:1360-8).

Quantitative Western Blotting of fHbp.

*N. meningitidis* cells were grown in broth cultures to early log phase, heat-killed (56° C. for 1 h), collected by centrifugation, and resuspended in PBS to an optical density of 0.6. Proteins in the heat-killed cells ($1-4 \times 10^7$ CFU) were separated by SDS-PAGE using 4-12% NuPAGE gels (Invitrogen, Carlsbad, Calif., US) as specified by the manufacturer, and were transferred to PVDF membranes (Immobilon-FL; Millipore, Billerica, Mass., US) using a Western blot module (Invitrogen, Carlsbad Calif., US). After blocking overnight at 4° C. in blocking buffer (Li-Cor Biosciences, Lincoln, Nebr., US), fHbp modular groups I and IV (variant 1 group) were detected with anti-fHbp JAR 5 or, JAR 31, for modular groups II, III, V or VI (variant groups 2 or 3) (Beernink P T et la. (2008) *Infect Immun* 76:4243-40). The secondary antibody was goat anti-mouse IgG-IRDye800CW (1:10,000, Rockland Immunochemicals, Gilbertsville, Pa., US).

Figure 11:
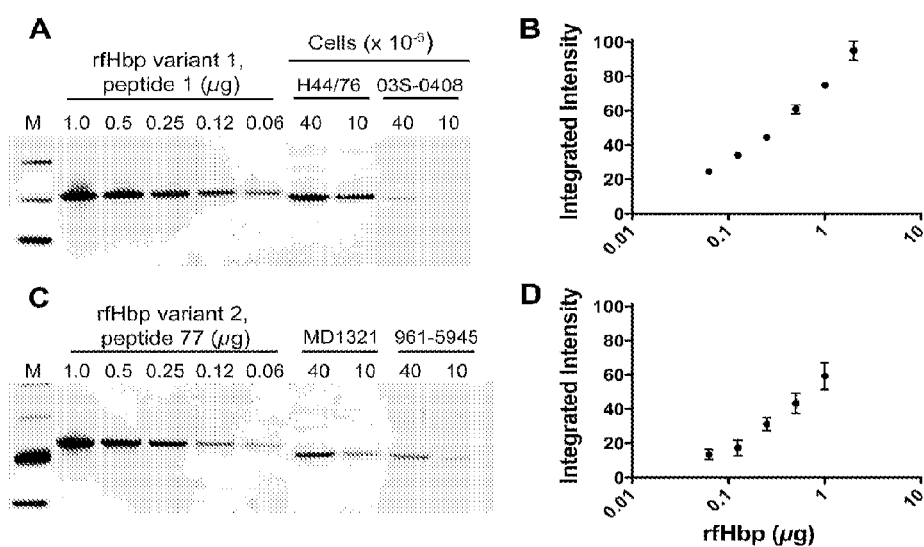
FIG. 11 shows fHbp expression measured by immunoblotting with infrared detection. Panels A and C, Recombinant proteins in modular groups I (ID 1) or VI (ID 77), or heat-killed bacterial cells from strains expressing fHbp in the corresponding modular groups. The modular group I proteins were detected with murine anti-fHbp mAb JAR 5, which recognizes nearly all fHbps in modular groups I and IV. The modular group VI proteins were detected with anti-fHbp mAb JAR 31, which recognizes nearly all proteins in modular groups II, III, V and VI (See Table 6 in example section). Panels B and D, Standard curves from the corresponding binding of the recombinant proteins shown in Panels A and C.

To determine the quantity of bound protein, the membranes were scanned at 800 nm wavelength using an infrared scanner (Li-Cor Odyssey, Lincoln, Nebr., US), and the integrated intensities of the bands were calculated with software provided by the manufacturer (version 3.0.21). The results of testing purified, recombinant fHbp from each of the six modular groups indicated that the IR signal intensities were proportional to the $\log_{10}$ of the quantities loaded in the range of 0.03 to 2 µg (representative data for control proteins in modular groups I and VI are shown in FIG. 11). Representative expression data are shown for two strains with fHbp in modular group I, and two strains in modular group VI (FIG. 11).

Statistical Analysis.

Statistical calculations were performed using Prism 5 for Mac OSX, version 5.0a (GraphPad Software, La Jolla, Calif., US). The proportion of isolates with fHbp in different modular groups in each country was computed along with the respective 95 percent confidence intervals calculated from the binomial distribution. Differences found in the proportion of isolates in the respective modular groups were compared by Fisher Exact Test (two-tailed) or chi-square analyses.

OVERVIEW OF EXAMPLES

Based on previous analyses of the sequences of the mature peptide, fHbp was classified into two sub-families (Fletcher et al. *Infect Immun* 2004, 72:2088-2100) or three variant groups (Masignani et al., 2003) (FIG. 3). Analysis presented herein indicated that the overall architecture of meningococcal fHbp contains a limited number of specific modular combinations of five variable segments, with each segment corresponding to one of two types, designated as α or β, based on sequence similarity to the respective segments of fHbp peptides 1 (variant 1 group) or 28 (variant 3 group). As described in the Examples section below and shown in FIG. 4, the amino acid sequences of two *N. gonorrhoeae* orthologs had architectures corresponding to natural chimeras in modular group V (FIG. 8). The propensity for *Neisseria* to transfer genes horizontally (Hotopp et al. *Microbiology* 2006, 152:3733-3749), coupled with the similar modular architectures of meningococcal and gonococcal fHbp peptides described here, suggests that during evolution, the respective progenitor genes recombined at conserved sequences encoding the invariant blocks of residues hypothesized to be points of junction.

Among the 69 distinct meningococcal fHbp peptides, 65 (94%) could be assigned to one of six modular groups (FIG. 8). Nearly 60% of the peptides were in modular groups I or II, which comprised only α or β type segments, respectively. The remaining peptides were natural chimeras of α and β segments. Modular fHbp groups, III, IV, and V (FIG. 8), could each have been generated from the two progenitor types by a single recombination event. The modular fHbp group VI could have been generated by two recombination events. Similarly the four exceptional sequences described in the Examples section could each have been generated through recombination at loci encoding alternative blocks of other conserved residues. For a protein comprising five segments, each of which can be of one of two types, there are $2^5=32$ theoretical independent modular combinations. That we identified only six modular groups suggests that there are functional or structural constraints on the molecule that select for certain combinations of the modules found in the prevalent fHbp modular groups.

fHbp structural data are available from two recent NMR studies (Cantini et al., *J Biol Chem* 2009, doi:10.1074/jbc.C800214200; Mascioni et al. *J Biol Chem* 2009, doi: 10.1074/jbc.M808831200) and a crystallographic study of fHbp in a complex with a complement regulatory protein (Cantini et al., 2009; Mascioni et al., 2009; Schneider et al. *Nature* 2009, doi:10.1038/nature07769). In the crystal structure, Schneider et al reported that binding to residues located on the short consensus repeat region 6 (SCR 6) of fH was mediated by charged amino acid residues in the fHbp structure that mimicked portions of sugar molecules known to bind to fH (Schneider et al. 2009). Analysis as presented in FIG. 9 indicated that these fH contact residues were located on three of the five variable segments identified in the present study. Of the 21 fH contact residues, five were invariant among the 69 unique fHbp peptides analyzed in our study and ten other contact residues were conserved.

All three fHbp variable segments with fH contact residues also contained amino acids that affected epitopes recognized by bactericidal murine anti-fHbp mAbs (FIG. 9). The central locations of the fH contact residues in the amino- or carboxyl-terminal domains appeared to be distinct from the peripheral locations of the residues affecting epitope expression. This reciprocal relationship suggests that the fHbp structures in contact with fH infrequently elicited bactericidal antibodies.

One limitation of fHbp as a vaccine candidate is antigenic variability (Beernink & Granoff, 2009; Masignani et al., 2003). Thus, serum antibodies to recombinant fHbp in the variant 1 group were bactericidal primarily only against strains with variant 1 proteins (Beernink et al. 2007; Fletcher et al. *Infect Immun* 2004, 72; 2088-2100; Masignani et al. 2003), while antibodies to fHbp in the variant 2 or 3 groups had activity primarily against strains with homologous variant 2 or 3 proteins but had no activity against strains with fHbp in the variant 1 group. These observations suggest that epitopes in the C and E segments of fHbp, for which variant 1 proteins were phylogenetically separated from those of variant 2 and 3 proteins (FIGS. 6 and 7), are more important for eliciting bactericidal antibodies than those in the A, B or D segments, where variant 1 proteins clustered together with variant 2 and/or 3 proteins (FIGS. 5 and 6). However, all of the variable segments with the exception of segment B contained residues previously identified as affecting epitopes recognized by murine bactericidal anti-fHbp mAbs (Beernink et al. 2008; Beernink et al. *Mol Immunol* 2009b, doi:10.1016/j.molimm.2009.02.021; Guiliani et al *Infect Immun* 2005, 73:1151-1160). Further, some of the mAbs inhibited binding of fH to the bacterial surface (Madico et al. *J Immunol* 2006, 177:501-510), and some combinations of mAbs that individually were not bactericidal elicited cooperative bactericidal activity (Beernink et al. 2008; Beernink et al. 2009b; Welsch et al. *J Infect Dis* 2008, 197:1053-1061). The latter included mAb JAR 4, which was specific for an epitope on variable segment A (Beernink et al. 2009b), and elicited cooperative bactericidal activity with second mAbs with epitopes on variable segment C (for example JAR 3 or 5) or variable segment E (for example, JAR 13 or mAb502).

To minimize the possibility of fHbp escape mutants, an ideal meningococcal vaccine should include antigenic targets other than fHbp (Giuliani et al., 2006). However, there may be limits to the number of recombinant proteins that can be combined in a multicomponent vaccine because of the large dose of total protein required, poor tolerability, or loss of immunogenicity of the individual components. To decrease the number of individual fHbp components, we engineered chimeric fHbp molecules containing the amino-terminal domain of a variant 1 fHbp with the carboxyl-terminal domain of a variant 2 protein using G136 as the junctional point (Beernink & Granoff, 2008). The resulting chimeric protein expressed epitopes from all three variant groups, and the chimeric fHbp vaccines elicited serum antibodies with bactericidal activity against a panel of genetically diverse strains expressing fHbp variant 1, 2 or 3. The junctional point selected for creation of the recombinant chimeric vaccines was located in an invariant portion of the middle of the variable C segment, which, in the present study, was not identified as a junctional point for any of the natural fHbp chimeric proteins described here. The use of natural junctional points that flank the C segment may result in improved recombinant chimeric fHbp vaccines that elicit broad bactericidal antibodies than other vaccines. It may also be possible to introduce amino acid mutations in one or more of the variable segments to introduce epitopes from heterologous fHbp variants (Beernink & Granoff 2008; Beernink et al. 2009b). Thus, the presence of such fH-binding epitopes in the chimeric fHbp polypeptides can provide for production of antibodies that can facilitate protection against *N. meningitidis*.

In conclusion, the analysis herein shows that the overall architecture of fHbp can be defined by a limited number of specific modular combinations of variable segments flanked by invariant sequences. Collectively, the data suggest that recombination occurred between *N. meningitidis* and *N. gonorrhoeae* progenitor sequences to generate an antigenically diverse family of meningococcal factor H-binding proteins. The data presented in the Examples thus provide insights into the evolution of fHbp variants, and provide a rational basis for classification of groups of peptide variants. Population-based surveillance studies will be required to define the prevalence of fHbp from different modular groups among strains causing carriage and/or disease, and the relationship between the fHbp modular group and other strain characteristics such as capsular group, clonal complex and PorA variable regions.

Details of the studies that led to this discovery are set out below.

Example 1

Phylogenic Analysis 69 unique fHbp amino acid sequences were aligned to generate a phylogram shown in FIG. 3. For each sequence, the peptide identification number assigned in fHbp peptide database at neisseria.org is shown and, if known, the multi-locus sequence type (MLST) clonal complex is shown in parentheses. The lower left branch shows variant group 1 as defined by Masignani et al 2003 (sub-family B of Fletcher et al 2004); sub-family A contained two branches, variant groups 2 and 3. Prototype peptides for each of the variant groups 1, 2 and 3 are indicated with arrows and labeled with the name of the source strain of the respective genes. The phylogram was constructed by multiple sequence alignment as described in Methods. The scale bar shown at the bottom indicates 5 amino acid changes per 100 residues.

The analysis showed the two major branches previously designated as sub-families A and B (Fletcher et al. 2004). Sub-family A contained fHbp sequences in antigenic variant groups 2 and 3, and sub-family B corresponded to fHbps in the antigenic variant group 1 (Masignani et al. 2003). For some clonal complexes, there were examples of strains with fHbp in each of the variant groups (for example, for ST-11, peptides 2, 3, 6, 9, 10, 11 and 78 in the variant 1 group, peptides 17, 22, 23 and 27 in the variant 2 group and peptide 59 in the variant 3 group). The strains from the ST-32 clonal complex had fHbp in two of the variant groups (peptides 1 and 89 in the variant 1 group and peptide 76 in the variant 3 group) and the ST-8 clonal complex had fHbp only in one variant group (peptides 16, 50, and 77 in the variant 2 group). The distribution of fHbp variants in all of the observed clonal complexes is given in Table 2 below. Peptide IDs listed are assigned by the fHbp peptide database at neisseria.org.

TABLE 2

Distribution of factor H binding protein variants in each clonal complex.

| Clonal Complex | Number in Variant group (peptide ID) | | | Total |
|---|---|---|---|---|
| | Variant 1 | Variant 2 | Variant 3 | |
| ST-4 | 1 (5) | 0 | 0 | 1 |
| ST-8 | 0 | 3 (16, 50, 77) | 0 | 3 |
| ST-11 | 7 (2, 3, 6, 9, 10, 11, 78) | 4 (17, 22, 23, 27) | 1 (59) | 12 |
| ST-32 | 2 (1, 89) | 0 | 1 (76) | 3 |
| ST-35 | 1 (7) | 0 | 0 | 1 |
| ST-41/44 | 6 (4, 8, 12, 14, 86, 87) | 2 (19, 20) | 2 (28, 84) | 10 |
| ST-162 | 1 (88) | 1 (21) | 2 (29, 82) | 4 |
| ST-213 | 1 (90) | 1 (24) | 3 (30, 31, 85) | 5 |
| ST-269 | 10 (13, 15, 60-63, 65, 66, 69, 71) | 2 (68, 83) | 3 (64, 70, 72) | 15 |
| ST-4821 | 1 (80) | 0 | 0 | 1 |
| Unassigned | 2 (73, 74) | 0 | 1 (79) | 3 |
| Not done | 6 (40, 54-58) | 2 (25, 49) | 3 (45-47) | 11 |

Example 2

The Architecture of fHbp is Modular

Blocks of two to five invariant residues were identified that separate the proteins into segments of variable residues. See FIG. 4 for detail. The invariant residues are shown as vertical rectangles. The top three panels show representative architectures of three *N. meningitidis* fHbp variants in groups 1, 2 and 3 (peptide ids, 1, 16 and 28, respectively). Each of the three variants had repetitive amino-terminal elements (N-term), and variable segments A through E, which in some cases differed in length among the variants. The amino acid positions of the last residue in each variable segment are shown.

With the exception of the amino-terminal element, there were identical respective invariant amino acid sequences and homologous variable segments in two *N. gonorrhoeae* orthologs (Genbank accession numbers AE004969 and CP001050), which overall had 96% amino acid sequence identity with meningococcal fHbp peptide 79 (variant 3 meningococcal proteins). In the first study, all 69 fHbp sequence variants had blocks of 2 to 5 invariant residues that flanked five modular variable segments (FIG. 4). These invariant residues were also conserved in 170 of the 172 additional fHbp variants analyzed in study 2. One exception, protein ID 33, had SHFDF (SEQ ID NO: 279) instead of SRFDF (SEQ ID NO: 3) between the A and B segments, and the other exception, protein, ID 150, had IEHLE (SEQ ID NO:6) instead of IEHLK (SEQ ID NO: 5) between the D and A segments (FIG. 4).

The blocks of invariant residues appeared to represent natural junctional points for recombination of the respective genes encoding the meningococcal and gonococcal proteins. The phylogeny of each the variable segments defined by these junctional points was analyzed. In the analysis of the 69 distinctive meningococcal fHbp peptide variants described below, the numbering of the amino acid residues is based on the mature fHbp peptide 1 encoded by a gene from MC58 in the variant 1 group (Masignani et al. 2003). The numbering for the respective variant 2 and 3 proteins differ from that of the variant 1 protein by −1 and +7, respectively (FIG. 4).

Example 3

The Amino-Terminal Repetitive Element

For all 69 sequences, the mature fHbp began with a cysteine residue that is lipidated by signal peptidase II, which was followed by three invariant amino acid residues, SSG. This invariant sequence was followed by a repetitive variable sequence consisting of 1 to 6 glycine and/or serine residues and then by two invariant glycine residues (FIG. 4). The variable portion of the amino-terminal element consisted of a single glycine residue for 34 of the 69 peptides (nearly all in the variant 1 group, Table 3 shown below), or GG residues for 12 of the peptides (all in the variant 2 group). The other common variable sequence was GGGSGG (SEQ ID NO: 9) (8 in the variant 1 group and 7 in the variant 3 group).

TABLE 3

Sequence and distribution of amino-terminal repetitive element

| Variable Sequence[1] | Number of Peptides in Variant Group | | |
|---|---|---|---|
| | Variant 1 | Variant 2 | Variant 3 |
| G | 29 | 3 | 2 |
| GG | 0 | 12 | 0 |
| SGG | 0 | 0 | 1 |
| GGGS (SEQ ID NO: 1) | 0 | 0 | 2 |
| SGSGG (SEQ ID NO: 2) | 0 | 0 | 1 |
| GGGSGG (SEQ ID NO: 3) | 8 | 0 | 6 |
| GGGSGS (SEQ ID NO: 4) | 1 | 0 | 4 |

[1]The mature fHbp begins with an invariant tetrapeptide, CSSG (SEQ ID NO: 2), which is followed by a repetitive variable sequence consisting of 1 to 6 glycine and/or serine residues, which is then followed by two invariant glycine residues.

Example 4

Downstream Variable Segments

There were five variable segments, which we designated A, B, C, D or E (FIG. 4). Based on the presence of certain signature amino acid residues and sequence similarity (Table 4), each of the five segments could be segregated into one of two types. One of the types had signature amino acid residues and sequence similarity to peptides in the antigenic variant 1 group. The other type had signature amino acid residues and sequence similarity to peptides in the antigenic variant 3 group, which also were similar to those of the gonococcal ortholog (see FIG. 4). Also see Table 4 presented below.

TABLE 4

Amino acid identity within and between sequence groups by segment.

| | | | α Sequence Types | | | β Sequence Types | | | Identity |
|---|---|---|---|---|---|---|---|---|---|
| Variable Segment | Residue Range[1] | Invariant Block[2] | Signature residues[3] | No.[4] | Identity Range (%) | Signature residues[3] | No.[4] | Identity Range (%)[4] | between α and β Types (%)[4] |
| A | 8-73 | SRFDF[7] | QSV | 48 | 89-100 | DSI and KDN | 21 | 89-100[5] | 69-78[5] |
| B | 79-93 | GEFQ[8] | IRQ | 53 | 80-100[5] | VQK | 16 | 100 | 60-66[5] |
| C | 98-159 | DD | QDS | 38 | 85-100 | NNP | 31 | 93-100 | 32-45 |
| D | 162-180 | IEHLK[9] | AG or AS | 58 | 89-100 | PN | 11 | 84-100 | 52-63 |
| E | 186-253 | KQ[6] | SLGI | 38 | 86-100 | HLAL[10] | 31 | 94-100[5] | 48-57[5] |

[1]Amino acid numbering based on the mature fHbp from strain MC58.
[2]Invariant block of residues immediately following each variable segment. The invariant sequence immediately before segment A was GG (See FIG. 4).
[3]See FIG. 2A-2E: (Table 8) for complete sequences of each variable segment.
[4]Number of sequences in each sequence type for each variable segment (N = 61 peptides).
[5]Four fHbp sequences with exceptional junctional positions at other conserved blocks of residues were excluded from the percent identity analyses (see text).
[6]Corresponds to carboxyl-terminal end of fHbp sequence
[7]SEQ ID NO: 3
[8]SEQ ID NO: 4
[9]SEQ ID NO: 5
[10]SEQ ID NO: 280
[11]SEQ ID NO: 281

For purposes of classification, the first group of segments is designated as α types and the second group as β types. The amino acid identity of the respective segments within an α or β type ranges from 80 to 100% (Table 4). In contrast, the identity of segments between types ranged from 69-78% for segment A, which was located in a conserved region of the N-terminal portion of the molecule, to 32-45% in the C segment, which encompassed resides 98-159 in a much less conserved region of the protein (Table 4). For each segment, distinct sequence variants were assigned a unique identifier beginning with a letter, A through E, to represent the variable segment; followed by an α or β to indicate the presence of residues with the respective types described above, followed by a number for each distinct sequence (listed in FIG. 2A-2E (Table 8)).

Segment A began at amino acid residue 8 immediately after the invariant GG sequence and extended to position 73 (Table 4). Among the 69 fHbp variants, segment A contained 16 distinctive α sequence variants, and 9 distinctive β sequence variants (FIG. 5). Where multiple peptides possessed an identical sequence in a segment, the number of peptides is given in parentheses. The scale bar indicates 5 amino acid changes per 100 residues. Based on the phylogram, the A segments of most of the fHbps in the variant 1 group (shown in FIG. 5) clustered with those in the variant 2 group, whereas the A segments of fHbps in the variant 3 group were in a separate cluster. The most common α variant (N=14) was designated A.α.1, which was present in 4 fHbp peptides in the variant 1 group and 10 in the variant 2 group. The most common β variant was designated A.β.1, which was present in 6 peptides, all in the variant 3 group.

Segment B began at position 79 immediately after an invariant SRFDF (SEQ ID NO: 3) sequence and extended to position 93 (Table 4). Among the 69 fHbp peptides, segment B contained 7 different α variant sequences and a single β sequence (FIG. 5). The phylogenic analysis showed that the B segments of fHbp peptides in the variant 1 and 2 groups clustered together (FIG. 5), which were distinct from those in the variant 3 group. The most common B segment, B.α.1, was present in 40 fHbp peptides (28 in the variant 1 group and 12 in the variant 2 group).

Figure 7:
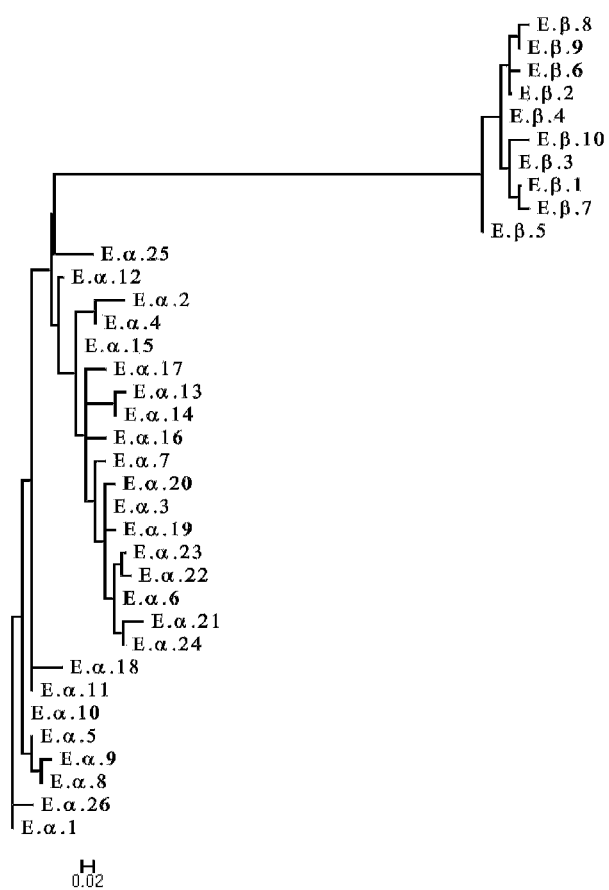
FIG. 7 is a phylogram of unique fHbp amino acid sequences in variable segment E (residues 186-253).

In contrast to the A and B segments, the respective C (residues 98-159) and E (residues 186-253) segments of fHbp in the variant 2 and 3 groups clustered together and were separated from those of fHbps in the variant 1 group 1 (FIG. 6). All of the D segments (residues 162-180) of strains with fHbp in the variant group 1 were α types while those of fHbp peptides in the variant 2 or 3 groups were α or β (FIG. 7). The most common D segment, D.α.1 (N=39), was present in 21 fHbp v.1 peptides, 9 v.2 peptides and 9 v.3 peptides.

Example 5

Classification of fHbp Variants by Modular Groups

Based on the phylogenic analysis of the variable segments of fHbp described above, the majority of these different fHbp variants studied were categorized into six distinct fHbp modular groups (I to VI) (FIG. 8). Forty of the 69 fHbp peptides (58%) comprised only α (N=33) or β (N=7) type segments, which were designated fHbp modular groups I and II, respectively (FIG. 8). The α segments are shown in gray and the β segments are shown in white. The remaining 29 peptides (42%) could be classified into one of four chimeras derived from recombination of different α or β segments (designated fHbp modular groups III, IV, V or VI; N=25) or, as described below, were other chimeras (N=4) in which one of the five segments used an exceptional junctional position at other conserved blocks of sequences. As seen in FIG. 6, a representative peptide in each modular group is indicated by the peptide identification number from the fHbp database at neisseria.org. The number of unique sequences observed within each fHbp modular group is indicated at the right. This analysis excluded four peptides sequences with exceptional junctional points at one of their segments.

Although the amino-terminal repetitive segment described above was not used to define the modular fHbp groups, the majority (88 to 100%) of modular group I, III and VI peptides sequences had amino-terminal repetitive elements of 1 or 2 glycine residues (Table 3). In contrast, the majority (75 to 100%) of the peptides in modular groups II, IV and V had amino-terminal elements of 3 to 6 glycine and serine residues. The length of this amino-terminal element may affect the distance of the protein from the bacterial membrane and surface-accessibility of certain epitopes.

In the second study, all but three of the 172 new fHbp variants could be classified into one of the six modular groups (I to VI, FIG. 4, Panel A). The three exceptions (protein ID 207, 67 and 175) had distinctive combinations of modular segments derived from α or β type lineages and were assigned to one of three new modular groups (VII, VIII and IX, respectively).

Of 242 distinct fHbp variants in the expanded database, 125 proteins were in modular group I (FIG. 4), which contained only α segments, and 20 proteins were in modular group II (entirely β segments). The remaining 97 fHbp sequence variants were natural chimeras of α and β segments and were assigned to modular groups III through IX (together, 40 percent of all variants). FIG. 4 shows the fHbp variant groups as described by Masignani et al. (2003) *J Exp Med* 1997:789-99 for each of the modular groups. The variant groups were assigned based on the relatedness of the overall amino acid sequences of the respective proteins.

Example 6

Chimeric fHbp Peptides Containing Junction Points within a Variable Segment

Four fHbp sequences had modular structures similar to those described above except that one of the junctional points between two of the segments utilized alternative invariant sequences. For example, fHbp peptide 55 was similar to peptides in modular group IV (FIG. 8) except that the A segment switched from a β type sequence to an α type sequence at an invariant AQGAE (SEQ ID NO: 278) starting at residue 50 rather than at SRFDF (SEQ ID NO: 3) starting at residue 74. This A segment was designated A.β.9 (β because of its higher sequence identity to other β type A segments than to the α type A segments; FIG. 5). Two other fHbp peptides, 24 and 25 (FIG. 2A-2E (Table 8)), had modular structures similar to peptides in modular group III (FIG. 8) but had B segments that switched from an α type to a β type sequence at an invariant IEV beginning at residue 82 instead of GEFQ (SEQ ID NO: 4 at position 94. This exceptional B segment, designated B.α.3, was categorized as an α type because of its higher sequence identity to other α type B segments than to the β type B segments (FIG. 5). The fourth exceptional fHbp modular structure, peptide 82 (FIG. 2A-2E (Table 8)), was similar to type V, except that its E segment, designated E.β.10, switched from an α type sequence to a β type at residue A196 instead of at IEHLK (SEQ ID NO: 5) starting at position 181 (FIG. 6).

Example 7

Structural Features of the Variable and Invariant fHbp Segments

The respective variable and invariant segments of fHbp were mapped onto a molecular model based on the published coordinates from the fHbp crystal structure (FIG. 9) (Schneider et al. 2009). The amino- and carboxyl-termini, labeled N and C, respectively, in panel A are in identical positions in panels B and C. The figure was constructed with PyMol (pymol.org). The models in the center of panels A, B and C have been rotated 180 degrees on the Y-axis from the corresponding models on the far left, while the models on the far right have been rotated 90 degrees on the X-axis as compared with the models in the middle.

The ribbon models in panel A show the two previously described major domains of fHbp (Cantini et al. 2009; Mascioni et al. 2009; Schneider et al. 2009), each containing independently folded beta-structures, which are connected together by a structured, four amino acid residue linker located in variable segment C. The amino-terminal domain, which begins at residue 8 and extends to residue 136, includes variable segments A and B and part of C (note that the first 14 residues of the mature protein are not present in the crystal structure). The carboxyl-terminal domain, which extends from residue 141 to 255, includes the carboxyl-terminal portion of the C and the entire D and E variable segments.

Panel B shows the corresponding space-filled models. The amino acid residues previously reported to be in contact with fH based on the structure of the fHbp-fH complex are depicted in black. These residues form clusters on variable segments A, C and E and are visible in the models shown in the middle and far right of panel B. Since fH is known to bind to fHbp on live bacteria (Madico et al. 2006; Schneider et la. 2006), this binding site must be surface-exposed. The invariant blocks of residues that flank each of the five variable segments, are localized on the opposite face of the protein and shown in white in panels B and C (far left model). Since the amino-terminus, which contains the signal anchor, extends from this face of the protein (bottom surface of model at far right, panel B), the invariant residues are predicted to be located entirely on the surface of the molecule anchored to the cell wall. The presence of these invariant sequences on the membrane-associated surface suggests that there are structural constraints, perhaps a requirement for a partner protein, for anchoring and/or orienting fHbp on the bacterial cell membrane.

Previous studies mapped the epitopes of eleven bactericidal anti-fHbp mAbs (Beernink et al. 2008; Beernink et al. 2009b; Giuliani et al. 2005; Scarselli et al J Mol Biol 2009, 386:97-108). In panel C (FIG. 9), the amino acids affecting expression of each of these epitopes are depicted in black and the previously defined fH contact residues (shown in black as in panel B). With the exception of segment B, all of the variable segments contained epitopes recognized by bactericidal mAbs. The amino acids affecting the epitopes generally were located on the periphery of the amino- and carboxyl-terminal domains of fHbp whereas the residues in contact with fH were located in clusters in the central portions of each of the two domains. The epitopes of certain mAbs such as JAR 3, 5 or 13, which were previously reported to inhibit binding of fH to fHbp (Beernink et al. 2008; Beernink et al. 2009b), involved amino acids located in proximity to some of the fH contact residues. However, there was no example of overlap between the two sets of residues.

Example 8

Frequency of fHbp Modular Groups Among Isolates Causing Disease in Different Countries The analysis described above provided information on the extent of fHbp modular group diversity. For this following analysis, the fHbp sequence data from systematically collected group B isolates in the U.S. and Europe reported by Murphy et al. (2009) *J Infect Dis* 200:379-89 were used. The isolates were from cases in the United States between 2001 and 2005 (N=432), and from the United Kingdom (N=536), France (N=244), Norway (N=23) and the Czech Republic (N=27) for the years 2001 to 2006. The U.S. data were supplemented with fHbp sequences of 143 additional isolates that had been systematically collected at multiple sites in the U.S. as part of another study (Beernink P T et al. (2007) *J Infect Dis* 195:1472-9).

Figure 12:
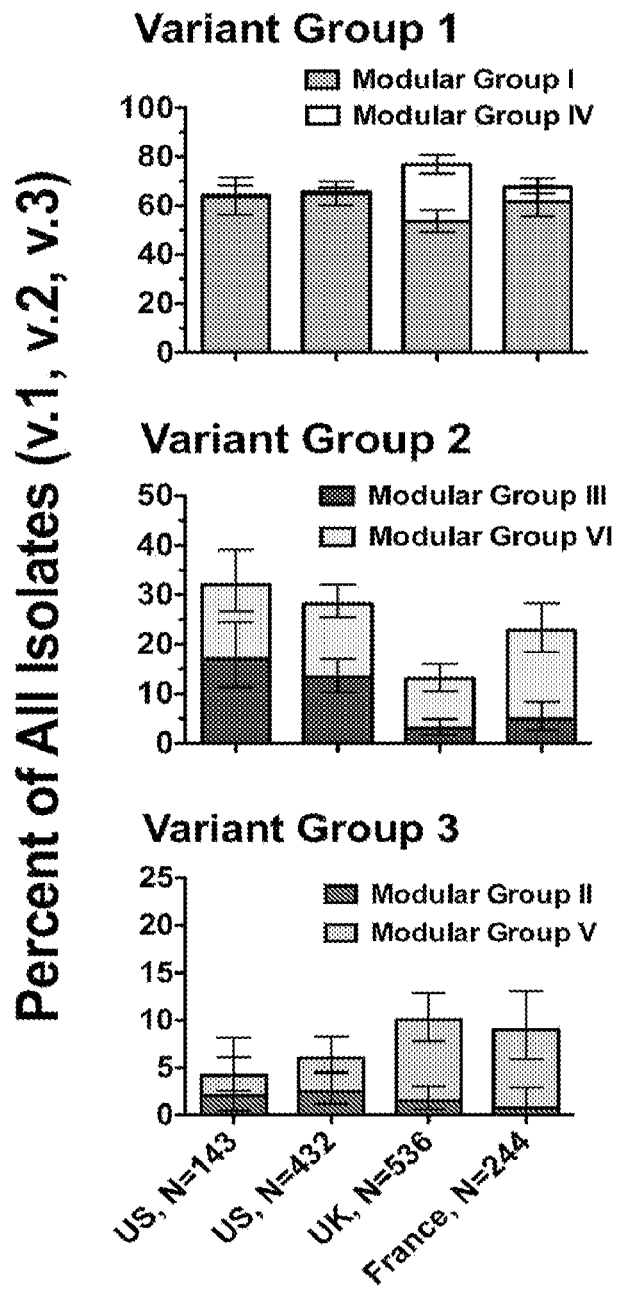
FIG. 12 shows the frequencies of fHbp modular groups among systematically collected *N. meningitidis* group B case isolates. Data are from sequences of isolates collected in the United States (N=432), United Kingdom (N=536) and France (N=244) reported by Murphy et al [16], and newly obtained sequences of 143 additional U.S. isolates from California (2003-2004), Maryland (1995 and 2005), and pediatric hospitals in 9 states (2001-2005).

Among the total of 1405 systematically collected group B isolates, modular group I was found in 59.7%, group II in 1.7%, group III in 8.1%, group IV in 10.6%, group V in 6.1%, and group VI in 13.6%. The new modular groups, VII, VIII and IX, were each found in ≤0.1%. The respective distributions of the fHbp modular groups in the different countries as stratified by the variant group classification of Masignani et al. (2003) *J Exp Med* 197:789-99 are shown in FIG. 12. For this analysis, the data from Norway and Czech Republic were excluded, since the number of isolates in each of these collections was too small for precise estimates of the respective frequencies of the modular groups. The respective percentages of the modular groups in the two U.S. collections are shown separately.

Isolates in variant 1 group of Masignani consisted of modular groups I, IV and VII. Modular group I strains, which have entirely α-type segments, predominated in all three countries (54 to 64 percent of all isolates). In the UK, however, 23% of all isolates were modular group IV, which are natural chimeras of α- and β-type segments (FIG. 8), as compared with <1% in the two U.S. collections, and 3 percent of isolates from France (P<0.001 by chi square). Since there was only one isolate in modular group VII (France), the frequency of this modular group is not shown in FIG. 12.

Isolates in variant 2 group included modular groups III and VI, which are all natural chimeras of α- and β-type segments. Modular groups III or VI were present in approximately equal proportions of isolates in the two U.S. collections, while modular group VI predominated among variant 2 isolates from the UK and France.

Isolates with variant 3 group included modular group II (entirely β-type segments) and modular groups V, VIII and IX, which are chimeras. In France and the UK, modular group V accounted for the majority of the isolates with variant 3 fHbp, while in the two U.S. collections there were approximately equal numbers of modular group II or V proteins. Modular groups VIII and IX accounted for <0.1% of the isolates. Because of the low percentages, these groups are not shown on FIG. 12.

Example 9

Figure 13:
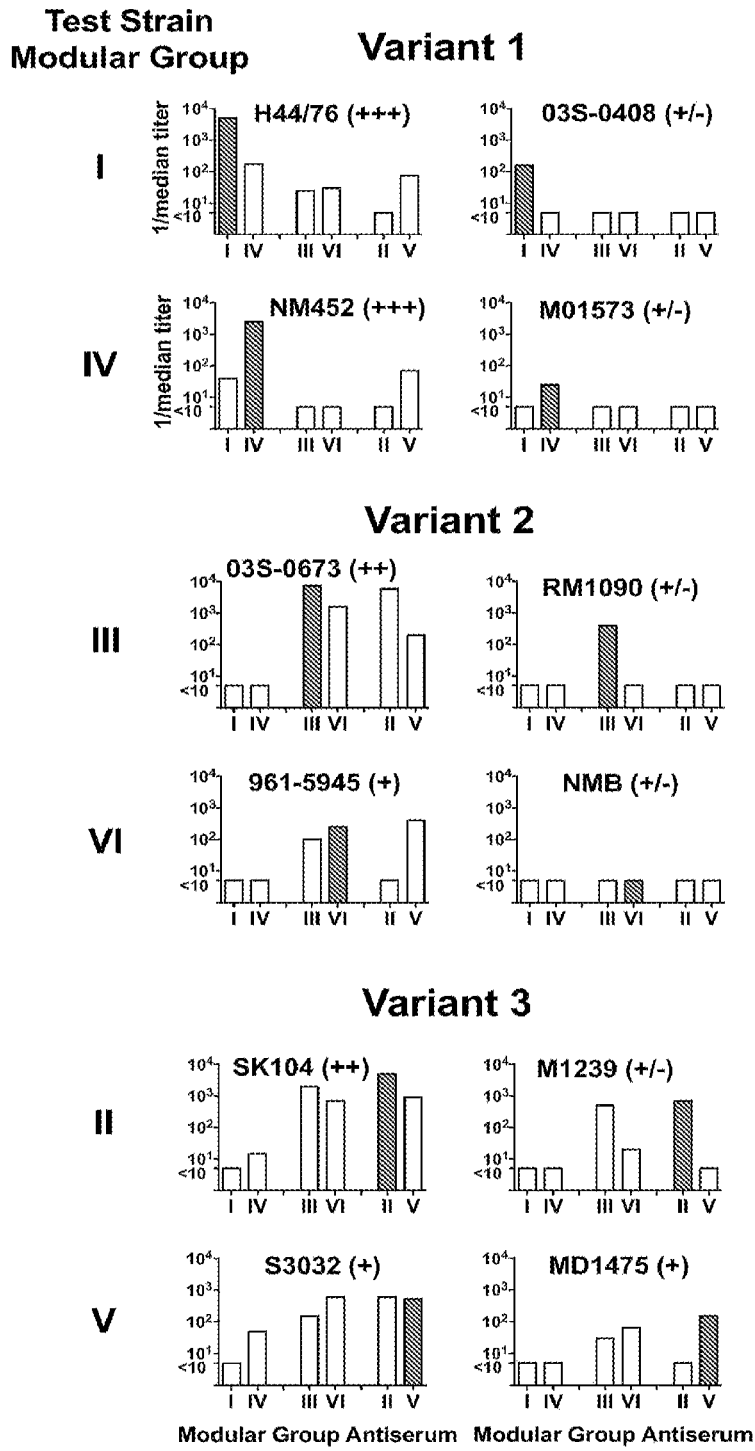
FIG. 13 shows serum bactericidal activities of serum pools from mice immunized with fHbps from modular groups I to VI. The black bars represent the median titers of 3 to 4 serum pools for each modular group tested against homologous test strains. The white bars represent the median titer of the respective heterologous serum pools against the test strain. +, refers to relative expression of fHbp by each of the strains; strains with +/− representing low fHbp-expressing strains (see values in Table 5 in example section)

Strain Susceptibility to Anti-fHbp Serum Bactericidal Activity in Relation to Modular Group and fHbp Expression FIG. 13 depicts human complement bactericidal titers of serum pools from mice immunized with recombinant fHbp vaccines representative of modular groups I-VI. The heights of the bars represent the respective median titers of each of the six antisera (3 to 4 pools per modular group) when tested against the specific test strain. For example, the upper left panel shows the data for strain H44/76, which is a high expresser of fHbp in modular group I (relative expression is designated by +++; actual values are shown in Table 5 below). The median bactericidal titer of the homologous anti-fHbp modular group I antiserum (black bar) was ~1:6000. The respective titers of the five heterologous anti-fHbp modular group antisera (white bars) against strain H44/76 were 1 to 2 $\log_{10}$ lower, ranging from <1:10 (antisera to modular group II) to ~1:200 (antisera to modular group IV). The corresponding median titers of the anti-modular group II and IV antisera when tested against control strains with homologous fHbp modular groups II (strain SK104 in the Variant 3 panel) or IV (NM452 in the Variant 1 panel) were >1:2000. Thus, these and the other heterologous antisera had high antibody activity when measured against control strains with the respective homologous fHbp modular groups.

There were lower bactericidal titers against low fHbp expressing strains than against high expressing strains (compare respective graphs on the right side of FIG. 13 showing data for low expressing strains [designated +/–], with those on the left showing higher expressers). For example the anti-modular group I antiserum had a titer of 1:6000 against H44/76, a high fHbp modular group I expressing strain, but a titer of ~1:100 against strain 03S-0408, a low fHbp modular group I expresser. (For modular group V, both test strains were intermediate expressers, since a pair of high and low fHbp expressing strains were not available).

There was a trend for lower cross-reactivity of anti-fHbp bactericidal activity against strains with low expression of fHbp from heterologous modular groups than for high expressing strains (see for example, data for low expressing strains 03S-0408 (modular group I), M01573 (modular group IV), and RM1090 (modular group III), which were killed only by their respective homologous modular group antisera as compared with the broader bactericidal activity against the respective higher fHbp expressing strains (H44/76, NM452, and 03S-0673; FIG. 13). Strain NMB (fHbp modular group VI) was completely resistant to anti-fHbp bactericidal activity (titer <1:10), which apparently was a result of low fHbp expression (Table 5). The amino acid sequence of the vaccine used to prepare the anti-modular group VI antisera differed by a single amino acid from fHbp expressed by NMB, and the resulting antisera were bactericidal against a higher expressing strain (961-5945) with fHbp modular group VI. Further, the resistant strain, NMB, was killed by a control anti-PorA mAb at a concentration of 0.15 μg/ml, which was identical to that of an anti-PorA mAb required for killing of the anti-fHbp susceptible 961-5945 strain.

TABLE 5

Characteristics of *N. meningitidis* strains used for measuring serum bactericidal activity.

| Strain name | sequence types | clonal complex | Factor H-binding protein | | | | |
|---|---|---|---|---|---|---|---|
| | | | Variant group | Protein ID | Modular group | Expression (ng/$10^6$ cells) | Genbank accession number |
| H44/76 | 32 | 32 | 1 | 1 | I | 31 | AY548370 |
| 03S-0408 | 11 | 11 | 1 | 78 | I | 3 | ACF35432 |
| SK104 | 5748 | 162 | 3 | 99 | II | 11 | GQ219769 |
| M1239 | 437 | 41/44 | 3 | 28 | II | 2 | ABF82029 |
| 03S-0673 | 1364 | 32 | 2 | 23 | III | 14 | GU056306 |

TABLE 5-continued

Characteristics of *N. meningitidis* strains used for measuring serum bactericidal activity.

| Strain name | sequence types | clonal complex | Factor H-binding protein | | | | |
|---|---|---|---|---|---|---|---|
| | | | Variant group | Protein ID | Modular group | Expression (ng/10⁶ cells) | Genbank accession number |
| RM1090 | 11 | 11 | 2 | 22 | III | 2 | ABY26518 |
| NM452 | 283 | 269 | 1 | 15 | IV | 20 | ABL14232 |
| M01573 | 44 | 41/44 | 1 | 55 | IV | 1 | AAR84481 |
| S3032 | 6874 | n/a | 3 | 79 | V | 8 | ACH48234 |
| MD1475 | 162 | 162 | 3 | 82 | V | 7 | GQ219772 |
| 961-5945 | 153 | 8 | 2 | 16 | VI | 5 | AAR84453 |
| NMB | 8 | 8 | 2 | 50 | VI | 1 | AY330379 |

The antibodies used for the quantitative measurement of fHbp and the reactivity of various modular group proteins for each antibody is shown in the Table below.

TABLE 6

Anti-fHbp monoclonal antibody reactivity of recombinant proteins used to prepare antisera in relationship to locations of epitopes.

| Anti-fHbp mAb | | JAR1 | JAR 4 | JAR 3 or JAR 5 | JAR 10 | JAR 11 | JAR 13 | JAR 31 | JAR 32 JAR 35 | JAR 33 |
|---|---|---|---|---|---|---|---|---|---|---|
| Epitope location | Amino acid residue(s) | R204 | (25-27) YGN (57-59) KDN | G121, K122 | K180 and E192[4] | A174 | S216 | Unk[6] | K174 | R180 and E192[4] |
| | Modular segment | Eα | Aα | Cα | Dα and Eβ | Dα | Eβ | UD[6] | Dβ | Dβ and Eβ |

| Modular Group | Variant Group | Protein ID No. | Reactivity of Recombinant Protein by ELISA[5] | | | | | | | |
|---|---|---|---|---|---|---|---|---|---|---|
| I | 1 | 1 | 1 | 1 | 1 | 0 | 0 | 0 | 0 | 0 | 0 |
| II | 3 | 28 | 0 | 0 | 0 | 0 | 0 | 1 | 1 | 1 | 1 |
| III | 2 | 22 | 0 | 1 | 0 | 0 | 0 | 0 | 1 | 1 | 1 |
| IV | 1 | 15 | 0 | 0 | 1 | 0 | 0 | 0 | 0 | 0 | 0 |
| V | 3 | 79 | 0 | 0 | 0 | 1 | 1 | 1 | 1 | 0 | 0 |
| VI | 2 | 77 | 0 | 1 | 0 | 1 | 1 | 1 | 1 | 0 | 0 |

[1]All of the MAbs were bactericidal when tested in certain combinations with human complement
[3]Discontinuous epitope; presence of KDN suppresses epitope [1]
[4]Discontinuous epitope requiring specific combinations of charged residues
[5]Assigned "1" if Optical density >3 SD above background binding when tested at 1 µg/ml, "0", negative.
[6]UD, location of epitope undetermined

What is claimed is:

1. A non-naturally occurring factor H binding protein (fHbp), comprising a non-naturally occurring amino acid sequence, contiguously from its N-terminus to C-terminus:

$$V_A\alpha\text{-}I_3\text{-}V_B\alpha\text{-}I_4\text{-}V_C\alpha\text{-}I_5\text{-}V_D\beta\text{-}I_6\text{-}V_E\beta$$

wherein the $V_{A\alpha}$, $V_{B\alpha}$, $V_{C\alpha}$, $V_{D\beta}$, and $V_{E\beta}$ are variable segments,
wherein combination of alleles for each of the variable segments is not found in nature, and wherein:
the $V_{A\alpha}$ has an amino acid sequence at least 85% identical to SEQ ID NO: 15,
the $I_3$ is the amino acid sequence SRFDF (SEQ ID NO: 3),
the $V_{B\alpha}$ has an amino acid sequence at least 90% identical to SEQ ID NO: 85,
the $I_4$ is the amino acid sequence GEFQ (SEQ ID NO: 4),
the $V_{C\alpha}$ has an amino acid sequence at least 85% identical to SEQ ID NO: 96,
the $I_5$ is the amino acid sequence DD,
the $V_{D\beta}$ has an amino acid sequence at least 85% identical to SEQ ID NO: 192,
the $I_6$ is the amino acid sequence IEHLK (SEQ ID NO: 5) or IEHLE (SEQ ID NO: 6), and
the $V_{E\beta}$ has an amino acid sequence at least 85% identical to SEQ ID NO: 262.

2. The non-naturally occurring fHbp of claim 1, wherein said non-naturally occurring fHbp comprises, contiguously from N-terminus to C-terminus:

$$I_1\text{-}Nte\text{-}I_2\text{-}V_A\alpha\text{-}I_3\text{-}V_B\alpha\text{-}I_4\text{-}V_C\alpha\text{-}I_5\text{-}V_D\beta\text{-}I_6\text{-}V_E\beta\text{-}I_7,$$

wherein the $I_1$ is CSSG (SEQ ID NO: 2),
wherein the Nte is a N-terminal element having the sequence G, GG, SGG, GGGS (SEQ ID NO: 7), SGSGG (SEQ ID NO: 8), GGGSGG (SEQ ID NO:9), GGGSGS (SEQ ID NO:10), GSGG (SEQ ID NO:11), GGGSGGGG (SEQ ID NO:12), GGGSGGGSGG (SEQ ID NO:13), or GGSGG (SEQ ID NO:14),
the $I_2$ is GG, and
the $I_7$ is the amino acid sequence KQ.

3. An immunogenic composition comprising a first non-naturally occurring fHbp, wherein the first non-naturally occurring fHbp is the non-naturally occurring fHbp of claim 1, and a pharmaceutically acceptable excipient.

4. The immunogenic composition of claim 3, further comprising a second *N. meningitidis* fHbp, wherein said second fHbp is different from said first non-naturally occurring fHbp.

5. The immunogenic composition of claim 3, wherein said non-naturally occurring fHbp is in a vesicle preparation, wherein vesicles are prepared from a *Neisseria* bacterium.

6. The immunogenic composition of claim 5, wherein said *Neisseria* bacterium is genetically modified to disrupt production of an endogenous fHbp polypeptide.

7. The immunogenic composition of claim 3, wherein said non-naturally occurring fHbp is produced by a *Neisseria* bacterium that is genetically modified to produce said fHbp.

8. The immunogenic composition of claim 6, wherein said vesicle preparation is from the *Neisseria* bacterium producing said non-naturally occurring fHbp.

9. The immunogenic composition of claim 6, wherein said *Neisseria* bacterium is deficient in capsular polysaccharide synthesis.

10. The non-naturally occurring fHbp of claim 1, wherein
the $V_{A\alpha}$ has an amino acid sequence at least 90% identical to SEQ ID NO: 15,
the $V_{B\alpha}$ has an amino acid sequence at least 90% identical to SEQ ID NO: 85,
the $V_{C\alpha}$ has an amino acid sequence at least 90% identical to SEQ ID NO: 96,
the $V_{D\beta}$ has an amino acid sequence at least 90% identical to SEQ ID NO: 192, and
the $V_{E\beta}$ has an amino acid sequence at least 90% identical to SEQ ID NO: 262.

11. The non-naturally occurring fHbp of claim 1, wherein
the $V_{A\alpha}$ has an amino acid sequence at least 95% identical to SEQ ID NO: 15,
the $V_{B\alpha}$ has an amino acid sequence at least 90% identical to SEQ ID NO: 85,
the $V_{C\alpha}$ has an amino acid sequence at least 95% identical to SEQ ID NO: 96,
the $V_{D\beta}$ has an amino acid sequence at least 90% identical to SEQ ID NO: 192, and
the $V_{E\beta}$ has an amino acid sequence at least 95% identical to SEQ ID NO: 262.

12. The non-naturally occurring fHbp of claim 2, wherein
the $V_{A\alpha}$ has an amino acid sequence at least 90% identical to SEQ ID NO: 15,
the $V_{B\alpha}$ has an amino acid sequence at least 90% identical to SEQ ID NO: 85,
the $V_{C\alpha}$ has an amino acid sequence at least 90% identical to SEQ ID NO: 96,
the $V_{D\beta}$ has an amino acid sequence at least 90% identical to SEQ ID NO: 192, and
the $V_{E\beta}$ has an amino acid sequence at least 90% identical to SEQ ID NO: 262.

13. The non-naturally occurring fHbp of claim 2, wherein
the $V_{A\alpha}$ has an amino acid sequence at least 95% identical to SEQ ID NO: 15,
the $V_{B\alpha}$ has an amino acid sequence at least 90% identical to SEQ ID NO: 85,
the $V_{C\alpha}$ has an amino acid sequence at least 95% identical to SEQ ID NO: 96,
the $V_{D\beta}$ has an amino acid sequence at least 90% identical to SEQ ID NO: 192, and
the $V_{E\beta}$ has an amino acid sequence at least 95% identical to SEQ ID NO: 262.

14. The non-naturally occurring fHbp of claim 1, wherein said fHbp comprises an epitope that is specifically bound by JAR 5 monoclonal antibody.

15. A method of eliciting an antibody response to *Neisseria meningitidis* in a mammal, the method comprising administering to said mammal a composition comprising an immunologically effective amount of the non-naturally occurring fHbp of claim 1.

16. The method of claim 15, wherein the mammal is a human.

17. The method of claim 15, wherein said non-naturally occurring fHbp is in a preparation comprising outer membrane vesicles, microvesicles, or a mixture thereof.

18. The method of claim 17, wherein said vesicles are prepared from two or more different strains of *N. meningitidis*, each of which is genetically different from the other.

\* \* \* \* \*